(12) United States Patent
Anderson et al.

(10) Patent No.: US 7,070,556 B2
(45) Date of Patent: Jul. 4, 2006

(54) TRANSOBTURATOR SURGICAL ARTICLES AND METHODS

(75) Inventors: Kimberly A. Anderson, Eagan, MN (US); Brian R. Watschke, Eden Prairie, MN (US); Georges Mellier, Lyons (FR); Johann J. Neisz, Coon Rapids, MN (US)

(73) Assignee: AMS Research Corporation, Minnetonka, MN (US)

( * ) Notice: Subject to any disclaimer, the term of this patent is extended or adjusted under 35 U.S.C. 154(b) by 347 days.

(21) Appl. No.: 10/306,179

(22) Filed: Nov. 27, 2002

(65) Prior Publication Data

US 2003/0171644 A1 Sep. 11, 2003

Related U.S. Application Data

(60) Provisional application No. 60/362,806, filed on Mar. 7, 2002, provisional application No. 60/380,797, filed on May 14, 2002, provisional application No. 60/402,007, filed on Aug. 8, 2002, and provisional application No. 60/414,865, filed on Sep. 30, 2002.

(51) Int. Cl.
*A61F 2/00* (2006.01)
*A61B 17/12* (2006.01)
*A61B 17/06* (2006.01)
*D05B 1/00* (2006.01)

(52) U.S. Cl. .................. 600/29; 606/144; 606/225; 112/169

(58) Field of Classification Search ............ 600/30, 600/37; 128/898, DIG. 25; 606/73, 75, 139, 606/232, 223, 144, 118, 119, 185, 147, 148, 606/191, 225; 112/169

See application file for complete search history.

(56) References Cited

U.S. PATENT DOCUMENTS

| 2,738,790 | A | 3/1956 | Todt et al. |
| 3,124,136 | A | 3/1964 | Usher |
| 3,182,662 | A | 5/1965 | Shirodkar |

(Continued)

FOREIGN PATENT DOCUMENTS

| DE | 2305815 | 2/1973 |
| DE | 43 04 353 A1 | 4/1994 |
| DE | 4220283 C2 | 5/1994 |

(Continued)

OTHER PUBLICATIONS

Beck, Peter R. et al., Treatment of Urinary Stress Incontinence With Anterior Colporrhaphy. Obstetrics and Gynecology, vol. 59 (No. 3), pp. 269–274 (Mar. 1982).
Benderev, Theodore V., MD, A Modified Percutaneous Outpatient Bladder Neck Suspension System, Journal of Urology, vol. 152, pp. 2316–2320 Idec. 1994).
Das, Sakti et al., Laparoscopic Colpo–Suspension, The Journal of Urology, vol. 154, pp. 1119–1121 (Sep. 1995).

(Continued)

*Primary Examiner*—Samuel G. Gilbert
(74) *Attorney, Agent, or Firm*—Jose W. Jimenez

(57) ABSTRACT

Described is a surgical instrument and method for treating female urinary stress incontinence. The instrument includes a first curved needle-like element defining in part a curved shaft having a distal end and a proximal, a mesh for implanting into the lower abdomen of a female to provide support to the urethra; a second curved needle element having a proximal end and a distal end, and a coupler for simultaneous attachment to the distal end of the first needle and the distal end of the second needle.

26 Claims, 36 Drawing Sheets

U.S. PATENT DOCUMENTS

| | | | |
|---|---|---|---|
| 3,311,110 A | 3/1967 | Singerman et al. | |
| 3,384,073 A | 5/1968 | Van Winkle, Jr. | |
| 3,472,232 A | 10/1969 | Earl | |
| 3,580,313 A | 5/1971 | McKnight | |
| 3,763,860 A | 10/1973 | Clarke | |
| 3,789,828 A | 2/1974 | Schulte | |
| 3,858,783 A | 1/1975 | Kapitanov et al. | |
| 3,924,633 A | 12/1975 | Cook et al. | |
| 3,995,619 A | 12/1976 | Glatzer | |
| 4,019,499 A | 4/1977 | Fitzgerald | |
| 4,037,603 A | 7/1977 | Wendorff | |
| 4,128,100 A | 12/1978 | Wendorff | |
| 4,172,458 A | 10/1979 | Pereyra | |
| 4,204,541 A * | 5/1980 | Kapitanov | 606/145 |
| 4,235,238 A | 11/1980 | Ogiu et al. | |
| 4,246,660 A | 1/1981 | Wevers | |
| 4,265,231 A | 5/1981 | Scheller, Jr. et al. | |
| 4,441,497 A | 4/1984 | Paudler | |
| 4,509,516 A | 4/1985 | Richmond | |
| 4,632,100 A | 12/1986 | Somers et al. | |
| 4,775,380 A | 10/1988 | Seedhom et al. | |
| 4,857,041 A | 8/1989 | Annis et al. | |
| 4,865,031 A | 9/1989 | O'Keeffe | |
| 4,920,986 A | 5/1990 | Biswas | |
| 5,053,043 A | 10/1991 | Gottesman et al. | |
| 5,085,661 A | 2/1992 | Moss | |
| 5,112,344 A * | 5/1992 | Petros | 606/148 |
| 5,123,428 A | 6/1992 | Schwarz | |
| 5,188,636 A | 2/1993 | Fedotov | |
| 5,207,694 A * | 5/1993 | Broome | 606/148 |
| 5,209,756 A | 5/1993 | Seedhom et al. | |
| 5,250,033 A | 10/1993 | Evans et al. | |
| 5,256,133 A | 10/1993 | Spitz | |
| 5,281,237 A | 1/1994 | Gimpelson | |
| 5,328,077 A | 7/1994 | Lou | |
| 5,336,239 A * | 8/1994 | Gimpelson | 606/223 |
| 5,337,736 A * | 8/1994 | Reddy | 600/217 |
| 5,362,294 A | 11/1994 | Seitzinger | |
| 5,368,595 A | 11/1994 | Lewis | |
| 5,383,904 A | 1/1995 | Totakura et al. | |
| 5,386,836 A | 2/1995 | Biswas | |
| 5,403,328 A | 4/1995 | Shallman | |
| 5,413,598 A | 5/1995 | Moreland | |
| 5,439,467 A | 8/1995 | Benderev et al. | |
| 5,520,700 A | 5/1996 | Beyar et al. | |
| 5,520,703 A * | 5/1996 | Essig et al. | 606/148 |
| 5,544,664 A | 8/1996 | Benderev et al. | |
| 5,562,685 A | 10/1996 | Mollenauer et al. | |
| 5,562,689 A | 10/1996 | Green et al. | |
| 5,571,139 A | 11/1996 | Jenkins, Jr. | |
| 5,591,163 A | 1/1997 | Thompson | |
| 5,611,515 A | 3/1997 | Benderev et al. | |
| 5,628,756 A | 5/1997 | Barker, Jr. et al. | |
| 5,633,286 A | 5/1997 | Chen | |
| 5,662,683 A * | 9/1997 | Kay | 606/232 |
| 5,669,935 A | 9/1997 | Rosenman et al. | |
| 5,683,349 A | 11/1997 | Makower et al. | |
| 5,807,403 A | 9/1998 | Beyar et al. | |
| 5,810,882 A * | 9/1998 | Bolduc et al. | 606/213 |
| 5,836,314 A * | 11/1998 | Benderev et al. | 128/898 |
| 5,836,315 A | 11/1998 | Benderev et al. | |
| 5,842,478 A | 12/1998 | Benderev et al. | |
| 5,860,425 A | 1/1999 | Benderev et al. | |
| 5,899,909 A * | 5/1999 | Claren et al. | 606/119 |
| 5,904,696 A * | 7/1999 | Rosenman | 606/151 |
| 5,919,232 A | 7/1999 | Chaffringeon et al. | |
| 5,934,283 A | 8/1999 | Willem et al. | |
| 5,935,122 A | 8/1999 | Fourkas et al. | |
| 5,935,138 A | 8/1999 | McJames, II et al. | 606/139 |
| 5,944,732 A | 8/1999 | Raulerson et al. | |
| 5,972,000 A | 10/1999 | Beyar et al. | |
| 5,988,171 A | 11/1999 | Sohn et al. | |
| 5,992,269 A * | 11/1999 | Puig et al. | 81/3.35 |
| 5,997,554 A | 12/1999 | Thompson | |
| 6,010,447 A | 1/2000 | Kardjian | |
| 6,030,393 A | 2/2000 | Corlew | |
| 6,031,148 A | 2/2000 | Hayes et al. | |
| 6,042,534 A | 3/2000 | Gellman et al. | |
| 6,042,536 A | 3/2000 | Tihon et al. | |
| 6,048,351 A * | 4/2000 | Gordon et al. | 606/144 |
| 6,050,937 A | 4/2000 | Benderev | |
| 6,053,935 A * | 4/2000 | Brenneman et al. | 606/232 |
| 6,068,591 A | 5/2000 | Bruckner et al. | |
| 6,071,290 A | 6/2000 | Compton | |
| 6,099,538 A * | 8/2000 | Moses et al. | 606/144 |
| 6,106,545 A | 8/2000 | Egan | |
| 6,110,101 A | 8/2000 | Tihon et al. | |
| 6,117,067 A | 9/2000 | Gil-Vernet | |
| 6,168,611 B1 | 1/2001 | Risvi | |
| 6,221,005 B1 | 4/2001 | Bruckner et al. | |
| 6,273,852 B1 * | 8/2001 | Lehe et al. | 600/30 |
| 6,302,840 B1 | 10/2001 | Benderev | |
| 6,306,079 B1 | 10/2001 | Trabucco | |
| 6,328,744 B1 | 12/2001 | Harari et al. | |
| 6,334,446 B1 * | 1/2002 | Beyar | 128/898 |
| 6,352,553 B1 | 3/2002 | van der Burg et al. | |
| 6,367,353 B1 * | 4/2002 | Puig et al. | 81/3.48 |
| 6,382,214 B1 | 5/2002 | Raz et al. | |
| D458,679 S | 6/2002 | Thompson et al. | |
| 6,406,423 B1 | 6/2002 | Scetbon | |
| 6,406,480 B1 | 6/2002 | Beyar et al. | |
| 6,440,154 B1 | 8/2002 | Geltman et al. | |
| 6,475,139 B1 | 11/2002 | Miller | |
| 6,478,727 B1 * | 11/2002 | Scetbon | 600/30 |
| 6,478,803 B1 | 11/2002 | Kapec et al. | |
| 6,482,214 B1 | 11/2002 | Sidor, Jr. et al. | |
| 6,494,906 B1 | 12/2002 | Owens | |
| 6,502,578 B1 | 1/2003 | Raz et al. | |
| 6,530,943 B1 | 3/2003 | Hoepffner et al. | |
| 6,582,443 B1 | 6/2003 | Cabak et al. | |
| 6,626,917 B1 * | 9/2003 | Craig | 606/144 |
| 6,663,633 B1 * | 12/2003 | Pierson, III | 606/72 |
| 6,673,010 B1 | 1/2004 | Skiba et al. | |
| 6,802,807 B1 | 10/2004 | Anderson et al. | |
| 2001/0000533 A1 | 4/2001 | Kovac | |
| 2001/0049467 A1 | 12/2001 | Lehe et al. | |
| 2002/0022841 A1 | 2/2002 | Kovac | |
| 2002/0028980 A1 | 3/2002 | Thierfelder et al. | |
| 2002/0055748 A1 | 5/2002 | Gellman et al. | |
| 2002/0058959 A1 | 5/2002 | Gellman | |
| 2002/0068948 A1 | 6/2002 | Stormby et al. | |
| 2002/0072694 A1 | 6/2002 | Snitkin et al. | |
| 2002/0077526 A1 | 6/2002 | Kammerer et al. | |
| 2002/0078964 A1 | 6/2002 | Kovac et al. | |
| 2002/0091373 A1 | 7/2002 | Berger | |
| 2002/0099258 A1 | 7/2002 | Staskin et al. | |
| 2002/0099259 A1 | 7/2002 | Anderson et al. | |
| 2002/0099260 A1 | 7/2002 | Suslaine et al. | |
| 2002/0107430 A1 | 8/2002 | Neisz et al. | |
| 2002/0107525 A1 | 8/2002 | Harari et al. | |
| 2002/0115906 A1 | 8/2002 | Miller | |
| 2002/0128670 A1 | 9/2002 | Ulmsten et al. | |
| 2002/0138025 A1 | 9/2002 | Gellman et al. | |
| 2002/0147382 A1 | 10/2002 | Neisz et al. | |
| 2002/0151762 A1 | 10/2002 | Rocheleau et al. | |
| 2002/0151909 A1 | 10/2002 | Gellman et al. | |
| 2002/0151910 A1 | 10/2002 | Gellman et al. | |
| 2002/0156487 A1 | 10/2002 | Gellman et al. | |
| 2002/0156488 A1 | 10/2002 | Gellman et al. | |
| 2002/0188169 A1 | 12/2002 | Kammerer et al. | |
| 2003/0004395 A1 | 1/2003 | Therin | |

| | | | |
|---|---|---|---|
| 2003/0009181 | A1 | 1/2003 | Gellman et al. |
| 2003/0023136 | A1 | 1/2003 | Raz |
| 2003/0023137 | A1 | 1/2003 | Gellman |
| 2003/0023138 | A1 | 1/2003 | Luscombe |
| 2003/0036676 | A1 | 2/2003 | Scetbon |
| 2003/0045774 | A1 | 3/2003 | Staskin et al. |
| 2003/0050530 | A1 | 3/2003 | Neisz et al. |
| 2003/0065246 | A1 | 4/2003 | Inman et al. |
| 2003/0065402 | A1 | 4/2003 | Anderson et al. |
| 2003/0130670 | A1 | 7/2003 | Anderson et al. |
| 2003/0149440 | A1 | 8/2003 | Kammerer et al. |
| 2003/0176762 | A1 | 9/2003 | Kammerer |
| 2003/0199732 | A1 | 10/2003 | Suslian et al. |
| 2004/0267088 | A1 | 12/2004 | Kammerer |

FOREIGN PATENT DOCUMENTS

| | | |
|---|---|---|
| DE | 101 38 950 | 2/2003 |
| DE | 10211360 | 10/2003 |
| DE | 102 11 360 | 10/2003 |
| EP | 0 470 308 A1 | 2/1992 |
| EP | 0 650 703 A1 | 6/1994 |
| EP | 0 643 945 A2 | 7/1994 |
| EP | 1 093 758 A1 | 4/2001 |
| SU | 1225547 A1 | 4/1986 |
| SU | 1342486 A | 10/1987 |
| WO | WO 93/17635 A1 | 9/1993 |
| WO | WO 93/19678 A2 | 10/1993 |
| WO | WO 97/16121 | 5/1997 |
| WO | WO 98/19606 A1 | 5/1998 |
| WO | WO 98/35606 | 8/1998 |
| WO | WO 98/35616 A1 | 8/1998 |
| WO | WO 98/35632 | 8/1998 |
| WO | WO 99/52450 A1 | 10/1999 |
| WO | WO 00/13601 A1 | 3/2000 |
| WO | WO 00/18319 A1 | 4/2000 |
| WO | WO 00/57812 A1 | 10/2000 |
| WO | WO 00/64370 A1 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 01/78609 | 10/2001 |
| WO | WP 02/02031 | 1/2002 |
| WO | WO 02/26108 | 4/2002 |
| WO | WO 02/28312 A1 | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/069781 | 9/2002 |
| WO | WO 02/071953 A2 | 9/2002 |
| WO | WO 02/078552 A1 | 10/2002 |
| WO | WO 2004/016196 A2 | 2/2004 |
| WO | WO 2004/019786 | 3/2004 |

OTHER PUBLICATIONS

Gija, Ivan et all, A Modified Raz Bladder Neck Suspension Operation (Transvaginal Burch), The Journal of Urology, vol. 153, pp. 1455–1457 (May 1995).

Holschneider, C.H., et al., The Modified Pereyra Procedure in Recurrent Stress Urinary Incontinence: A 15-year Review, obstetrics & Gynecology, vol. 83, No. 4, pp. 573–578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648–652 (Apr. 1998).

Klutke, Carl et al., The Anatomy of Stress Incontinence: Magentic Resonance Imaging of the Female Bladder Neck and Urethra, The Journal Urology, vol. 143, pp. 563–566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294–296 (Aug. 1996).

Kovac, S. Robert, et al, Pubic Bone Suburethral Stabilization Sling for Recurrent Urinary Incontinence, Obstetrics & Gynecology, vol. 89, No. 4, pp. 624–627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow–up of the Pubic Bone Suburethral Stabilization Sling Operation for Recurrent Urinary Incontinence (Kovac Procedure), Journal of Pelvic Surgery, pp. 156–160 (May 1999).

Leach, Gary E., et al, Female Stress Urinary Incontinence Clinical Guidelines Panel Report on Surgical Management of Female Stress Urinary Incontinence, American Urological Association, vol. 158, pp. 875–880 (Sep. 1997).

Leach, Gary E., MD, Bone Fixation Technique for Transvaginal Needle Suspension, Urology vol. XXXI, No. 5, pp. 388–390 (May 1988).

McGuire, Edward J. et al., Experience With Pubovaginal Slings for Urinary Incontinence at the University of Michigan, Journal of Urology, vol. 138, pp. 90–93 (1987).

McGuire, Edward J. et al., Abdominal Fascial Slings, Slings, Raz Female Urology, pp. 369–375 (1996).

Morgan, J.E. et al., The Marlex Sling Operation for the Treatment of Recurrent Stress Urinary Incontinence: A 16–Year Review, American Obstetrics Gynecology, vol. 151, No. 2, pp. 224–226 (Jan. 1998).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45–50 (1999).

Pereyra, Armand J. et al, Pubourethral Supports in Perspective: Modified Pereyra Procedure for Urinary Incontinence, Obstetrics and Gynecology, vol. 59, No. 5, pp. 643–648 (May 1982).

Petros, Peter E. Papa et al., Part IV: Surgical Applications of the Theory–Development of the Intravaginal Sling Plasty (IVS) Procedure, Scandinavian Journal of Neurology and Urodynamics, Sup 153, pp. 53–54 (1993).

Stanton, Stuart, Springer–Veglag, Surgery of Female Incontinence, pp. 105–113 (1986).

Staskin, David R. et al., The Gore–Tex Sling Procedure for Female Sphincteric Incontinence: Indications, Technique, and Results, World Journal of Urology, vol. 15, pp. 295–299 (1997).

TVT Tension–free Vaginal Tape, Gynecare, Ethicon, Inc., 23 pages (1999).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93–100, vol. 21 (Mar. 1996).

Zimmern, Phillippe E. et al., Four–Corner Bladder Neck Suspension, Vaginal Surgery for the Urologist, vol. 2, No. 1, pp. 29–36 (Apr. 1994).

Document entitled "Access Instrument System™ with AlloSling™ Fascia" (5 pages with two pages of Instructions for Use).

Document with heading "Introducing: AlloSling™ Fascia the *Natural Choice* for Suburethral Sling Procedures", Advertisement from UroMed Corp.

AlloSource product literature (11 pages).

Staskin et al., A Comparison of Tensile Strength among Three Preparations of Irradiated and Non–Irradiated Human Fascia Lata Allografts (2 pages).

UroMed Access™ Instrument System for the Sub–urethral Sling Procedure Catalog No. 120235, Directions for Use, (3 pages).

U.S. patent application Ser. No. 09/661,620, Suslaine et al., filed Sep. 27, 2002.

"*Safyre and Transobturator*", DVD.

"The Strength of Suspend" *Mentor*, Marketing Material, 6 pages.

*Gynecare TVT*, "Tension–Free Support for Incontinence" Marketing Material, Gynecare Worldwide (02/02), 6 pages.

Sender Hershorn, M.D. et al., "Gynecare TVT With Abdominal Guides Early Clinical Experience" *Gynecare TVT*, Marketing Material, Gynecare Worldwide (05/02), 12 pages.

"Uretex Polypropylene Urethral Support—Safety, Simplicity, Flexibility" *Bard*, Marketing Material, 8 pages.

Sabre, "Generation Now" *Mentor*, Marketing Material (05/02), 4 pages.

Safyre, "The Essence of a Contemporary Synthetic Sling—Self–Anchoring Complete Adjustability Elastic" *Promedon*, Marketing Material (01/02), 4 pages.

Porges U.K. Ltd., "Uratape Perineal Hammock Urethral Support Tape—New Generation of Tape Perineal Implantation" *Mentor*, Marketing Material (01/02), 6 pages.

Boston Scientific Microvasive, "Precision Twist Transvaginal Anchor System—Low Profile Design for Precise Anchor Placement" *Boston Scientific Corp.*, Marketing Material (2000), 2 pages.

Boston Scientific Microvasive, "Precision Tact Transvaginal Anchor System—The Precise Approach to Transvaginal Sling Procedures" *Boston Scientific Corp.*, Marketing Material (1998), 4 pages.

Boston Scientific Microvasive, "Vesica Sling Kits with Press–In Percutaneous Anchor System—Simplifying Sling Procedures" *Boston Scienficic Corp.*, Marketing Material (1998), 4 pages.

"T–Sling (Totally Tension–free) Urinary Incontinence Procedure" *Herniamesh USA Inc.*, Marketing Material (01/00), 2 pages.

"IVS Tunneller—Australian Medical Design Breakthrough for GSI, Mixed Incontinence and Vault Prolapse", *AMA Medical Products T/A AMA Services (WA) Pty Ltd.*, Marketing Material, 4 pages.

"Advantage A/T—Surgical Mesh Sling Kit", *Boston ScientificCorp.*, Marketing Material (2002) 1 page.

"Durasphere—Injectable Bulking Agent", *Boston Scientific-Corp.*, Marketing Material (2002) 1 page.

"Precision SpeedTac—Transvaginal Anchor System", *Boston ScientificCorp.*, Marketing Material (2002) 1 page.

Boston Scientific Microvasive, "Stone Cone—Nitinol Urological Retrieval Coil", *Boston ScientificCorp.*, Marketing Material (2002) 1 page.

"Swiss LithoClast Ultra—Combination Ulrasonic and Pneumatic Urological Lithotriptor", *Boston ScientificCorp.*, Marketing Material (2002) 1 page.

Boston Scientific Microvasive, "Polaris—Dual Durometer Percuflex Ureteral Stent with HydroPlus Coating", *Boston ScientificCorp.*, Marketing Material (2001) 1 page.

G. A. J. McIndoe et al., National Women's Hospital, Auckland, "The Aldridge Sling Procedure in the Treatment of Urinary Stress Incontinence" Aust NZ J Obstet Gynaecol, 1987; 27:238.

Charles F. McKiel, Jr. et al., "Marshall–Marchetti Procedure: Modification" *1st Journal in Urology*, vol. 96, pp. 737–739, Nov. 1966, The Williams & Wilkins Co.

Valenzio C. Mascio, M.D., "Therapy of Urinary Stress Incontinence In Women Using Mitek GII Anchors" *Mitek Surgical Products, Inc.*, 5 pages (1993).

Edward J. McGuire, M.D., "The Sling Procedure for Urinary Stress Incontinence" *Profiles in Urology*, pp. 3, 5–19.

Edward J. McGuire, et al., "Pubovaginal Sling Procedure for Stress Incontinence" *The Journal of Urology*, vol. 119, pp. 82–84, Jan. 1978, The Williams & Wilkins Co.

Edward J. McGuire, M.D., "Abdominal Procedures for Stress Incontinence" Symposium on Female Urology, *Urologic Clinics of North America*—vol. 12, No. 2, pp. 285–290, May 1985.

Victor Fray Marshall, M.D., F.A.C.S. et al., "The Correction of Stress Incontinence by Simple Vesicourethral Suspension" *Surgery, Gynecology and Obstetrics*, pp. 509–518.

Kevin R. Loughlin, et al., "Review of an 8–Year Experience With Modifications of Endoscopic Suspension of the Bladder Neck for Female Stress Urinary Incontinence" *The Journal of Urology*, vol. 143, pp. 44–45, Jan. 1990 The American Urological Association, Inc.

Irving L. Lichtenstein, M.D., et al., "The Tension–Free Hernioplasty" *The American Journal of Surgery*, vol. 157, Feb. 1989, pp. 188–193.

Andrew Korda, et al., "Experience with Silastic Slings for Female Urinary Incontinence" *Aust NZ J Obstet Gynaecol*, 1989, vol. 29, pp. 150–154.

Mickey M. Karram, M.D. et al., "Patch Procedure: Modified Transvaginal Fascia Lata Sling for Recurrent or Severe Stress Urinary Incontinence" *Obstetrics & Gynecology*, vol. 75, No. 3, Part 1, Mar. 1990, pp. 461–464.

J. Kersey, "The gauze hammock sling operation in the treatment of stress incontinence" *British Journal of Obstetrics and Gynaecology*, vol. 90 pp. 945–949, Oct. 1983.

A. Ingelman–Sundberg, et al., "Surgical Treatment of Female Urinary Stress Incontinence" *Contr. Gynec. Obstet.* vol. 10, pp. 51–69 (Karger. Basel 1983).

T. N. A. Jeffcoate, M.D., F.R.C.S.E., F.R.C.O.G., "The Results of the Aldridge Sling Operation for Stress Incontinence" *Journal of Obstetrics and Gynaecology*, pp. 36–39.

C. Paul Hodgkinson, M.D., et al., "Urinary Stress Incontinence in the Female—III. Round–ligament technic for retropubic suspension of the urethra" *Obstetrics and Gynecology*, vol. 10, No. 5, Nov. 1957, pp. 493–499.

L. Henriksson, M.D. et al., "A urodynamic evaluation of the effects of abdominal urethrocystopexy and vaginal sling urethroplasty in women with stress incontinence" *Am. J. Obstet. Gynecol*, May 1, 1978, pp. 77–82.

Victoria L. Handa, M.D. et al., "Banked Human Fascia Lata for the Suburethral Sling Procedure: A Preliminary Report" *Obstetrics and Gynecology*, vol. 88, No. 6, May 20, 1996, pp. 1045–1049.

C. Falconer, et al., "Influence of different Sling Materials on Connective Tissue Metabolism in Stress Urinary Incontinent Women" *International Urogynecology Journal*, (2001) (Supp. 2) pp. S19–S23.

H. Enzelsberger et al., "Urodynamic and Radiologic Parameters Before and After Loop Surgery for Recurrent Urinary Stress Incontinence" *Acta Obstet Gynecol Scand 1990*; 69 pp. 51–54.

Bjarne C. Eriksen, et al., "Long–Term Effectiveness of the Burch Colposuspension in Female Urinary Stress Incontinence" *Acta Obstet Gynecol Scand* 1990; 69 pp. 45–50.

John O. L. DeLancey, M.D., "Structural support of the urethra as it relates to stress urinary incontinence: The hammock hypothesis" *Am. J Obstet Gynecol*, pp. 1713–1723, Jun. 1994.

Ross M. Decter, "Use of the Fascial Sling for Neurogenic Incontinence: Lessons Learned" *The Journal of Urology*, vol. 150, pp. 683–686, Aug. 1993, American Urological Association, Inc.

Jong M. Choe, et al., "Gore–Tex Patch Sling: 7 Years Later" *Urology, 54 (4)* pp. 641–646, Apr. 1999, Elsevier Science Inc.

Fred E. Bryans, M.D., F.R.C.S.(C.), "Marlex gauze hammock sling operation with Cooper's ligament attachment in the management of recurrent urinary stress incontinence" *Am. J. Obstet. Gynecol.*, vol. 133, No. 3, pp. 292–294, Feb. 1, 1979.

John C. Burch, M.D., "Urethrovaginal fixation to Cooper's ligament for correction of stress incontinence, cystocele, and prolapse" *Am. J. Obstet. & Gynecol.*, vol. 81 No. 2, pp. 281–290, Feb. 1961.

Jerry G. Blaivas, et al., "Pubovaginal Fascial Sling for the Treatment of Complicated Stress Urinary Incontinence" *The Journal of Urology*, vol. 145, Jun. 1991, pp. 1214–1218, American Urological Association, Inc.

Jerry G. Blaivas, M.D., et al., "Type III Stress Urinary Incontinence: Importance of Proper Diagnosis and Treatment" *Gynecology and Obstetrics Surgical Forum*, pp. 473–475.

Arieh Bergman, M.D. et al., "Three surgical procedures for genuine stress incontinence: Five–year follow–up of a prospective randomized study", *Am. J. Obstet Gynecol*, vol. 173 No. 1, pp. 66–71, Jul. 1995.

M. Asmussen, et al., "Simultaneous Urethro–Cystometry With a New Technique" *Scand J Urol Nephrol 10*, pp. 7–11, 1976.

Tohru Araki, et al, "The Loop–Loosening Procedure for Urination Difficulties After Stamey Suspension of the Vesical Neck" *The Journal of Urology*, vol. 144, pp. 319–323, Aug. 1990, American Urological Association, Inc.

Albert H. Aldridge, B.S., M.D., F.A.C.S., "Transplantation of Fascia for Relief of Urinary Stress Incontinence" *Am. J. of Obstet. and Gynec.*, pp. 398–411.

Peter E. Papa Petros et al., "The Role of a Lax Posterior Vaginal Fornix in the Causation of Stress and Urgency Symptoms: A Preliminary Report" *Acta Obstet Gynecol Scand.*, 69 Suppl. 153, pp. 71–73, 1990.

Peter E. Papa Petros et al., "The Tethered Vagina Syndrome, Post Surgical Incontinence and I–Pasty Operation for Cure" *Acta Obstet Gynecol Scand.* pp. 63–67, 69 Suppl. 153, 1990.

Peter E. Papa Petros et al., "The Tuck Procedure: A Simplified Vaginal Repair for Treatment of Female Urinary Incontinence" *Acta Obstet Gynecol Scand*, 1990. pp. 41–42, 69 Suppl. 153.

Peter E. Papa Petros et al., "The Posterior Fornix Syndrome: A Multiple Symptom Complex of Pelvic Pain and Abnormal Urinary Symtoms Deriving From Laxity in the Posterior Fornix of Vagina" *Scand J Urol Nephrol*, pp. 89–93, Suppl. No. 153, 1993.

Peter E. Papa Petros et al., "The Intravaginal Slingplasty Procedure: IVS VI—further development of the 'double-–breasted' vaginal flap repair—attached flap" *Scand J Urol Nephrol*, pp. 81–84, Suppl. No. 153, 1993.

Peter E. Papa Petros et al., "The Further Development of the Intravaginal Slingplasty Procedure: IVS IV—(with "double-–breasted" unattached vaginal flap repair and "free" vaginal tapes)" *Scand J Urol Nephrol*, pp. 73–79, Suppl. No. 153, 1993.

Peter E. Papa Petros et al., "The Free Graft Procedure for Cure of the Tethered Vagina Syndrome" *Scand J Urol Nephrol*, pp. 85–87, Suppl. No. 153, 1993.

Peter E. Papa Petros et al., "Pinch Test for Diagnosis of Stress Urinary Incontinence" *Acta Obstet Gynecol Scand.* pp. 33–35, 69 Suppl. 153, 1990.

Peter E. Papa Petros et al., "Pregnancy Effects on the Intravaginal Sling Operation" *Acta Obstet Gynecol Scand.* pp. 73–78, 69 Suppl. 153, 1990.

Peter E. Papa Petros et al., "Pelvic floor rehabilitation according to the integrated theory of female urinary incontinence" *Pelvic Floor Dysfunction—Investigations & Conservative Treatment*, Chapter 7, pp. 249–258.

Peter E. Papa Petros et al., "Part IV: Surgical Applications of the Theory—Development of the Intravaginal Sling Plasty (IVS) Procedure" *Scand J Urol Nephrol*, pp. 53–54, Suppl. No. 153,1993.

Peter E. Papa Petros et al., "Part III: Surgical Principles Deriving From the Theory" *Scand J Urol Nephrol*, pp. 41–52, Suppl. No. 153, 1993.

Peter E. Papa Petros et al., "Part II: The Biomechanics of Vaginal Tissue and Supporting Ligaments With Special Relevance to the Pathogenesis of Female Urinary Incontinence" *Scand J Urol Nephrol*, pp. 29–40, Suppl. No. 153, 1990.

W. R. Sloan, et al., "Stress Incontinence of Urine: A Retrospective Study of the Complications and Late Results of Simple Suprapubic Fascial Slings" *The Journal of Urology*, vol. 110, pp. 533–536, Nov. 1973.

Pat D. O'Donnell, M.D., "Combined Raz Urethral Suspension and McGuire Pubovaginal Sling For Treatment of Complicated Stress Urinary Incontinence" *Journal of The Arkansas Medical Society*, vol. 88, No. 8, pp. 389–392, Jan. 1992.

Nicollette S. Horbach, "Suburethral Sling Procedures" *Urolgynecology and Urodynamics Theory and Practice*, Fourth Edition, Chapter 42, pp. 569–579, 1996, Williams & Wilkins.

Armand J. Pereyra, M.D., F.A.C.S., "A Simplified Surgical Procedure for the Correction of Stress Incontinence in Women" *West J. Surg. Obst. & Gynec.* pp. 223–226, Jul.–Aug. 1959.

M. Asmussen, et al., "Simultaneous Urethro–Cystometry With a New Technique" *Scand J Urol Nephrol 10*, pp. 7–11, 1976.

P. E. Papa Petros "Development of Generic Models for Ambulatory Vaginal Surgery—Preliminary Report" *International Urogynecology Journal*, 9 pages (1998).

Peter E. Papa Petros et al., "An analysis of rapid pad testing and the history for the diagnosis of stress incontinence" *Acta Obstet Gynecol Scand 71*, pp. 529–536 (1992).

Peter E. Papa Petros et al., "An Anatomical Basis for Success and Failure of Female Incontinence Surgery" *Scand J Urol Nephrol*, pp. 55–60, Suppl. No. 153.

Peter E. Papa Petros et al., "An integral theory of female urinary incontinence—Experimental and clinical considerations" *Acta Obstet Gynecol Scand*, vol. 69, Suppl. 153, pp. 7–31 (1990), The Scandinavian Association of Obstetricians and Gynecologists.

Rafael F. Nickel et al., "Evaluation of a Transpelvic Sling Procedure With and Without Colposuspension for Treatment of Female Dogs With Refractory Urethral Sphincter Mechanism Incompetence" *Veterinary Surgery*, vo. 27, pp. 94–104, (1998), The American College of Veterinary Surgeons.

Peter E. Papa Petros et al., "Bladder Instability in Women: A Premature Activation of the Micturition Reflex" *Neurourology and Urodynamics*, vol. 12, pp. 235–238 (1993).

Peter E. Papa Petros et al., "Cough Transmission Ratio: An Indicator of Suburethral Vaginal Wall Tension Rather Than Urethral Closure?" *Acta Obstet Gynecol Scand*, vol. 69 Suppl. 153. pp. 37–39 (1990).

Jeffrey R. Woodside, et al., "Suprapubic Endoscopic Vesical Neck Suspension for the Management of Urinary Incontinence in Myelodysplastic Girls" *The Journal of Urology*, vol. 135, pp. 97–99, Jan. 1986.

Robert F. Zacharin, FRCS, FRCOG, et al, "Pulsion Enterocele: Long–Term Results of an Abdominoperineal Technique" *Obstetrics & Gynecology*, pp. 141–148, vol. 55, No. 2, Feb. 1980, The American College of Obstetricians & Gynecologists.

Robert F. Zacharin, "The suspensory mechanism of the female urethra" *Journal of Anatomy*, vol. 97, Part 3, pp. 423–427, (1963).

George D. Webster, "Female Urinary Incontinence" *Urologic Surgery*, Ch. 66, pp. 665–679.

Peter E. Papa Petros et al., "Cure of Stress Incontinence by Repair of External Anal Spincter: Two Case Reports" *Acta Obstet Gynecol Scand*, vol. 69 Suppl. 153, p. 75 (1990).

Peter E. Papa Petros et al., "Cure of Urge Incontinence by the Combined Intravaginal Sling and Tuck Operation" *Acta Obstet Gynecol Scand*, vol. 69 Suppl. 153, pp. 61–62 (1990).

Peter E. Papa Petros et al., "Further Development of the Intravaginal Slingplasty Procedure—IVS III—(with midline "tuck")" *Scand J Urol Nephrol*, Suppl. 153, pp. 69–71 (1993).

Peter E. Papa Petros, "Medium–term Follow–up of the Intravaginal Slingplasty Operation Indicates Minimal Deterioration of Urinary Continence With Time" *International Urogynecology Journal and Pelvic Floor Dysfunction*, Reprinted from vol. 7, No. 3, pp. 133–137 (1996).

Peter E. Papa Petros, "New Ambulatory Surgical Methods Using an Anatomical Classification of Urinary Dysfunction Improve Stress, Urge and Abnormal Emptying" *Urogynecology Journal*, 8 pages.

Peter E. Papa Petros et al., "Non Stress Non Urge Female Urinary Incontinence—Diagnosis and Cure: A Preliminary Report" *Acta Obstet Gynecol Scand*, vol. 69 Suppl. 153. pp. 69–70 (1990).

Peter E. Papa Petros et al., "Part I: Theoretical, Morphological, Radiographical Correlations and Clinical Perspective" *Scand J Urol Nephrol*, Suppl. 153. pp. 5–28.

Shlomo Raz, M.D., "Modified Bladder Neck Suspension for Female Stress Incontinence" *Urology*, vol. XVII, No. 1, pp. 82–85, Jan. 1981, University of California Health Sciences Center, Los Angeles, CA.

David A. Richardson, M.D., et al., "Delayed Reaction to the Dacron Buttress Used in Urethropexy" *The Journal of Reproductive Medicine*, vol. 29 No. 9, Sep. 1984, pp. 689–692.

Henry Roberts, M.D., M.R.C.O.G., "Cystourethrography in Women" *Ethel Bovce University Fellowship* vol. 25 No. 293, pp. 253–259, May 1952, University of Liverpool.

W. R. Sloan et al., "Stress Incontinence of Urine: A Retrospective Study of the Complications and Late Results of Simple Suprapubic Suburethral Fascial Slings", *The Journal of Urology*, vol. 110, pp. 533–536, Nov. 1973.

Julia R. Spencer, et al., "A Comparison of Endoscopic Suspension of the Vesical Neck With Suprapubic Vesicourethropexy for Treatment of Stress Urinary Incontinence" *The Journal of Urology*, vol. 137, pp. 411–415, Mar. 1987.

Stuart L. Stanton, FRCS, FRCOG, "Suprapubic Approaches for Stress Incontinence in Women" *JAGS*, vol. 38, No. 3, pp. 348–351 (1990), The American Geriatrics Society.

William E. Studdiford, M.D., "Transplantation of Abdominal Fascia for the Relief of Urinary Stress Incontinence" *American Journal of Obstetrics and Gynecology*, pp. 764–775, Bellevue Hospital and New York University College of Medicine.

Cousin Biotech SAS—Medical Division, "Suport—Sub–Urethral Perineal Retro–Pubic Tensionless Sling" Marketing Brochure, 1 page.

Ulf Ulmsten et al., "Different Biochemical Composition of Connective Tissue in Continent and Stress Incontinent Women" *Acta Obstet Gynecol Scand*, vol. 66 pp. 455–457 (1987).

Ulf Ulmsten et al., "The unstable female urethra" *Am. J. Obstet. Gynecol.*, vol. 144 No. 1, pp. 93–97, May 3, 1982.

U. Ulmsten, "Female Urinary Incontinence—A Symptom, Not a Urodynamic Disease. Some Theoretical and Practical Aspects on the Diagnosis and Treatment of Female Urinary Incontinence" *The International Urogynecology Journal*, vol. 6, pp. 2–3 (1995).

Microvasive Boston Scientific, "Vesica–Percutaneous Bladder Neck Stabilization Kit" Marketing Brochure, 4 pages, Boston Scientific Corp.

Peter Papa Petros et al., "Anchoring the midurethra restores bladder–neck anatomy and continence" *The Lancet*, vol. 354, pp. 997–998, Sep. 18, 1999.

Edward J. McGuire, et al., "Experience With Pubovaginal Slings for Urinary Incontinence at the University of Michigan" *The Journal of Urology*, vol. 138, pp. 525–526, Sep. 1987.

G. Narik, M.D., "A simplified sling operation suitable for routine use" *The Am J. Obst. & Gynec.*, vol. 84, No. 3, pp. 400–405, Aug. 1, 1962.

Chester C. Winter, M.D., "Peripubic Urethropexy for Urinary Stress Incontinence in Women" *Urology* vol. XX, No. 4, Oct. 1982.

J. Chassar Moir, "The Gauze–Hammock Operation (A Modified Aldridge Sling Prcedure)" *The Journal of Obstetrics and Gynaecology of the British Commonwealth*, vol. 75 No. 1, pp. 1–9, Jan. 1968.

George D. Webster, et al., "Voiding Dysfunction Following Cystourethropexy: Its Evaluation and Management" *The Journal of Urology*, vol. 144, Sep. 1990,pp. 670–673, American Urological Association, Inc.

J. E. Morgan, M.D., "A sling operation, using Marlex polypropylene mesh, for treatment of recurrent stress incontinence" *Amer. J. Obstet. Gynec.* vol. 106, No. 3, Feb. 15, 1970, pp. 369–377.

David H. Nichols, MD, FACOG, "The Mersilene Mesh Gauze–Hammock For Severe Urinary Stress Incontinence" *Obstetrics and Gynecology*, vol. 41, No. 1, pp. 88–93, Jan. 1973.

Jeffrey P. Norris, M.D., et al., "Use of Synthetic Material in Sling Surgery: A Minimally Invasive Approach" *Journal of Endourology*, vol. 10 No. 3, pp. 227–230, Jun. 1996, Mary Ann Liebert, Inc.

Peter Papa Petros et al., "The Autogenic Ligament Procedure: A Technique for Planned Formation of an Artificial Neo–Ligament" *Acta Obstet Gynecol Scand*, vol. 69 Suppl 153, pp. 43–51 (1990).

Peter Papa Petros et al., "The Combined Intravaginal Sling and Tuck Operation. An Ambulatory Procedure for Cure of Stress and Urge Incontinence" *Acta Obstet Gynecol Scand*, vol. 69 Suppl 153, pp. 53–59 (1990).

Peter Papa Petros et al., "The Development of the Intravaginal Slingplasty Procedure: IVS II—with bilateral 'tucks')", *Scand J Urol Nephrol*, Suppl. 153. pp. 61–67.

Peter Papa Petros et al., "Urethral Pressure Increase on Effort Originates From Within the Urethra, and Continence From Musculovaginal Closure" *Neurourology and Urodynamics*, vol. 14, pp. 337–350 (1995).

R. O. Parra, et al., "Experience with a Simplified Technique for the Treatment of Female Stress Urinary Incontinence" *British Journal of Urology*, vol. 66, pp. 615–617 (1990).

Raymond R. Rackley, M.D., et al. "Tension–free Vaginal Tape and Percutaneous Vaginal Tape Sling Procedures" *Techniques in Urology*, vol. 7, No. 2, pp. 90–100 (2001).

Raymond Rackley, M.D., "Synthetic slings: Five steps for successful placement" *Urology Times*, pp. 46, 48–49, Jun. 2000.

Shlomo Raz, M.D. et al., "Female Urology—Second Edition" *University of California at Los Angeles School of Medicine*, articles pp. 80–86, 369–381, 382–391, 392–394, 395–398, 435–442, (1983) W.B. Saunders Company.

John H. Ridley, M.D., "Appraisal of the Goebell–Frangenheim–Stoeckel sling procedure" *Am. J. Obst. & Gynec.* vol. 95, No. 5, pp. 714–721, Jul. 1, 1966.

Thomas A. Stamey, M.D., "Endoscopic Suspension of the Vesical Neck for Urinary Incontinence in Females" *Ann Surg.*, vol. 192, No. 4, pp. 465–471, Oct. 1980.

Rudolf Hohenfellner, et al., "Sling Procedures" *Surgery of Female Incontinence–Second Edition*, Chapter 7, pp. 105–113, (no date) Springer–Verlag.

David R. Staskin, et al., "The Gore–tex sling procedure for female sphincteric incontinence: indications, technique, and results" *World J Urol.*, 1997, vol. 15, pp. 295–299 , Springer–Verlag.

Gynecare, "TVT—Tension–Free Vaginal Tape, Minimally Invasive, Highly Effective Treatment for Female Stress Urinary Incontinence" Marketing Brochure, *Ethicon, Inc.* (1999) 6 pages.

U. Ulmsten et al., "A Multicenter Study of Tension–Free Vaginal Tape (TVT) for Surgical Treatment of Stress Urinary Incontinence" *The International Urogynecology Journal*, 1998, vol. 9, pp. 210–213.

U. Ulmsten et al., "A three–year follow up of tension free vaginal tape for surgical treatment of female stress urinary incontinence" *The British Journal of Obstetrics and Gynaecology*, Apr., 1999, vol. 106, pp. 345–350.

U. Ulmsten et al., "An Ambulatory Surgical Procedure Under Local Anesthesia for Treatment of Female Urinary Incontinence" *The International Urogynecology Journal*, 1996, vol. 7, pp. 81–86.

U. Ulmsten et al., "Intravaginal Slingplasty (IVS): An Ambulatory Surgical Procedure for Treatment of Female Urinary Incontinence" *Scand J Urol Nephrol*,vol. 29 pp. 75–82, 1995, Scandinavian University Press ISSN.

C. Falconer et al., "Clinical Outcome and Changes in Connective Tissue Metabolism After Intravaginal Slingplasty in Stress Incontinent Women" *International Urogynecol J*, vol. 7, pp. 133–137, (1996).

Ruben F. Gittes et al, "No–Incision Pubovaginal Suspension for Stress Incontinence" *The Journal of Urology*, vol. 138, pp. 568–570, Sep. 1987.

AMA Medical Products "IVS Tunneller—A universal delivery instrument for all tension free vaginal tape procedures", Marketing Brochure, 4 pages.

John Klutke, M.D. et al., "The promise of tension–free vaginal tape for female SUI" *Focus on Technology 2000*, pp. 59–60, 65–66, 69–70, 73, Oct. 2000, *Contemporary Urology*.

Urogynecology, Product Catalog, eg. SIS Technology, Bladder Suspension, Urodynamics and Urinary Diversion, Incontinence, 36 pages, Cook, Urological Inc. (1996).

Jerry G. Blaivas, "Commentary: Pubovaginal Sling Procedure" *Surgery for Female Urinary Incontinence*, pp. 93–101.

Theodore V. Benderev. M.D., "Anchor Fixation and Other Modifications of Endoscopic Bladder Neck Suspension" *Urology*, vol. 40, No. 5, pp. 409–418, Nov. 1992.

Martin, Surgical Products Catalog, 8 pages, Martin Medizin–Technik, Gebrüder Martin GmbH & Co. KG (1998).

Mentor–Porges, *Trans–obturator tape, Le hamac perinial, Nos references*, Marketing Material in French language, 1 page (01/03).

Mentor–Porges, *Come See Us at Booth #28*, Marketing Material, 1 page (07/02).

Mentor, Sabre™ Bioabsorbable Sling, *Surgical Procedure*, Marketing Material, 6 pages (08/02).

Raz, Shlomo, et al., *The Raz Bladder Neck Suspension Results in 206 Patients*, The Journal of Urology, pp. 845–850 (09/92).

Marco A. Pelosi II, et al., *New Tranobturator Sling Reduces Risk of Injury*, OBG Management , pp. 17–20, 30, 32, 35–38 (Jul. 2003).

Dargent, D., et al. *Pos d'un ruban sous uretral oblique par voie obturatrice dans le traitement de l'incontinence urinaire feminine*, Gynecol Obstet Fertil 2002; 30: 576–582 (2002) (Provided in both French and English languages), 13 pages.

de Leval, Jean "Novel Surgical Technique for the Treatment of Female Stress Urinary Incontinence: Transobturator Vaginal Tape Inside–Out", *European Urology* 44 (2003) 724–730.

Delorme, Emmanuel et al.,"Transobturator Tape (Uratape®): A New Minimally–Invasive Procedure to Treat Female Urinary Incontinence", *European Urology* 45 (2004) 203–207.

Letters To The Editor, R. Villet's response to the article by D. Dargent et al., "Placement of an oblique transpsobturator suburethral tape in the treatment of female urinary incontinence", *Gynecology Obstetrics & Fertility* 31 (2003) 96–101 (English Translation).

H.P. Dietz et al., "Mechanical Properties of urogynecologic implant Materials", *International Urogynecology Journal* (2003) 14:239–243.

C.B. Iglesia et al.,"The Use of Mesh in Gynecologic Surgery", *International Urogynecology Journal* (1997) 8:105–115, ©1997 Springer–Vertag London Ltd.

C.C. Chu and L. Welch, "Characterization of Morphologic and Mechanical Properties of Surgical Mesh Frabrics", *Journal of Biomedical Materials Research*, vol. 19, 903–916 (1985), ©1985 John Wiley & Sons, Inc.

J.E. Morgan, M.D., "A sling operation, using Marlex Polypropylene mesh, for treatment of recurrent stress incontinence", *America Journal of Obstetrics and Gynecology*, Feb. 15, 1970, 106:3, pp. 369–377.

J.E. Morgan, M.D. et al., "The Marlex sling operation for the treatment of recurrent stress urinary incontinence: A 16–year review", *American Journal of Obstetrics and Gynecology*, Jan. 15, 1985, pp. 224–227.

Pourdeyhimi, "Porosity of surgical mesh fabrics: New technology", *J. Biomed, Mater, Res.:Applied Biomaterials*, vol. 23, No. A1, 145–152 (1989), ©1989 John Wiley & Sons, Inc.

"Urinary Incontinence: Easier Operation", Artide from *La Liber Belgique*, Wednesday, Oct. 15, 2003 (English Translation).

Declaration of Johann J. Neisz with Attachment.

Delorme, "La bandelette trans–obturatrice: un procede mini-–invasif pour traiter l'incontinence urinaire d'effort de la femme", *Urologie de la Femme*, 2001:11, pp. 1306–1313 with English Translation.

*AMS Monarc Sling System Instructions for Use*, American Medical Systems, Inc., Sep. 2002, English version, 7 pages.

*AMS Monarc Subfacial Hammock Instructions for Use*, American Medical Systems, Inc., Nov. 2003, English version, 11 pages.

\* cited by examiner

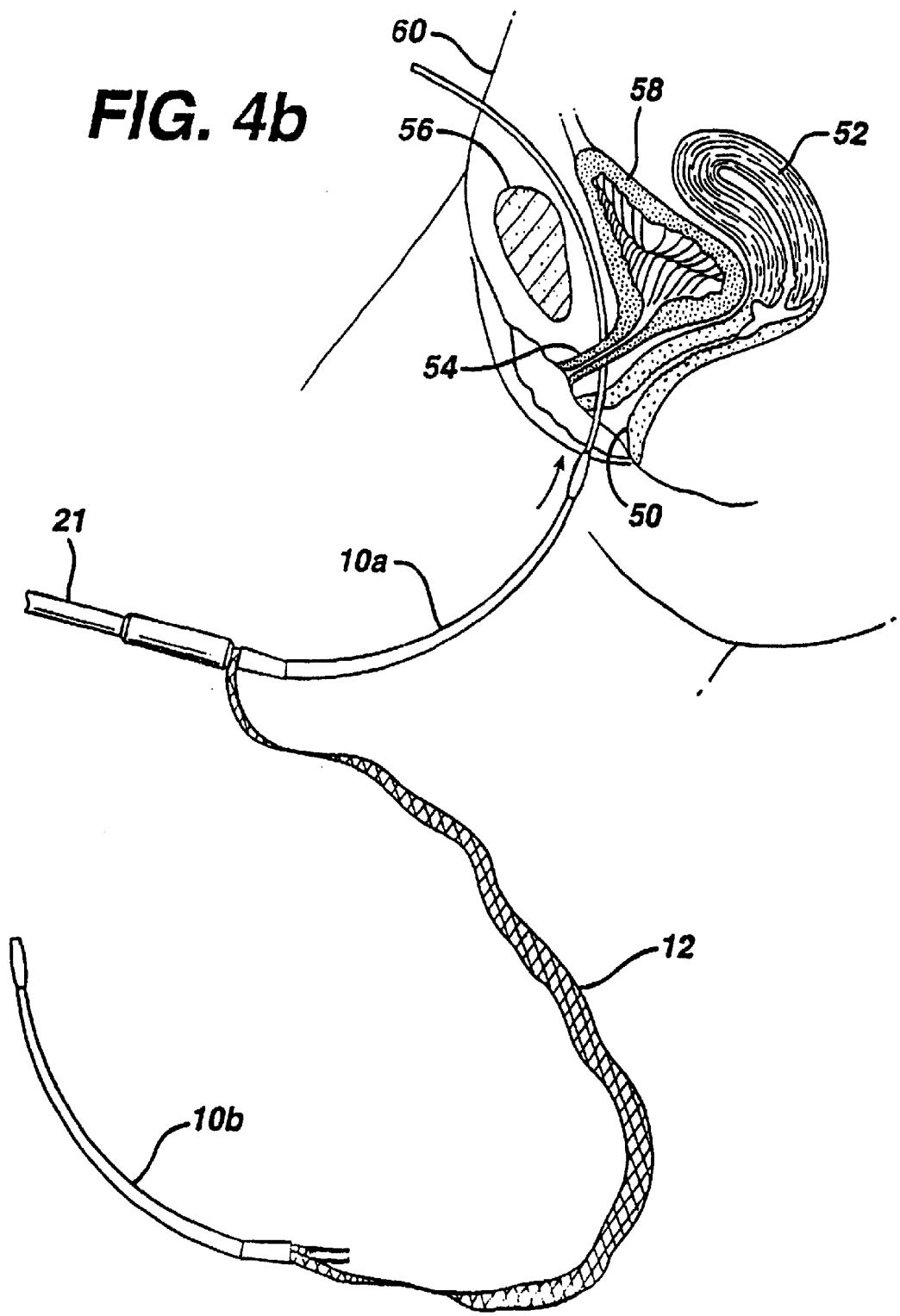

TRANSOBTURATOR SURGICAL ARTICLES AND METHODS

CROSS REFERENCE TO RELATED APPLICATION

The present invention is a continuation-in-part of co-pending U.S. patent application, Ser. No. 09/521,801, filed on Mar. 9, 2000, which claims the benefit of earlier-filed U.S. provisional patent application, Ser. No. 60/138,231, filed on Jun. 9, 1999, which are both incorporated by reference in their entirety herein.

BACKGROUND OF THE INVENTION

1. Field of the Invention

The present invention relates generally to a surgical instrument and a method for treating female urinary incontinence and in particular to a needle and mesh configuration for creating a sling beneath the urethra.

2. Background Discussion

Women account for more than 11 million of incontinence cases. Moreover, a majority of women with incontinence suffer from stress urinary incontinence (SUI). Women with SUI involuntarily lose urine during normal daily activities and movements, such as laughing, coughing, sneezing and regular exercise. SUI may be caused by a functional defect of the tissue or ligaments connecting the vaginal wall with the pelvic muscles and pubic bone. Common causes include repetitive straining of the pelvic muscles, childbirth, loss of pelvic muscle tone, and estrogen loss. Such a defect results in an improperly functioning urethra. Unlike other types of incontinence, SUI is not a problem of the bladder.

Normally, the urethra, when properly supported by strong pelvic floor muscles and healthy connective tissue, maintains a tight seal to prevent involuntary loss of urine. When a woman suffers from the most common form of SUI, however, weakened muscle and pelvic tissues are unable to adequately support the urethra in its correct position. As a result, during normal movements when pressure is exerted on the bladder from the diaphragm, the urethra cannot retain its seal, permitting urine to escape. Because SUI is both embarassing and unpredictable, many women with SUI avoid an active lifestyle, shying away from social situations.

U.S. Pat. No. 5,112,344 describes a method and apparatus for treating female incontinence. The surgical instrument for the application of a filamentary element into the body comprises a tubular shaft having a handle at one end and a flexible needle slidably receivable in the shaft and adapted at one end to receive filamentary element. The method of treating female incontinence comprises looping a filamentary element between the wall of the vagina and the rectus abdomens sheath in the anterior wall of the abdomen whereby it passes to each side of the urethra, tightening the loop to bring the vaginal wall and the urethra into the correct spatial relationship to the pubis allowing the development of scar tissue between the vaginal wall and the anterior wall of the abdomen pubic symphysis and removing the filamentary element.

U.S. Pat. No. 5,899,909 discloses a surgical instrument comprising a shank having a handle at one end and connecting means at the other end to receive, one at a time, two curved needle-like elements which are connected at one end to one of a mesh intended to be implanted into the body. In practice, the mesh is passed into the body via the vagina first at one end and then at the other end at one side and the other, respectively, of the urethra to foam a loop around the end at one side and the other, respectively, of the urethra to form a loop around the urethra, located between the urethra and vaginal wall. The mesh is extended over the pubis and through the abdominal wall and is tightened. The mesh ends are cut at the abdominal wall, and the mesh is left implanted in the body. The trans-vaginal procedure is exemplified by the TVT product sold by the Gynecare franchise of Ethicon Inc., a Johnson & Johnson Company, of Somerville, NJ, USA. In this procedure two 5 mm needles pass a PROLENE mesh trans-vaginally and through the abdomen to create a tension-free support around the mid urethra. U.S. Pat. No. 5,899,909 is incorporated herein by reference in its entirety.

An alternate method to treat SUI is the sling procedure. In this procedure a needle or other suture-retrieving device is first inserted through the abdomen, above the pubic bone. The needle is guided behind the pubic bone, through the subrapubic fascia around the urethra, and out of the body through an incision in the anterior vaginal wall. At this point sutures are attached to the needle(s) and pulled up back through the abdominal cavity, where the sutures are fastened to the rectus muscle.

Techniques for protecting against the puncture of the internal structures during this type of procedure have included laparoscopic procedures. This involves making an incision in the abdomen and inserting a video scope to watch the progress of the needles as they pass through the abdominal cavity. These additional incisions are not optimal for the patient. Also, the needles which pass through the abdomen are not designed to capture a mesh but rather a suture which has been previously attached to the mesh or harvested fascia. These needles are generally in the diameter range of about 0.090 ins. to about 0.120 inches. Therefore, the needles do not create a large channel through the fascia. The channel is only wide enough to pass the suture. Accordingly, the sutures do not possess the elongation properties of the PROLENE mesh and therefore can not provide the tension-free support of the TVT. Also attaching a mesh directly to these needles is not optimal because it is very difficult, if at all possible, to pull the mesh through the narrow channel created by the needle.

It would be beneficial to provide a surgical system for use in implanting a mesh within a female body to prevent incontinence that can be implanted either through a trans-vaginal approach of a trans-abdominal approach.

This invention addresses that need and overcomes the deficiencies of the prior art.

SUMMARY OF THE INVENTION

The invention overcomes the deficiencies of the prior art and provides for a surgical apparatus and a method for the treatment of female stress urinary incontinence. The invention provides a surgical instrument comprising a handle at one end and connecting means at the other end to receive, one at a time, two curved needle-like elements, each of which have a blunt tip and a constant or varying diameter. The distal end of the needle comprises an interlocking coupling means for accepting a guide needle or, alternatively, a mesh.

In one embodiment each curved needle connects at its proximal end to separate ends of a mesh to be implanted within the body. A guide needle, similar in structure to a Stamey needle, is passed through the abdomen and behind the pubic bone, passes along one side of the urethra and to an incision site at the anterior vaginal wall. After the guide needle exits the body through the vagina, the guide needle couples to the distal end of the curved needle. The curved needle is then pushed back through the vagina and through the fascia, following the path of the guide needle. The curved needle and first end of the mesh pass over the pubis and through the abdominal wall. The guide needle is again passed behind the pubic bone from the abdomen, passes along the other side of the urethra to the incision site in the vaginal wall. The guide needle again couples to the distal end of the second curved needle, which then passes through the vagina and fascia, following the second path created by the guide needle. The second end of the mesh is extended over the pubis and through the abdominal wall. The mesh ends are cut at the abdominal wall, and the mesh is left in the body, creating a tension- free support between the vaginal wall and the mid urethra.

In an alternate embodiment a curved needle is passed through the abdomen and behind the pubic bone, passes along one side of the urethra and to an incision site in the anterior vaginal wall. After the curved needle exits the body through the vagina, the distal end of the curved needle couples to one end of the mesh to be implanted within the body. The curved needle is then pulled back through the vagina and through the fascia, following the path it originally created. The curved needle and first end of the mesh pass over the pubis and out through the abdominal wall. The first end of the mesh de-couples from the curved needle and the needle is again passed behind the pubic bone from the abdomen, passes along the other side of the urethra to the incision site in the vaginal wall. The needle couples to second end of the mesh and is then pulled back through the vagina and fascia, following the second path created by the needle. The second end of the mesh is extended over the pubis and through the abdominal wall. The mesh ends are cut at the abdominal wall, and the mesh is left in the body, creating a tension-free support between the vaginal wall and the mid urethra.

The invention is also compatible for use in a trans-vaginal approach as described in U.S. Pat. No. 5,899,909.

The object of the invention is to provide a surgical instrument that implants a mesh for treatment of SUI and is capable for using in a trans-vaginal or a trans-abdominal procedure.

An advantage of the invention is that it is useful across different medical specialties depending on preferred surgical approaches.

These and other features and advantages of the present invention will become apparent from the following more detailed description, when taken in conjunction with the accompanying drawings which illustrate, by way of example, the principles of the invention.

BRIEF DESCRIPTION OF THE DRAWINGS

FIGS. 3b–d are alternate embodiments of a connector for use in FIG. 3a;

DETAILED DESCRIPTION OF THE INVENTION

Before explaining the present invention in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways.

The invention discloses an apparatus and method for treating SUI. A mesh or tape is passed through pelvic tissue and positioned between the urethra and vaginal wall, creating a supportive sling. The mesh provides a structure means for tissue ingrowth and thereby provides a newly created body tissue supporting means for the urethra. When pressure is exerted upon the lower abdomen, such as during a cough or sneeze, the mesh provides support to the urethra, allowing it to keep its seal and prevent the unwanted discharge of urine.

Figure 1:
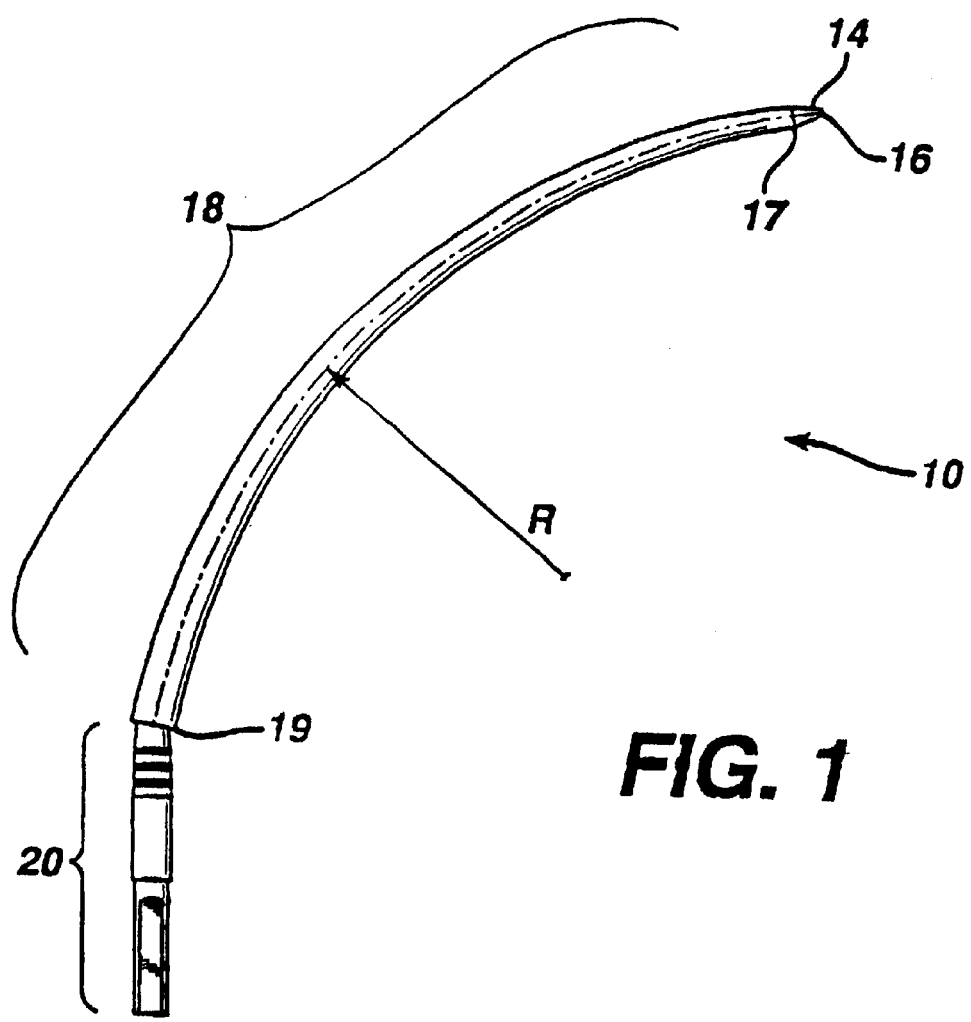
FIG. 1 is a side view of the needle in one embodiment thereof.
Figure 2A:
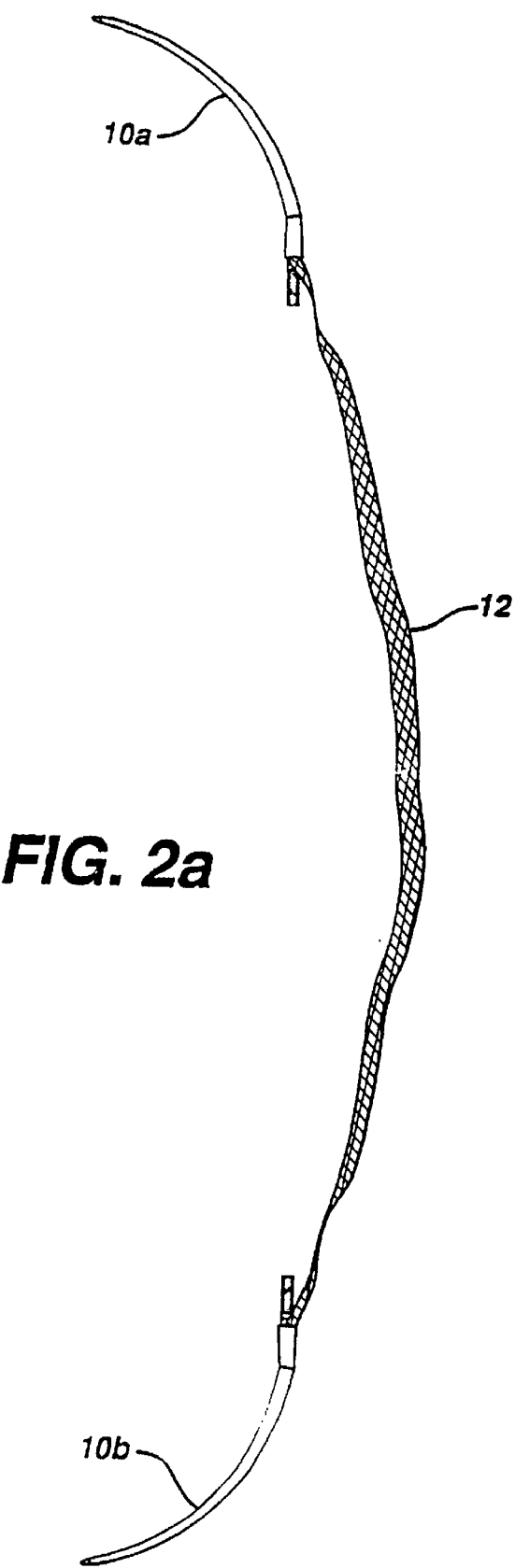
FIG. 2a is a side view of two needles and a mesh interconnecting the needles.

Referring to FIGS. 1 and 2a, in one embodiment the surgical instrument comprises a needle-like element 10 that attaches to a mesh 12. Needle element 10 defines a certain radius R to perform the surgical procedure discussed herein. The distal end of needle element 10 terminates at a conical section 14 having a tip 16. Alternate configurations, such as a blade-like, arrow or burr tips are also possible. Preferably, tip 16 is blunt, wherein the tip 16 has a radius of about 0.6 millimeters. A blunt tip is preferred since it is less likely to stick in bone or penetrate bladder wall tissue or blood vessel wall tissue as will be appreciated from the method of implanting the mesh as described below.

The proximal end of needle 10 terminates in an attachment segment 20 that is adapted to mate and lock into a handle 21 as disclosed in U.S. Pat. No. 5,899,909.

Disposed between tip 14 and segment 20 is a curved shaft segment 18 having a distal end 17 and a proximal end 19. The shape of shaft 18 extends substantially a quarter of a circle in order to follow substantially the profile of the pubis between the vagina and the abdominal wall. For the purposes of the method as will be discussed in more detail below, shaft 18 has a preferred radius R of about 106 millimeters. The diameter of shaft 18 may be constant, for example, about 5 mm. Alternatively, the diameter of segment 18 may transition from a smaller diameter at distal end 17 to a larger diameter at proximal end 19. The minimum diameter of distal end 17 may be as small as 0.5 mm due to the minimal stresses at this point. The minimal diameter of proximal end 19 is about 4 mm.

Needle 10 is preferably tubular with a circular cross section and is made from a material that is compatible with the human body. Preferably, needle 10 is made from AISI 303 stainless steel. The surface of shaft 18 may be smooth, preferably polished, to facilitate penetration of the soft tissue. Alternatively, the surface of needle 10 may have a somewhat rougher surface. A rougher surface would result in slightly additional tissue trauma, which in turn stimulates fibroblast activity around the mesh 12. The surface of needle 10 may also be darkened in shade or color to provide higher visibility while in place in the body during a cystoscopy.

Needle 10 may be manufactured as a single, continuous unit, or alternatively, curved portion 18 may be manufactured separately from linear portion 20. In this manner the two pieces would attach using any conventional attaching means, such as, screwing, or other conventional means as is known to those skilled in the art.

Figure 2B:
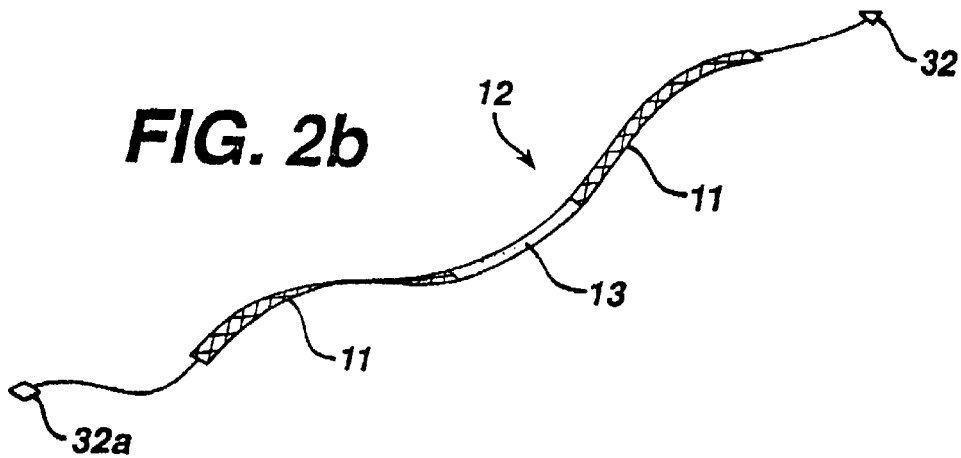
FIGS. 2b–d are alternate embodiments of the mesh and connecting means between the mesh and needle.
Figure 2C:
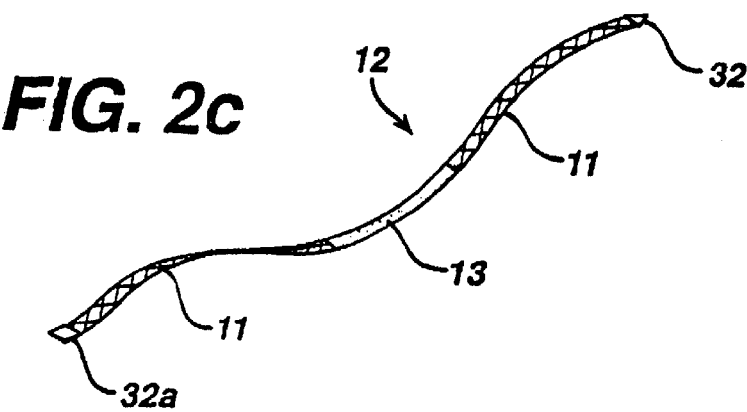
Figure 2D:
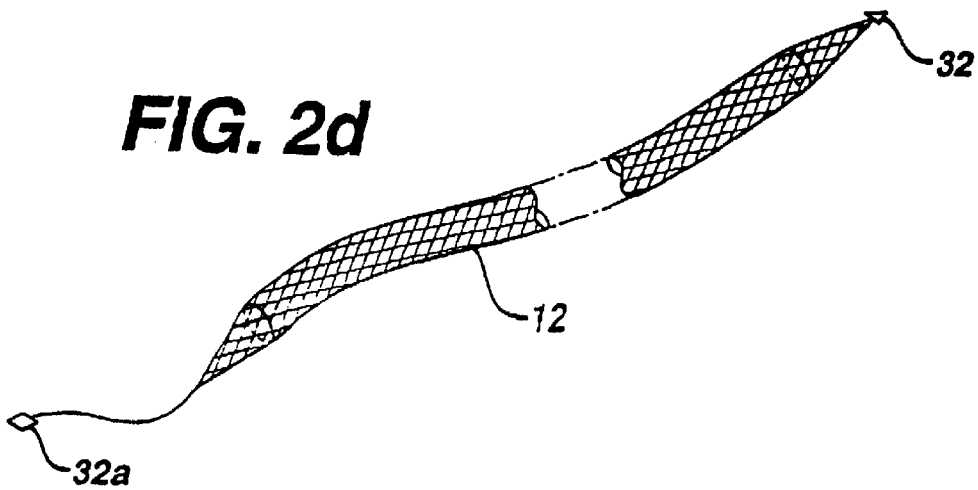

Referring to FIGS. 2a–d, mesh 12 comprises any tissue-compatible synthetic material, or any natural material, including, but not limited to, autologous, allograft, xenograft, a tissue engineered matrix, or a combination thereof. An exemplary synthetic material is PROLENE®polypropylene mesh, a mesh having a thickness of 0.7 mm and openings of about 1 mm manufactured by Ethicon, Inc., Somerville, New Jersey, U.S.A. This material is approved by the U.S. Food and Drug Administration for implantation into the human body. A still further embodiment of the mesh 12 is a combination of a synthetic material 11 and a natural material 13 centered between the synthetic material 11 as shown in FIGS. 2b–c. A still further embodiment of the mesh 12 includes a combination of synthetic material 11 and natural material 13, whereby the natural material is placed over or incorporated within a generally central portion of the synthetic material 11. One advantage of the mesh configurations is that natural material 13 is along the center region of mesh 12 so that after installation of mesh 12, natural material 13 is positioned below the urethra and eliminates possible erosion issues at the interface of the urethra and mesh. Natural material 13 may be connected to the synthetic material 11 by means of sewing, a bio-compatible glue, cell culturing techniques or other known means.

Mesh 12 may be of any convenient shape that suits the intended purpose of the invention. An exemplary width is about 1 cm and the length would be dependent upon the size of the female undergoing the procedure. Mesh 12 may be single or double ply, generally planar in structure, or tubular (FIG. 2d) to provide additional supporting strength and more surface area on which tissue fibers may attach. Moreover, mesh 12 may consist of different types of material, such as a bioabsorbable and non-bioabsorbable material. Mesh 12 may also be coated with an antimicrobial additive to prevent or minimize infection and a lubricous coating, for example, a bioabsorbable hydrogel, to facilitate the mesh passing through the tissue as discussed below. Preferably, mesh 12 is covered by a removal plastic sheath as disclosed in U.S. Pat. No. 5,899,909. The mesh may also be made radio-opaque and/or of a contrasting color to the body tissue to allow for future diagnostic visualization. In one embodiment mesh 12 may be attached to needle segment 20 by means of tying, gluing or other suitable attaching means. Preferably, a bio-compatible heat shrink tube fixes mesh 12 onto needle portion 20, FIG. 2a.

Figure 3A:
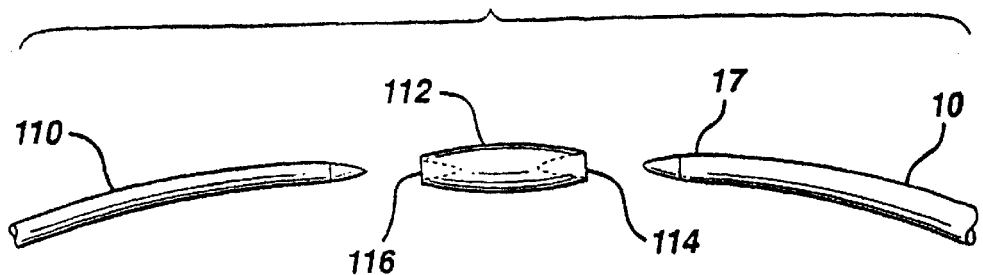
FIG. 3a is an assembly diagram for two needles and a connector.

FIG. 3a illustrates a needle 10 for use in conjunction with a guide needle 110 and coupler 112. Guide needle 110 may be configured to have a similar radius R as needle 10. Preferably, guide needle 110 has a smaller diameter, about 2 mm. It is possible, however, for guide needle 110 to have the same diameter as needle 10. A coupler 112 acts as an interfacing element useful to couple guide needle 110 to needle 10. Coupler 112 is substantially elliptical-shaped having a first bore opening 114 for accepting distal end 17 and a second bore opening 116 for accepting the distal end of guide needle 110. Preferably, openings 116 and 114 are configured to allow for a press fit connection with needles 110 and 10, respectively. Alternatively, openings 114 and 116 may comprise a bio-compatible glue or high-friction material to facilitate a strong connection between the needles 10/110 and coupler 112. Coupler 10 may be made from any bio-compatible metal, such as stainless steel or polyurethane, silicone, rubber or other similar compound.

Figure 3B:
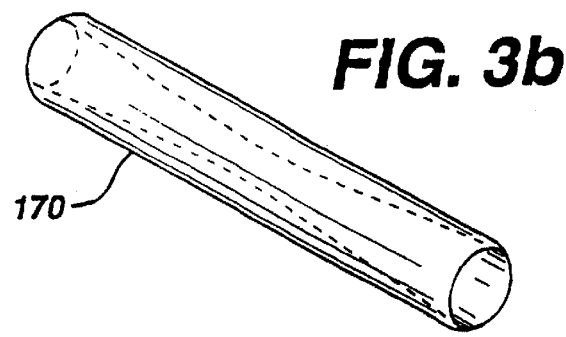
Figure 3C:
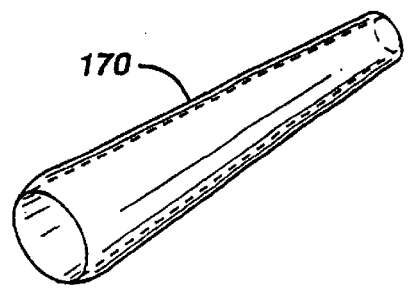
Figure 3D:
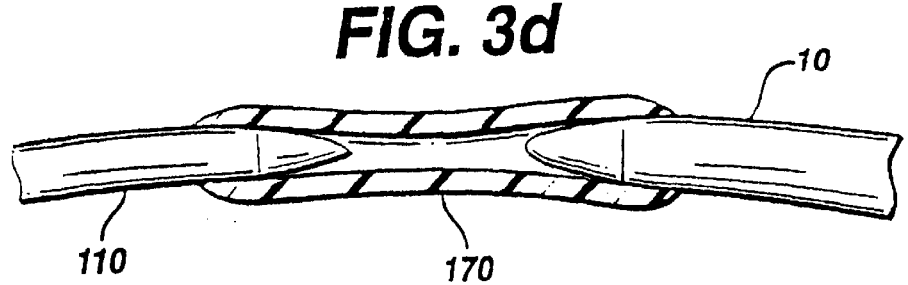

FIGS. 3b–d illustrate alternate connector means utilizing a high friction tube 170, such as Tygon. FIG. 3b discloses a tube having a constant O.D., but a varying I.D. The larger I.D. would accept needle 10 and the smaller I.D. accepts the guide needle 110. FIG. 3c illustrates a tube 172 having both a varying O.D. and I.D. As the needles are placed within the tube the decreasing I.D. compresses around the distal ends of the respective needles and the high coefficient of friction securely anchors the needles. FIG. 3d illustrates the needles within the tube 172. Preferably, the ends of tube 170 and 172 are tapered to eliminate any abrupt surface that adds additional drag to the needles as they are pulled through the abdominal cavity.

The surgical procedure for trans-abdominally implanting mesh 12 using two needles is shown in FIGS. 4a–j. In the figures the relevant parts of the female lower abdomen are disclosed, the vagina being 50, the uterus 52, the urethra 54, the pubic bone 56, the urinary bladder 58 and the abdominal wall 60. A guide needle 110 penetrates the abdominal wall 60, anterior to the pubic bone 56, FIG. 4a and follows the contour of the pubic bone 56 to one side of the urethra 54 and exits the body through an incision having been made in the anterior wall of the vagina 50. Coupler 112 attaches to the distal end of guide needle 110, extending out from the body, and needle 10a, FIG. 4b. One end of mesh 12 is attached to the proximal end of needle 10a. The surgeon then retracts guide needle 110 back through the abdomen and advances needle 10a through the vaginal incision following the same path guide needle 110 created, FIG. 4c. The needles pass through the vaginal wall and through the soft tissue on one side of the urethra 54, the needles then according to FIG. 4d being passed close to the back of the pubic bone 56, through additional layers of fat, muscle and fascia, and then out the abdominal wall 60 above the pubic bone 56. The surgeon uncouples handle 21 from the needle 10a and pulls needle 10a out of the body through the abdominal wall 60, FIG. 4e. Guide needle 110 is disconnected from needle 10a, and the surgeon repeats the same procedure, but passing the guide needle 110 on the opposite side of the urethra 54, FIGS. 4f–j, to complete the implantation of the mesh between the mid- urethra and vaginal wall using needle 10b.

FIGS. 8a–i illustrate an alternate preferred embodiment. A first guide needle 110a penetrates the abdominal wall 60, anterior to the pubic bone 56 and follows the contour of the pubic bone 56 to one side of the urethra 54 and exits the body through an incision having been made in the anterior wall of the vagina 50. A second guide needle 110b penetrates the abdominal wall 60, anterior to the pubic bone 56 and follows the contour of the pubic bone 56 to the opposite side of the urethra 54 as guide needle 110a and exits the body through an incision having been made in the anterior wall of the vagina 50, FIG. 8a. At this point, the surgeon may perform a single cystoscopy to confirm the integrity of the bladder 58. Couplers 112a,b attach to the distal ends of needles 10a,b. Needle 10a, having one end of mesh 12 attached to the proximal end of needle 10a attaches to guide needle 110a via coupler 112a, FIG. 8b. The surgeon then retracts guide needle 110a back through the abdomen and advances needle 10a through the vaginal incision following the same path guide needle 110a created. The needles pass through the vaginal wall and through the soft tissue on one side of the urethra 54, the needles being passed close to the back of the pubic bone 56, through additional layers of fat, muscle and fascia, and then out the abdominal wall 60 above the pubic bone 56, FIGS. 8c–d. The surgeon uncouples handle 21 from the needle 10a and pulls needle 10a out of the body through the abdominal wall 60, FIG. 8e.

The surgeon repeats the same procedure, but removing guide needle 110b and advancing needle 10b on the opposite side of the urethra 54, to complete the implantation of the mesh between the mid-urethra and vaginal wall using needle 10b, FIGS. 8f–i.

Figure 5A:
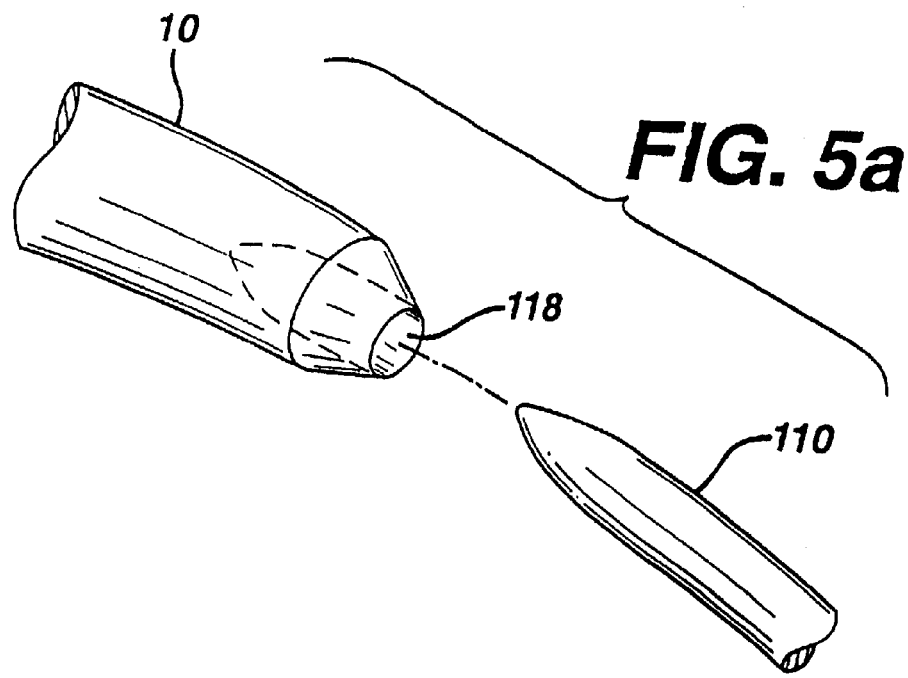
FIGS. 5a–d illustrate alternate embodiments of coupling the guide needle to the needle.
Figure 5B:
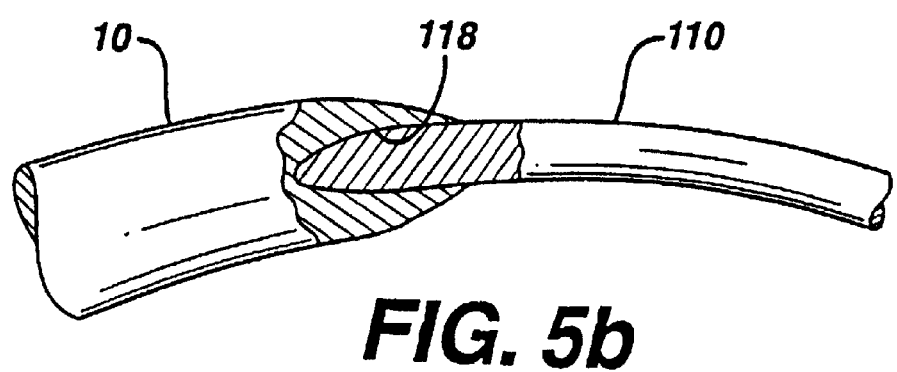

FIGS. 5a–d illustrate alternate embodiments for coupling needle 10 to guide needle 110 to implant a mesh 12 trans-abdominally as indicated above. In FIGS. 5a–b, the distal end of needle 10 is modified to include a bore opening 118 to allow for a press fit connection with the distal end of guide needle 110. Alternatively, bore-opening 118 may comprise other connection means, such as glue or a high-friction material.

Figure 5C:
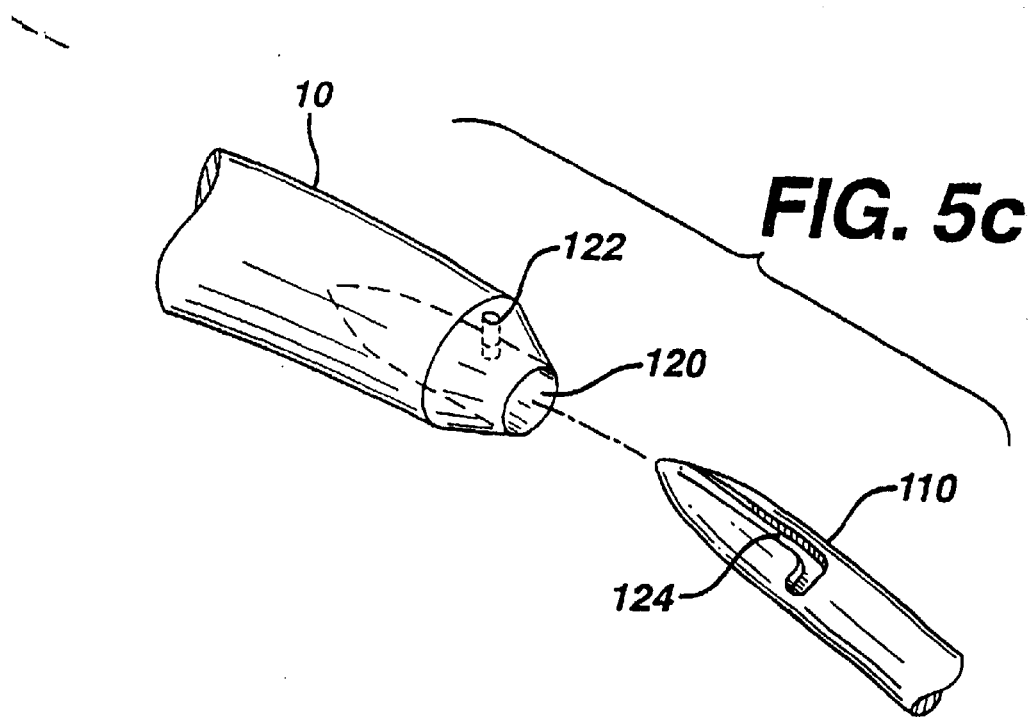

In FIG. 5c, the distal end of needle 10 is modified to include a bore opening 120 and a locking pin 122. Guide needle 110 is modified to include an L-shaped groove 124. The distal end of guide needle 110 inserts into opening 120 and groove 124 engages locking pin 122 and locks thereto with a quarter-turn twist.

Figure 5D:
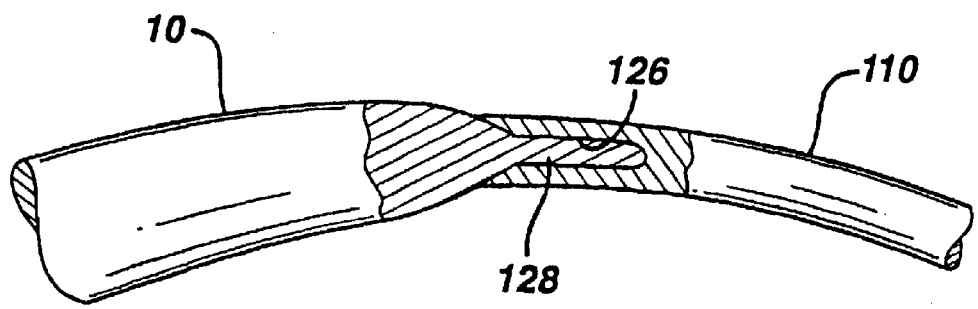

FIG. 5d illustrates a bore opening 126 in guide needle 110 to accept a protruding element 128 at the distal end needle 10. Protruding element 128 press fits into bore opening 126.

Figures 2, 3:
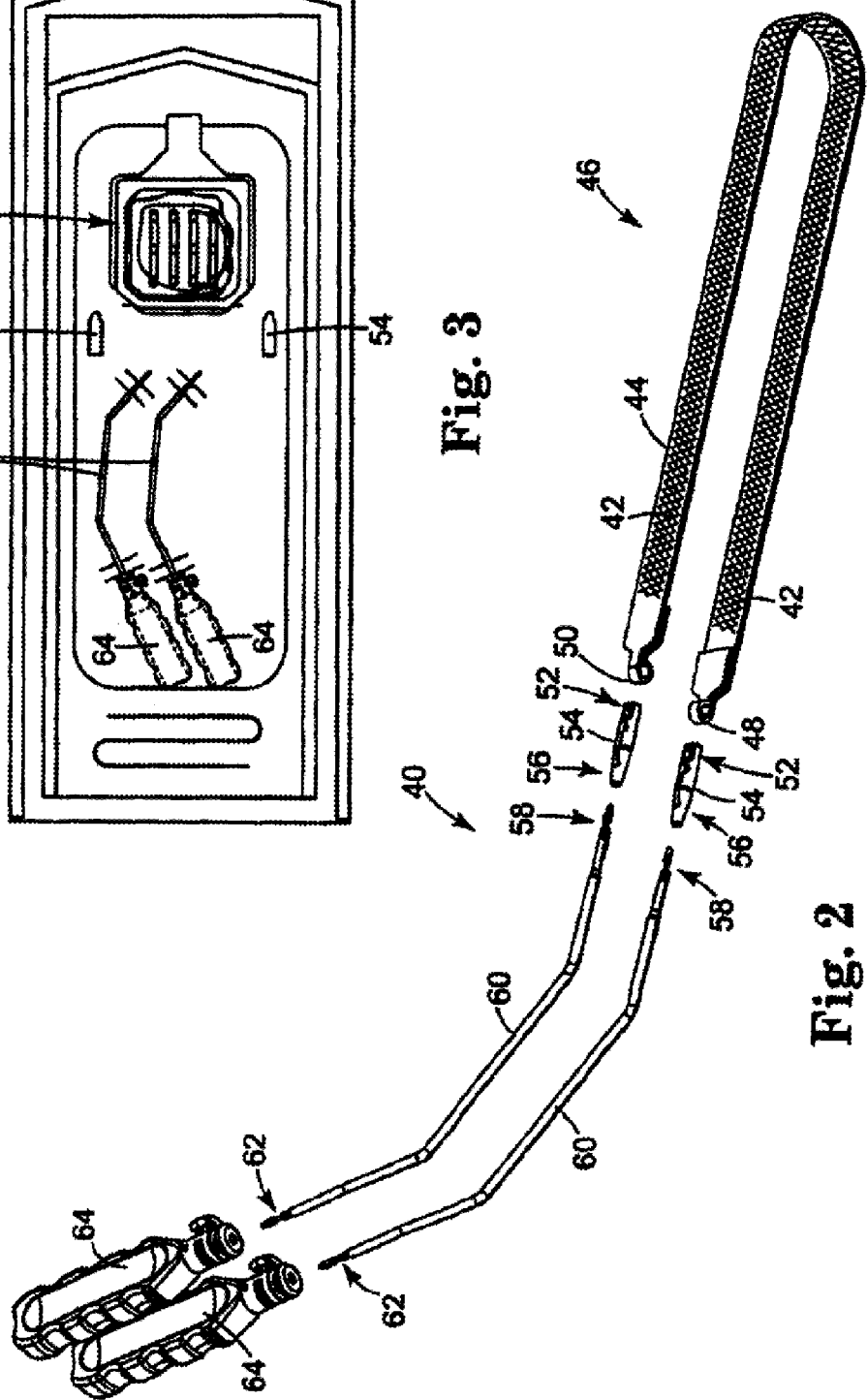

One advantage of the embodiment shown in FIG. 3 is that the needle 10 can be used for either a trans-abdominal approach or a trans-vaginal approach. In this approach, a kit comprising two needles 10, attached to a mesh 12, at least one coupler and at least one guide needle may be distributed for use by multiple surgeon specialists. For example, a gynecologist may prefer the trans-vaginal approach and will simply discard the connector and guide needle from the kit. On the other hand, a urologist may prefer the trans-abdominal approach and utilize the connector(s) and guide needle(s).

Referring now to FIGS. 6a–h, an alternate embodiment of the invention utilizes the needle 10 to penetrate the abdominal wall 60 and couple to the mesh 12. In this embodiment, the mesh 12 is modified to create a connection means for connecting to the distal end of the needle 10. The connection means is preferably detachable so that when the mesh is pulled out of the abdominal wall, the mesh may be detached from the needle and the needle reused to retrieve the other end of the mesh. This embodiment allows for the use of a single needle for the procedure. This embodiment also allows for the use of a mesh constructed, at least in part, of natural materials, which are otherwise not suitable in the pre-affixed embodiment due to the inability of the natural material to survive extended periods in inventory.

Figure 6A:
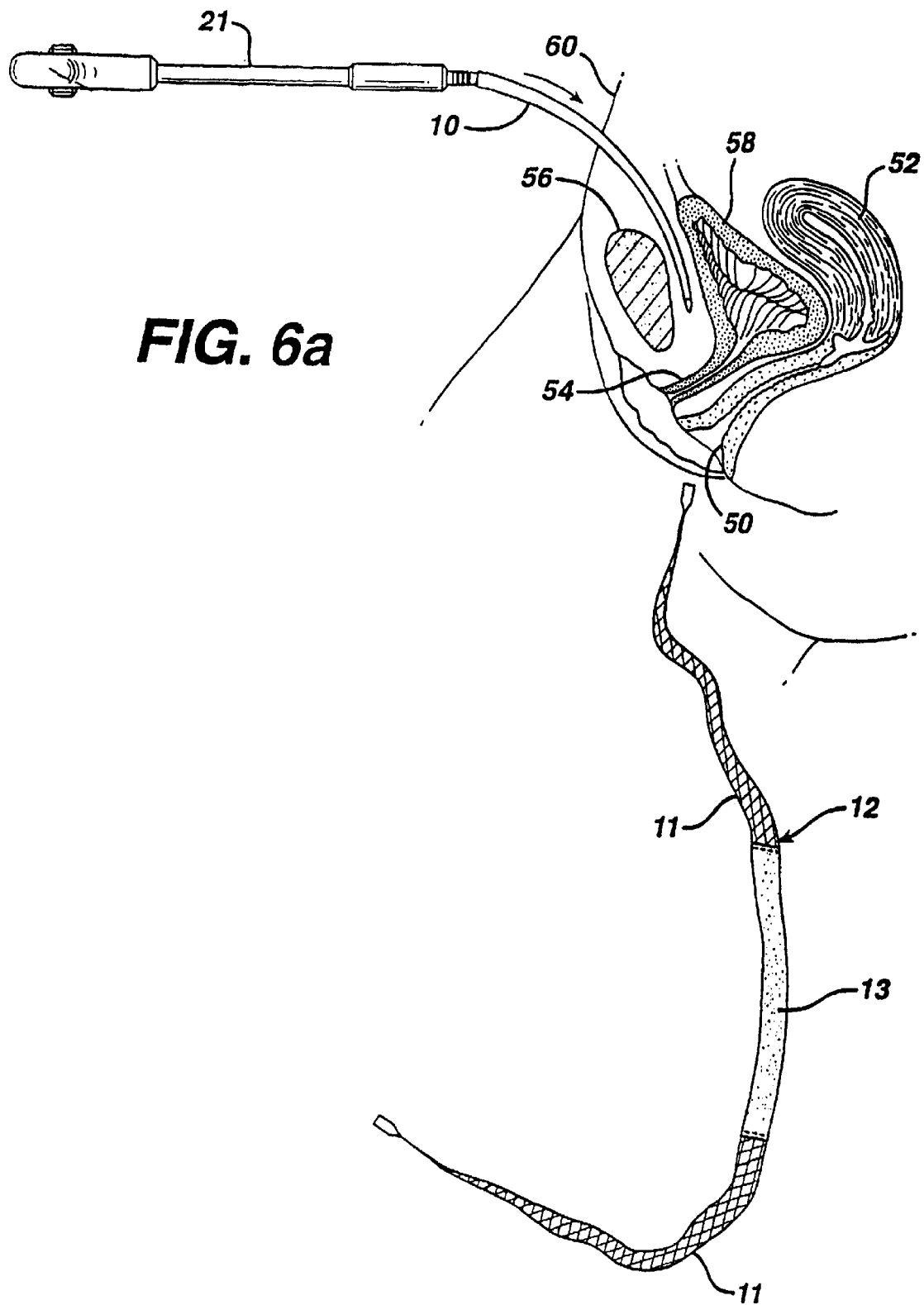
FIGS. 6a–h diagrammatically illustrate several surgical steps of a trans- abdominal method utilizing a single needle according to an alternate embodiment of the invention to treat SUI.
Figure 6B:
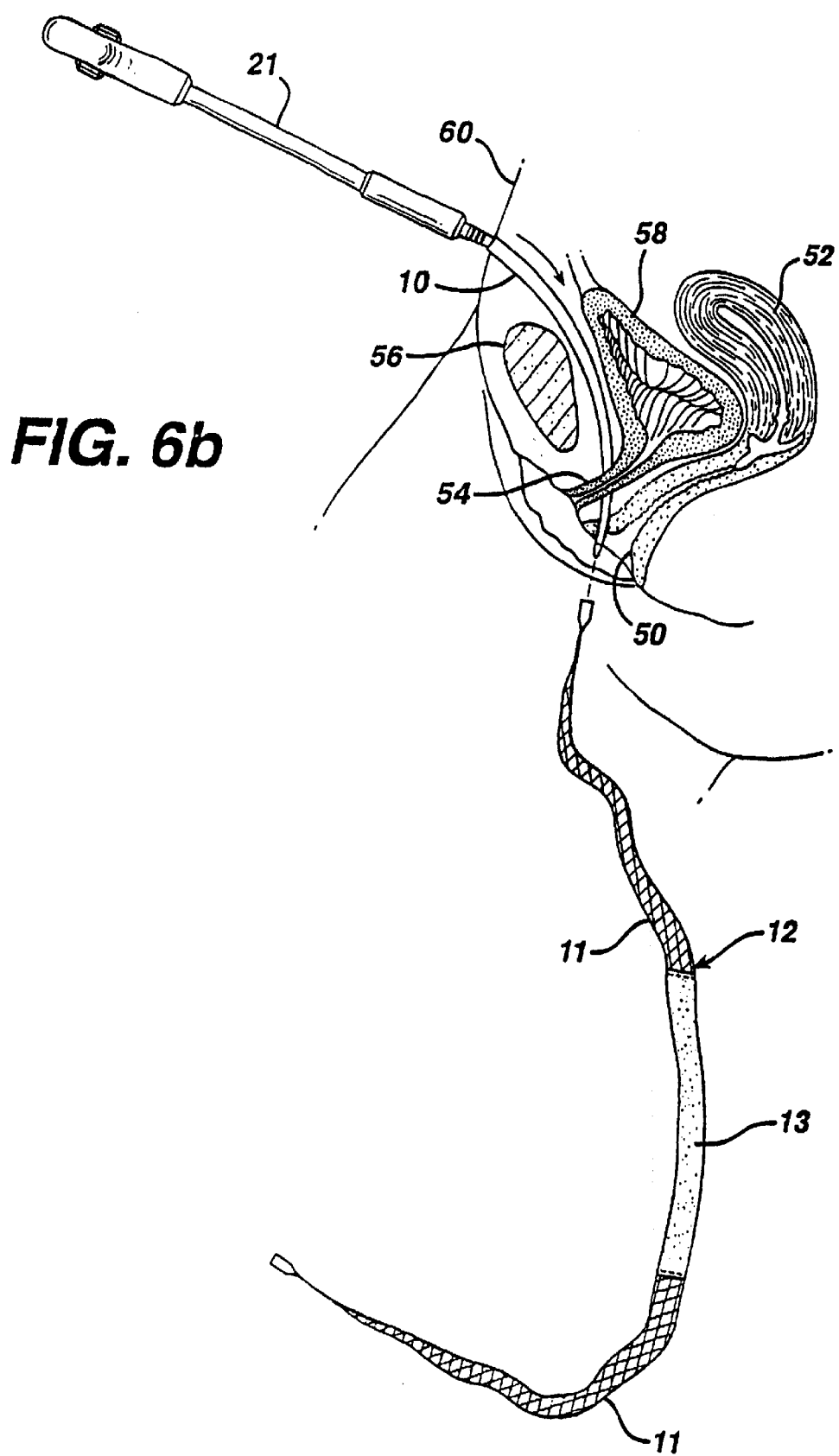
Figure 6C:
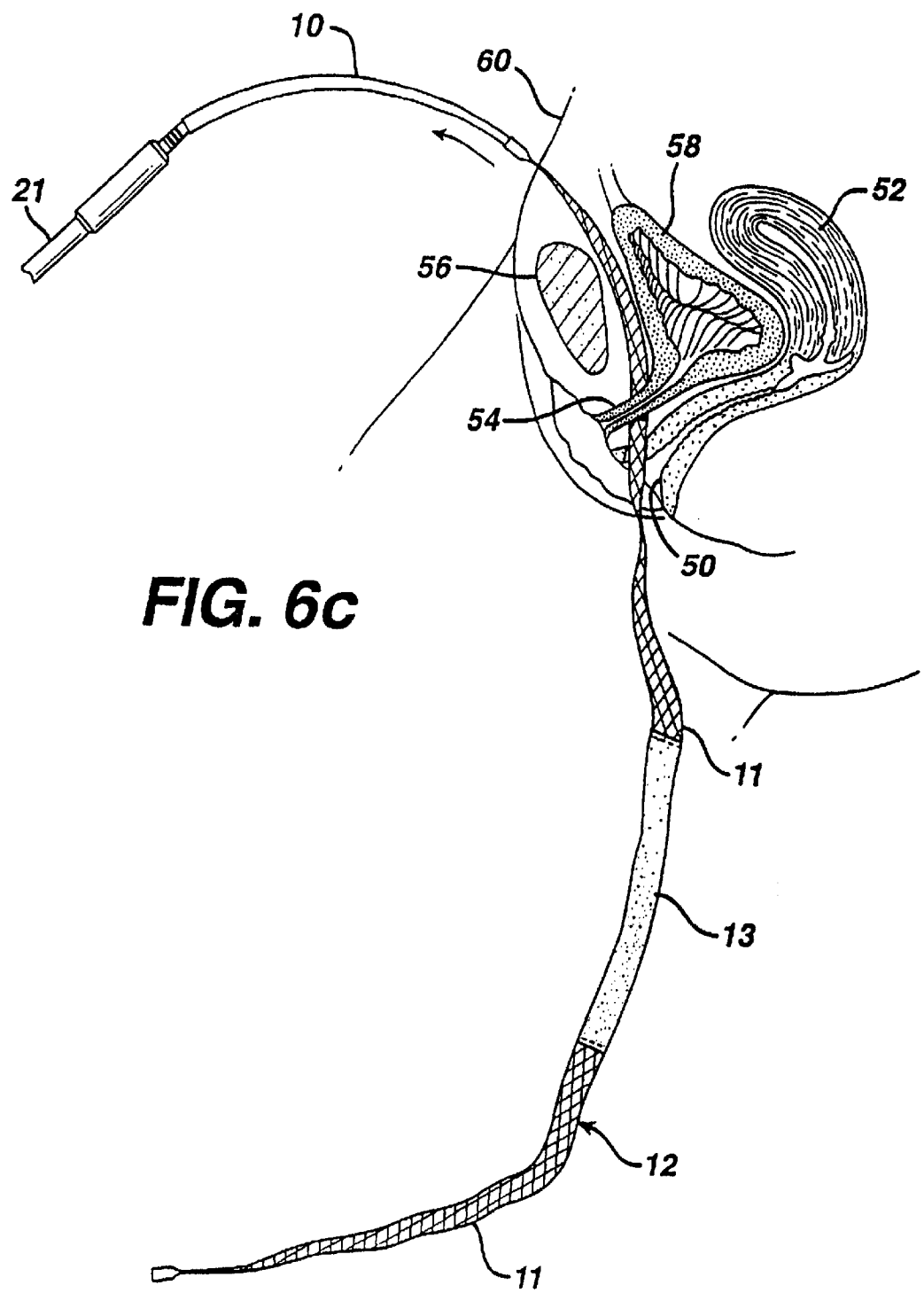
Figure 6D:
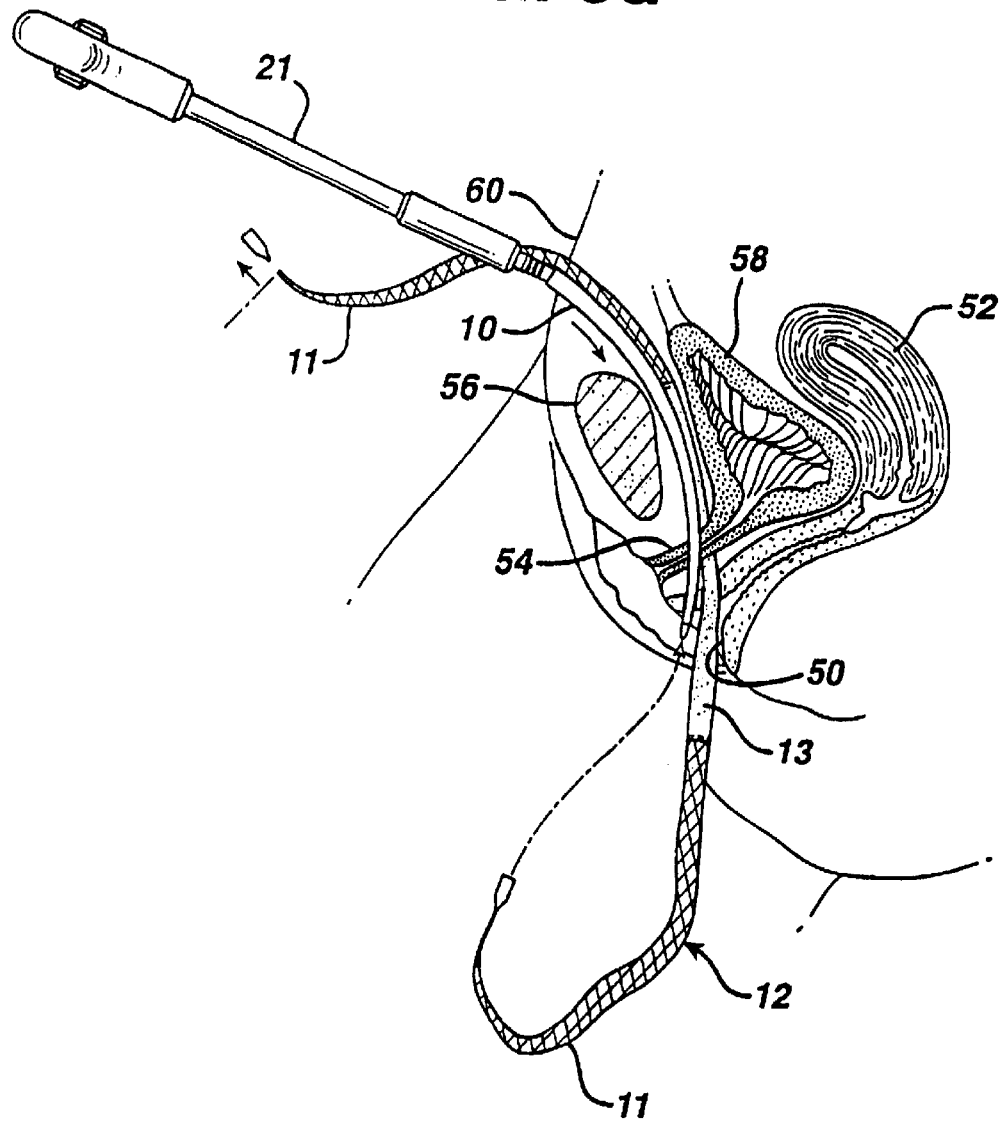
Figure 6E:
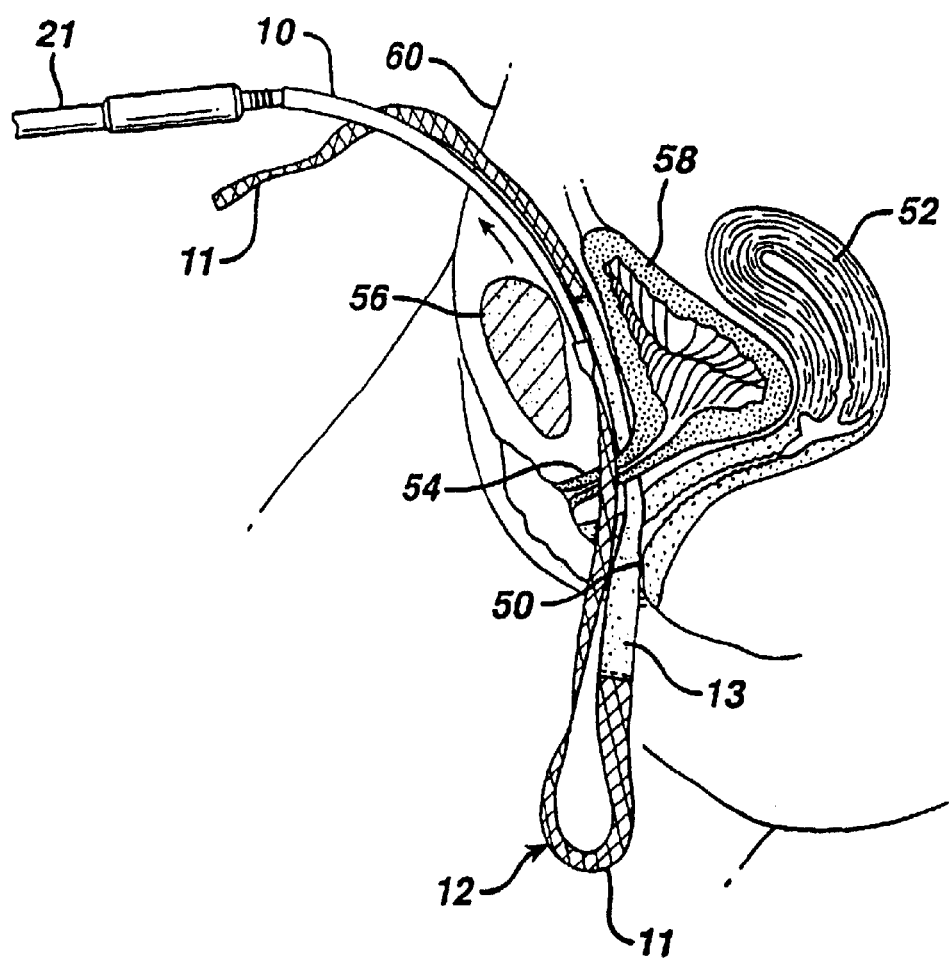
Figure 6F:
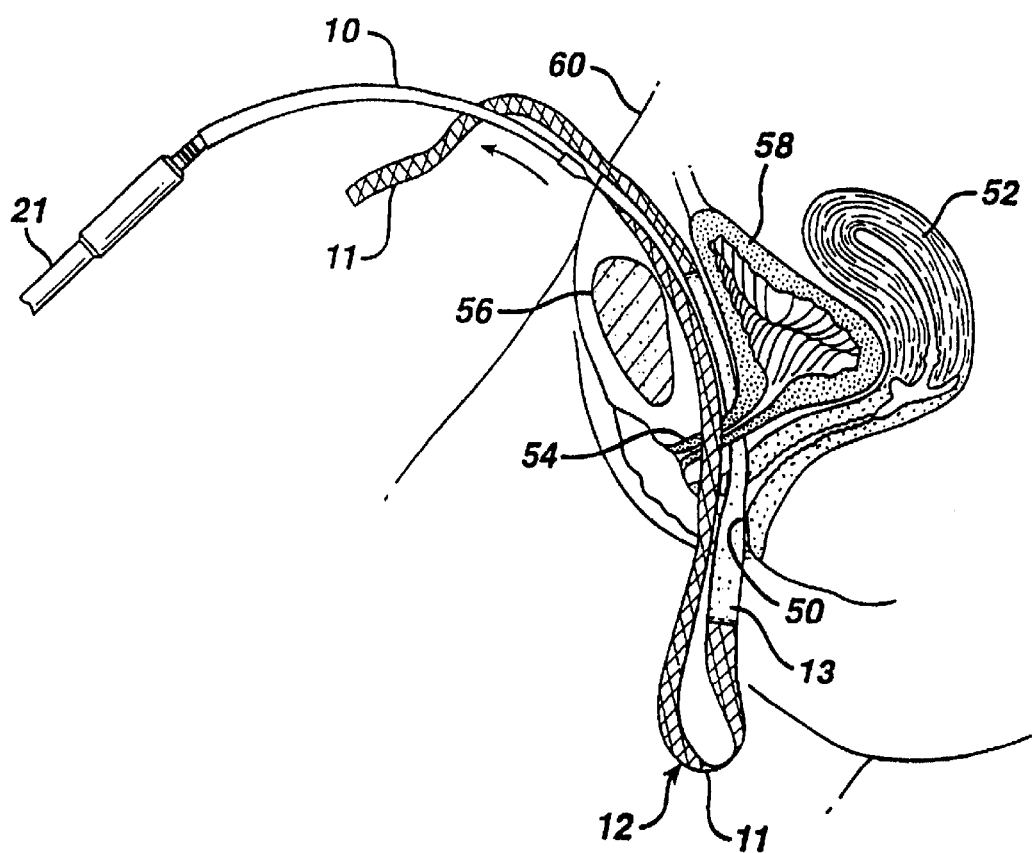
Figure 6G:
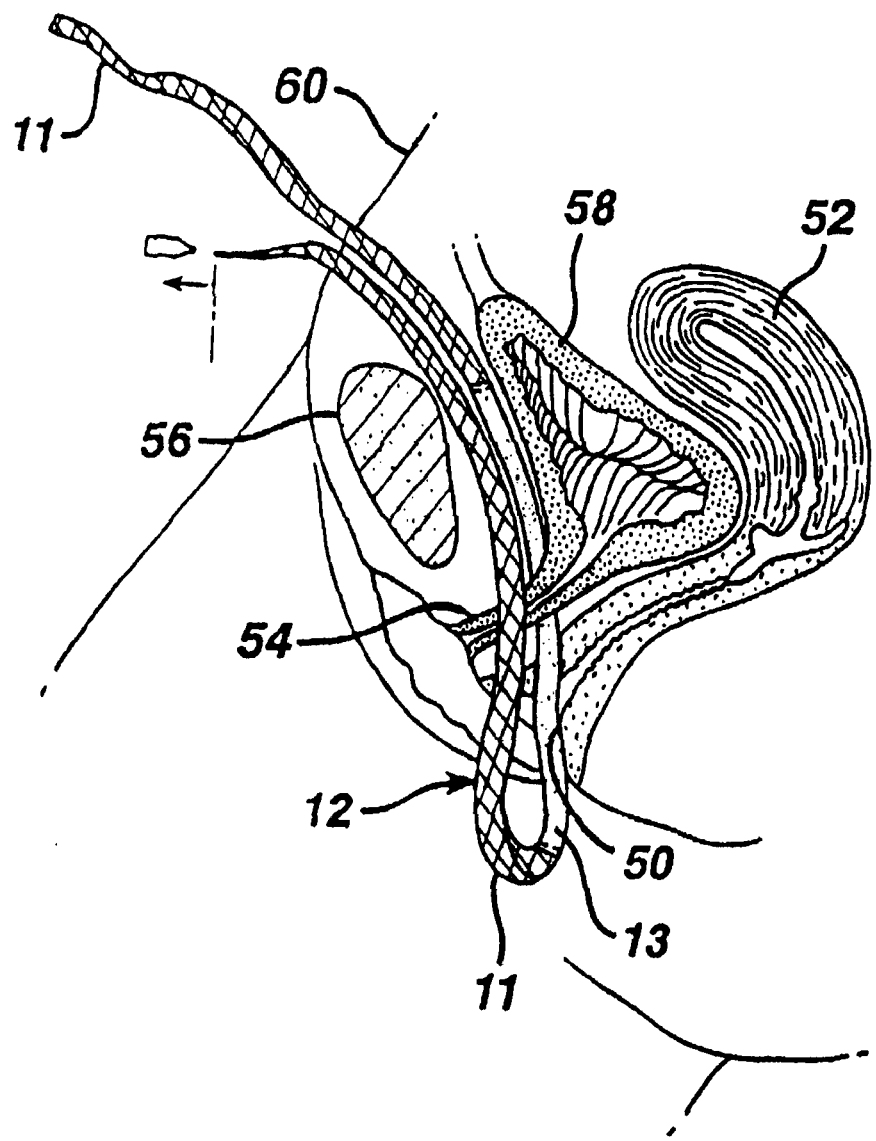
Figure 6H:
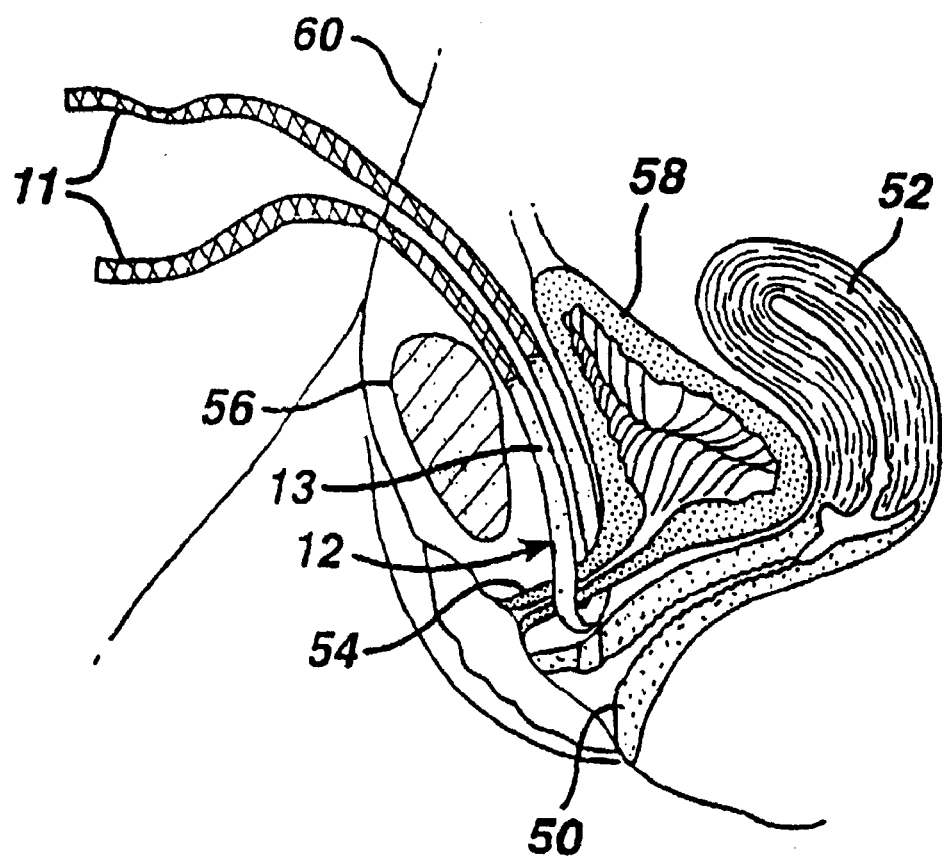

A needle 10 with coupling means at the distal end penetrates the abdominal wall 60, anterior to the pubic bone 56, FIG. 6a and follows the contour of the pubic bone 56 to one side of the urethra 54 and exits the body through an incision having been made in the anterior wall of the vagina 50, FIG. 6b. A first end of mesh 12 attaches to the distal end of needle 10 via coupling means. The surgeon then retracts needle 10 back through the pelvic cavity, following the same path created by needle 10, while at the same time causing mesh 12 to follow the needle, FIG. 4c, The needle 10 and mesh 12 pass through the vaginal wall and through the soft tissue on one side of the urethra 54. The needle and mesh then according to FIG. 4f being passed close to the back of the pubic bone 56, through additional layers of fat, muscle and fascia, and then out the abdominal wall 60 above the pubic bone 56.

Needle 10 disconnects from the first mesh end, and the surgeon repeats the same procedure, but this time passes the needle 10 on the opposite side of the urethra 54, FIGS. 6d–h, to complete the implantation of the mesh 12 between the mid urethra and vaginal wall.

Figure 7A:
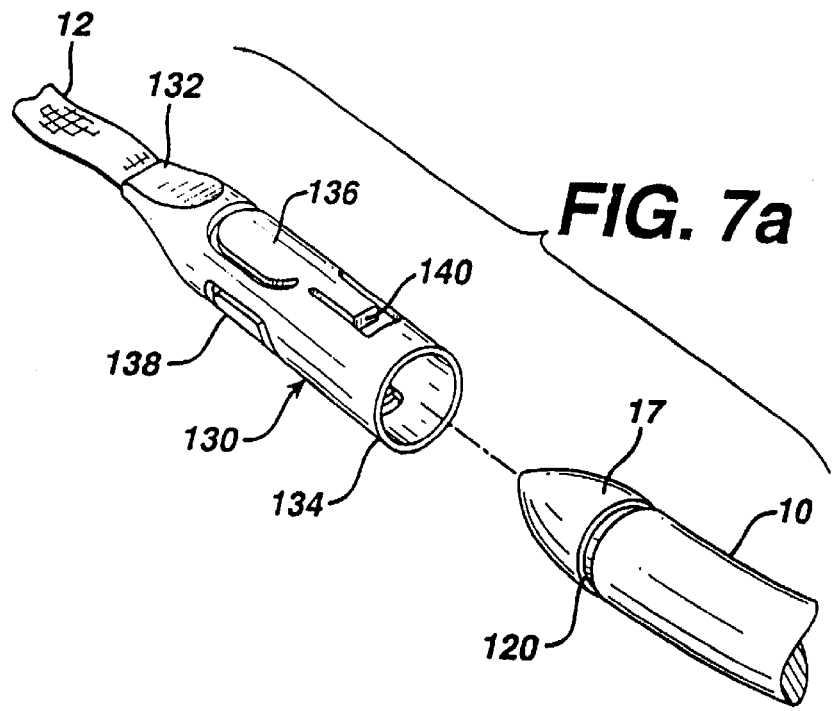
FIGS. 7a–g illustrate alternate embodiments of coupling the needle to the mesh.
Figure 7B:
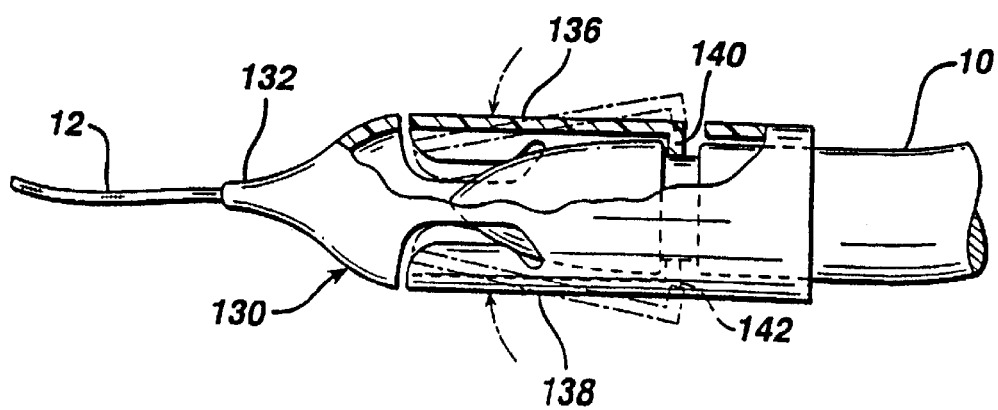

Referring to FIGS. 7a–g, alternate embodiments for connecting the needle 10 to the mesh 12 are disclosed. FIGS. 7a–b disclose a coupler 130 having a proximal end 132 configured to accept the mesh 12 and a distal end 134 for accepting the distal end 17 of needle 10. Distal end 17 comprises a contiguous groove 120 for detachably coupling with coupler 130. Coupler 130 further comprises two spring tabs 136 and 138, each with fingers 140 and 142 for engaging groove 120. Mesh 12 is preferably attached to the distal end 132 using a biocompatible glue or other appropriate mechanical fastening means. The surgeon may simply attach or detach needle 10 from coupler 130 by depressing spring tabs 136 and 138 forcing fingers 140 and 142 upward to allow distal end 17 to slide in or out of coupler 130. Fingers 140 and 142 engage groove 120 to hold needle 10 firmly in place within coupler 130.

Figure 7C:
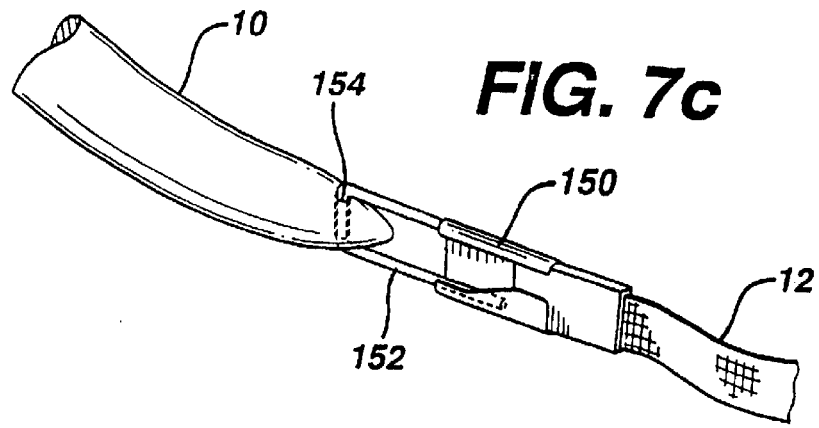
Figure 7D:
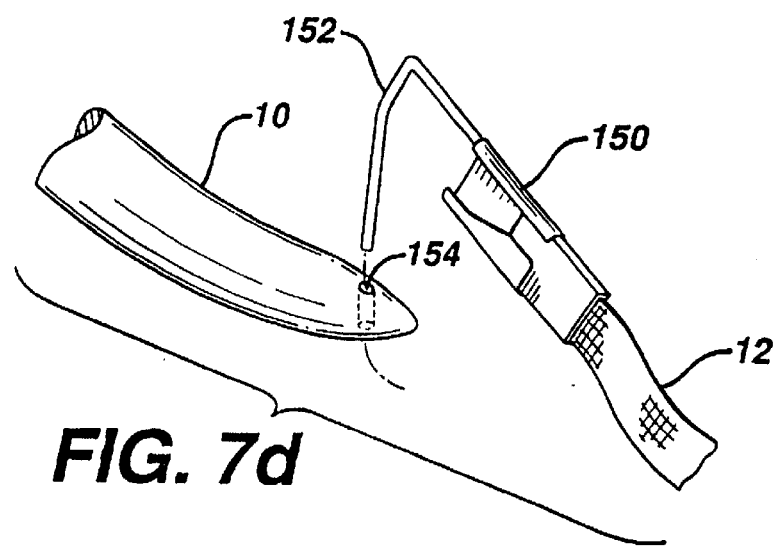
Figure 7E:
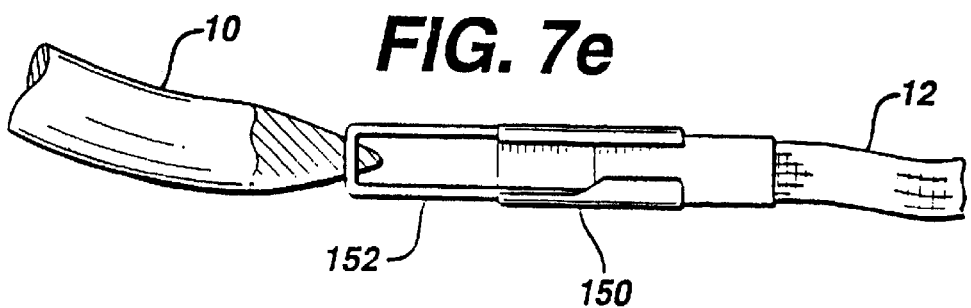

FIGS. 7c–e illustrate a coupling mechanism 150 similar in function to a safety pin. Spring arm 152 engages with a bore 154 at the distal end 17 of needle 10.

Figure 7F:
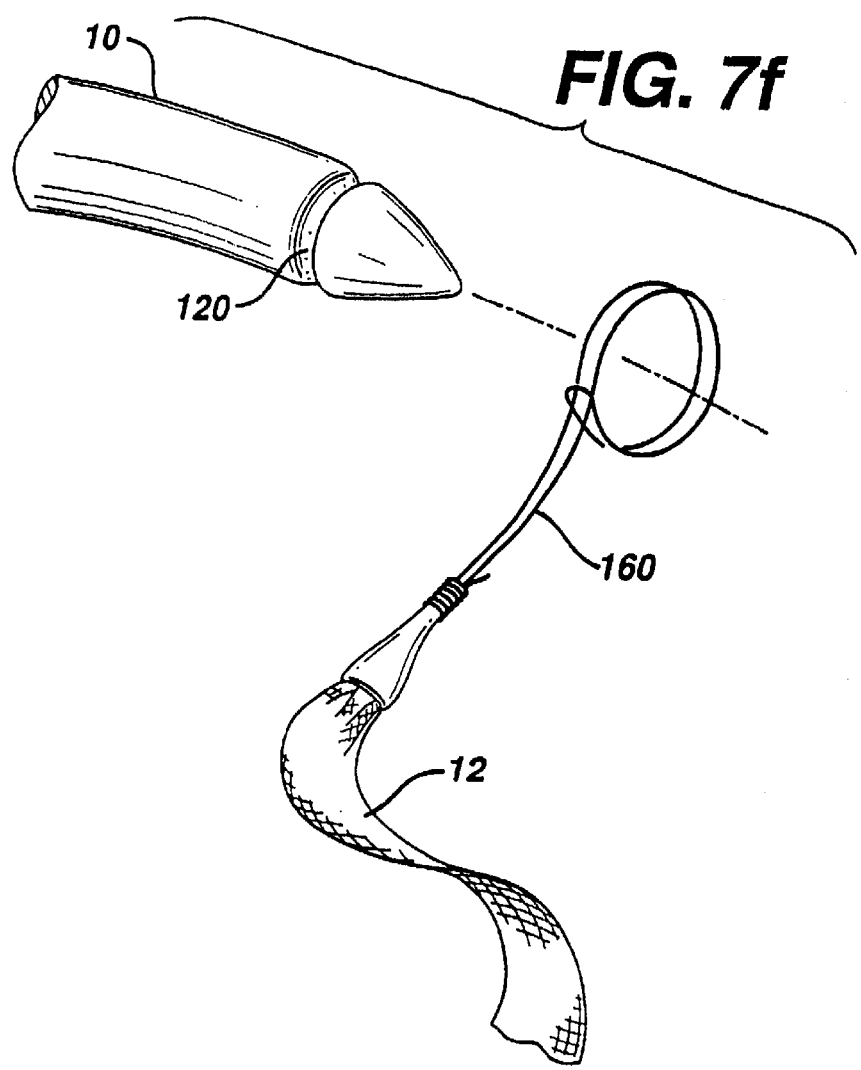
Figure 7G:
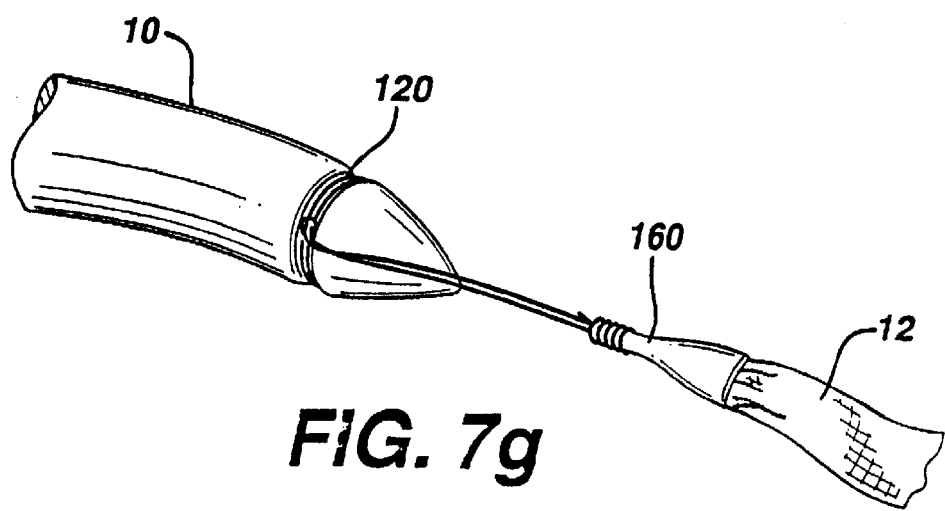
Figure 8A:
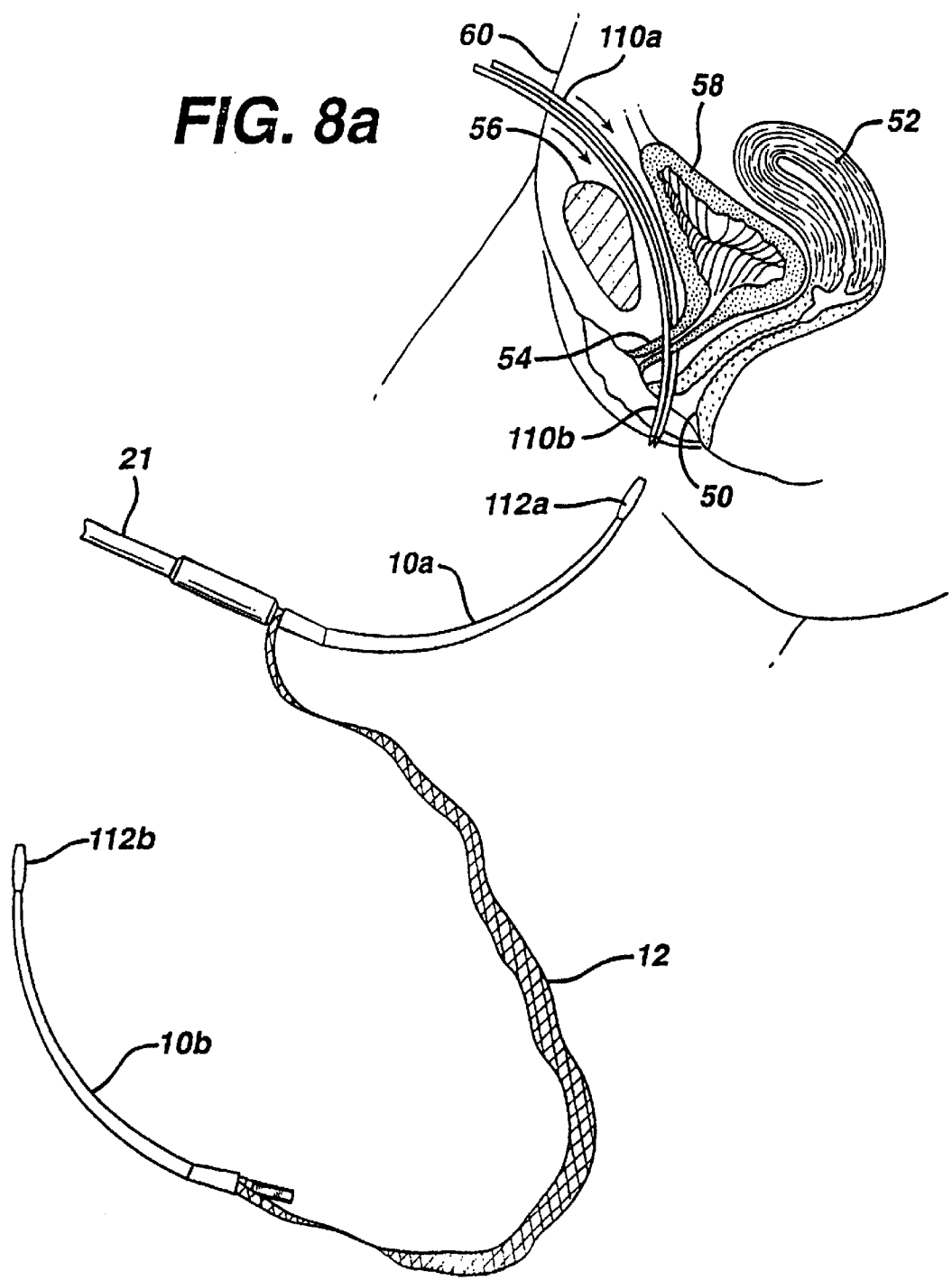
FIGS. 8a–i diagrammatically illustrate several surgical steps of a trans. abdominal method utilizing two needles and two guide needles according to the invention to treat SUI.
Figure 8B:
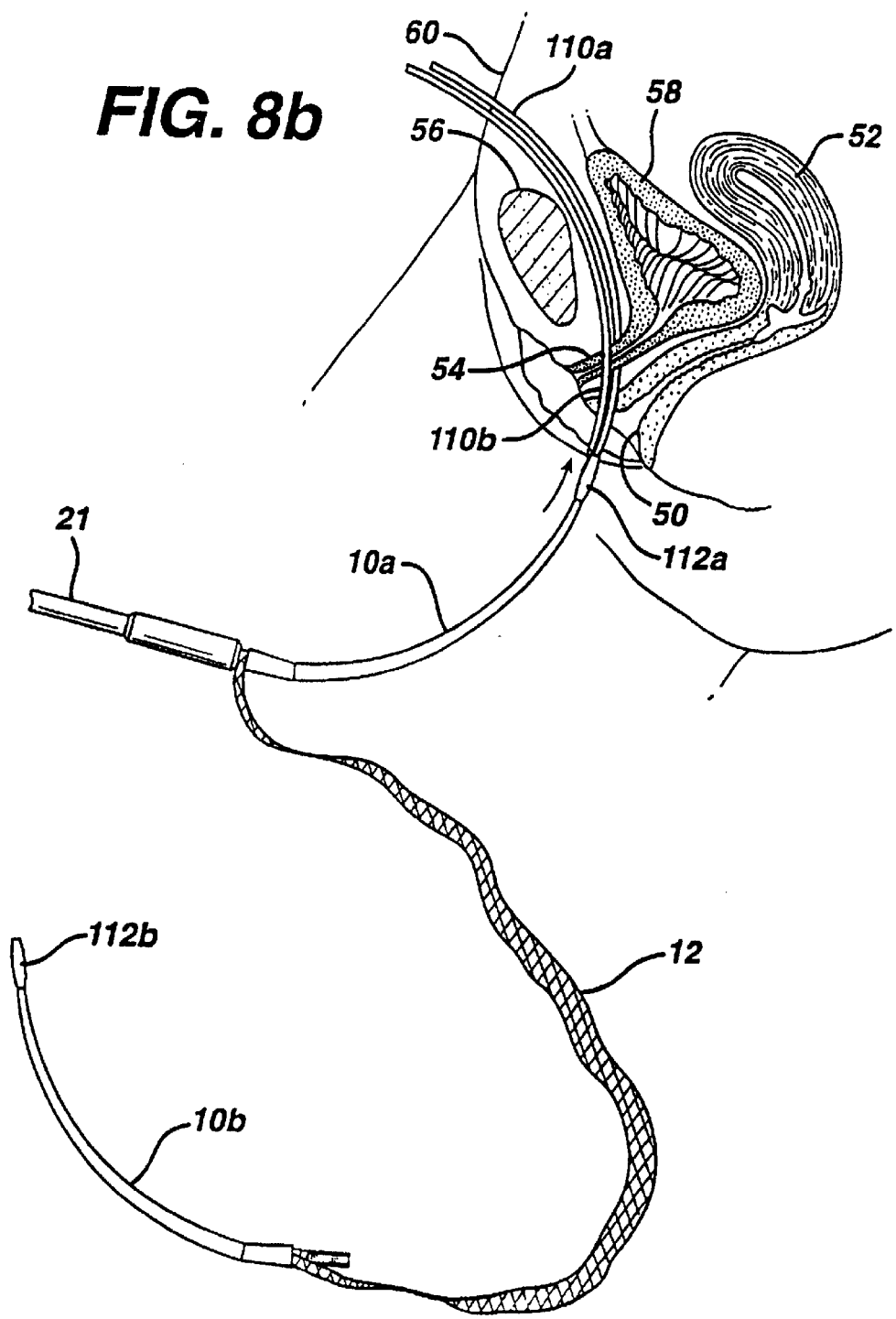
Figure 8C:
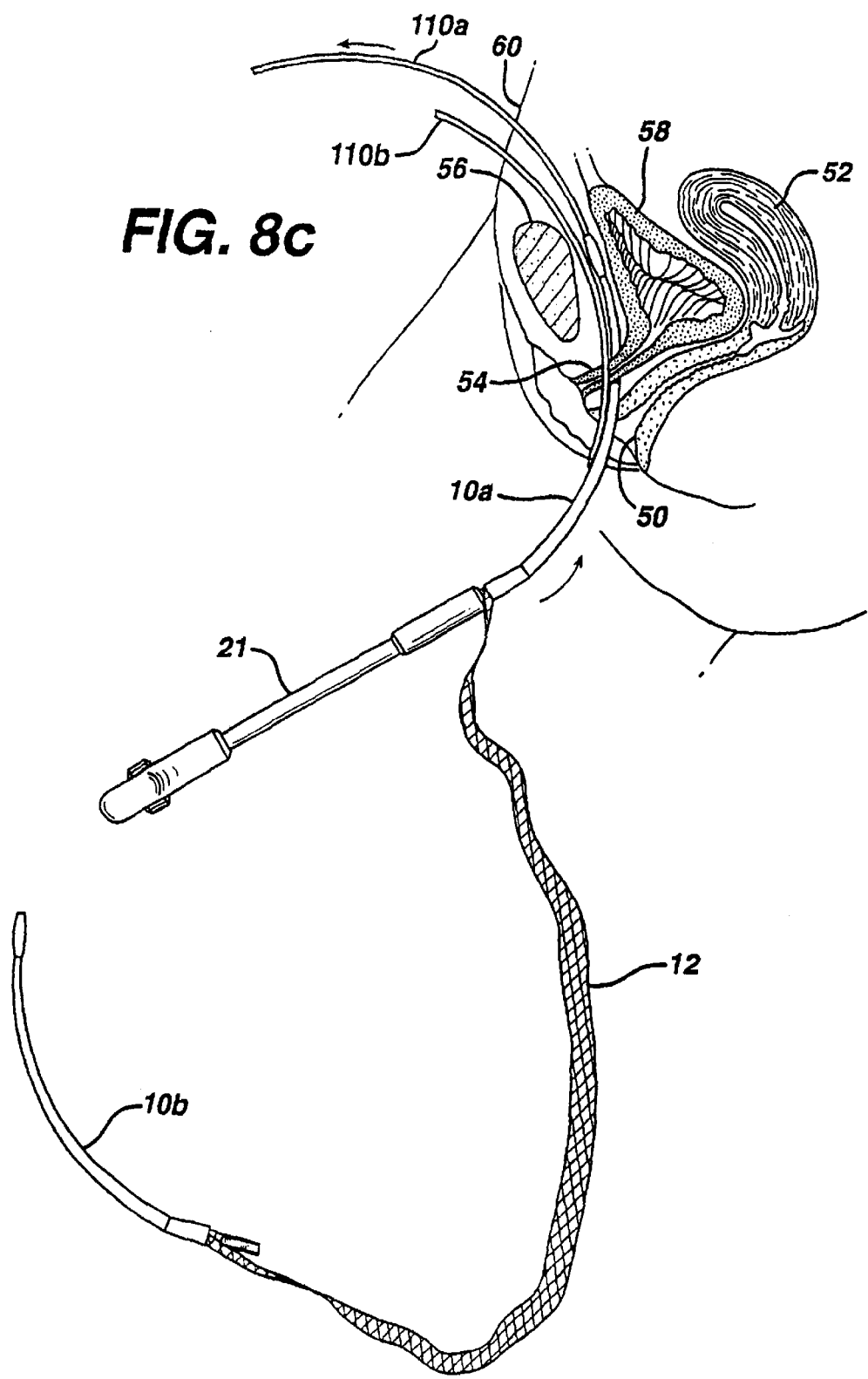
Figure 8D:
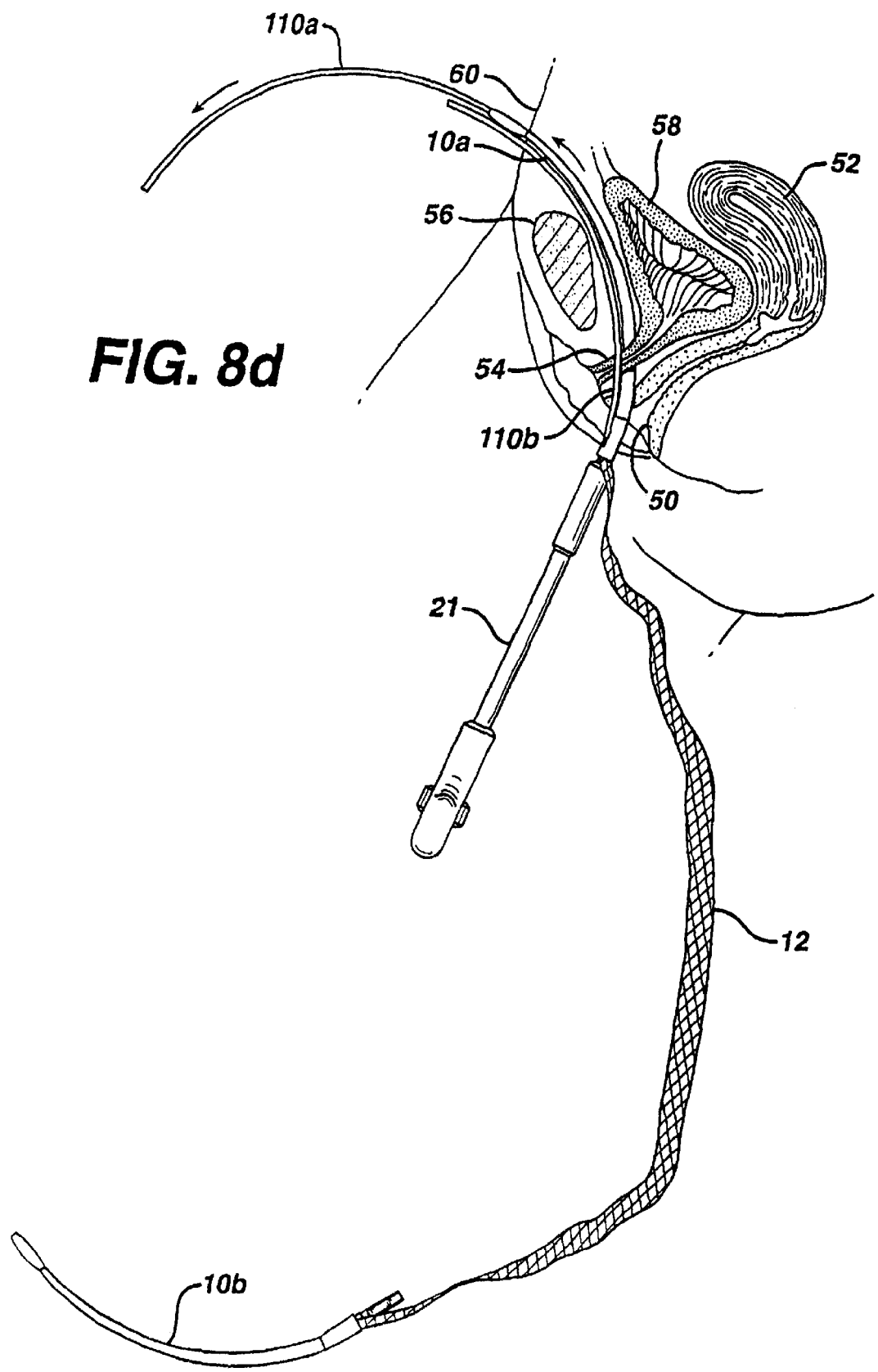
Figure 8E:
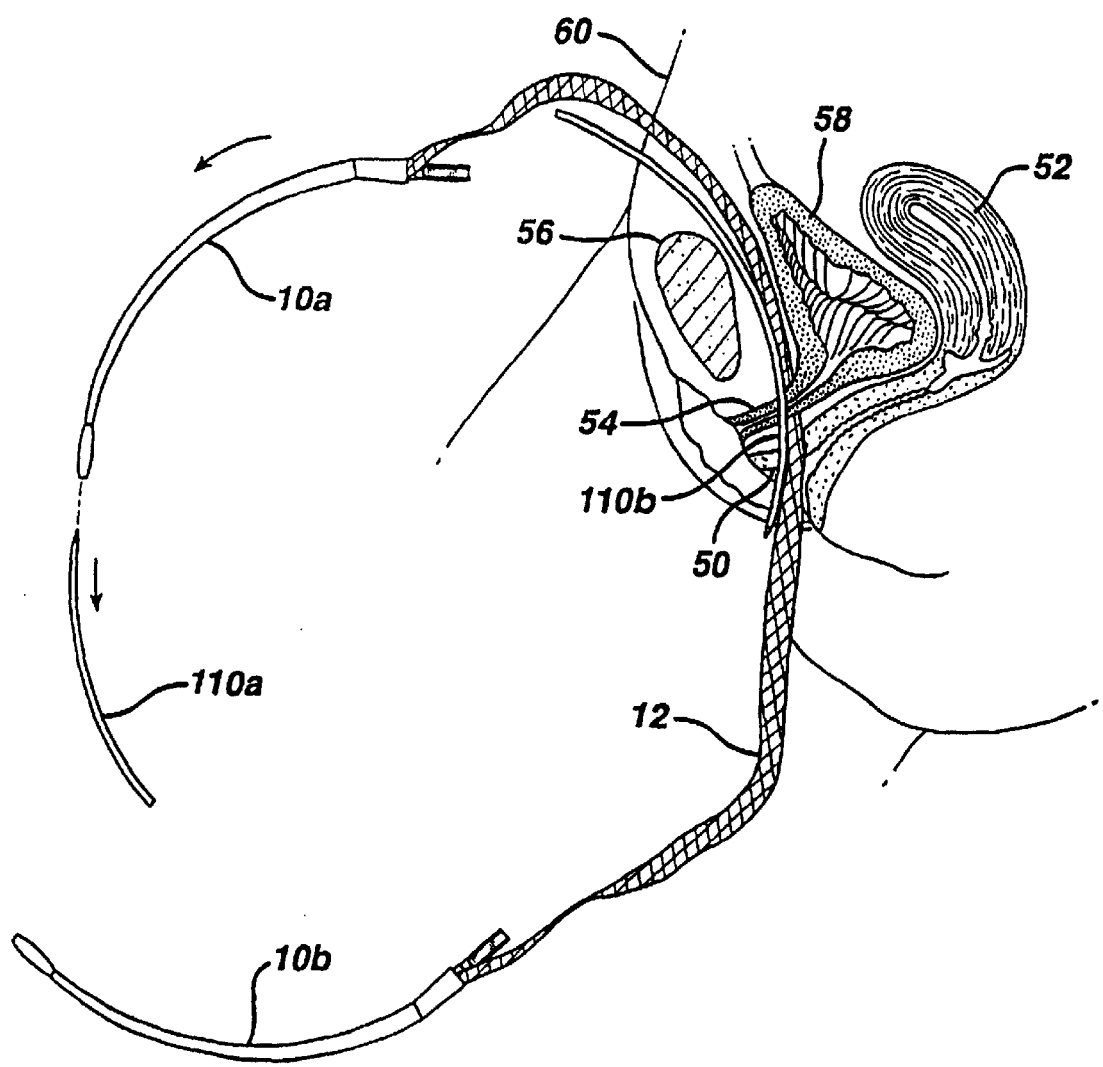
Figure 8F:
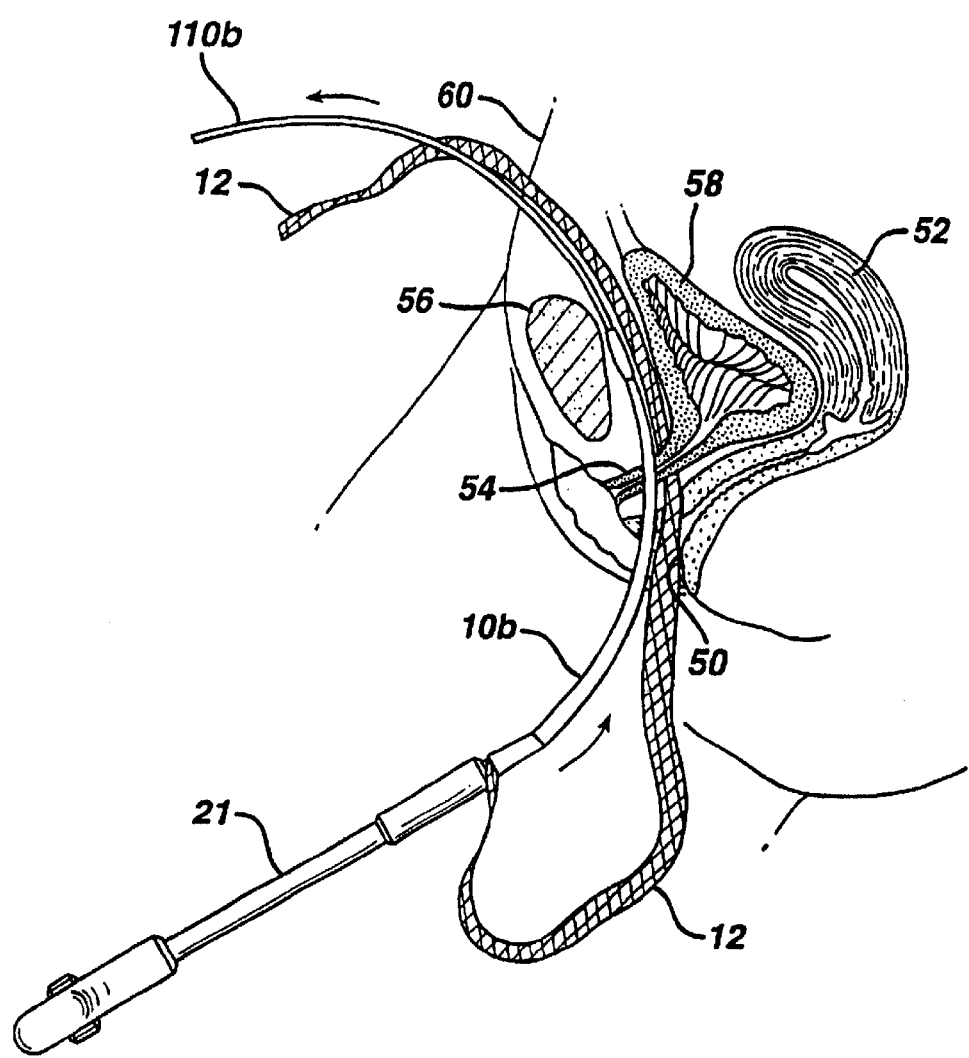
Figure 8G:
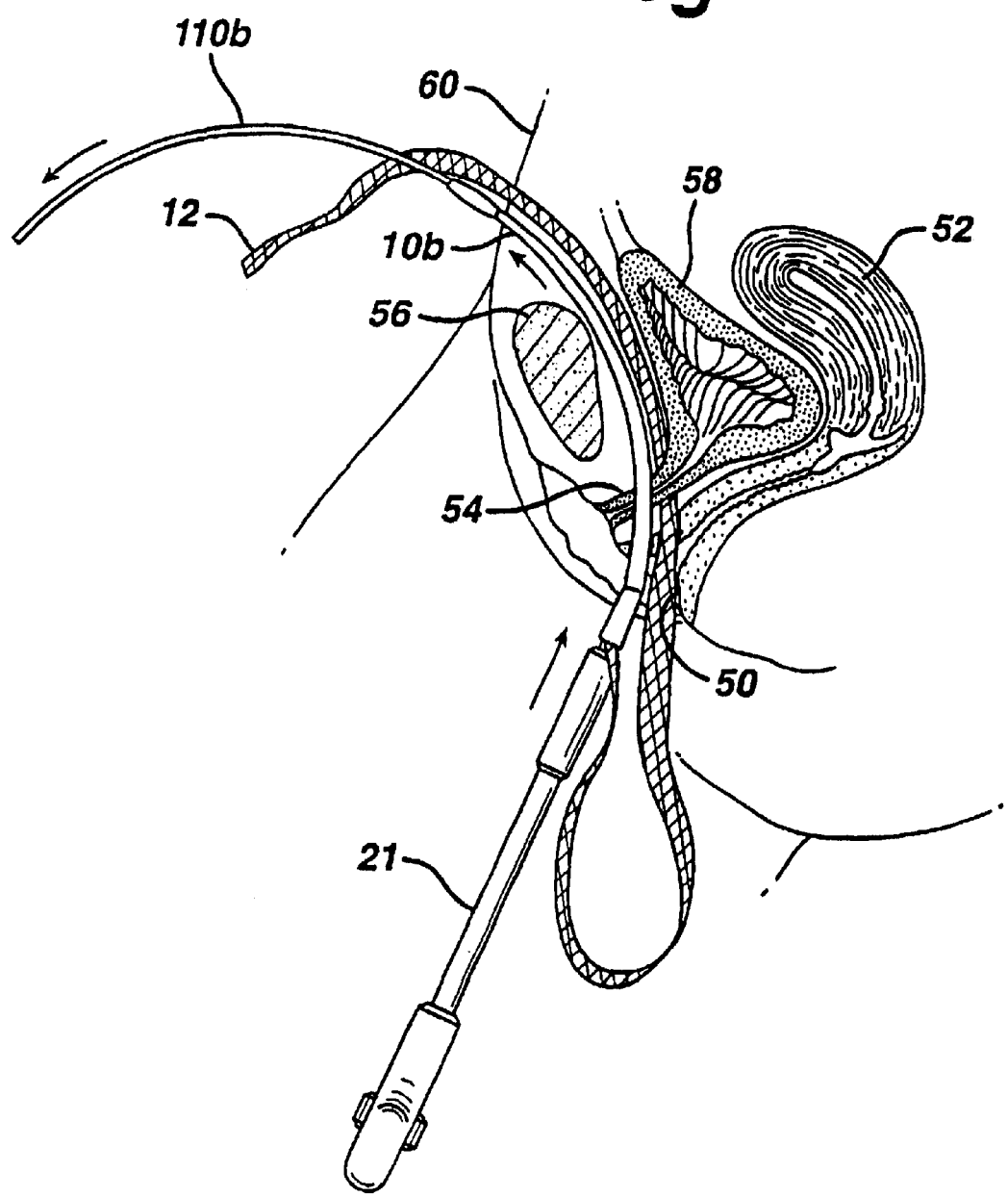
Figure 8H:
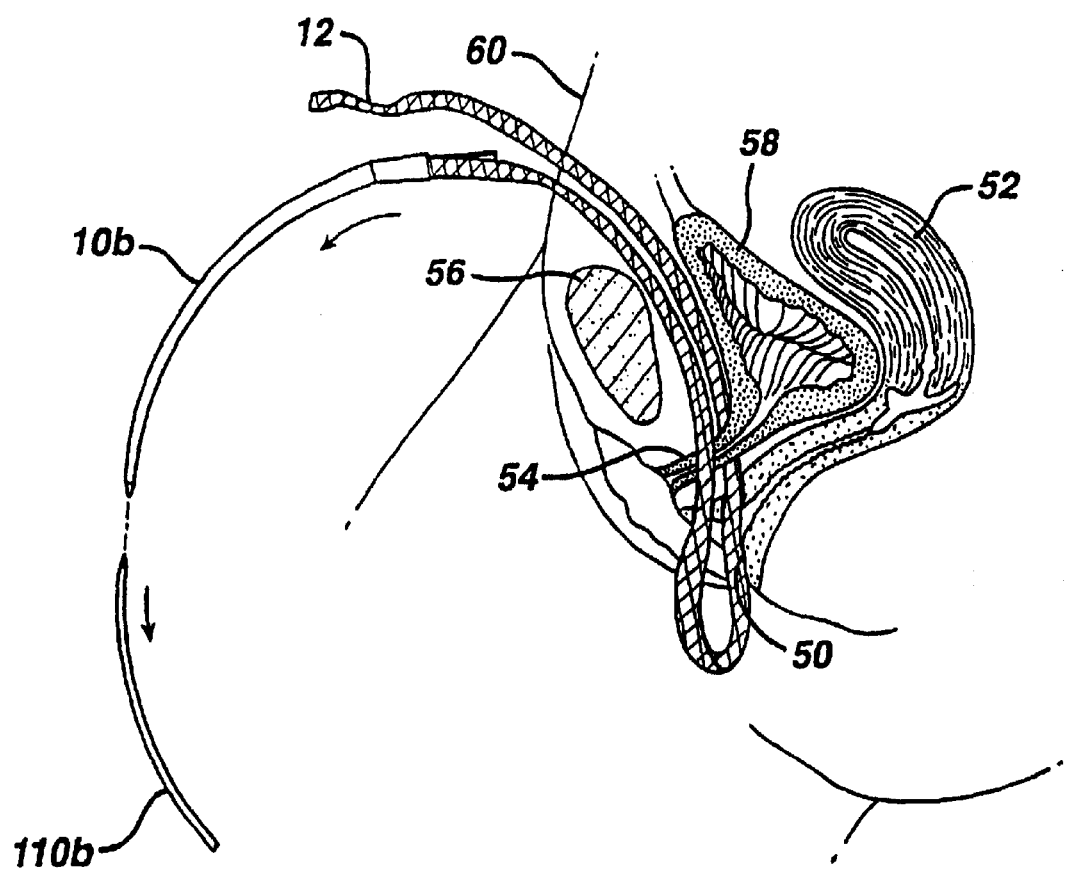
Figure 8I:
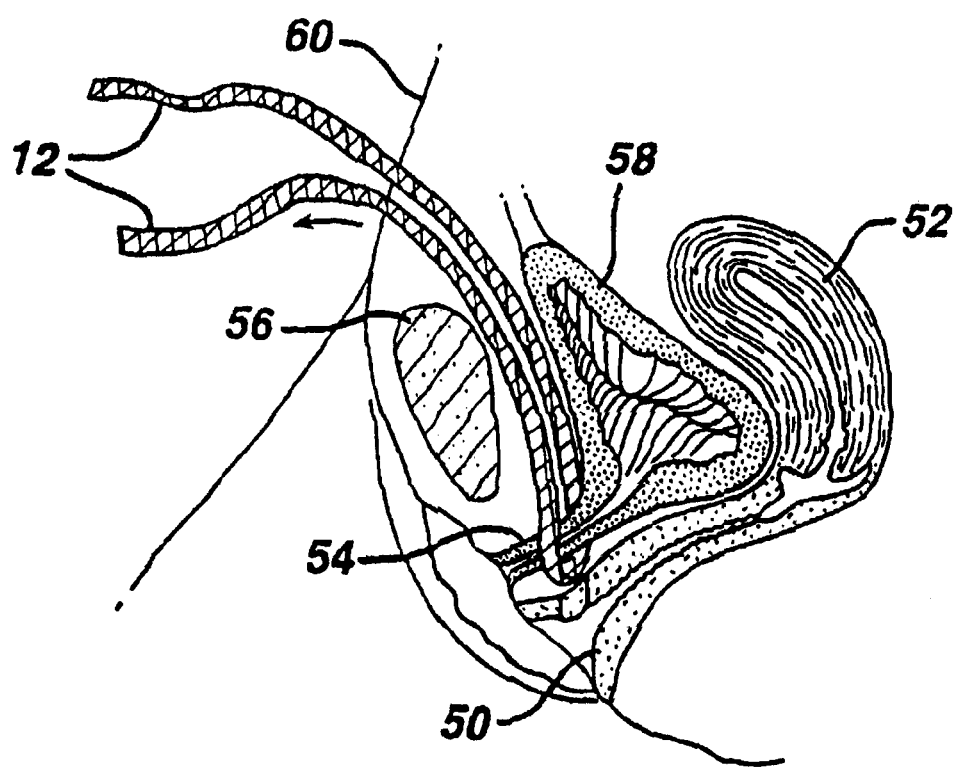
Figure 1:
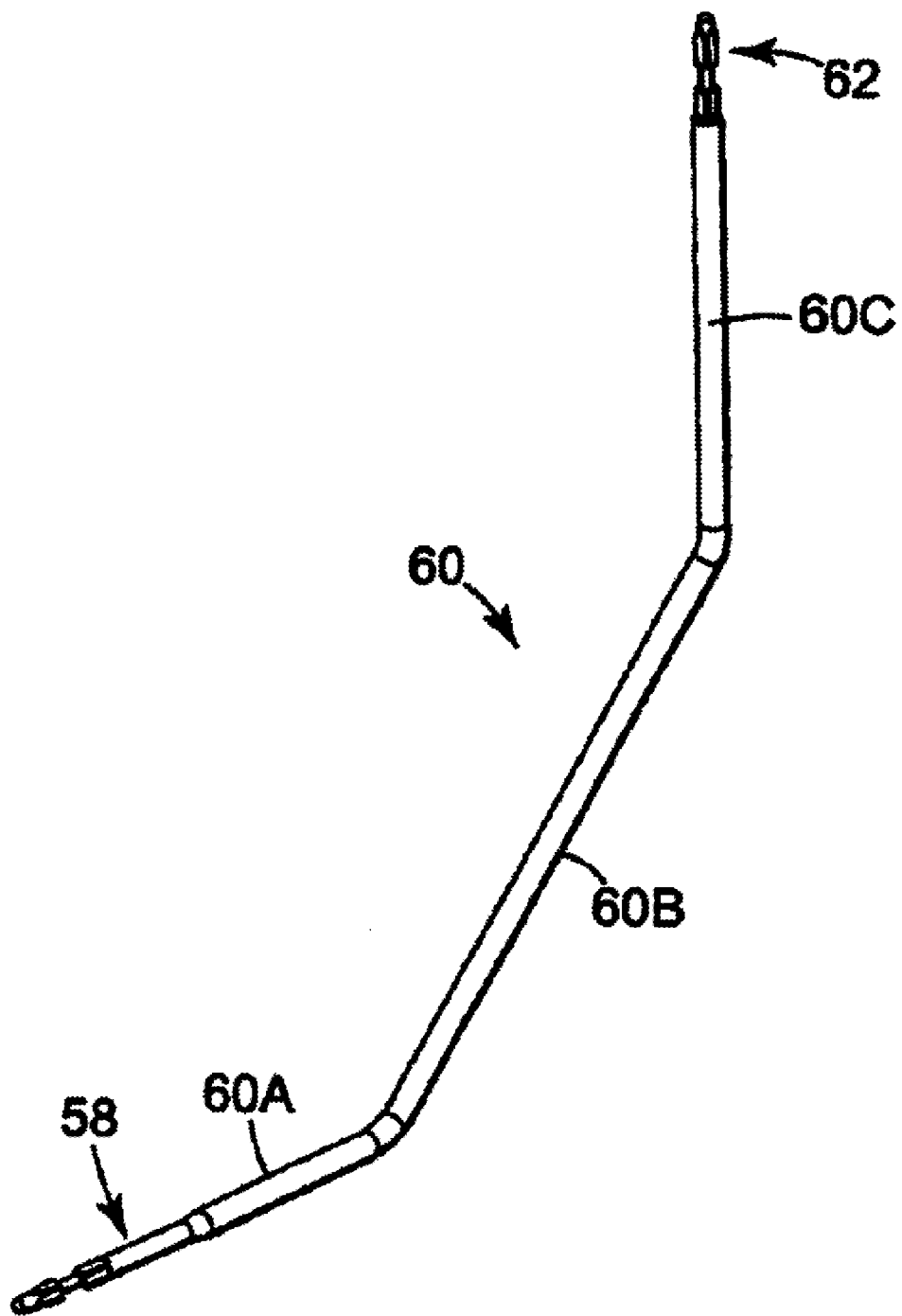

FIGS. 7f–g illustrate a loop coupling mechanism 160 attached to mesh 12 for engaging groove 120.

As would be appreciated by one skilled in the art, there exist multiple means for detachably connecting the mesh to the needle.

Since all procedures may be performed using a local anesthesia, the patient is able to provide feedback to the surgeon after mesh 12 is in place. Typically, the urinary bladder 58 is filled with a fluid, such as water, using a catheter and the patient is requested to cough. The surgeon is able to determine the operation of the urethra and may adjust the placement of the mesh 12, as necessary, by adjusting the ends of mesh 12 located at the outside of the abdomen 60, FIGS. 4h and 5h. After adjustments, the surplus mesh at the abdomen is cut off, and the ends of the mesh are secured within the abdomen and the abdomen is closed. Likewise, the incision at the vaginal wall is dosed whereby the tissue flap seals the mesh between the urethra 54 and the wall of vagina 50.

Mesh 12 is left in the body and forms an artificial ligament attached to the abdominal wall that provides the support for the urethra as required in order to restore urinary continence to the patient.

It will be apparent from the foregoing that, while particular forms of the invention have been illustrated and described, various modifications can be made without departing from the spirit and scope of the Invention. Accordingly, it is not intended that the invention be limited, except as by the appended claims.

A modification to the idea of using guides to assist in placing the mesh within the abdominal cavity to repair stress urinary incontinence is to complete the repair of pelvic floor defects. A mesh is placed within the pelvic floor to correct a cystocele or enterocele or rectocele or other prolapse. This concept discloses the method and instrumentation to place the mesh using, either a laparoscopic technique or blind approach with the guides to affix the mesh.

Prolapse is a condition in which organs, namely the bladder, bowel and uterus, which are normally supported by the pelvic floor, herniate or protrude into the vagina. This occurs as a result of damage to the muscles and ligaments making up the pelvic floor support. Childbirth is the most common cause of damage to the pelvic floor, particularly where prolonged labor, large babies and instrumental deliveries were involved. Other factors include past surgery such as hysterectomy, lack of estrogen due to the menopause, and conditions causing chronically raised intra abdominal pressure such as chronic constipation, coughing, and heavy lifting.

Vaginal surgery is the usual method of repair. Abdominal surgery, on the other hand, Is usually performed when there is urinary stress incontinence or when vaginal surgery has failed. The choice of technique will generally depend upon the type, the severity of the prolapse and the surgeon's experience. Recent advances in laparoscopic surgery have helped surgeons repair many pelvic floor defects, which are often difficult to reach by the vaginal method. Examples include prolapse of the vaginal vault, enterocele and paravaginal cystocele.

In the laparoscopic procedure, the surgeons insert a tiny telescope (laparoscope) through a small incision at the umbilicus. This is attached to a camera-television setup, giving the surgeons a magnified view of the pelvic floor. Via three keyhole incisions in the abdomen, the surgeons use specially designed instruments to lift and attach the prolapsed organs back to the ligament and muscle support with many non-absorbable sutures. The sutures act as a bridge allowing scar tissue to form the long-term support.

Surgeons can also make this repair by inserting a layer of mesh through the anterior vaginal wall. The corners of the mesh are attached with sutures to the ligaments and muscles on the sidewalls of the pelvis. The suturing can be done via access through the abdomen as above or by access through the vaginal incision.

Instead of suturing the sheet of mesh to the ligaments, the mesh is suspended from one or more strips of mesh attached at the edges of the main portion of the sheet. The suspension is completed to the abdominal rectus muscle or to the pelvic bone or other ligaments or muscles within the pelvis such as Cooper's ligament or the obturator muscle. Repair of a prolapse can also include passage of the guides and mesh through the obturator fossa or any other fossa in the pelvic bone. Alternately it can be attached along the levator ani muscle at the level of the arcus tendoneius. Portions of the mesh strips are pulled up through the abdominal rectus muscle or other muscle or are attached to the pelvic bone and held in place there by the friction between the mesh and muscle, similar to the TVT attachment.

To accomplish this, a long blunt needle or shaft is passed, under laparoscopic view or blindly with palpation, from the abdomen through the rectus muscle and out the vaginal incision. The mesh is attached to the tip of the needle similar to the attachment of the TVT AA device. The needle is pulled back out of the vagina and abdomen. This is repeated on all corners of the mesh suspending it under the bladder or other organ to hold it in place.

The mesh can be shaped into configurations, which would provide areas of support. Based on the requirements of the repair these configurations can consist of straight strips, crossed strips, a broad or elongated sheet with strips attached to the edges, or diagonal connections.

FIG. #9 shows the configuration of a sheet of mesh with strips extending from two edges. The strips would be pulled through the muscle or ligaments to hold the sheet in place under the organ to be supported. The strips would be inserted through the tissue by attaching them to a needle or shaft. The needle could then be attached to a guide which has been passed through the tissue from the opposite direction, and which has created a path for the needle and strip to egress.

Alternately, the needles could be passed through the tissue pulling the mesh strip behind without the aid of the guide.

FIG. #10 shows a side view of the mesh placed in a front to back position in the body.

FIG. #11 shows a frontal view of the strips, which are placed front to back.

FIG. #12 shows a side view of the front to back placement with the front end of the strip attached to the pubic bone or pubic symphysis.

FIG. #13 shows the strips with crossing bands connecting them under the area, which is to be supported. This band could also be a solid sheet between the two strips.

FIG. #14 is a frontal view of the mesh as it is suspended from two strips with a central connecting section.

FIG. #15 shows the strips in a side view, placed front to back and crossing each other under the organs to be supported.

Positioning of the tape under the organs to be supported is also disclosed here. FIG. #16 shows a side view of the female urogenital organs with an incision made In the mid vagina on the anterior wall. This incision would be approximately 1.5 cm and cut with a scalpel. Blunt dissection would be performed to separate the layers of the vagina. The guide is inserted into a puncture incision along the rim of the pubic bone about 2 cm from mid line. The guide is advanced to the inferior rim of the pubic bone. A finger is inserted into the vaginal incision and is advance toward the pubic symphysis. The tip of the guide is rotated or angled to the posterior section of the vagina and the finger palpates the guide tip. Once the finger and tip are in contact the guide is advanced through the thin layer of tissue on the top of the vagina. The guide is then push out of the vagina where the needle is connected to it via a coupling device. The guide is extracted from the vagina and abdomen pulling the mesh strip and needle with it. FIG. #17 shows the placement of the mesh strip under the bladder.

Additional incisions can be made on each side of the abdomen further along the lateral rim of the pelvic bone. The guide is inserted through these incisions, one at a time. and into the vagina by means of the finger guiding it. Additional strips of the mesh are attached to the guides via the needle and extracted out of the vagina and abdomen. FIG. #18 shows positions of the incisions. FIG. #19 shows a side view with two strips of mesh in place to provide a wider support area. FIG. #20 shows a frontal view of the procedure with a sheet of mesh inserted in the anterior vaginal wall, and strips of mesh extending from its edges and exiting either out of the abdomen, or being secured onto the soft tissue of the pelvic bone, i.e. the tendonous arch or white line.

The position of the mesh is not restricted to the anterior wall of the vagina. It may be placed under the vagina, under the bladder, under the rectum and along the levator ani muscle. When the organs are supported by strips alone the strips can be placed alongside or on top of or underneath the ligaments which are attached to these organs or which are supporting the organs either directly of indirectly. Examples of these type tissues are external anal sphincter, ischiocaverous muscle, central tendon of the perineum, endopelvic fascia such as; urethrovesical, vagino-uterine and rectal. Some examples of ligamentous tissue which can be supported as well are sacrotuberous ligament, sacrospinous ligament, broad ligament and cardinal ligaments.

Passage of the guides and mesh are not limited to, through the vagina. The guides can also be inserted through the anus and penetrate the rectum to exit the ischial fossa or obturator fossa to suspend mesh through those portals. Additional combinations of passage routes include; from the iliac crest to the pubis; from the Ischial spine to the pubis; from right Ischial spine to left Ischial spine and others.

Additional configurations of the mesh include:

FIG. #21 a ladder shape with multiple strands connecting the strips.

FIG. #22 an "X" connecting the strips.

FIG. #23 perpendicular and diagonal strands connecting the strips.

FIG. #25 diagonal strands connecting the strips In order to enhance the passage of the guide through the abdominal cavity it will be necessary for some procedures to have guides, which have different shapes and lengths. The basic guide has a single curve in the shaft, FIG. #26. Other configurations can have "S" curves, FIG.#27. Further shapes can be curves in multiple planes. The shaft can also contain a hinged section which is rotateable and lockable The direction of the guide can be accomplished with a simple hinge or complex hinges along the shaft. Additional designs can include flexible shafts, directable shafts, and stearable shafts. Other designs can incorporate sections, which are rigid and sections, which are flexible or stearable. The use of certain materials can also enhance the passage of the guides through the body. Materials, which can be used, are shape memory alloys and plastics, which deploy to specific shapes under changes in temperature. These materials can also include a super elastic property, which allows significant bending with low force applied and without permanent deformation. The superelastic material can be combined with a cannula so that the cannula makes the initial passage and the memory material is extended beyond the cannula to finish the curved track. Additionally, the superelastic material can be passed through a curved cannula and as it exits continues on a straight path. In this instance the shaft can be constructed from a single or double central core wire which is wrapped with a tight coil of wire producing a configuration which has the flexibility of a spring without the elongation.

The invention claimed is:

1. A surgical assembly for treating incontinence comprising: a first surgical instrument for use on a right side of a patient, the first surgical instrument comprising a handle portion and a substantially helical needle portion having substantial structure in three dimensions and a distal end, the needle portion having a portion that is sized and shaped to extend between an incision substantially adjacent the obturator foramen on the patient's right side and a vaginal incision;

a second surgical instrument for use on a left side of a patient, the second surgical instrument comprising a handle portion and a substantially helical needle portion having substantial structure in three dimensions and a distal end, the needle portion having a portion that is sized and shaped to extend between an incision substantially adjacent the obturator foramen on the patient's left side and a vaginal incision; and a sling assembly including a mesh material.

2. The assembly of claim 1 wherein the sling assembly comprises a synthetic material.

3. The assembly of claim 1 wherein the sling assembly comprises a knitted polypropylene material.

4. The assembly of claim 1 wherein the sling assembly comprises a sheath.

5. The assembly of claim 1 wherein at least a portion of the sling assembly comprises a non-synthetic material.

6. The assembly of claim 1 wherein the mesh material comprises a woven or knitted material.

7. The assembly of claim 1 wherein the mesh material comprises interlinked fibers that form multiple junctions.

8. The assembly of claim 1 wherein the needle portions of the first and second surgical instruments have structure near the distal ends for associating the first and second surgical instruments with the sling assembly.

9. The assembly of claim 1 wherein the needle portions of the first and second surgical instruments further comprise substantially straight spacer portions along an elongate axis of the handles.

10. The assembly of claim 1 wherein the substantially helical needle portions of the first and second surgical instruments are variable spiral portions.

11. The assembly of claim 1 wherein the needle portions of the first and second surgical instruments include a substantially circular cross sectional shape with a diameter of less than about 4 mm.

12. The surgical assembly of claim 1 wherein the handle portion of the first surgical instrument includes indicia indicating the first surgical instrument is for use on the right side of the patient, and the handle portion of the second surgical instrument includes indicia indicating the second surgical instrument is for use on the left side of the patient.

13. The assembly of claim 1 wherein the handle portions of the first and second surgical instruments are detachable from the substantially helical needle portions.

14. The assembly of claim 1 wherein the handle portions of the first and second surgical instruments consist of a single handle adapted to removably attach to the substantially helical needle portions of the first and second surgical instruments.

15. A surgical assembly for treating incontinence comprising: a first surgical instrument for use on a right side of a patient, the first surgical instrument comprising a handle portion, and a needle portion having a substantially straight portion projecting from the handle and a variable spiral portion with a distal end, the variable spiral portion being sized and shaped to extend between an incision substantially adjacent the obturator foramen on the patient's right side and a vaginal incision;

a second surgical instrument for use on a left side of a patient, the second surgical instrument comprising a handle portion, and a needle portion having a substantially straight portion projecting from the handle and a variable spiral portion with a distal end, the variable spiral portion being sized and shaped to extend between an incision substantially adjacent the obturator foramen on the patient's left side and a vaginal incision; and a sling assembly including a mesh material.

16. The assembly of claim 15 wherein the variable spiral portions of the first and second surgical instruments have a tissue clearance depth of greater than about 1.5 inches and less than about 2.5 inches.

17. The assembly of claim 15 wherein the variable spiral portions of the first and second surgical instruments have a maximum width of greater than about 1.25 inches and less than about 3 inches.

18. A surgical assembly for treating incontinence comprising: a first substantially helical needle having a leading end, a trailing end and substantial structure in three dimensions, the needle having a portion that is sized and shaped to extend between an incision substantially adjacent the obturator foramen on a patient's right side and a vaginal incision;

a second substantially helical needle having a leading end, a trailing end and substantial structure in three dimensions, the needle portion having a portion that is sized and shaped to extend between an incision substantially adjacent the obturator foraxnen on the patient's left side and a vaginal incision;

a handle removably attachable to the trailing ends of the first and second substantially helical needles; and a sling assembly including a mesh material.

19. The surgical assembly of claim 18 wherein the handle is removably attachable to the leading ends of the first and second substantially helical needles.

20. A method of treating incontinence in a patient comprising the steps of:

creating a vaginal incision, creating an incision substantially adjacent the patient's obturator foramen, providing an elongate, substantially helical surgical instrument comprising first and second ends, with at least one of the ends having a securement surfaces, providing a sling assembly having an implantable sling for treating the incontinence, the sling assembly having surfaces complementary to the securement surfaces.

passing the instrument between the incisions, then snap fitting the instrument to the sling assembly to provide a substantially permanent attachment between the instrument and the assembly, then passing the implantable material through tissue from the vaginal incision toward the incision substantially adjacent the patient's obturator foramen.

21. A method of treating incontinence in a patient comprising the steps of:

creating a vaginal incision, creating an incision substantially adjacent the patient's obturator foranien, providing a substantially helical, elongate surgical instrument comprising first and second ends, the instrument having substantial structure in three dimensions, providing an implant for treating the incontinence, passing the instrument between the incisions, then associating the implant with the instrument, and passing the implant through tissue and through the patient's obturator foramen with the instrument.

22. A method according to claim 21 wherein the step of passing the implant through tissue includes the step of passing the implant along a substantially three dimensional path.

23. A method according to claim 21 wherein the step of providing an elongate surgical instrument includes the step of providing an instrument with an elongate handle portion having an axis, and the step of passing the instrument between the incisions includes the step of rotating the instrument about the axis of the handle portion.

24. A method of treating incontinence in a patient comprising the steps of:

creating a vaginal incision, creating an incision substantially adjacent the patient's obturator foramen, providing an elongate surgical instrument comprising a handle portion,, a needle portion having a substantially straight portion projecting from the handle portion and a variable spiral portion with a distal end, providing an implant for treating the incontinence, passing at least a portion of the variable spiral portion between the incisions by initially passing the distal end through the incision substantially adjacent the patient's obturator foramen and then through the vaginal incision, then associating the implant with a portion of the instrument that has emerged from the vaginal incision, and then moving the distal end of the instrument with the implant associated therewith from the vaginal incision toward the patient's obturator foramen to pass the implant through tissue.

25. A method according to claim 24 wherein the step of associating the implant with a portion of the instrument that has emerged from the vaginal incision includes the step of using a suture to tie the implant to an eyelet in the distal end of the needle.

26. A method of treating incontinence in a patient comprising the steps of:

creating a vaginal incision, creating an incision substantially adjacent the patient's obturator foramen, providing a substantially helical, elongate surgical instrument comprising a pair of ends, providing an assembly having an implant for treating incontinence, initially passing one end of the instrument initially through the vaginal incision toward the incision substantially adjacent the patient's obturator foramen in a path through the patient's obturator foramen until one end of the instrument emerges from the incision substantially adjacent the patient's obturator foramen, leaving the other end of the needle projecting from the vaginal incision, then associating the end of the instrument that projects from the vaginal incision with the assembly, and then moving the instrument Out of the patient's body to pass the implant through tissue from the vaginal incision toward the incision substantially adjacent the patient's obturator foramen to place the implant in a therapeutically effective position.

* * * * *

UNITED STATES PATENT AND TRADEMARK OFFICE
CERTIFICATE OF CORRECTION

PATENT NO. : 7,070,556 B2
APPLICATION NO. : 10/306179
DATED : July 4, 2006
INVENTOR(S) : Anderson et al.

It is certified that error appears in the above-identified patent and that said Letters Patent is hereby corrected as shown below:

Delete title pages, showing and substitute therefore the attached title pages.

Delete the drawing sheets containing figures 1-36 and substitute therefore the attached sheets containing figures 1-40

Delete columns 1 line 1 through columns 14 line 55 and Insert columns 1 line 1 through columns 30 line 38 as attached Signed and Sealed this Seventeenth Day of June, 2008

JON W. DUDAS
*Director of the United States Patent and Trademark Office*

(12) United States Patent
Anderson et al.

(10) Patent No.: US 7,070,556 B2
(45) Date of Patent: Jul. 4, 2006

(54) TRANSOBTURATOR SURGICAL ARTICLES AND METHODS

(75) Inventors: Kimberly A. Anderson, Eagan, MN (US); Brian R. Watschke, Eden Prairie, MN (US); Georges Mellier, Lyons (FR); Johann J. Neisz, Coon Rapids, MN (US)

(73) Assignee: AMS Research Corporation, Minnetonka, MN (US)

( * ) Notice: Subject to any disclaimer, the term of this patent is extended or adjusted under 35 U.S.C. 154(b) by 347 days.

(21) Appl. No.: 10/306,179

(22) Filed: Nov. 27, 2002

(65) Prior Publication Data

US 2003/0171644 A1 Sep. 11, 2003

Related U.S. Application Data

(60) Provisional application No. 60/414,865, filed on Sep. 30, 2002, provisional application No. 60/402,007, filed on Aug. 8, 2002, provisional application No. 60/380,797, filed on May 13, 2002, and provisional application No. 60/362,806, filed on Mar. 7, 2002.

(51) Int. Cl.
*A61F 2/00* (2006.01)
*A61B 17/12* (2006.01)
*A61B 17/06* (2006.01)
*D05B 1/00* (2006.01)

(52) U.S. Cl. .................. 600/29; 606/144; 606/225; 112/169

(58) Field of Classification Search .............. 600/30, 600/37, 29; 128/898, DIG. 25; 606/73, 75, 606/139, 232, 223, 144, 118, 119, 185, 147, 606/148, 191, 225, 145, 221, 213, 72, 216, 606/151; 112/169; 81/3.35, 3.47, 3.48, 3.45, 81/3.46; 411/425
See application file for complete search history.

(56) References Cited

U.S. PATENT DOCUMENTS

| 2,738,790 A | 3/1956 | Todt et al. |
| 3,124,136 A | 3/1964 | Usher |
| 3,182,662 A | 5/1965 | Shirodkar |

(Continued)

FOREIGN PATENT DOCUMENTS

| DE | 2305815 | 2/1973 |
| DE | 43 04 353 A1 | 4/1994 |
| DE | 4220283 C2 | 5/1994 |

(Continued)

OTHER PUBLICATIONS

Beck, Peter R. et al., Treatment of Urinary Stress Incontinence With Anterior Colporrhaphy. Obstetrics and Gynecology, vol. 59 (No. 3), pp. 269-274 (Mar. 1982).

Benderev, Theodore V., MD, A Modifed Percutaneous Outpatient Bladder Neck Suspension System, Journal of Urology, vol. 152, pp. 2316-2320 (dec. 1994).

Das, Sakti et al., Laparoscopic Colpo-Suspension, The Journal of Urology, vol. 154, pp. 119-1121 (Sep. 1995).

(Continued)

*Primary Examiner*—Samuel G. Gilbert
(74) *Attorney, Agent, or Firm*—Jose W. Jimenez

(57) ABSTRACT

Surgical articles, implants and components suitable for a transobturator surgical procedure are described.

26 Claims, 40 Drawing Sheets

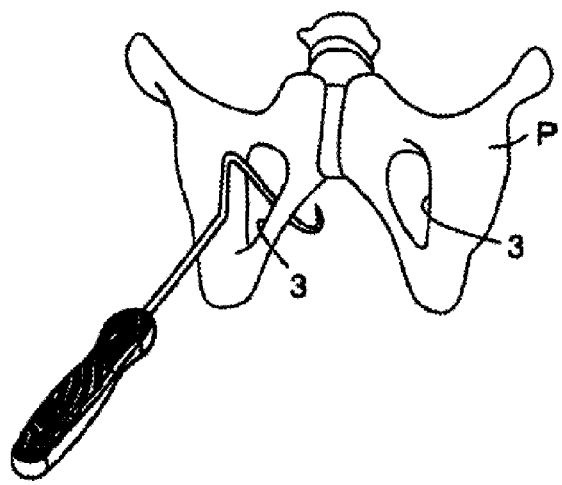

U.S. PATENT DOCUMENTS

| | | |
|---|---|---|
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,204,541 A * | 5/1980 | Kapitanov ............... 606/145 |
| 4,235,238 A | 11/1980 | Ogiu et al. |
| 4,246,660 A | 1/1981 | Wevers |
| 4,265,231 A | 5/1981 | Scheller, Jr. et al. |
| 4,441,497 A | 4/1984 | Paudler |
| 4,509,516 A | 4/1985 | Richmond |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,920,986 A | 5/1990 | Biswas |
| 5,053,043 A | 10/1991 | Gottesman et al. |
| 5,085,661 A | 2/1992 | Moss |
| 5,112,344 A * | 5/1992 | Petros ............... 606/148 |
| 5,123,428 A | 6/1992 | Schwarz |
| 5,188,636 A | 2/1993 | Fedotov |
| 5,207,694 A * | 5/1993 | Broome ............... 606/148 |
| 5,209,756 A | 5/1993 | Seedhom et al. |
| 5,250,033 A | 10/1993 | Evans et al. |
| 5,256,133 A | 10/1993 | Spitz |
| 5,281,237 A | 1/1994 | Gimpelson |
| 5,328,077 A | 7/1994 | Lou |
| 5,336,239 A * | 8/1994 | Gimpelson ............... 606/223 |
| 5,337,736 A * | 8/1994 | Reddy ............... 600/217 |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,520,700 A | 5/1996 | Beyar et al. |
| 5,520,703 A * | 5/1996 | Essig et al. ............... 606/148 |
| 5,544,664 A | 8/1996 | Benderev et al. |
| 5,562,685 A | 10/1996 | Mollenauer et al. |
| 5,562,689 A | 10/1996 | Green et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,662,683 A * | 9/1997 | Kay ............... 606/232 |
| 5,669,935 A | 9/1997 | Rosenman et al. |
| 5,683,349 A | 11/1997 | Makower et al. |
| 5,807,403 A | 9/1998 | Beyar et al. |
| 5,810,882 A * | 9/1998 | Bolduc et al. ............... 606/213 |
| 5,836,314 A * | 11/1998 | Benderev et al. ............... 128/898 |
| 5,836,315 A | 11/1998 | Benderev et al. |
| 5,842,478 A | 12/1998 | Benderev et al. |
| 5,860,425 A | 1/1999 | Benderev et al. |
| 5,899,909 A * | 5/1999 | Claren et al. ............... 606/119 |
| 5,904,696 A * | 7/1999 | Rosenman ............... 606/151 |
| 5,919,232 A | 7/1999 | Chaffringeon et al. |
| 5,934,283 A | 8/1999 | Willem et al. |
| 5,935,122 A | 8/1999 | Fourkas et al. |
| 5,935,138 A | 8/1999 | McJames, II et al. ...... 606/139 |
| 5,944,732 A | 8/1999 | Raulerson et al. |
| 5,972,000 A | 10/1999 | Beyar et al. |
| 5,988,171 A | 11/1999 | Sohn et al. |
| 5,992,269 A * | 11/1999 | Puig et al. ............... 81/3.35 |
| 5,997,554 A | 12/1999 | Thompson |
| 6,010,447 A | 1/2000 | Kardjian |
| 6,030,393 A | 2/2000 | Corlew |
| 6,031,148 A | 2/2000 | Hayes et al. |
| 6,042,534 A | 3/2000 | Gellman et al. |
| 6,042,536 A | 3/2000 | Tihon et al. |
| 6,048,351 A * | 4/2000 | Gordon et al. ............... 606/144 |
| 6,050,937 A | 4/2000 | Benderev |
| 6,053,935 A * | 4/2000 | Brenneman et al. ......... 606/232 |
| 6,068,591 A | 5/2000 | Bruckner et al. |
| 6,071,290 A | 6/2000 | Compton |
| 6,099,538 A * | 8/2000 | Moses et al. ............... 606/144 |
| 6,106,545 A | 8/2000 | Egan |
| 6,110,101 A | 8/2000 | Tihon et al. |
| 6,117,067 A | 9/2000 | Gil-Vernet |
| 6,168,611 B1 | 1/2001 | Risvi |
| 6,221,005 B1 | 4/2001 | Bruckner et al. |
| 6,273,852 B1 * | 8/2001 | Lehe et al. ............... 600/30 |
| 6,302,840 B1 | 10/2001 | Benderev |
| 6,306,079 B1 | 10/2001 | Trabucco |
| 6,328,744 B1 | 12/2001 | Harari et al. |
| 6,334,446 B1 * | 1/2002 | Beyar ............... 128/898 |
| 6,352,553 B1 | 3/2002 | van der Burg et al. |
| 6,367,353 B2 * | 4/2002 | Puig et al. ............... 81/3.48 |
| 6,382,214 B1 | 5/2002 | Raz et al. |
| D458,679 S | 6/2002 | Thompson et al. |
| 6,406,423 B1 | 6/2002 | Scetbon |
| 6,406,480 B1 | 6/2002 | Beyar et al. |
| 6,440,154 B2 | 8/2002 | Gellman et al. |
| 6,475,139 B1 | 11/2002 | Miller |
| 6,478,727 B2 * | 11/2002 | Scetbon ............... 600/30 |
| 6,478,803 B1 | 11/2002 | Kapec et al. |
| 6,482,214 B1 | 11/2002 | Sidor, Jr. et al. |
| 6,494,906 B1 | 12/2002 | Owens |
| 6,502,578 B2 | 1/2003 | Raz et al. |
| 6,530,943 B1 | 3/2003 | Hoepffner et al. |
| 6,582,443 B2 | 6/2003 | Cabak et al. |
| 6,626,917 B1 * | 9/2003 | Craig ............... 606/144 |
| 6,663,633 B1 * | 12/2003 | Pierson, III ............... 606/72 |
| 6,673,010 B2 | 1/2004 | Skiba et al. |
| 6,802,807 B2 | 10/2004 | Anderson et al. |
| 2001/0000533 A1 | 4/2001 | Kovac |
| 2001/0049467 A1 | 12/2001 | Lehe et al. |
| 2002/0022841 A1 | 2/2002 | Kovac |
| 2002/0028980 A1 | 3/2002 | Thierfelder et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslaine et al. |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0188169 A1 | 12/2002 | Kammerer et al. |
| 2003/0004395 A1 | 1/2003 | Therin |

| | | |
|---|---|---|
| 2003/0009181 A1 | 1/2003 | Gellman et al. |
| 2003/0023136 A1 | 1/2003 | Raz |
| 2003/0023137 A1 | 1/2003 | Gellman |
| 2003/0023138 A1 | 1/2003 | Luscombe |
| 2003/0036676 A1 | 2/2003 | Scetbon |
| 2003/0045774 A1 | 3/2003 | Staskin et al. |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0130670 A1 | 7/2003 | Anderson et al. |
| 2003/0149440 A1 | 8/2003 | Kammerer et al. |
| 2003/0176762 A1 | 9/2003 | Kammerer |
| 2003/0199732 A1 | 10/2003 | Suslian et al. |
| 2004/0267088 A1 | 12/2004 | Kammerer |

FOREIGN PATENT DOCUMENTS

| | | |
|---|---|---|
| DE | 101 38 950 | 2/2003 |
| DE | 10211360 | 10/2003 |
| DE | 102 11 360 | 10/2003 |
| EP | 0 470 308 A1 | 2/1992 |
| EP | 0 650 703 A1 | 6/1994 |
| EP | 0 643 945 A2 | 7/1994 |
| EP | 1 093 758 A1 | 4/2001 |
| SU | 1225547 A1 | 4/1986 |
| SU | 1342486 A | 10/1987 |
| WO | WO 93/17635 A1 | 9/1993 |
| WO | WO 93/19678 A2 | 10/1993 |
| WO | WO 97/16121 | 5/1997 |
| WO | WO 98/19606 A1 | 5/1998 |
| WO | WO 98/35606 | 8/1998 |
| WO | WO 98/35616 A1 | 8/1998 |
| WO | WO 98/35632 | 8/1998 |
| WO | WO 99/52450 A1 | 10/1999 |
| WO | WO 00/13601 A1 | 3/2000 |
| WO | WO 00/18319 A1 | 4/2000 |
| WO | WO 00/57812 A1 | 10/2000 |
| WO | WO 00/64370 A1 | 11/2000 |
| WO | WO 00/74594 A1 | 12/2000 |
| WO | WO 00/74613 A1 | 12/2000 |
| WO | WO 00/74633 A2 | 12/2000 |
| WO | WO 01/26581 A1 | 4/2001 |
| WO | WO 01/39670 A1 | 6/2001 |
| WO | WO 01/45589 A1 | 6/2001 |
| WO | WO 01/56499 A1 | 8/2001 |
| WO | WO 01/78609 | 10/2001 |
| WO | WP 02/02031 | 1/2002 |
| WO | WO 02/26108 | 4/2002 |
| WO | WO 02/28312 A1 | 4/2002 |
| WO | WO 02/32284 A2 | 4/2002 |
| WO | WO 02/34124 A2 | 5/2002 |
| WO | WO 02/39890 A2 | 5/2002 |
| WO | WO 02/069781 | 9/2002 |
| WO | WO 02/071953 A2 | 9/2002 |
| WO | WO 02/078552 A1 | 10/2002 |
| WO | WO 2004/016196 A2 | 2/2004 |
| WO | WO 2004/019786 | 3/2004 |

OTHER PUBLICATIONS

Gjia, Ivan et all, A Modified Raz Bladder Neck Suspension Operation (Transvaginal Burch), The Journal of Urology, vol. 153, pp. 1455-1457 (May 1995).

Holschneider, C.H., et al., The Modified Pereyra Procedure in Recurrent Stress Urinary Incontinence: A 15-year Review, obstetrics & Gynecology, vol. 83, No. 4, pp. 573-578 (Apr. 1994).

Horbach, Nicollette S., et al., Instruments and Methods, A Suburethral Sling Procedure with Polytetrafluoroethylene for the Treatment of Genuine Stress Incontinence in Patients with Low Urethral Closure Pressure, Obstetrics & Gynecology, vol. 71, No. 4, pp. 648-652 (Apr. 1998).

Klutke, Carl et al., The Anatomy of Stress Incontinence: Magentic Resonance Imaging of the Female Bladder Neck and Urethra, The Journal Urology, vol. 143, pp. 563-566 (Mar. 1990).

Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).

Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).

Kovac, S. Robert, et al, Pubic Bone Suburethral Stabilization Sling: A Long Term Cure for SUI?, Contemporary OB/GYN, 10 pages (Feb. 1998).

Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).

Leach, Gary E., et al, Female Stress Urinary Incontinence Clinical Guidelines Panel Report on Surgical Management of Female Stress Urinary Incontinence, American Urological Association, vol. 158, pp. 875-880 (Sep. 1997).

Leach, Gary E., MD, Bone Fixation Technique for Transvaginal Needle Suspension, Urology vol. XXXI, No. 5, pp. 388-390 (May 1988).

McGuire, Edward J. et al., Experience With Pubovaginal Slings for Urinary Incontinence at the University of Michigan, Journal of Urology, vol. 138, pp. 90-93 (1987).

McGuire, Edward J. et al., Abdominal Fascial Slings, Slings, Raz Female Urology, pp. 369-375 (1996).

Morgan, J.E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).

Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advanced Surgical Techniques, vol. 9, No. 1 pp. 45-50 (1999).

Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).

Petros, Peter E. Papa et al., Part IV: Surgical Applications of the Theory–Development of the Intravaginal Sling Plasty (IVS) Procedure, Scandinavian Journal of Neurology and Urodynamics, Sup 153, pp. 53-54 (1993).

Stanton, Stuart, Springer-Veglag, Surgery of Female Incontinence, pp. 105-113 (1986).

Staskin, David R. et al., The Gore-Tex Sling Procedure for Female Sphincteric Incontinence: Indications, Technique, and Results, World Journal of Urology, vol. 15, pp. 295-299 (1997).

TVT Tension-free Vaginal Tape, Gynecare, Ethicon, Inc., 23 pages (1999).

Walters, Mark D., Percutaneous Suburethral Slings: State of the Art, Presented at the conference of the American Urogynecologic Society, Chicago, 29 pages (Oct. 2001).

Waxman, Steve et al., Advanced Urologic Surgery for Urinary Incontinence, The Female Patient, pp. 93-100, vol. 21 (Mar. 1996).

Zimmern, Phillippe E. et al., Four-Corner Bladder Neck Suspension, Vaginal Surgery for the Urologist, vol. 2, No. 1, pp. 29-36 (Apr. 1994).

Document entitled "Access Instrument System™ with AlloSling™ Fascia" (5 pages with two pages of Instructions for Use).

Document with heading "Introducing: AlloSling™ Fascia the *Natural Choice* for Suburethral Sling Procedures", Advertisement from UroMed Corp.

AlloSource product literature (11 pages).

Staskin et al., A Comparison of Tensile Strength among Three Preparations of Irradiated and Non-Irradiated Human Fascia Lata Allografts (2 pages).

UroMed Access™ Instrument System for the Sub-urethral Sling Procedure Catalog No. 120235, Directions for Use, (3 pages).

U.S. patent application Ser. No. 09/661,620, Suslaine et al., filed Sep. 27, 2002.

"Safyre and Transobturator", DVD.

"The Strength of Suspend" *Mentor*, Marketing Material, 6 pages.

*Gynecare TVT*, "Tension-Free Support for Incontinence" Marketing Material, Gynecare Worldwide (02/02), 6 pages.

Sender Hershorn, M.D. et al., "Gynecare TVT With Abdominal Guides Early Clinical Experience" *Gynecare TVT*, Marketing Material, Gynecare Worldwide (05/02), 12 pages.

"Uretex Polypropylene Urethral Support—Safety, Simplicity, Flexibility" *Bard*, Marketing Material, 8 pages.

Sabre, "Generation Now" *Mentor*, Marketing Material (05/02), 4 pages.

Safyre, "The Essence of a Contemporary Synthetic Sling—Self-Anchoring Complete Adjustability Elastic" *Promedon*, Marketing Material (01/02), 4 pages.

Porges U.K. Ltd., "Uratape Perineal Hammock Urethral Support Tape—New Generation of Tape Perineal Implantation" *Mentor*, Marketing Material (01/02), 6 pages.

Boston Scientific Microvasive, "Precision Twist Transvaginal Anchor System—Low Profile Design for Precise Anchor Placement" *Boston Scientific Corp.*, Marketing Material (2000), 2 pages.

Boston Scientific Microvasive, "Precision Tact Transvaginal Anchor System—The Precise Approach to Transvaginal Sling Procedures" *Boston Scientific Corp.*, Marketing Material (1998), 4 pages.

Boston Scientific Microvasive, "Vesica Sling Kits with Press-In Percutaneous Anchor System—Simplifying Sling Procedures" *Boston Scienficic Corp.*, Marketing Material (1998), 4 pages.

"T-Sling (Totally Tension-free) Urinary Incontinence Procedure" *Herniamesh USA Inc.*, Marketing Material (01/00), 2 pages.

"TVS Tunneller—Australian Medical Design Breakthrough for GSI, Mixed Incontinence and Vault Prolapse", *AMA Medical Products T/A AMA Services (WA) Pty Ltd.*, Marketing Material, 4 pages.

"Advantage A/T—Surgical Mesh Sling Kit", *Boston ScientificCorp.*, Marketing Material (2002) 1 page.

"Durasphere—Injectable Bulking Agent", *Boston Scientific Corp.*, Marketing Material (2002) 1 page.

"Precision SpeedTac—Transvaginal Anchor System", *Boston ScientificCorp.*, Marketing Material (2002) 1 page.

Boston Scientific Microvasive, "Stone Cone—Nitinol Urological Retrieval Coil", *Boston ScientificCorp.*, Marketing Material (2002) 1 page.

"Swiss LithoClast Ultra—Combination Ultrasonic and Pneumatic Urological Lithotriptor", *Boston ScientificCorp.*, Marketing Material (2002) 1 page.

Boston Scientific Microvasive, "Polaris—Dual Durometer Percuflex Ureteral Stent with HydroPlus Coating", *Boston ScientificCorp.*, Marketing Material (2001) 1 page.

G. A. J. McIndoe et al., National Women's Hospital, Auckland, "The Aldridge Sling Procedure in the Treatment of Urinary Stress Incontinence" Aust NZ J Obstet Gynaecol, 1987; 27:238.

Charles F. McKiel, Jr. et al., "Marshall-Marchetti Procedure: Modification" *Ist Journal in Urology*, vol. 96, pp. 737-739, Nov. 1966, The Williams & Wilkins Co.

Valenzio C. Mascio, M.D., "Therapy of Urinary Stress Incontinence In Women Using Mitek GII Anchors" *Mitek Surgical Products, Inc.*, 5 pages (1993).

Edward J. McGuire, M.D., "The Sling Procedure for Urinary Stress Incontinence" *Profiles in Urology*, pp. 3, 5-19.

Edward J. McGuire, et al., "Pubovaginal Sling Procedure for Stress Incontinence" *The Journal of Urology*, vol. 119, pp. 82-84, Jan. 1978, The Williams & Wilkins Co.

Edward J. McGuire, M.D., "Abdominal Procedures for Stress Incontinence" Symposium on Female Urology, *Urologic Clinics of North America*—vol. 12, No. 2, pp. 285-290, May 1985.

Victor Fray Marshall, M.D., F.A.C.S. et al., "The Correction of Stress Incontinence by Simple Vesicourethral Suspension" *Surgery, Gynecology and Obstetrics*, pp. 509-518.

Kevin R. Loughlin, et al., "Review of an 8-Year Experience With Modifications of Endoscopic Suspension of the Bladder Neck for Female Stress Urinary Incontinence" *The Journal of Urology*, vol. 143, pp. 44-45, Jan. 1990 The American Urological Association, Inc.

Irving L. Lichtenstein, M.D., et al., "The Tension-Free Hernioplasty" *The American Journal of Surgery*, vol. 157, Feb. 1989, pp. 188-193.

Andrew Korda, et al., "Experience with Silastic Slings for Female Urinary Incontinence" *Aust NZ J Obstet Gynaecol*, 1989, vol. 29, pp. 150-154.

Mickey M. Karram, M.D. et al., "Patch Procedure: Modified Transvaginal Fascia Lata Sling for Recurrent or Severe Stress Urinary Incontinence" *Obstetrics & Gynecology*, vol. 75, No. 3, Part 1, Mar. 1990, pp. 461-464.

J. Kersey, "The gauze hammock sling operation in the treatment of stress incontinence" *British Journal of Obstetrics and Gynaecology*, vol. 90 pp. 945-949, Oct. 1983.

A. Ingelman-Sundberg, et al., "Surgical Treatment of Female Urinary Stress Incontinence" *Contr. Gynec. Obstet.* vol. 10, pp. 51-69 (Karger, Basel 1983).

T. N. A. Jeffcoate, M.D., F.R.C.S.E., F.R.C.O.G., "The Results of the Aldridge Sling Operation for Stress Incontinence" *Journal of Obstetrics and Gynaecology*, pp. 36-39.

C. Paul Hodgkinson, M.D., et al., "Urinary Stress Incontinence in the Female—III. Round-ligament technic for retropubic suspension of the urethra" *Obstetrics and Gynecology*, vol. 10, No. 5, Nov. 1957, pp. 493-499.

L. Henriksson, M.D. et al., "A urodynamic evaluation of the effects of abdominal urethrocystopexy and vaginal sling urethroplasty in women with stress incontinence" *Am. J. Obstet. Gynecol*, May 1, 1978, pp. 77-82.

Victoria L. Handa, M.D., et al., "Banked Human Fascia Lata for the Suburethral Sling Procedure: A Preliminary Report" *Obstetrics and Gynecology*, vol. 88, No. 6, May 20, 1996, pp. 1045-1049.

C. Falconer, et al., "Influence of different Sling Materials on Connective Tissue Metabolism in Stress Urinary Incontinent Women" *International Urogynecology Journal*, (2001) (Supp. 2) pp. S19–S23.

H. Enzelsberger et al., "Urodynamic and Radiologic Parameters Before and After Loop Surgery for Recurrent Urinary Stress Incontinence" *Acta Obstet Gynecol Scand 1990*; 69 pp. 51–54.

Bjarne C. Eriksen, et al., "Long–Term Effectiveness of the Burch Colposuspension in Female Urinary Stress Incontinence" *Acta Obstet Gynecol Scand* 1990; 69 pp. 45–50.

John O. L. DeLancey, M.D., "Structural support of the urethra as it relates to stress urinary incontinence: The hammock hypothesis" *Am. J. Obstet Gynecol*, pp. 1713–1723, Jun. 1994.

Ross M. Decter, "Use of the Fascial Sling for Neurogenic Incontinence: Lessons Learned" *The Journal of Urology*, vol. 150, pp. 683–686, Aug. 1993, American Urological Association, Inc.

Jong M. Choe, et al., "Gore–Tex Patch Sling: 7 Years Later" *Urology*, 54 (4) pp. 641–646, Apr. 1999, Elsevier Science Inc.

Fred E. Bryans, M.D., F.R.C.S.(C.), "Marlex gauze hammock sling operation with Cooper's ligament attachment in the management of recurrent urinary stress incontinence" *Am. J. Obstet. Gynecol.*, vol. 133, No. 3, pp. 292–294, Feb. 1, 1979.

John C. Burch, M.D., "Urethrovaginal fixation to Cooper's ligament for correction of stress incontinence, cystocele, and prolapse" *Am. J. Obstet. & Gynecol.*, vol. 81 No. 2, pp. 281–290, Feb. 1961.

Jerry G. Blaivas, et al., "Pubovaginal Fascial Sling for the Treatment of Complicated Stress Urinary Incontinence" *The Journal of Urology*, vol. 145, Jun. 1991, pp. 1214–1218, American Urological Association, Inc.

Jerry G. Blaivas, M.D., et al., "Type III Stress Urinary Incontinence: Importance of Proper Diagnosis and Treatment" *Gynecology and Obstetrics Surgical Forum*, pp. 473–475.

Arieh Bergman, M.D. et al., "Three surgical procedures for genuine stress incontinence: Five–year follow–up of a prospective randomized study", *Am. J. Obstet Gynecol*, vol. 173 No. 1, pp. 66–71, Jul. 1995.

M. Asmussen, et al., "Simultaneous Urethro–Cystometry With a New Technique" *Scand J Urol Nephrol 10*, pp. 7–11, 1976.

Tohru Araki, et al, "The Loop–Loosening Procedure for Urination Difficulties After Stamey Suspension of the Vesical Neck" *The Journal of Urology*, vol. 144, pp. 319–323, Aug. 1990, American Urological Association, Inc.

Albert H. Aldridge, B.S., M.D., F.A.C.S., "Transplantation of Fascia for Relief of Urinary Stress Incontinence" *Am. J. of Obstet. and Gynec.*, pp. 398–411.

Peter E. Papa Petros et al., "The Role of a Lax Posterior Vaginal Fornix in the Causation of Stress and Urgency Symptoms: A Preliminary Report" *Acta Obstet Gynecol Scand.*, 69 Suppl. 153, pp. 71–73, 1990.

Peter E. Papa Petros et al., "The Tethered Vagina Syndrome, Post Surgical Incontinence and I-Pasty Operation for Cure" *Acta Obstet Gynecol Scand.* pp. 63–67, 69 Suppl. 153, 1990.

Peter E. Papa Petros et al., "The Tuck Procedure: A Simplified Vaginal Repair for Treatment of Female Urinary Incontinence" *Acta Obstet Gynecol Scand*, 1990. pp. 41–42, 69 Suppl. 153.

Peter E. Papa Petros et al., "The Posterior Fornix Syndrome: A Multiple Symptom Complex of Pelvic Pain and Abnormal Urinary Symtoms Deriving From Laxity in the Posterior Fornix of Vagina" *Scand J Urol Nephrol*, pp. 89–93, Suppl. No. 153, 1993.

Peter E. Papa Petros et al., "The Intravaginal Slingplasty Procedure: IVS VI—further development of the 'double-breasted' vaginal flap repair—attached flap" *Scand J Urol Nephrol*, pp. 81–84, Suppl. No. 153, 1993.

Peter E. Papa Petros et al., "The Further Development of the Intravaginal Slingplasty Procedure: IVS IV—(with "double-breasted" unattached vaginal flap repair and "free" vaginal tapes)" *Scand J Urol Nephrol*, pp. 73–79, Suppl. No. 153, 1993.

Peter E. Papa Petros et al., "The Free Graft Procedure for Cure of the Tethered Vagina Syndrome" *Scand J Urol Nephrol*, pp. 85–87, Suppl. No. 153, 1993.

Peter E. Papa Petros et al., "Pinch Test for Diagnosis of Stress Urinary Incontinence" *Acta Obstet Gynecol Scand.* pp. 33–35, 69 Suppl. 153, 1990.

Peter E. Papa Petros et al., "Pregnancy Effects on the Intravaginal Sling Operation" *Acta Obstet Gynecol Scand.* pp. 73–78, 69 Suppl. 153, 1990.

Peter E. Papa Petros et al., "Pelvic floor rehabilitation according to the integrated theory of female urinary incontinence" *Pelvic Floor Dysfunction—Investigations & Conservative Treatment*, Chapter 7, pp. 249–258.

Peter E. Papa Petros et al., "Part IV: Surgical Applications of the Theory—Development of the Intravaginal Sling Plasty (IVS) Procedure" *Scand J Urol Nephrol*, pp. 53–54, Suppl. No. 153,1993.

Peter E. Papa Petros et al., "Part III: Surgical Principles Deriving From the Theory" *Scand J Urol Nephrol*, pp. 41–52, Suppl. No. 153, 1993.

Peter E. Papa Petros et al., "Part II: The Biomechanics of Vaginal Tissue and Supporting Ligaments With Special Relevance to the Pathogenesis of Female Urinary Incontinence" *Scand J Urol Nephrol*, pp. 29–40, Suppl. No. 153, 1990.

W. R. Sloan, et al., "Stress Incontinence of Urine: A Retrospective Study of the Complications and Late Results of Simple Suprapubic Fascial Slings" *The Journal of Urology*, vol. 110, pp. 533–536, Nov. 1973.

Pat D. O'Donnell, M.D., "Combined Raz Urethral Suspension and McGuire Pubovaginal Sling For Treatment of Complicated Stress Urinary Incontinence" *Journal of The Arkansas Medical Society*, vol. 88, No. 8, pp. 389–392, Jan. 1992.

Nicollette S. Horbach, "Suburethral Sling Procedures" *Urolgynecology and Urodynamics Theory and Practice*, Fourth Edition, Chapter 42, pp. 569–579, 1996, Williams & Wilkins.

Armand J. Pereyra, M.D., F.A.C.S., "A Simplified Surgical Procedure for the Correction of Stress Incontinence in Women" *West J. Surg. Obst. & Gynec.* pp. 223–226, Jul.–Aug. 1959.

M. Asmussen, et al., "Simultaneous Urethro–Cystometry With a New Technique" *Scand J Urol Nephrol 10*, pp. 7–11, 1976.

P. E. Papa Petros "Development of Generic Models for Ambulatory Vaginal Surgery—Preliminary Report" *International Urogynecology Journal*, 9 pages (1998).

Peter E. Papa Petros et al., "An analysis of rapid pad testing and the history for the diagnosis of stress incontinence" *Acta Obstet Gynecol Scand 71*, pp. 529–536 (1992).

Peter E. Papa Petros et al., "An Anatomical Basis for Success and Failure of Female Incontinence Surgery" *Scand J Urol Nephrol*, pp. 55–60, Suppl. No. 153.

Peter E. Papa Petros et al., "An integral theory of female urinary incontinence—Experimental and clinical considerations" *Acta Obstet Gynecol Scand*, vol. 69, Suppl. 153, pp. 7–31 (1990), The Scandinavian Association of Obstetricians and Gynecologists.

Rafael F. Nickel et al., "Evaluation of a Transpelvic Sling Procedure With and Without Colposuspension for Treatment of Female Dogs With Refractory Urethral Sphincter Mechanism Incompetence" *Veterinary Surgery*, vo. 27, pp. 94–104, (1998), The American College of Veterinary Surgeons.

Peter E. Papa Petros et al., "Bladder Instability in Women: A Premature Activation of the Micturition Reflex" *Neurourology and Urodynamics*, vol. 12, pp. 235–238 (1993).

Peter E. Papa Petros et al., "Cough Transmission Ratio: An Indicator of Suburethral Vaginal Wall Tension Rather Than Urethral Closure?" *Acta Obstet Gynecol Scand*, vol. 69 Suppl. 153, pp. 37–39 (1990).

Jeffrey R. Woodside, et al., "Suprapubic Endoscopic Vesical Neck Suspension for the Management of Urinary Incontinence in Myelodysplastic Girls" *The Journal of Urology*, vol. 135, pp. 97–99, Jan. 1986.

Robert F. Zacharin, FRCS, FRCOG, et al, "Pulsion Enterocele: Long–Term Results of an Abdominoperineal Technique" *Obstetrics & Gynecology*, pp. 141–148, vol. 55, No. 2, Feb. 1980, The American College of Obstetricians & Gynecologists.

Robert F. Zacharin, "The suspensory mechanism of the female urethra" *Journal of Anatomy*, vol. 97, Part 3, pp. 423–427, (1963).

George D. Webster, "Female Urinary Incontinence" *Urologic Surgery*, Ch. 66, pp. 665–679.

Peter E. Papa Petros et al., "Cure of Stress Incontinence by Repair of External Anal Spincter: Two Case Reports" *Acta Obstet Gynecol Scand*, vol. 69 Suppl. 153, p. 75 (1990).

Peter E. Papa Petros et al., "Cure of Urge Incontinence by the Combined Intravaginal Sling and Tuck Operation" *Acta Obstet Gynecol Scand*, vol. 69 Suppl. 153, pp. 61–62 (1990).

Peter E. Papa Petros et al., "Further Development of the Intravaginal Slingplasty Procedure—IVS III—(with midline "tuck")" *Scand J Urol Nephrol*, Suppl. 153, pp. 69–71 (1993).

Peter E. Papa Petros, "Medium-term Follow-up of the Intravaginal Slingplasty Operation Indicates Minimal Deterioration of Urinary Continence With Time" *International Urogynecology Journal and Pelvic Floor Dysfunction*, Reprinted from vol. 7, No. 3, pp. 133–137 (1996).

Peter E. Papa Petros, "New Ambulatory Surgical Methods Using an Anatomical Classification of Urinary Dysfunction Improve Stress, Urge and Abnormal Emptying" *Urogynecology Journal*, 8 pages.

Peter E. Papa Petros et al., "Non Stress Non Urge Female Urinary Incontinence—Diagnosis and Cure: A Preliminary Report" *Acta Obstet Gynecol Scand*, vol. 69 Suppl. 153. pp. 69–70 (1990).

Peter E. Papa Petros et al., "Part I: Theoretical, Morphological, Radiographical Correlations and Clinical Perspective" *Scand J Urol Nephrol*, Suppl. 153. pp. 5–28.

Shlomo Raz, M.D., "Modified Bladder Neck Suspension for Female Stress Incontinence" *Urology*, vol. XVII, No. 1, pp. 82–85, Jan. 1981, University of California Health Sciences Center, Los Angeles, CA.

David A. Richardson, M.D., et al., "Delayed Reaction to the Dacron Buttress Used in Urethropexy" *The Journal of Reproductive Medicine*, vol. 29 No. 9, Sep. 1984, pp. 689–692.

Henry Roberts, M.D., M.R.C.O.G., "Cystourethrography in Women" *Ethel Boyce University Fellowship* vol. 25 No. 293, pp. 253–259, May 1952, University of Liverpool.

W. R. Sloan et al., "Stress Incontinence of Urine: A Retrospective Study of the Complications and Late Results of Simple Suprapubic Suburethral Fascial Slings", *The Journal of Urology*, vol. 110, pp. 533–536, Nov. 1973.

Julia R. Spencer, et al., "A Comparison of Endoscopic Suspension of the Vesical Neck With Suprapubic Vesicourethropexy for Treatment of Stress Urinary Incontinence" *The Journal of Urology*, vol. 137, pp. 411–415, Mar. 1987.

Stuart L. Stanton, FRCS, FRCOG, "Suprapubic Approaches for Stress Incontinence in Women" *JAGS*, vol. 38, No. 3, pp. 348–351 (1990), The American Geriatrics Society.

William E. Studdiford, M.D., "Transplantation of Abdominal Fascia for the Relief of Urinary Stress Incontinence" *American Journal of Obstetrics and Gynecology*, pp. 764–775, Bellevue Hospital and New York University College of Medicine.

Cousin Biotech SAS—Medical Division, "Suport—Sub-Urethral Perineal Retro-Pubic Tensionless Sling" Marketing Brochure, 1 page.

Ulf Ulmsten et al., "Different Biochemical Composition of Connective Tissue in Continent and Stress Incontinent Women" *Acta Obstet Gynecol Scand*, vol. 66 pp. 455–457 (1987).

Ulf Ulmsten et al., "The unstable female urethra" *Am. J. Obstet. Gynecol.*, vol. 144 No. 1, pp. 93–97, May 3, 1982.

U. Ulmsten, "Female Urinary Incontinence—A Symptom, Not a Urodynamic Disease. Some Theoretical and Practical Aspects on the Diagnosis and Treatment of Female Urinary Incontinence" *The International Urogynecology Journal*, vol. 6, pp. 2–3 (1995).

Microvasive Boston Scientific, "Vesica-Percutaneous Bladder Neck Stabilization Kit" Marketing Brochure, 4 pages, Boston Scientific Corp.

Peter Papa Petros et al., "Anchoring the midurethra restores bladder-neck anatomy and continence" *The Lancet*, vol. 354, pp. 997–998, Sep. 18, 1999.

Edward J. McGuire, et al., "Experience With Pubovaginal Slings for Urinary Incontinence at the University of Michigan" *The Journal of Urology*, vol. 138, pp. 525–526, Sep. 1987.

G. Narik, M.D., "A simplified sling operation suitable for routine use" *The Am J. Obst. & Gynec.*, vol. 84, No. 3, pp. 400–405, Aug. 1, 1962.

Chester C. Winter, M.D., "Peripubic Urethropexy for Urinary Stress Incontinence in Women" *Urology* vol. XX, No. 4, Oct. 1982.

J. Chassar Moir, "The Gauze-Hammock Operation (A Modified Aldridge Sling Prcedure)" *The Journal of Obstetrics and Gynaecology of the British Commonwealth*, vol. 75 No. 1, pp. 1–9, Jan. 1968.

George D. Webster, et al., "Voiding Dysfunction Following Cystourethropexy: Its Evaluation and Management" *The Journal of Urology*, vol. 144, Sep. 1990,pp. 670-673, American Urological Association, Inc.

J. E. Morgan, M.D., "A sling operation, using Marlex polypropylene mesh, for treatment of recurrent stress incontinence" *Amer. J. Obstet. Gynec.* vol. 106, No. 3, Feb. 15, 1970, pp. 369-377.

David H. Nichols, MD, FACOG, "The Mersilene Mesh Gauze-Hammock For Severe Urinary Stress Incontinence" *Obstetrics and Gynecology*, vol. 41, No. 1, pp. 88-93, Jan. 1973.

Jeffrey P. Norris, M.D., et al., "Use of Synthetic Material in Sling Surgery: A Minimally Invasive Approach" *Journal of Endourology*, vol. 10 No. 3, pp. 227-230, Jun. 1996, Mary Ann Liebert, Inc.

Peter Papa Petros et al., "The Autogenic Ligament Procedure: A Technique for Planned Formation of an Artificial Neo-Ligament" *Acta Obstet Gynecol Scand*, vol. 69 Suppl 153, pp. 43-51 (1990).

Peter Papa Petros et al., "The Combined Intravaginal Sling and Tuck Operation. An Ambulatory Procedure for Cure of Stress and Urge Incontinence" *Acta Obstet Gynecol Scand*, vol. 69 Suppl 153, pp. 53-59 (1990).

Peter Papa Petros et al., "The Development of the Intravaginal Slingplasty Procedure: IVS II—with bilateral 'tucks')", *Scand J Urol Nephrol*, Suppl. 153. pp. 61-67.

Peter Papa Petros et al., "Urethral Pressure Increase on Effort Originates From Within the Urethra, and Continence From Musculovaginal Closure" *Neurourology and Urodynamics*, vol. 14, pp. 337-350 (1995).

R. O. Parra, et al., "Experience with a Simplified Technique for the Treatment of Female Stress Urinary Incontinence" *British Journal of Urology*, vol. 66, pp. 615-617 (1990).

Raymond R. Rackley, M.D., et al. "Tension-free Vaginal Tape and Percutaneous Vaginal Tape Sling Procedures" *Techniques in Urology*, vol. 7, No. 2, pp. 90-100 (2001).

Raymond Rackley, M.D., "Synthetic slings: Five steps for successful placement" *Urology Times*, pp. 46, 48-49, Jun. 2000.

Shlomo Raz, M.D. et al., "Female Urology—Second Edition" *University of California at Los Angeles School of Medicine*, articles pp. 80-86, 369-381, 382-391, 392-394, 395-398, 435-442, (1983) W.B. Saunders Company.

John H. Ridley, M.D., "Appraisal of the Goebell-Frangenheim-Stoeckel sling procedure" *Am. J. Obst. & Gynec.* vol. 95, No. 5, pp. 714-721, Jul. 1, 1966.

Thomas A. Stamey, M.D., "Endoscopic Suspension of the Vesical Neck for Urinary Incontinence in Females" *Ann Surg.*, vol. 192, No. 4, pp. 465-471, Oct. 1980.

Rudolf Hohenfellner, et al., "Sling Procedures" *Surgery of Female Incontinence-Second Edition*, Chapter 7, pp. 105-113, (no date) Springer-Verlag.

David R. Staskin, et al., "The Gore-tex sling procedure for female sphincteric incontinence: indications, technique, and results" *World J Urol.*, 1997, vol. 15, pp. 295-299, Springer-Verlag.

Gynecare, "TVT—Tension-Free Vaginal Tape, Minimally Invasive, Highly Effective Treatment for Female Stress Urinary Incontinence" Marketing Brochure, *Ethicon, Inc.* (1999) 6 pages.

U. Ulmsten et al., "A Multicenter Study of Tension-Free Vaginal Tape (TVT) for Surgical Treatment of Stress Urinary Incontinence" *The International Urogynecology Journal*, 1998, vol. 9, pp. 210-213.

U. Ulmsten et al., "A three-year follow up of tension free vaginal tape for surgical treatment of female stress urinary incontinence" *The British Journal of Obstetrics and Gynaecology*, Apr., 1999, vol. 106, pp. 345-350.

U. Ulmsten et al., "An Ambulatory Surgical Procedure Under Local Anesthesia for Treatment of Female Urinary Incontinence" *The International Urogynecology Journal*, 1996, vol. 7, pp. 81-86.

U. Ulmsten et al., "Intravaginal Slingplasty (IVS): An Ambulatory Surgical Procedure for Treatment of Female Urinary Incontinence" *Scand J Urol Nephrol*,vol. 29 pp. 75-82, 1995, Scandinavian University Press ISSN.

C. Falconer et al., "Clinical Outcome and Changes in Connective Tissue Metabolism After Intravaginal Slingplasty in Stress Incontinent Women" *International Urogynecol J*, vol. 7, pp. 133-137, (1996).

Ruben F. Gittes et al, "No-Incision Pubovaginal Suspension for Stress Incontinence" *The Journal of Urology*, vol. 138, pp. 568-570, Sep. 1987.

AMA Medical Products "IVS Tunneller—A universal delivery instrument for all tension free vaginal tape procedures", Marketing Brochure, 4 pages.

John Klutke, M.D. et al., "The promise of tension-free vaginal tape for female SUI" *Focus on Technology 2000*, pp. 59-60, 63-66, 69-70, 73, Oct. 2000, *Contemporary Urology*.

Urogynecology, Product Catalog, eg. SIS Technology, Bladder Suspension, Urodynamics and Urinary Diversion, Incontinence, 36 pages, Cook, Urological Inc. (1996).

Jerry G. Blaivas, "Commentary: Pubovaginal Sling Procedure" *Surgery for Female Urinary Incontinence*, pp. 93-101.

Theodore V. Benderev, M.D., "Anchor Fixation and Other Modifications of Endoscopic Bladder Neck Suspension" *Urology*, vol. 40, No. 5, pp. 409-418, Nov. 1992.

Martin, Surgical Products Catalog, 8 pages, Martin Medizin-Technik, Gebrüder Martin GmbH & Co. KG (1998).

Mentor-Porges, *Trans-obturator tape, Le hamac perinial, Nos references*, Marketing Material in French language, 1 page (01/03).

Mentor-Porges, *Come See Us at Booth #28*, Marketing Material, 1 page (07/02).

Mentor, Sabre™ Bioabsorbable Sling, *Surgical Procedure*, Marketing Material, 6 pages (08/02).

Raz, Shlomo, et al., *The Raz Bladder Neck Suspension Results in 206 Patients*, The Journal of Urology, pp. 845-850 (09/92).

Marco A. Pelosi II, et al., *New Transobturator Sling Reduces Risk of Injury*, OBG Management, pp. 17-20, 30, 32, 35-38 (Jul. 2003).

Dargent, D., et al. *Pos d'un ruban sous uretral oblique par voie obturatrice dans le traitement de l'incontinence urinaire feminine*, Gynecol Obstet Fertil 2002; 30: 576-582 (2002) (Provided in both French and English languages), 13 pages.

de Leval, Jean "Novel Surgical Technique for the Treatment of Female Stress Urinary Incontinence: Transobturator Vaginal Tape Inside-Out", *European Urology* 44 (2003) 724-730.

Delorme, Emmanuel et al.,"Transobturator Tape (Uratape®): A New Minimally-Invasive Procedure to Treat Female Urinary Incontinence", *European Urology* 45 (2004) 203-207.

Letters To The Editor, R. Villet's response to the article by D. Dargent et al., "Placement of an oblique transpsobturator suburethral tape in the treatment of female urinary incontinence", *Gynecology Obstetrics & Fertility* 31 (2003) 96-101 (English Translation).

H.P. Dietz et al., "Mechanical Properties of urogynecologic implant Materials", *International Urogynecology Journal* (2003) 14:239-243.

C.B. Iglesia et al.,"The Use of Mesh in Gynecologic Surgery", *International Urogynecology Journal* (1997) 8:105-115, ©1997 Springer-Verlag London Ltd.

C.C. Chu and L. Welch, "Characterization of Morphologic and Mechanical Properties of Surgical Mesh Frabrics", *Journal of Biomedical Materials Research*, vol. 19, 903-916 (1985), ©1985 John Wiley & Sons, Inc.

J.E. Morgan, M.D., "A sling operation, using Marlex Polypropylene mesh, for treatment of recurrent stress incontinence", *America Journal of Obstetrics and Gynecology*, Feb. 15, 1970, 106:3, pp. 369-377.

J.E. Morgan, M.D. et al., "The Marlex sling operation for the treatment of recurrent stress urinary incontinence: A 16-year review", *American Journal of Obstetrics and Gynecology*, Jan. 15, 1985, pp. 224-227.

Pourdeyhimi, "Porosity of surgical mesh fabrics: New technology", *J. Biomed. Mater. Res.:Applied Biomaterials*, vol. 23, No. A1, 145-152 (1989), ©1989 John Wiley & Sons, Inc.

"Urinary Incontinence: Easier Operation", Article from *La Liber Belgique*, Wednesday, Oct. 15, 2003 (English Translation).

Declaration of Johann J. Neisz with Attachment.

Delorme, "La bandelette trans-obturatrice: un procede mini-invasif pour traiter l'incontinence urinaire d'effort de la femme", *Urologie de la Femme*, 2001:11, pp. 1306-1313 with English Translation.

*AMS Monarc Sling System Instructions for Use*, American Medical Systems, Inc., Sep. 2002, English version, 7 pages.

*AMS Monarc Subfacial Hammock Instructions for Use*, American Medical Systems, Inc., Nov. 2003, English version, 11 pages.

\* cited by examiner

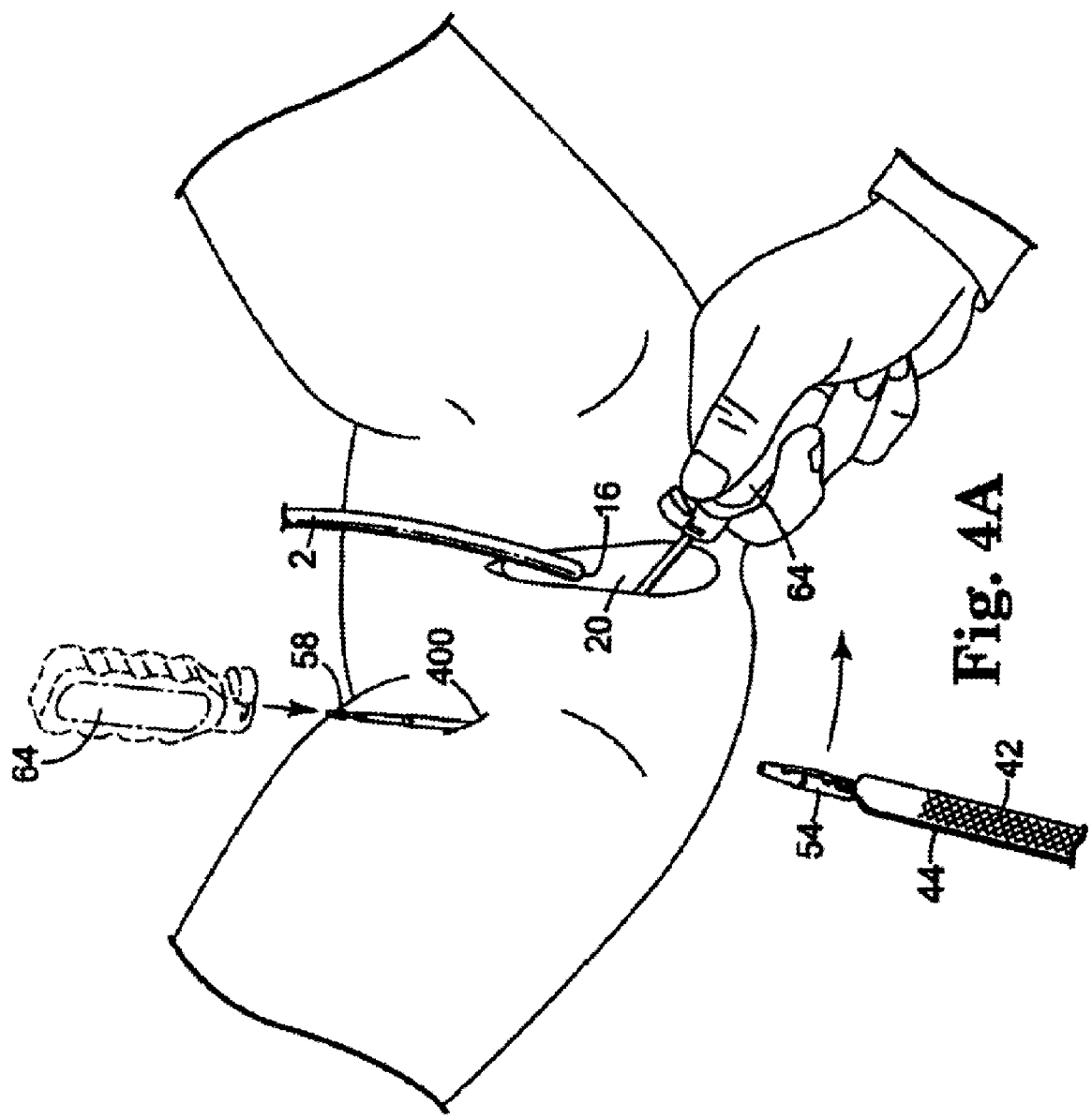

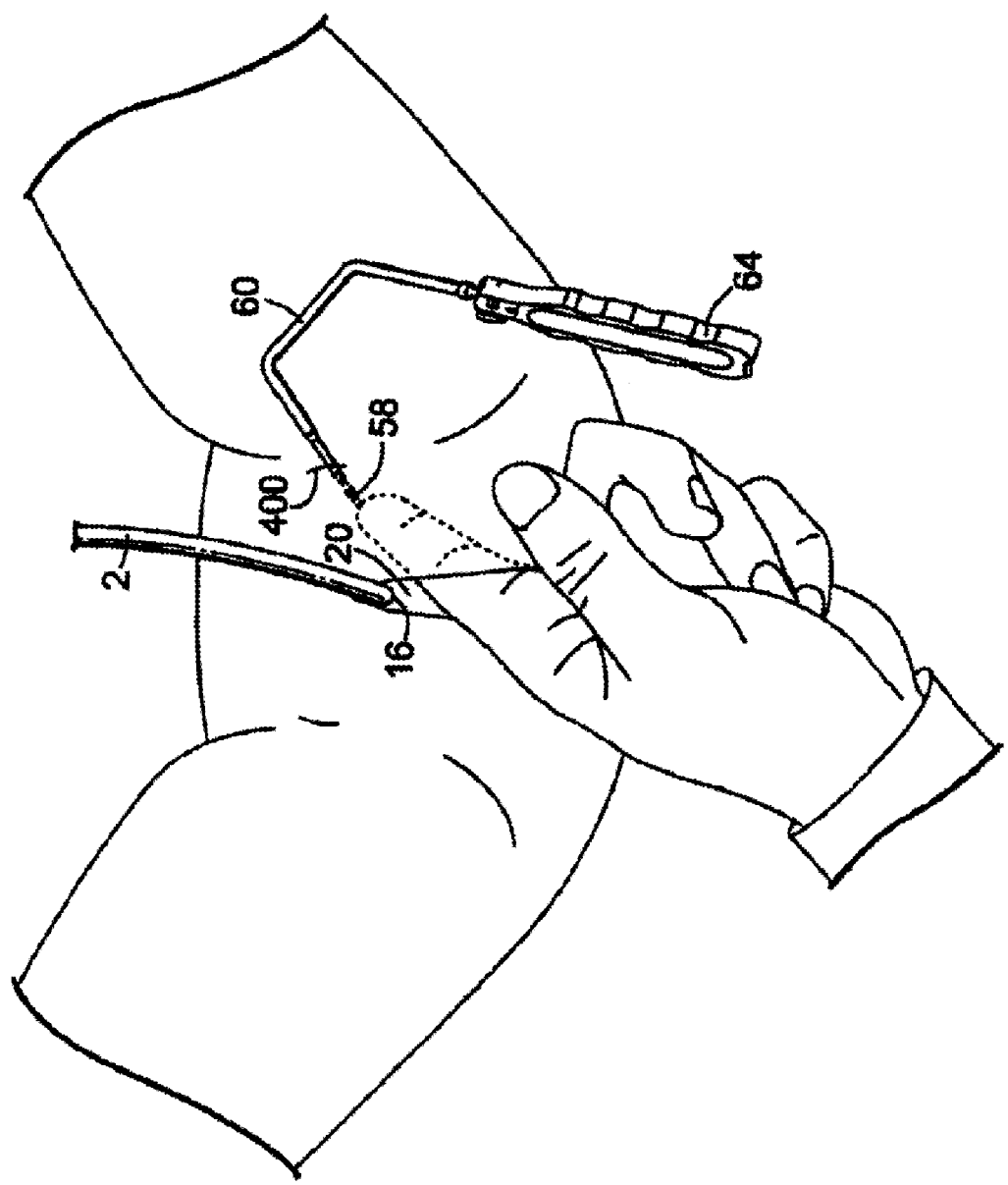

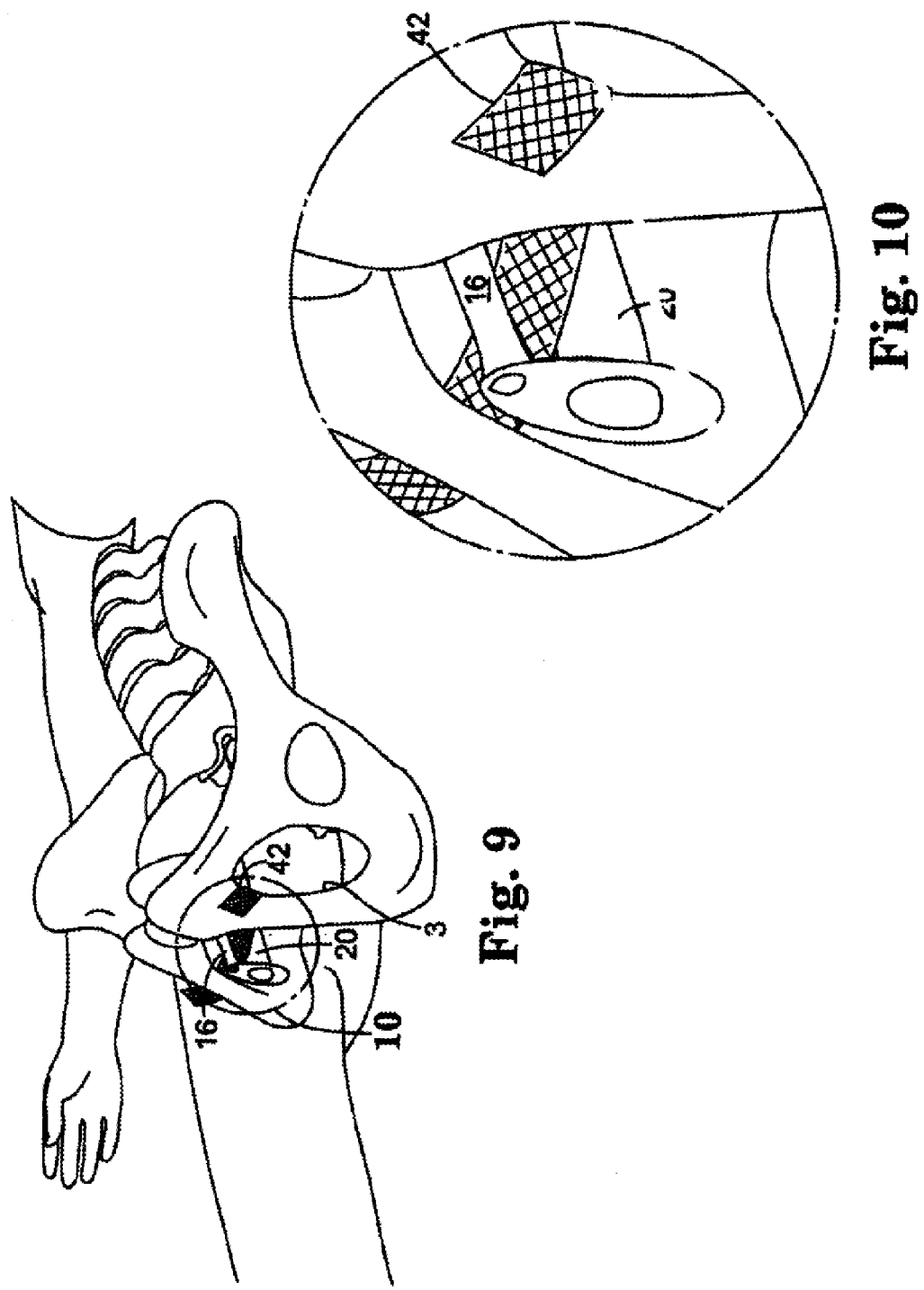

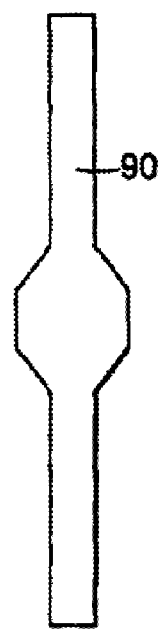
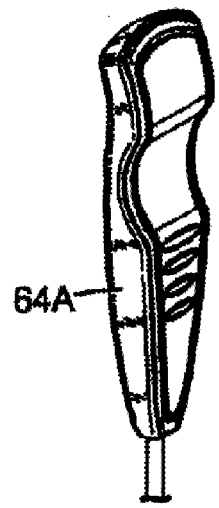
Fig. 12
Fig. 14
Fig. 13A
Fig. 13B

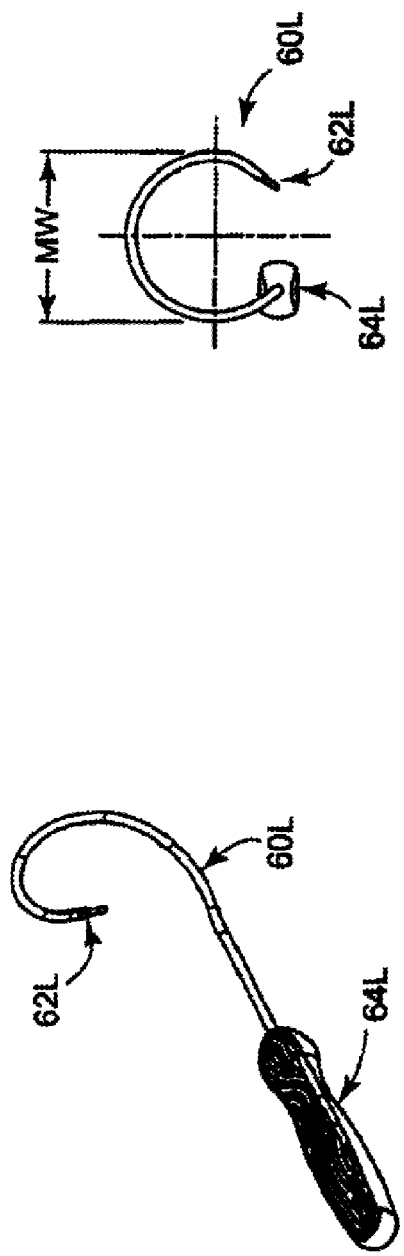
Fig. 19
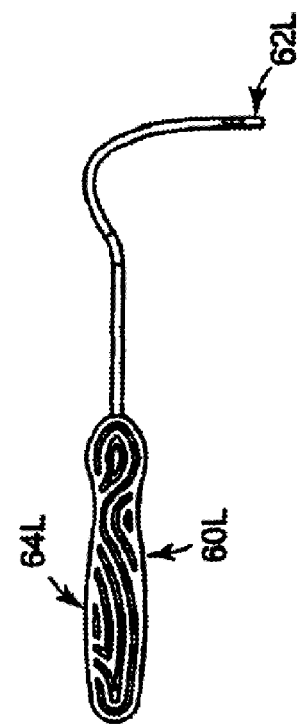
Fig. 20
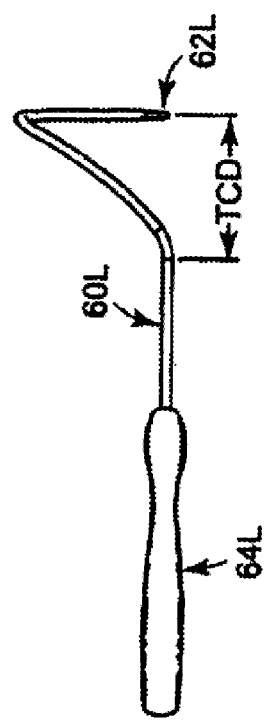
Fig. 21
Fig. 22

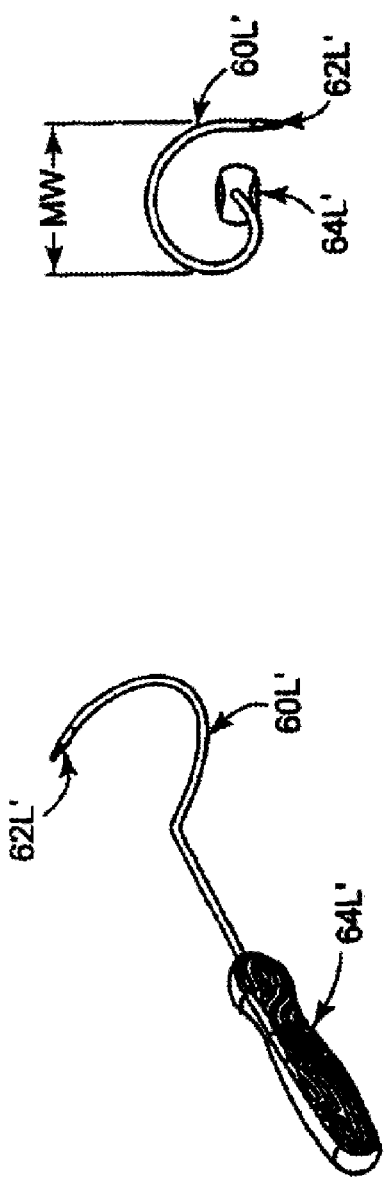
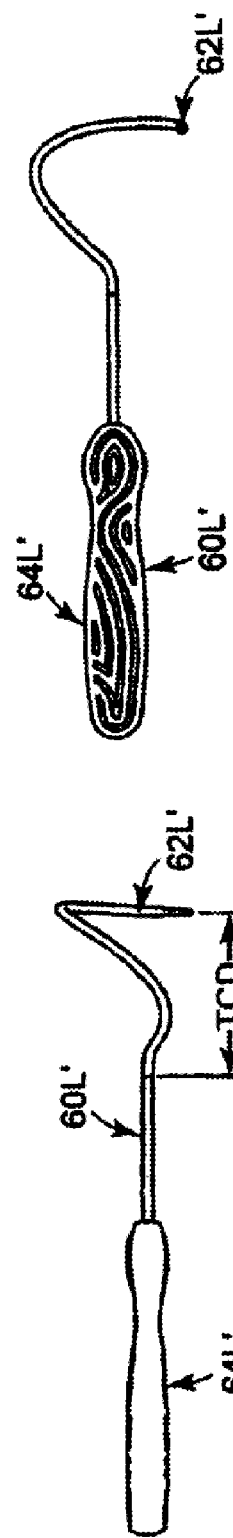
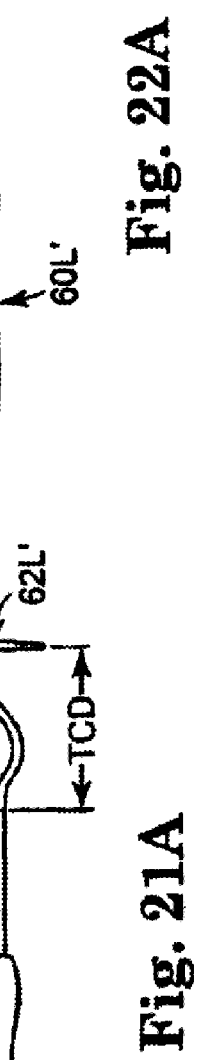
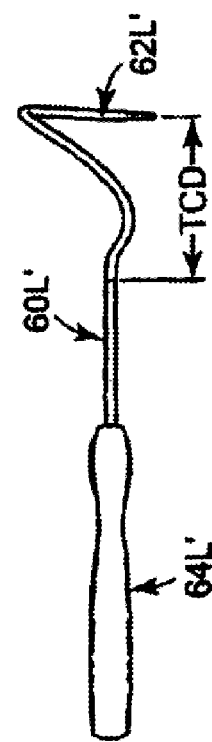
Fig. 19A
Fig. 20A
Fig. 21A
Fig. 22A

TRANSOBTURATOR SURGICAL ARTICLES AND METHODS

CROSS REFERENCE TO RELATED APPLICATIONS

The present application claims priority to U.S. Provisional Application Ser. No. 60/362,806, filed Mar. 7, 2002; and U.S. Provisional Application Ser. No. 60/380,797, filed May 13, 2002; and U.S. Provisional Application Ser. No. 60/402,007, filed Aug. 8, 2002; and U.S. Provisional Application Ser. No. 60/414,865 filed Sep. 30, 2002. The entire contents of all of the provisional patent applications are herein incorporated by reference.

BACKGROUND

Urinary incontinence is a significant health concern worldwide. In the urology field, needles, suture passers and ligature carriers are utilized in a variety of procedures, many of which are designed to treat incontinence. Examples of such surgical instruments included Stamey needles, Raz needles, and Pereyra needles. See Stamey, *Endoscopic Suspension of the Vesical Neck for Urinary Incontinence in Females*, Ann. Surgery, pp. 465-471, October 1980; and Pereyra, *A Simplified Surgical Procedure for the Correction of Stress Incontinence in Women*, West J. Surg., Obstetrics & Gynecology, pp. 243-246, July-August 1959.

A pubovaginal sling procedure is a surgical method involving the placement of a sling to stabilize or support the bladder neck or urethra. There are a variety of different sling procedures. Descriptions of different sling procedures are disclosed in U.S. Pat. Nos. 5,112,344; 5,611,515; 5,842,478; 5,860,425; 5,899,909; 6,039,686; 6,042,534 and 6,110,101.

Some pubovaginal sling procedures extend a sling from the rectus fascia in the abdominal region, to a position below the urethra, and back again to the rectus fascia. Although serious complications associated with sling procedures are infrequent, they do occur. Complications include urethral obstruction, prolonged urinary retention, bladder perforations, damage to surrounding tissue, and sling erosion.

The Tension-free Vaginal Tape (TVT) procedure (available from Ethicon, of N.J.) utilizes a Prolene™ nonabsorbable, polypropylene mesh. Problems with the TVT procedure are documented in the literature and patents. Problems associated with the TVT procedures and the like are acknowledged and described in PCT publication nos. PCT WO 00/74613 and PCT WO 00/74594, U.S. Pat. Nos. 6,273,852; 6,406,423; and 6,478,727, and published U.S. patent application Ser. Nos. 2002-0091373-A1, 2002-0107430-A1, 2002-0099258-A1 and US-2002-0099259-A1. A cadaver study indicated that the TVT needle is placed in close proximity to sensitive tissue such as superficial epigastric vessels, inferior epigastric vessels, the external iliac vessel and the obturator. See, Walters, Mark D., *Percutaneous Suburethral Slings: State of the Art*, presented at the conference of the American Urogynecologic Society, Chicago (October 2001) and PCT International Publication No. WO 02/26108.

Additional sling procedures are disclosed in Published U.S. patent application Ser. No. US 2001/0018549A1, and PCT Publication Nos. WO 02/39890 and WO 02/069781.

A significant percentage of pubovaginal sling procedures are conducted after previous pelvic surgery. A pubovaginal sling procedure can be particularly challenging if the patient has scarring as a result of previous pelvic surgeries or other anatomical problems. The additional complications presented by significant scarring present surgeons with a greater surgical challenge and may lead some surgeons to forego an otherwise beneficial sling procedure. Unfortunately, this reduces a patient's options for treating incontinence.

Published U.S. patent application Ser. No. 2002/0099260 discloses an implantable device or tape for use in correcting urinary incontinence. The tape includes sprayed polypropylene fibers that result in a strong implantable device. The tape also has a silicone-coated portion and tapered free ends. The procedure utilizes an Emmet needle that includes an eyelet. To create the eyelet, the distal portion of the Emmet needle is enlarged. A surgical procedure using an Emmet needle is believed to be described in the French publication D. Dargent, S. Bretones, P. George, and G. Mellier, *Pose dun ruban sous uretral oblique par voie obturatrice dans le traitement de l'incontinence urinairefeminine*, Gynecol. Obstet. Fertil. 2002; 30: 576-582.

In the procedure described in U.S. patent application Ser. No. 2002/0099260, an incision is made in the perineal skin facing the obturator and in the groin. The Emmet needle is first inserted through the cutaneous incision. The Emmet needle is first introduced perpendicular to the perineum for about 15 mm (passing through the internal obturator muscle as far as just outside the ischiopubic branch). The Emmet needle is then allowed to describe its curvature. The free end of the tape is then slipped into the eyelet of the needle. The needle/tape connection is thus reversible as one merely needs to unthread the tape from the eyelet to separate the tape from the needle. Separation of the tape and needle while both are within the body is undesirable as it would require the needle to be repassed through the body.

The needle with the tape extending through the eyelet is then pulled back though the skin incision. The eyelet and threaded tape present a sudden discontinuity encountered by the tissue that can make tape and needle passage inconvenient and unnecessarily irritative or traumatic to tissue. Additionally, the final placement of the sling may not be optimum in this procedure.

SUMMARY OF THE INVENTION

In one aspect, the present invention comprises a novel surgical instrument for treating incontinence. The instrument comprises a handle portion, and a needle portion with a distal end. Unlike the Emmet needle of the prior art, the novel instrument has substantial structure in three dimensions. The needle portion is sized and shaped to extend between an incision substantially adjacent the patient's obturator foramen and a vaginal incision. The needle portion also has structure near the distal end for associating the instrument with an implantable material for treating the incontinence. Preferably, the needle portion includes a portion that is substantially helically shaped, more preferably, it is a variable helix shape. The structure for associating the instrument with an implantable material can comprise an eyelet or a dilator or other structure.

The handle portion is preferably elongate along a handle axis, the needle portion includes a substantially straight spacer portion along the handle axis, and a variable spiral portion extending from the spacer portion. The variable spiral portion preferably has a tissue clearance depth of greater than about 1.5 inches and less than about 2.5 inches, and a maximum width of greater than about 1.25 inches and less than about 3 inches.

In one embodiment, the handle portion is elongate defining a mid plane, and the distal end of the novel needle includes a distal tip situated substantially near an extension of the mid plane that is spaced from the handle portion.

In another aspect, the present invention comprises a surgical instrument comprising first and second ends, the instrument having a portion that is sized and shaped to extend between a vaginal incision and an incision substantially adjacent the patient's obturator foramen. One of the ends has a handle, at least the other end having securement surfaces for snap fitting the instrument to another surgical component used to treat incontinence. The snap fit preferably provides a substantially permanent attachment between the instrument and the other surgical component. Preferably, the other surgical component comprises a dilator of a sling assembly. The instrument and the dilator preferably have complementary engagement surfaces for resisting separation of the instrument from the dilator once they are snap fitted together.

In another aspect, the novel instrument comprises a handle portion, a needle portion having a substantially straight portion projecting from the handle portion and a variable spiral portion with a distal end. The variable spiral portion is sized and shaped to extend between an incision substantially adjacent the patient's obturator foramen and a vaginal incision. The needle portion has structure near the distal end for associating the instrument with an implantable material for treating incontinence.

In yet another aspect, the present invention comprises a surgical assembly for treating incontinence. The assembly includes a surgical instrument having a handle portion, a needle portion having substantial structure in three dimensions and a distal end. The needle portion has a portion that is sized and shaped to extend between an incision substantially adjacent a patient's obturator foramen and a vaginal incision. The assembly may also include an implantable synthetic material and a sheath situated about the implantable synthetic material. In this aspect, the needle portion has structure near the distal end for associating the instrument with the implantable synthetic material. The assembly may further including a dilator. Alternatively, needle may comprise an eyelet.

When the assembly includes a dilator, the dilator preferably has engagement surfaces for connecting the dilator to the instrument. The dilator is preferably operatively associated with the sheath and implantable material. The structure of the needle portion near the distal end comprises surfaces complementary with the engagement surfaces of the dilator for resisting separation of the instrument from the dilator once they are engaged. Preferably, the needle portion is sized and shaped for a predetermined side of a patient, and the handle portion includes indicia indicating the predetermined side of the patient.

In another aspect, the present invention comprises a surgical assembly comprising a first surgical instrument for use on a right side of a patient. The first surgical instrument comprises a handle portion and a needle portion having substantial structure in three dimensions and a distal end. The needle portion has a portion that is sized and shaped to extend between an incision substantially adjacent the obturator foramen on the patient's right side and a vaginal incision. The assembly also has a second surgical instrument for use on a left side of a patient. The second surgical instrument comprises a handle portion and a needle portion having substantial structure in three dimensions and a distal end. The needle portion of the second instrument has a portion that is sized and shaped to extend between an incision substantially adjacent the obturator foramen on the patient's left side and a vaginal incision.

Preferably, the handle portion of the first surgical instrument includes indicia indicating the first surgical instrument is for use on the right side of the patient, and the handle portion of the second surgical instrument includes indicia indicating the second surgical instrument is for use on the left side of the patient. The assembly may also include an implantable knitted polypropylene material, and a sheath situated about the implantable synthetic material. The first and second surgical instruments may include an eyelet for receiving a suture to tie the surgical instrument to the implantable material. Alternatively, the assembly can have first and second dilators for associating the first and second surgical instruments with the implantable material.

In another aspect the present invention comprises a surgical instrument for treating incontinence comprising a needle sized and shaped to either a) initially extend through an incision substantially adjacent a patient's obturator foramen and then through a vaginal incision, or b) initially extend through a vaginal incision and subsequently through an incision substantially adjacent a patient's obturator foramen. Notably, such a surgical instrument need not have substantial structure in three dimensions. Preferably, the needle comprises a pair of ends having surfaces for affording association with either an implantable sling material or a removable handle. In one embodiment, the needle is sized and shaped for use on either the patient's right side or left side.

In another aspect, the present invention comprises methods for treating incontinence. Some methods may utilize substantially three dimensional needles, others need not require three dimension needles and other methods may utilize either three dimensional needles or substantially flat needles or both. One method comprises the steps of creating a vaginal incision, creating an incision substantially adjacent the patient's obturator foramen, providing an elongate surgical instrument comprising first and second ends, with at least one of the ends having securement surfaces, providing a sling assembly having an implantable sling for treating the incontinence, the sling assembly having surfaces complementary to the securement surfaces, passing the instrument between the incisions, then snap fitting the instrument to the sling assembly to provide a substantially permanent attachment between the instrument and the assembly, then passing the implantable material through tissue from the vaginal incision toward the incision substantially adjacent the patient's obturator foramen.

In another aspect a method comprises the steps of creating a vaginal incision, creating an incision substantially adjacent the patient's obturator foramen, providing an elongate surgical instrument comprising first and second ends, the instrument having substantial structure in three dimensions, providing an implant for treating the incontinence, passing the instrument between the incisions, then associating the implant with the instrument, and passing the implant through tissue and through the patient's obturator foramen with the instrument. Preferably, the step of providing an elongate surgical instrument includes the step of providing an instrument with a portion that is substantially helically shaped, and the step of passing the implant through tissue includes the step of passing the implant along a substantially three dimensional path. The step of providing an elongate surgical instrument preferably includes the step of providing an instrument with an elongate handle portion having an axis, and the step of passing the instrument between the incisions preferably includes the step of rolling the instrument about the axis of the handle portion.

In another aspect, the method comprises the steps of creating a vaginal incision, creating an incision substantially adjacent the patient's obturator foramen, providing an elongate surgical instrument comprising a handle portion, a needle portion having a substantially straight portion projecting from the handle portion and a variable spiral portion with a distal end, providing an implant for treating the incontinence, passing at least a portion of the variable spiral portion between the incisions by initially passing the distal end through the incision substantially adjacent the patient's obturator foramen and then through the vaginal incision, then associating the implant with a portion of the instrument that has emerged from the vaginal incision, and then moving the distal end of the instrument with the implant associated therewith from the vaginal incision toward the patient's obturator foramen to pass the implant through tissue. Optionally, the step of associating the implant with a portion of the instrument that has emerged from the vaginal incision includes the step of using a suture to tie the implant to an eyelet in the distal end of the needle.

In yet another aspect, the method comprises the steps of creating a vaginal incision, creating an incision substantially adjacent the patient's obturator foramen, providing an elongate surgical instrument comprising a pair of ends, providing an assembly having an implant for treating incontinence, initially passing one end of the instrument initially through the vaginal incision toward the incision substantially adjacent the patient's obturator foramen in a path through the patient's obturator foramen until one end of the instrument emerges from the incision substantially adjacent the patient's obturator foramen, leaving the other end of the needle projecting from the vaginal incision, then associating the end of the instrument that projects from the vaginal incision with the assembly, and then moving the instrument out of the patient's body to pass the implant through tissue from the vaginal incision toward the incision substantially adjacent the patient's obturator foramen to place the implant in a therapeutically effective position.

In another aspect, the present invention comprises the ornamental design for a surgical instrument, as shown in FIGS. 39 through 45 and described in the Brief Description of the Drawings. Also, the present invention comprises the ornamental design for a surgical instrument, as shown in FIGS. 46 through 52 and described in the Brief Description of the Drawings.

BRIEF DESCRIPTION OF THE DRAWINGS

Figure 4A:
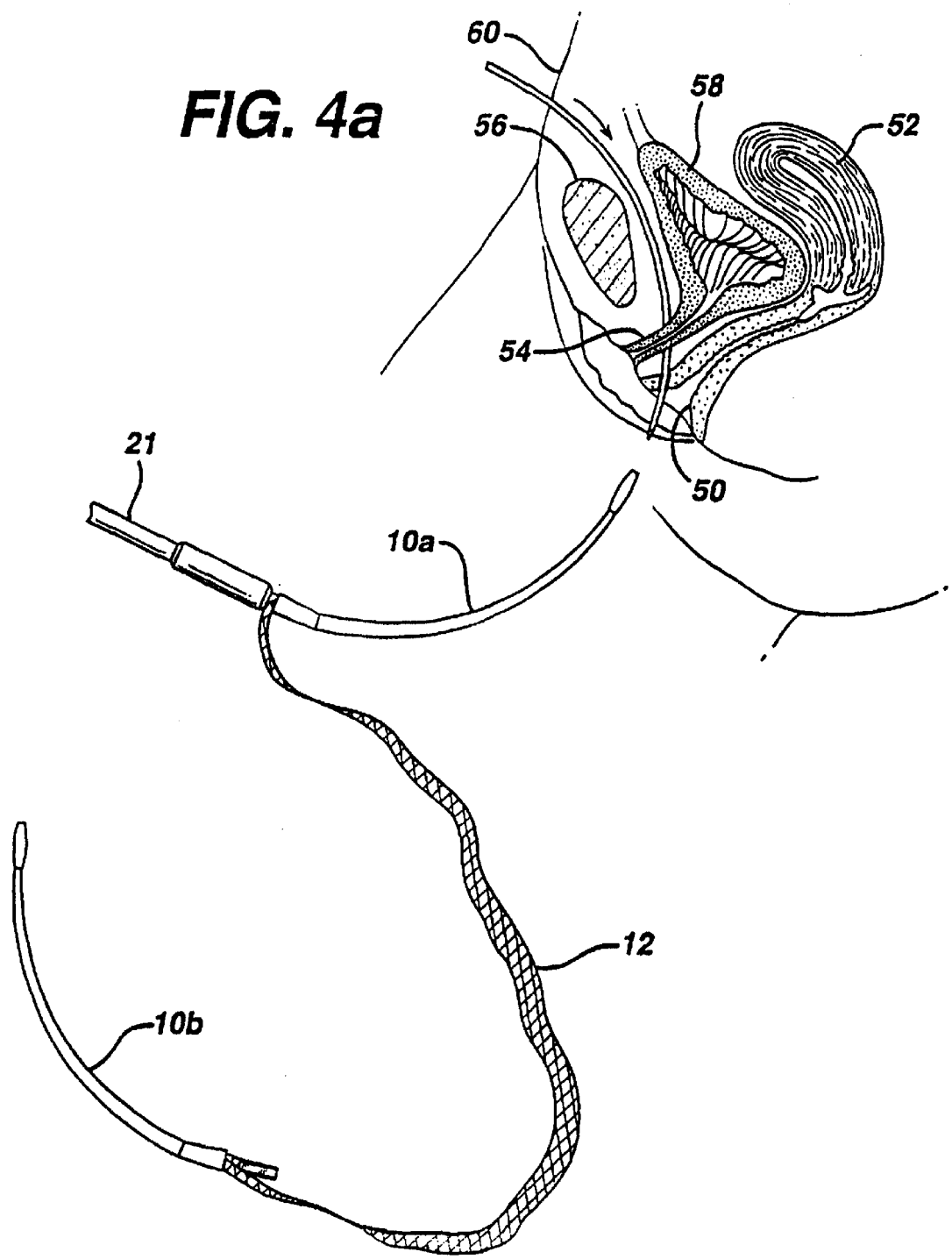
FIGS. 4a–j diagrammatically illustrate several surgical steps of a trans-abdominal method utilizing two needles and guide needle according to the invention to treat SUI.
Figure 4C:
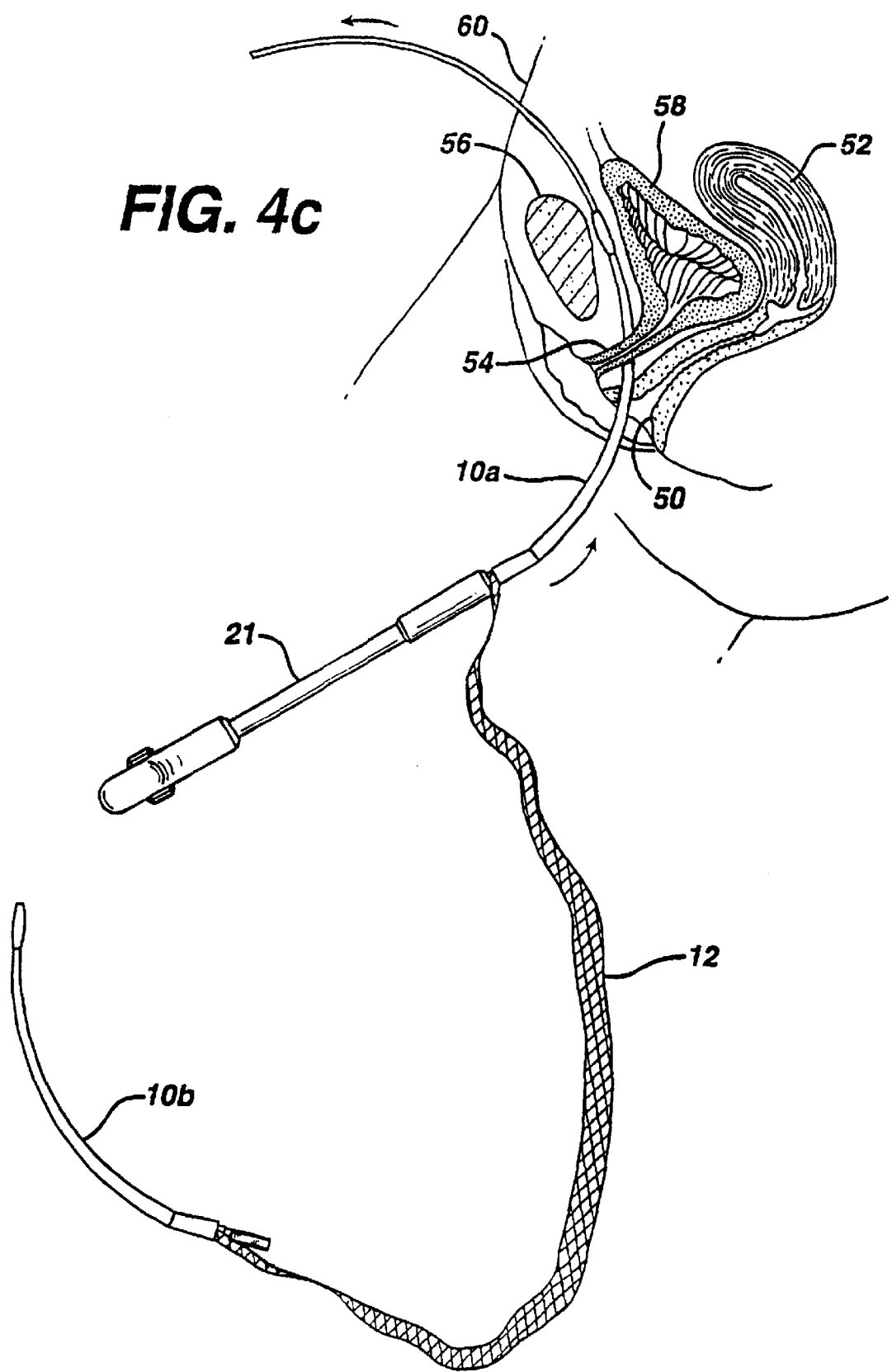
Figure 4D:
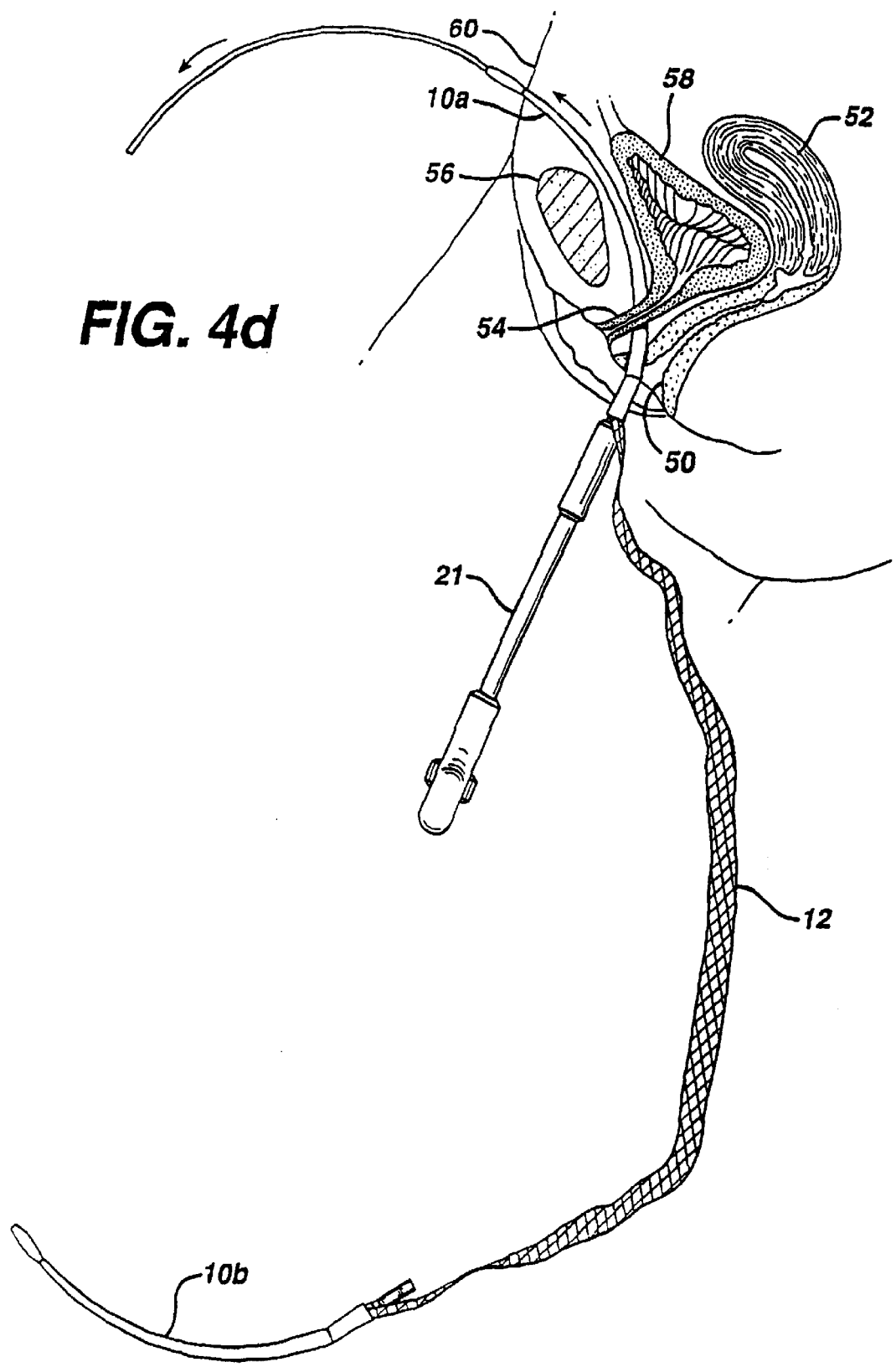
Figure 4E:
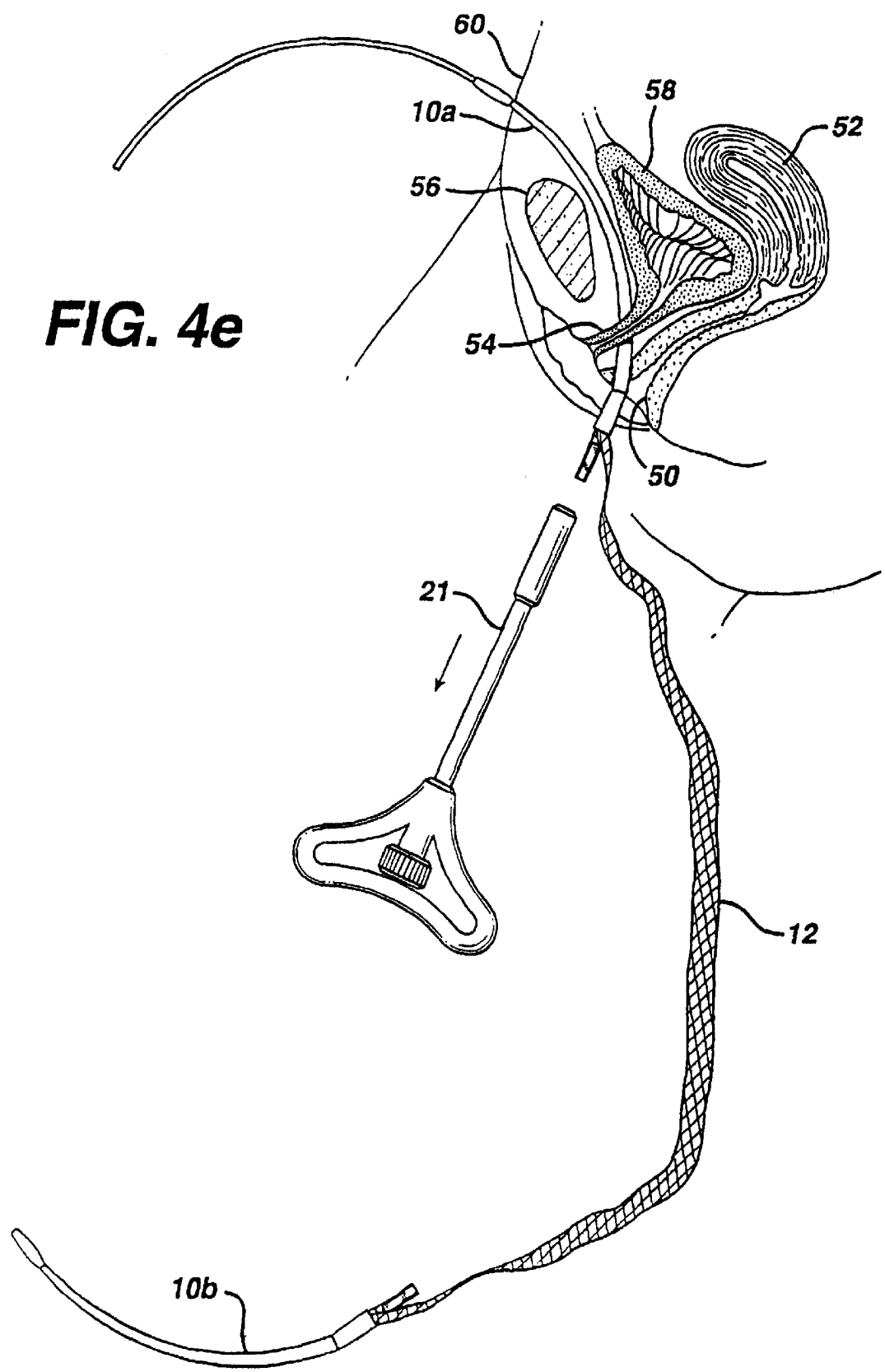
Figure 4F:
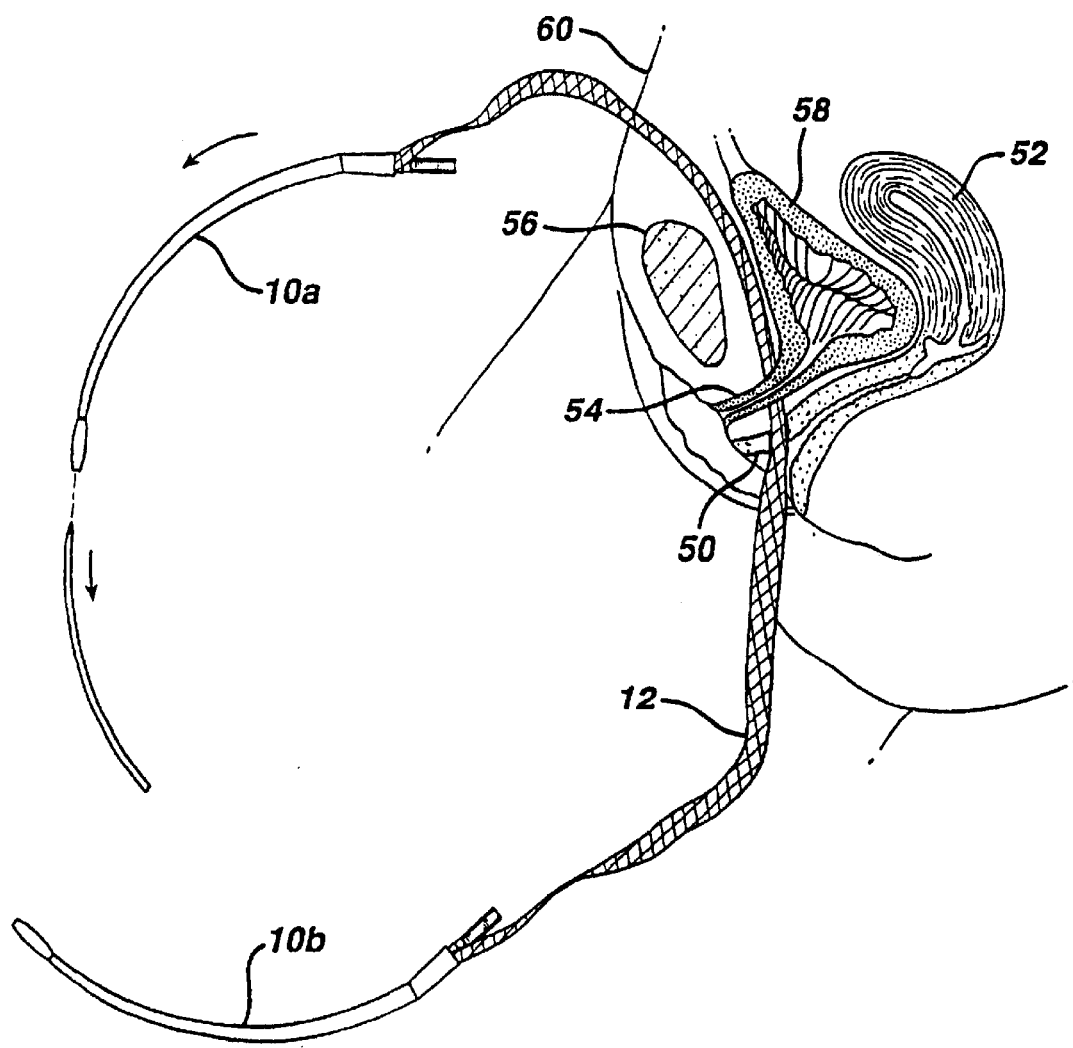
Figure 4G:
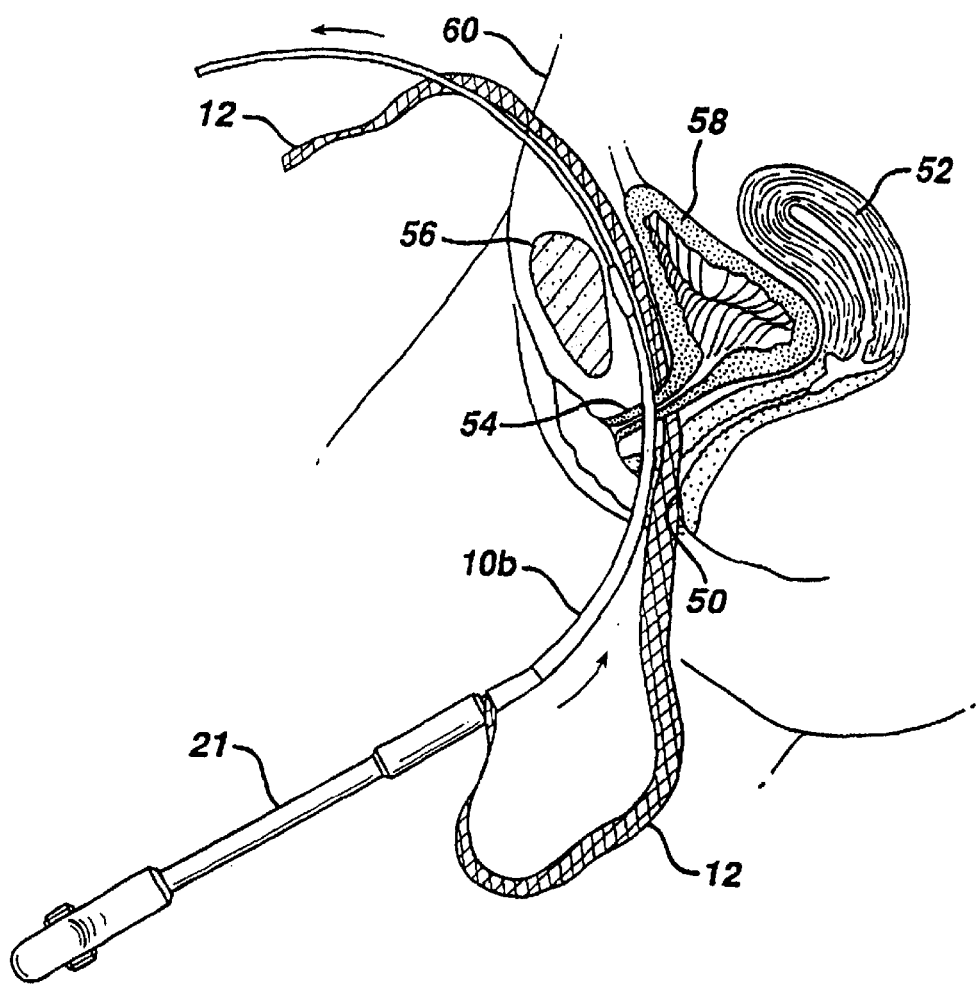
Figure 4H:
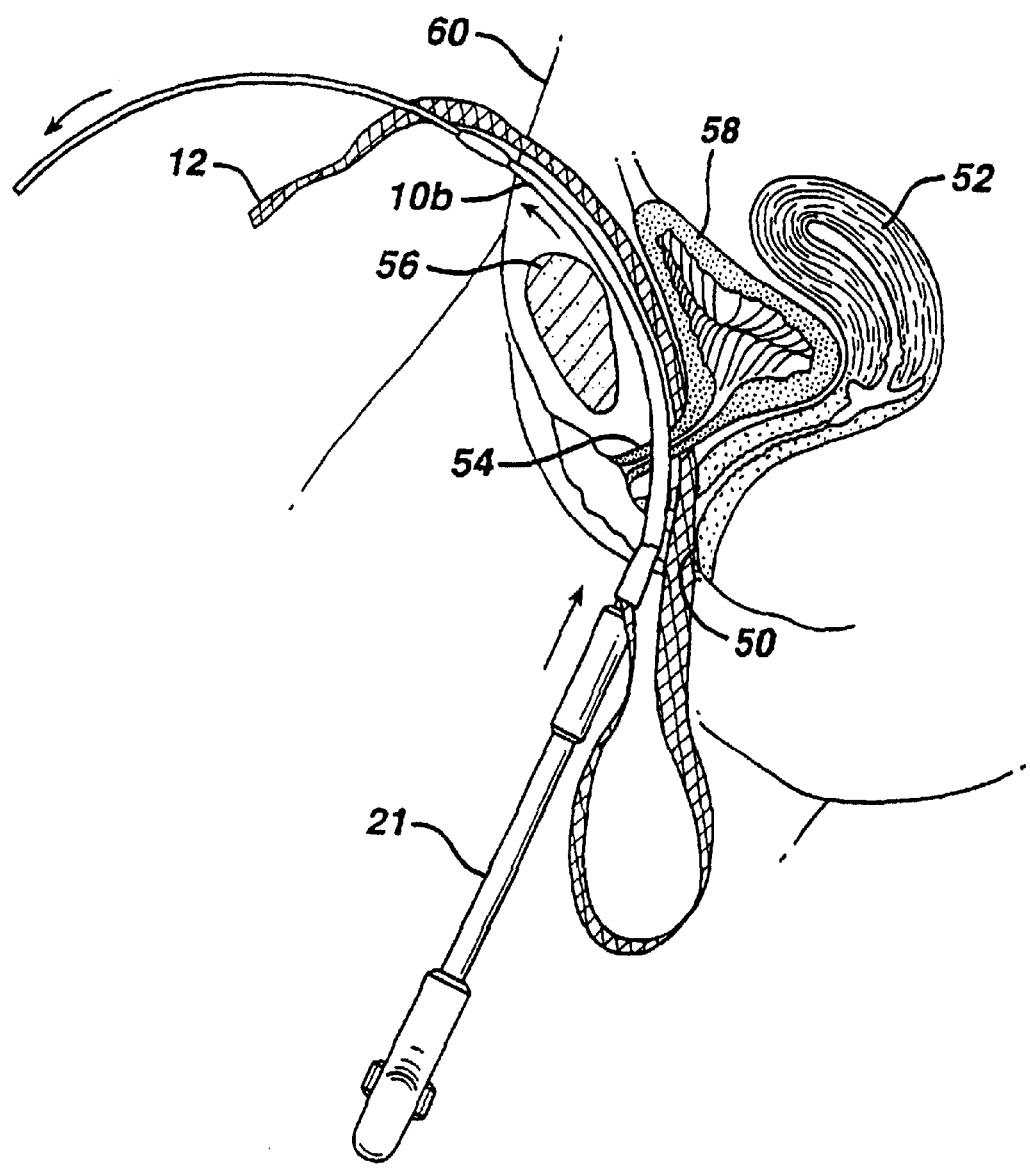
Figure 4I:
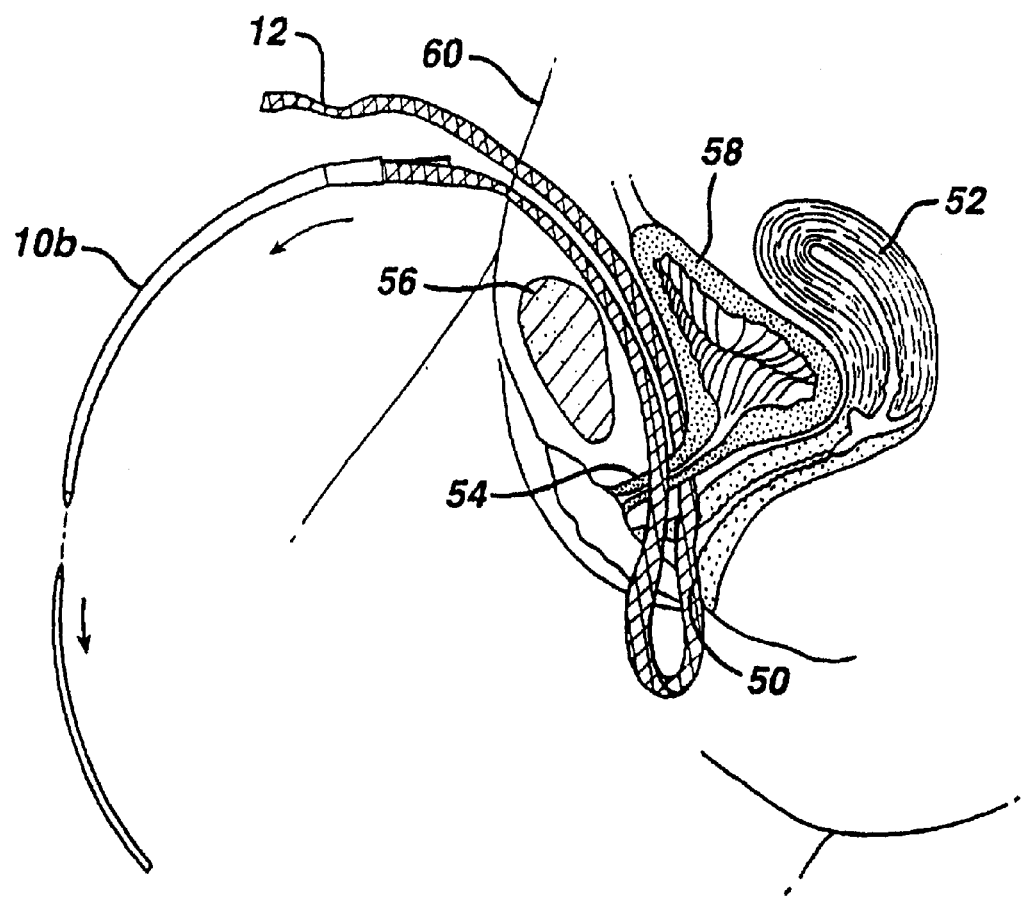
Figure 4J:
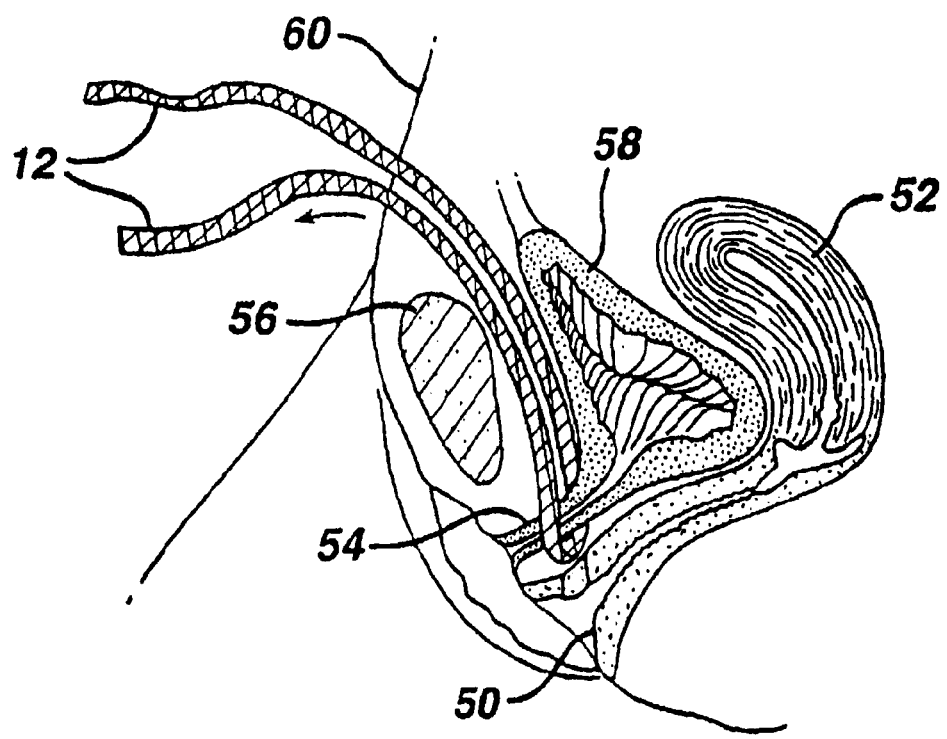
Figure 4:
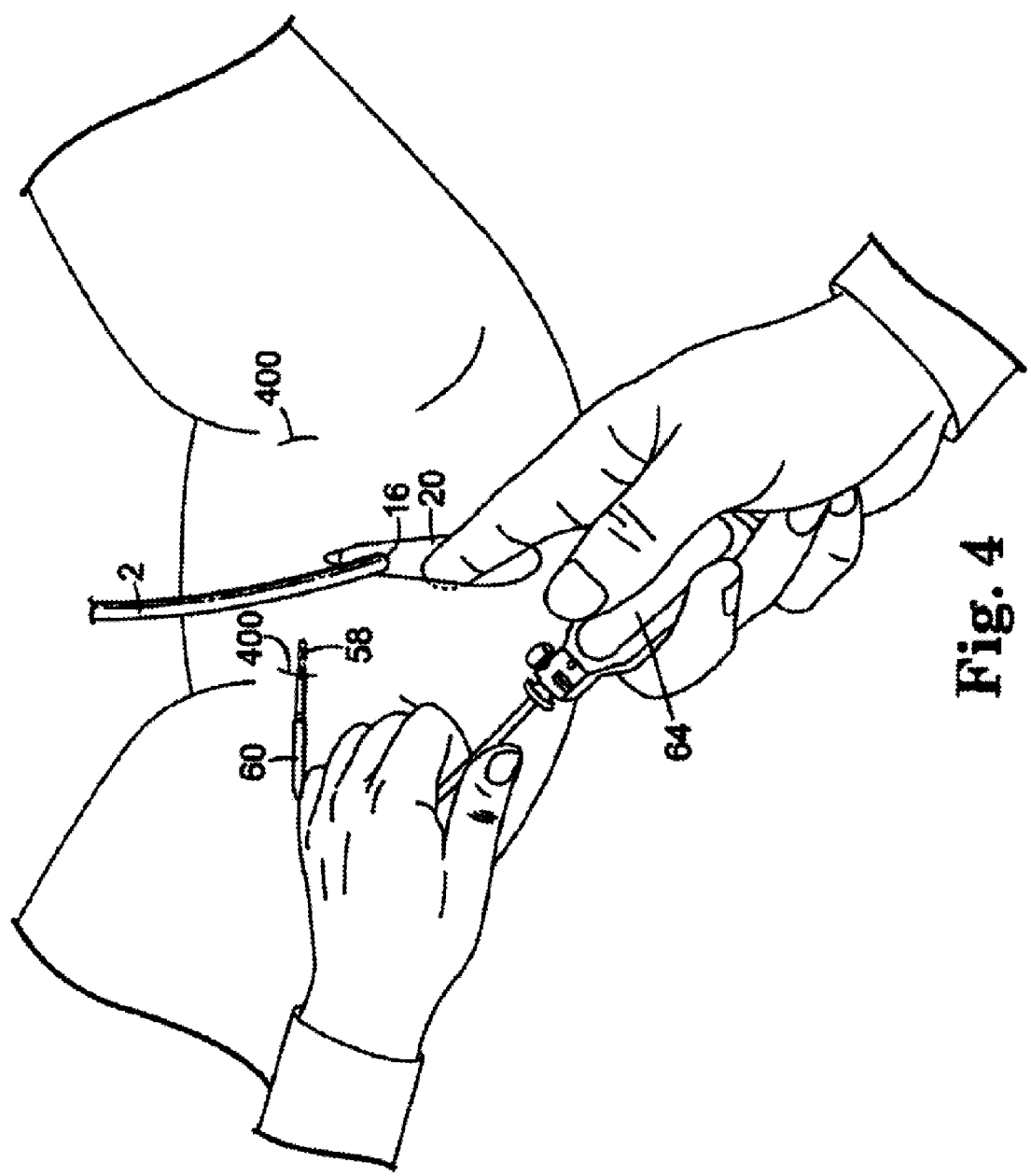
Figure 6:
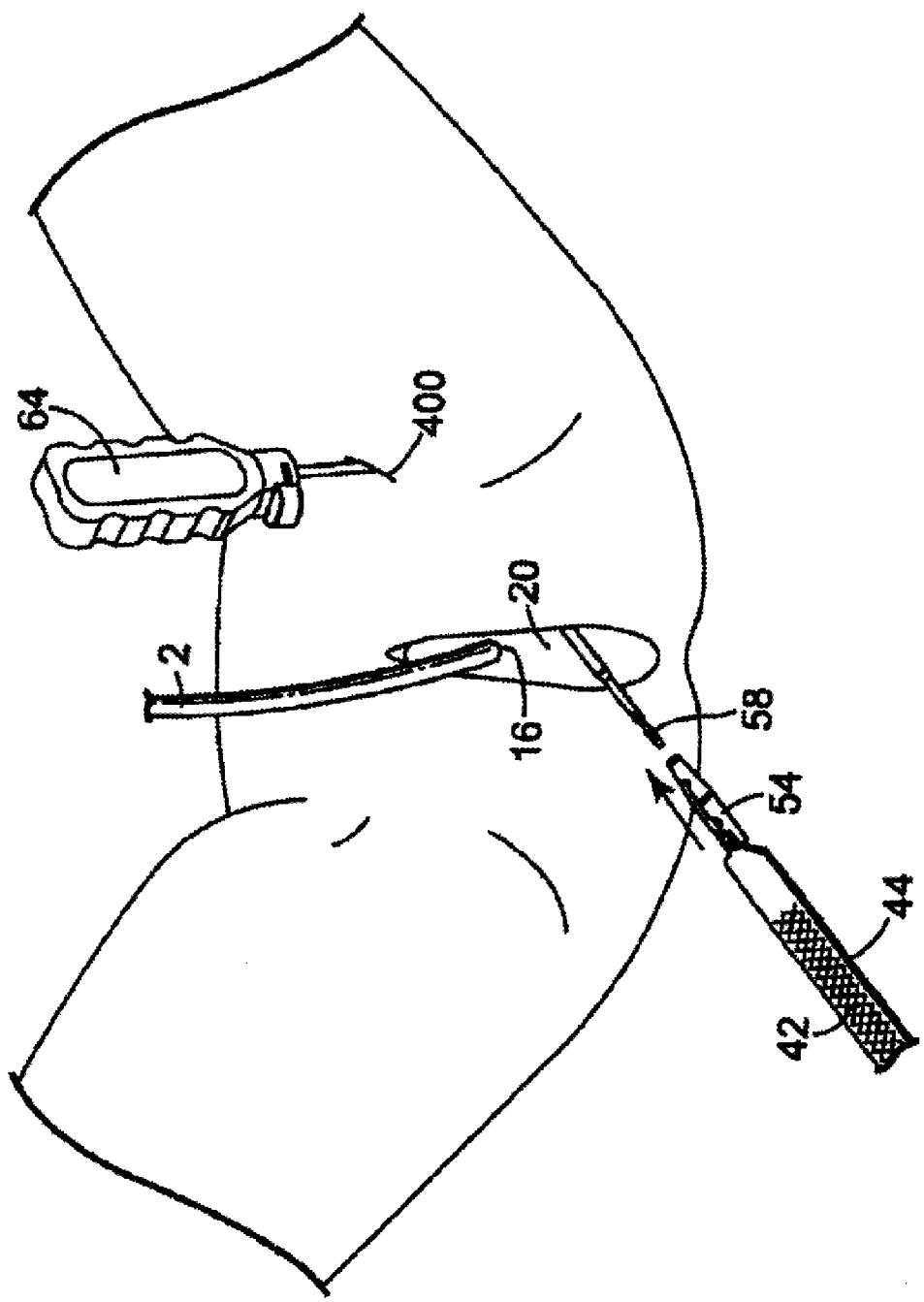
Figure 7:
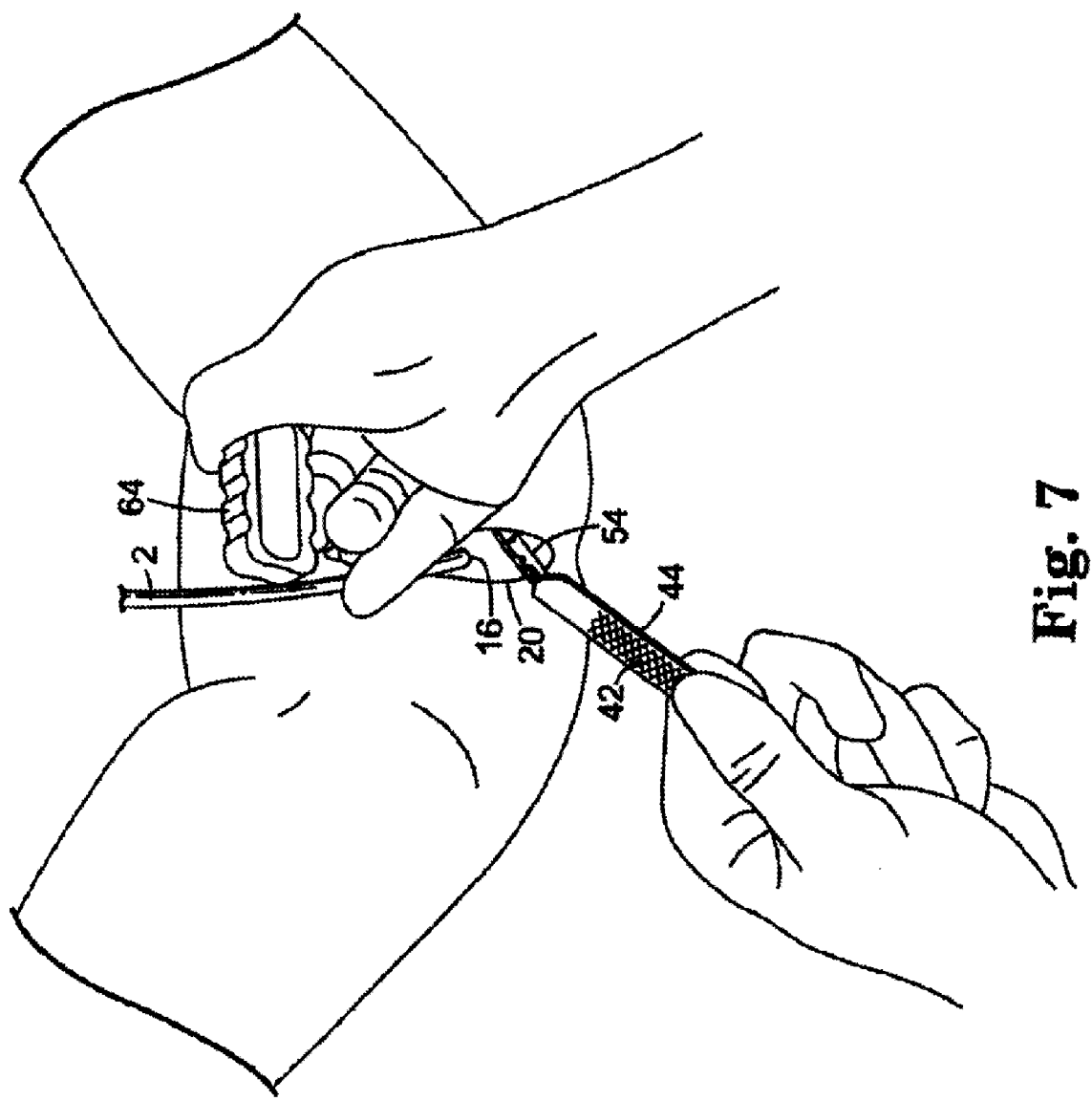
Figure 8:
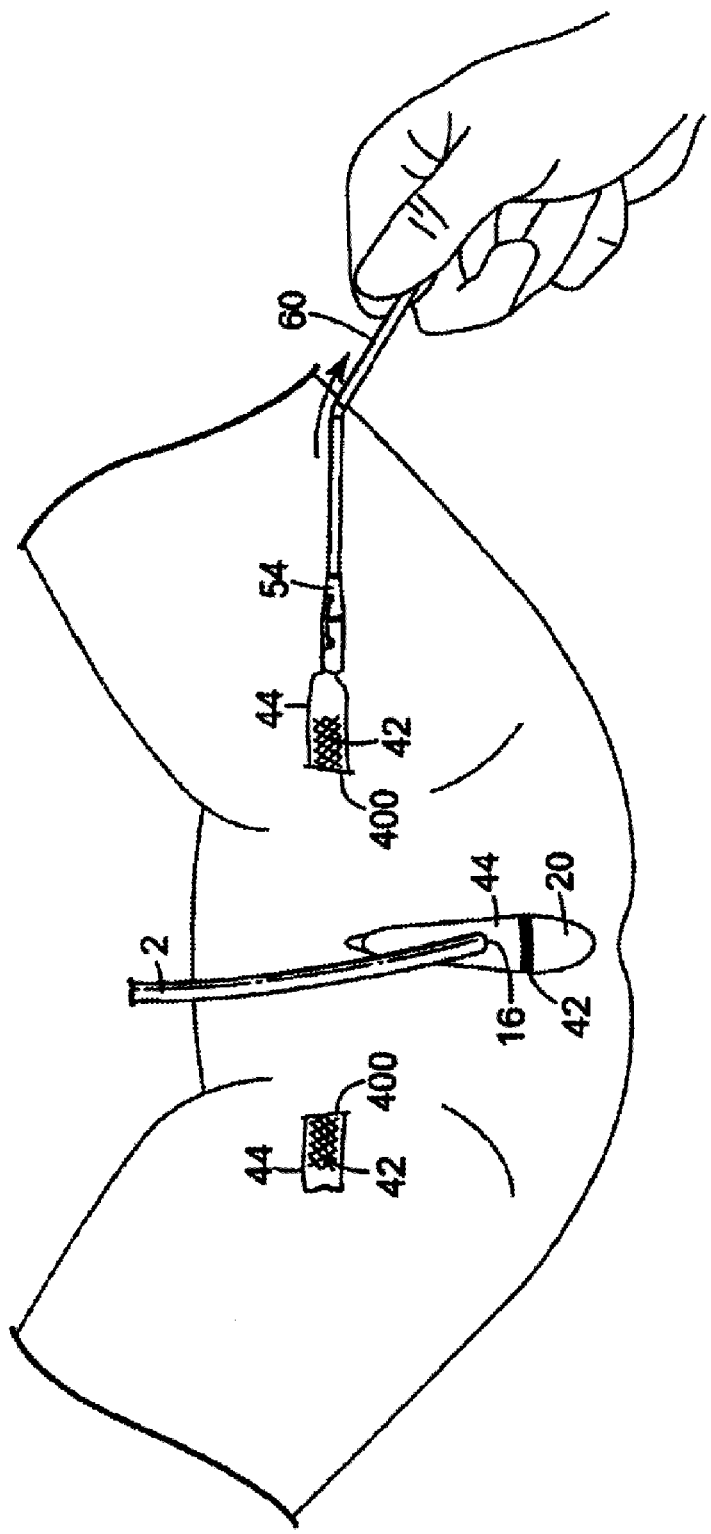
Figure 11:
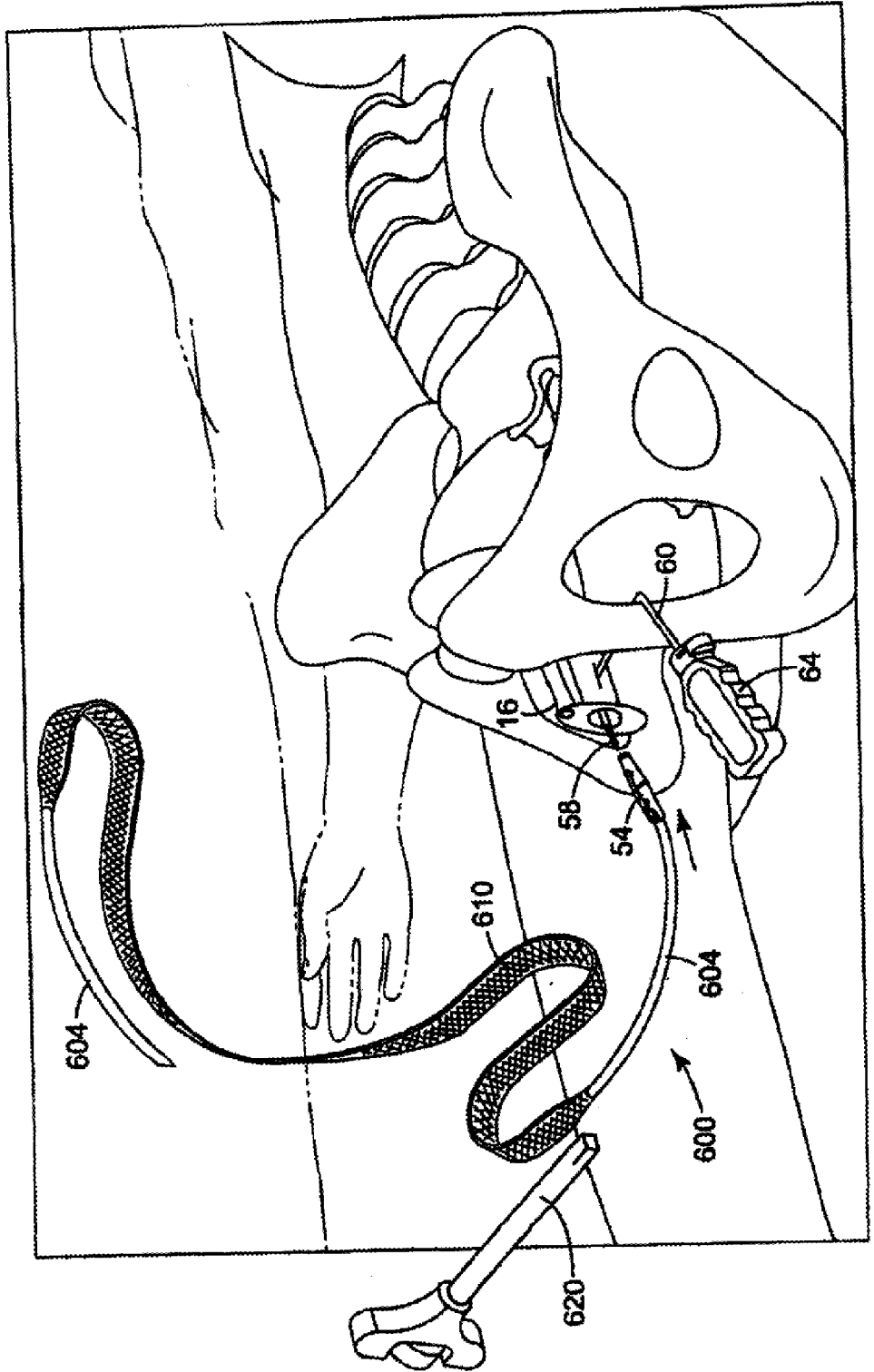
Figure 15:
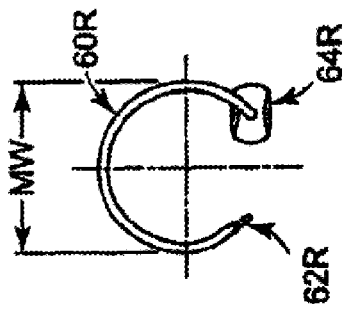
Figure 16:
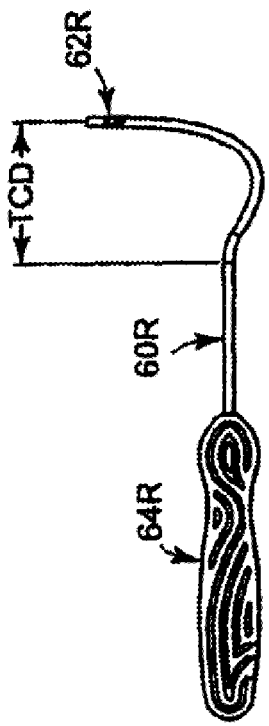
Figure 17:
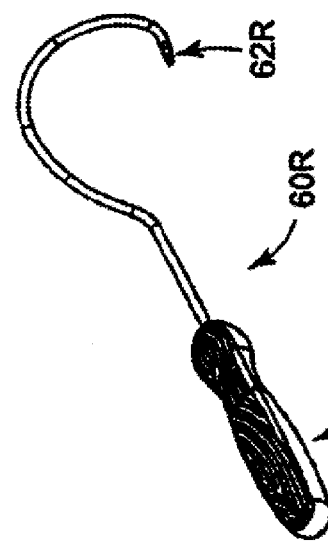
Figure 18:
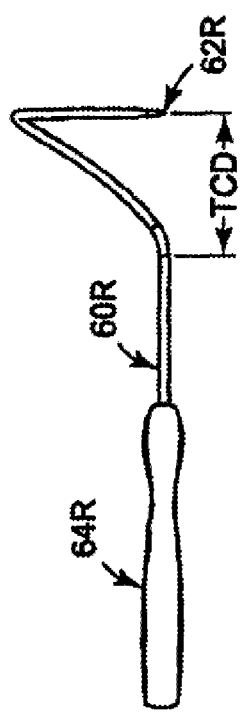
Figure 16A:
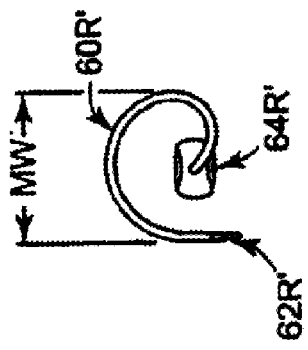
Figure 15A:
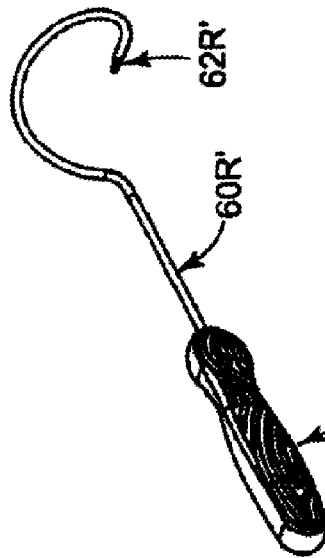
Figure 18A:
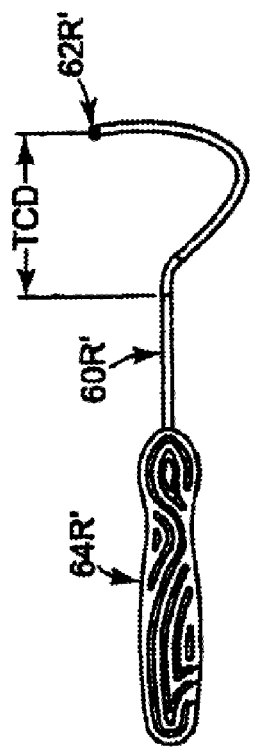
Figure 17A:
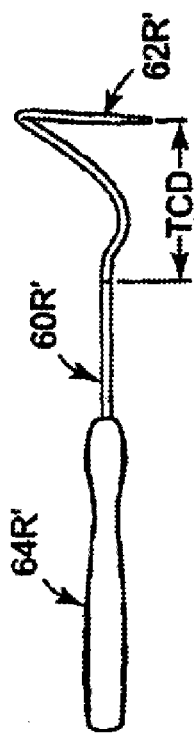
Figure 20B:
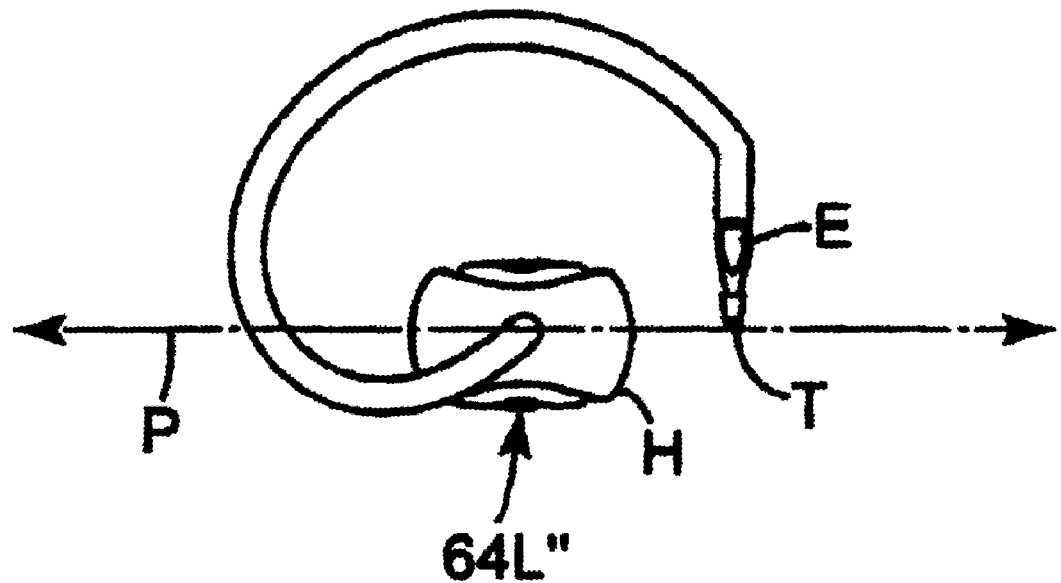
Figure 23:
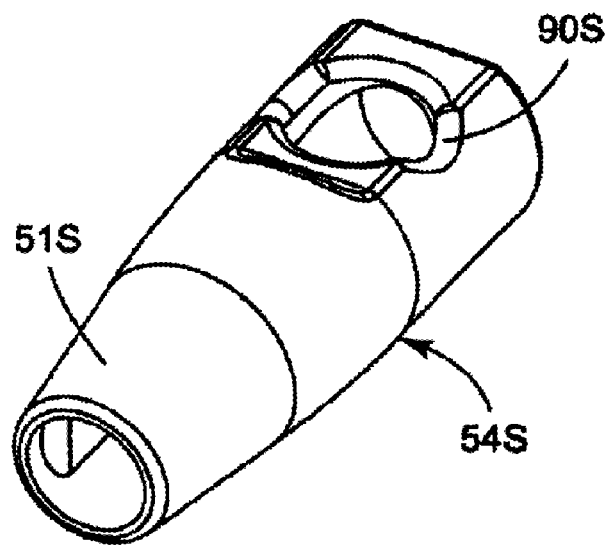
Figure 24:
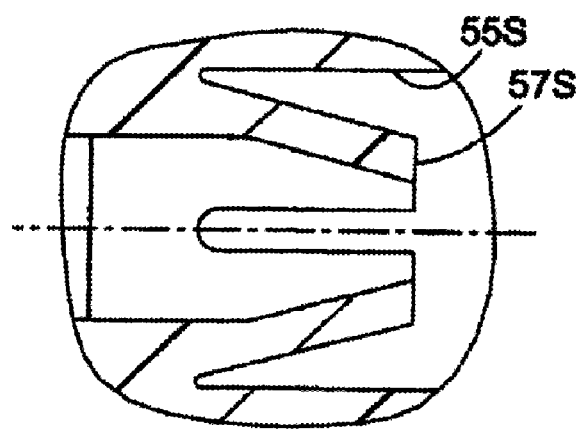
Figure 25:
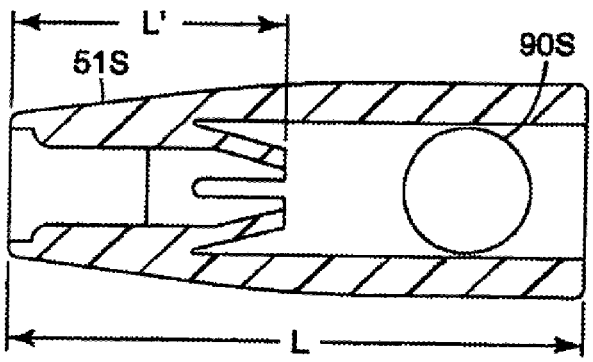
Figure 25A:
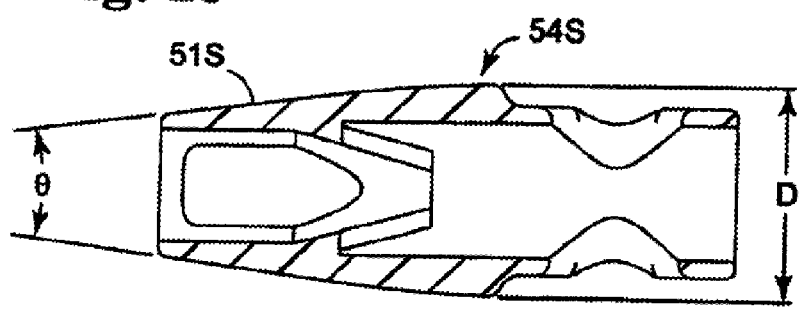
Figure 26:
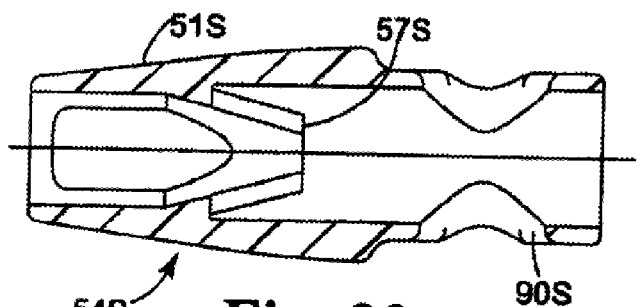
Figure 26A:
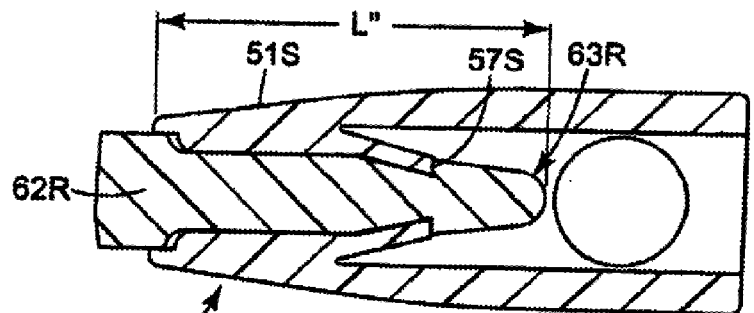
Figure 27:
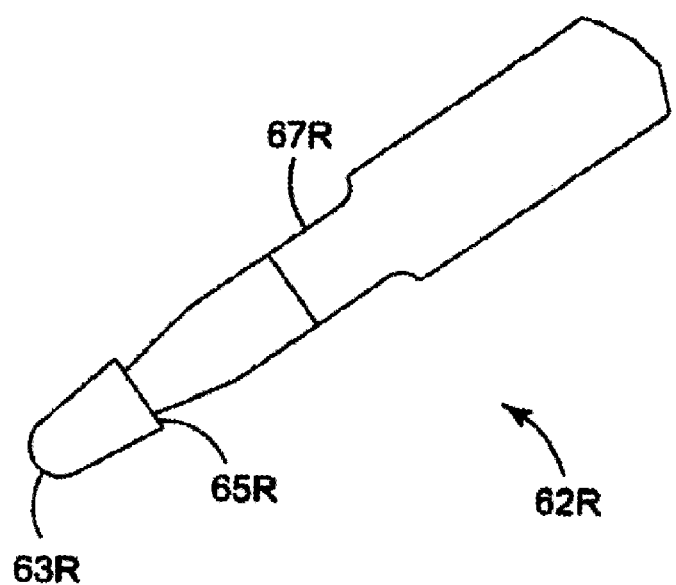
Figure 28:
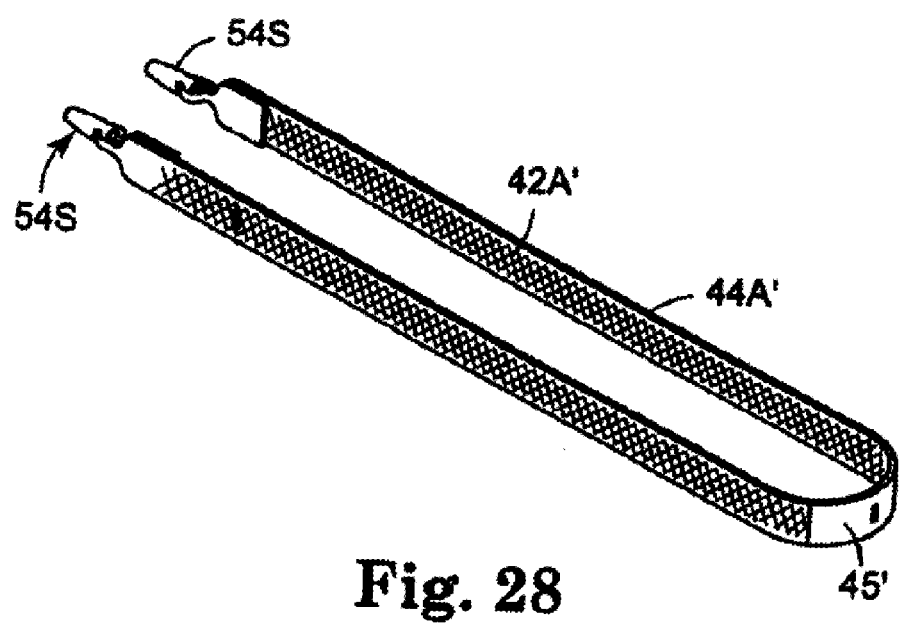
Figure 29:
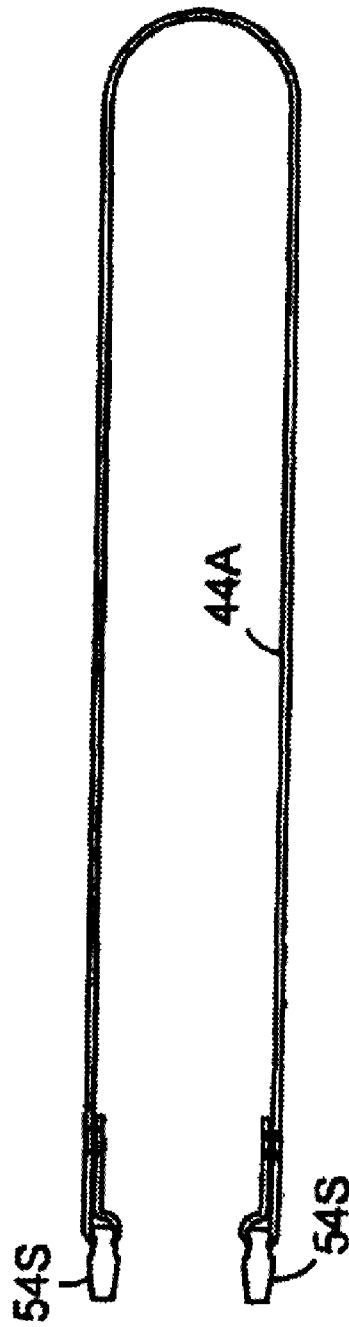
Figure 30:
Figure 31:
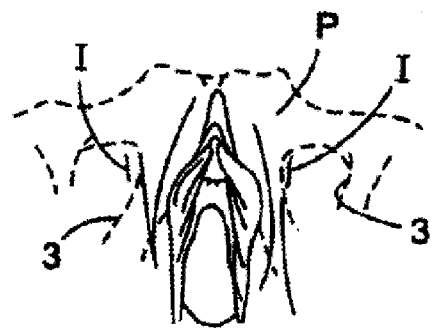
Figure 32:
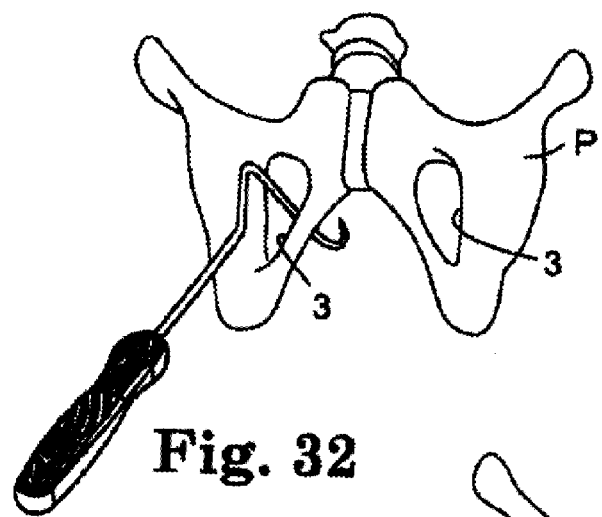
Figure 33:
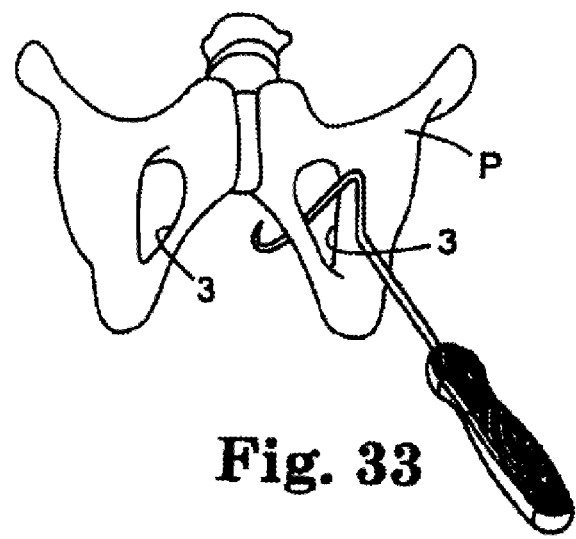
Figure 34:
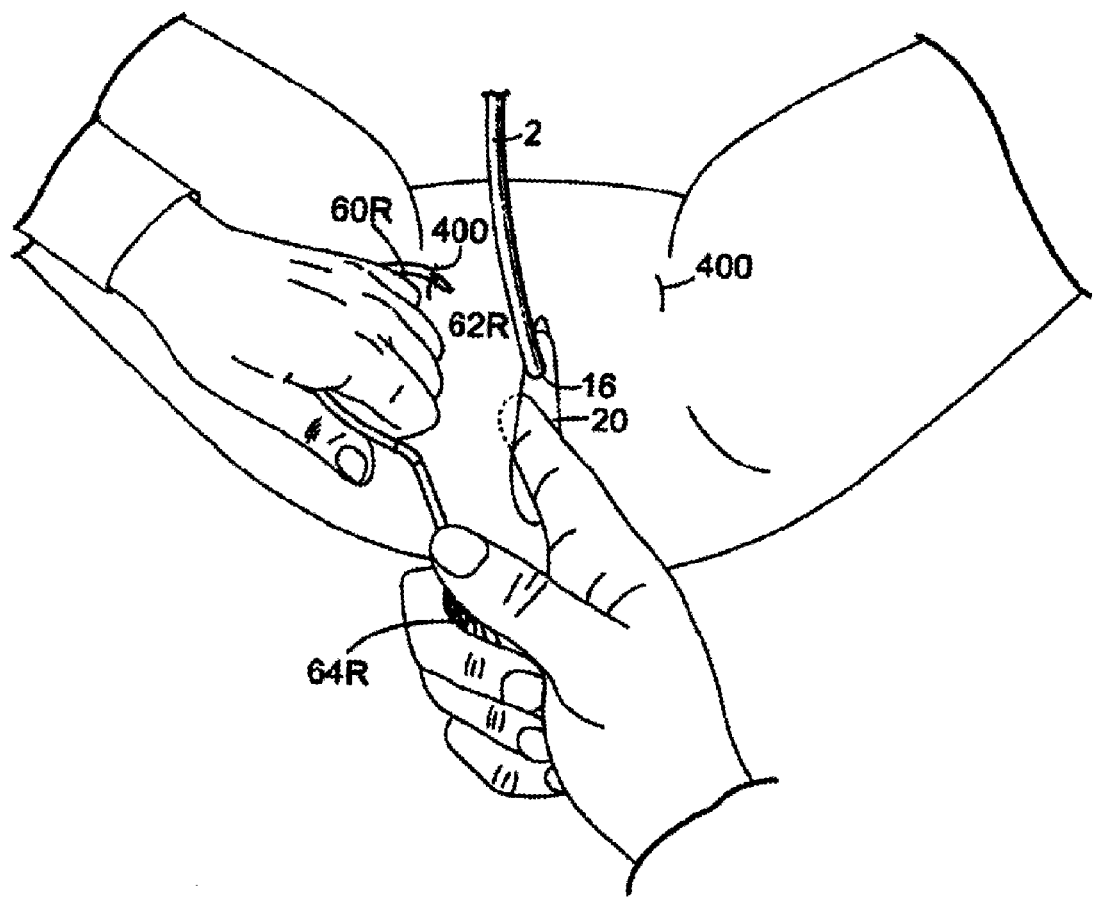
Figure 35:
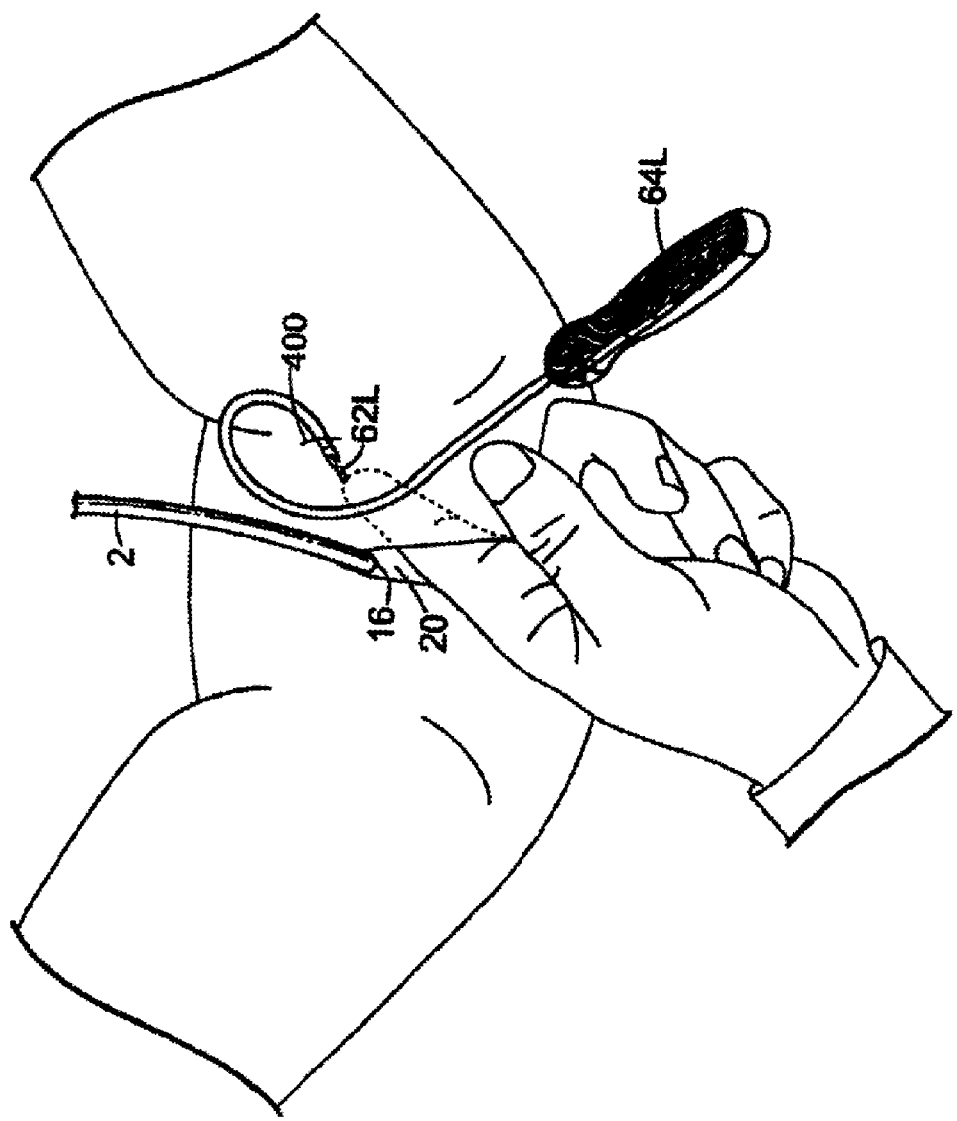
Figure 36:
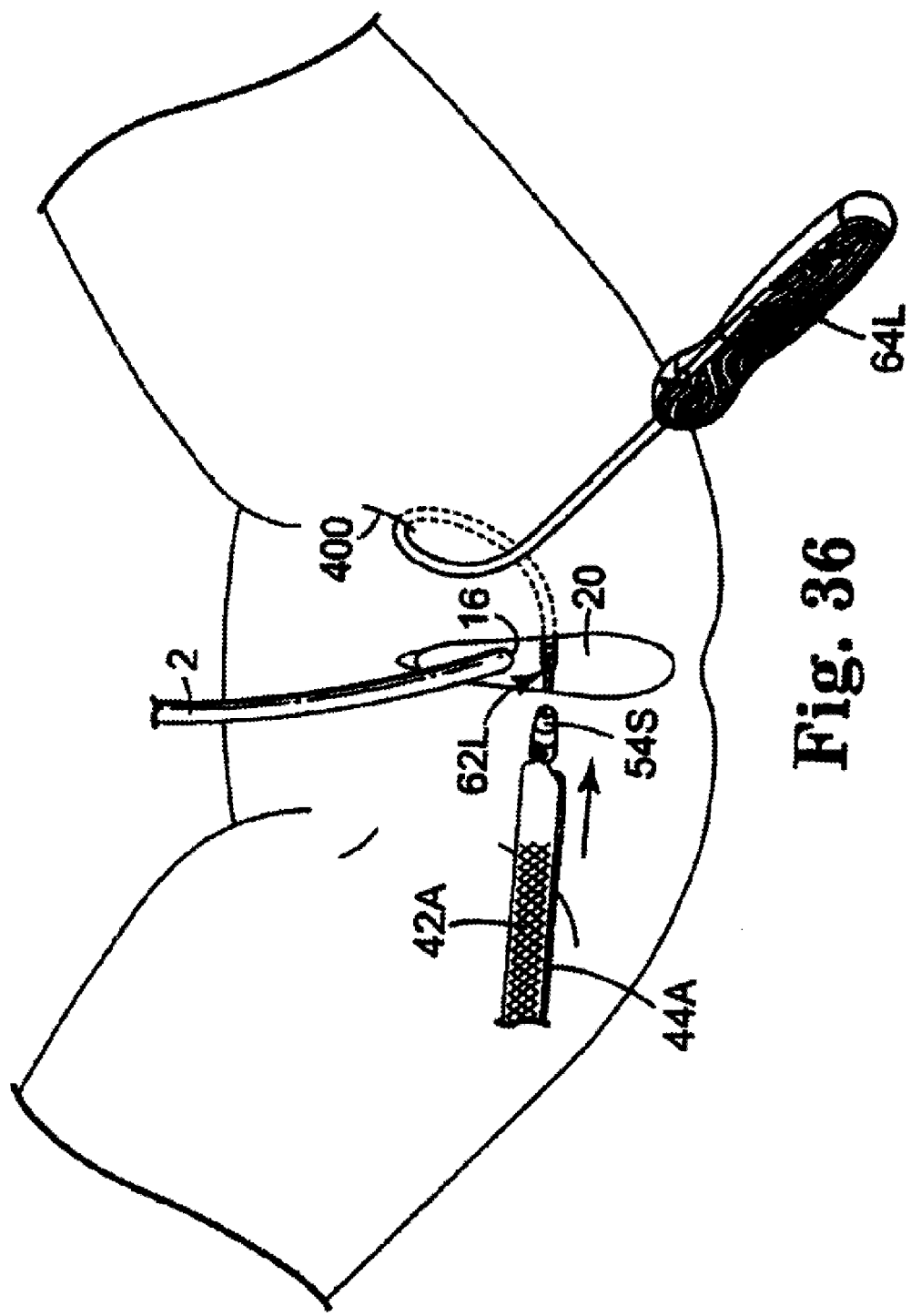
Figure 37:
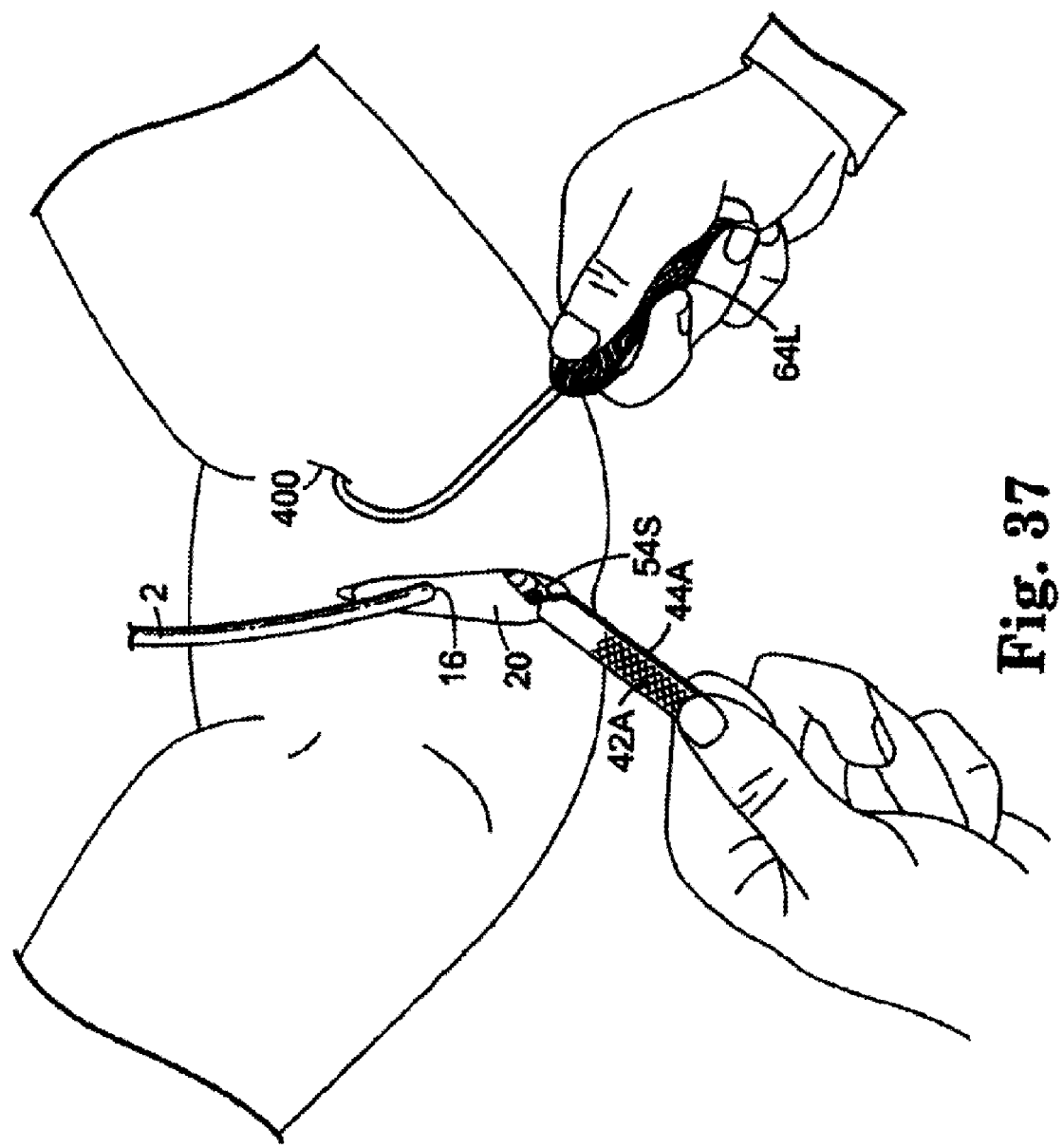
Figure 38:
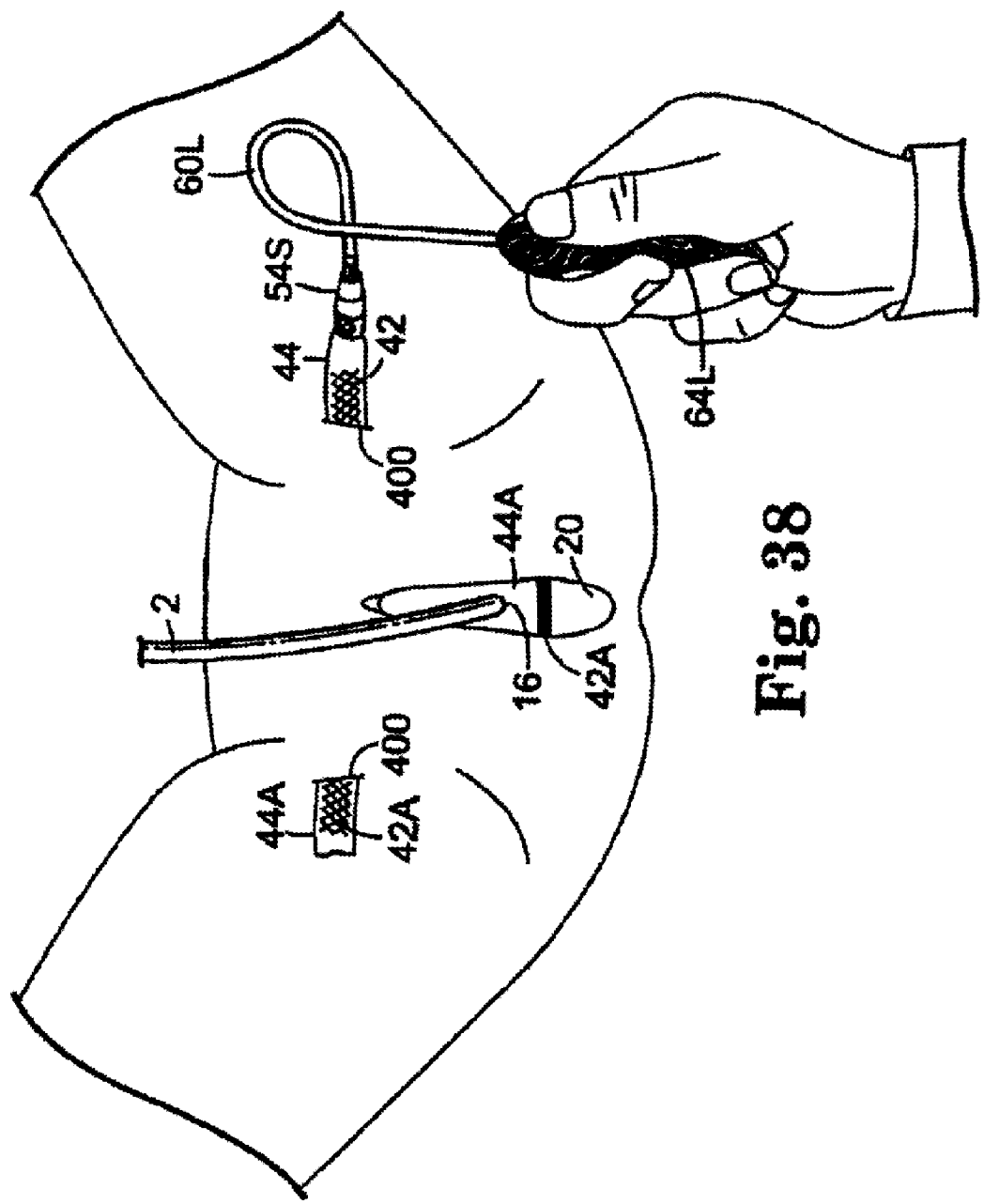
Figure 39:
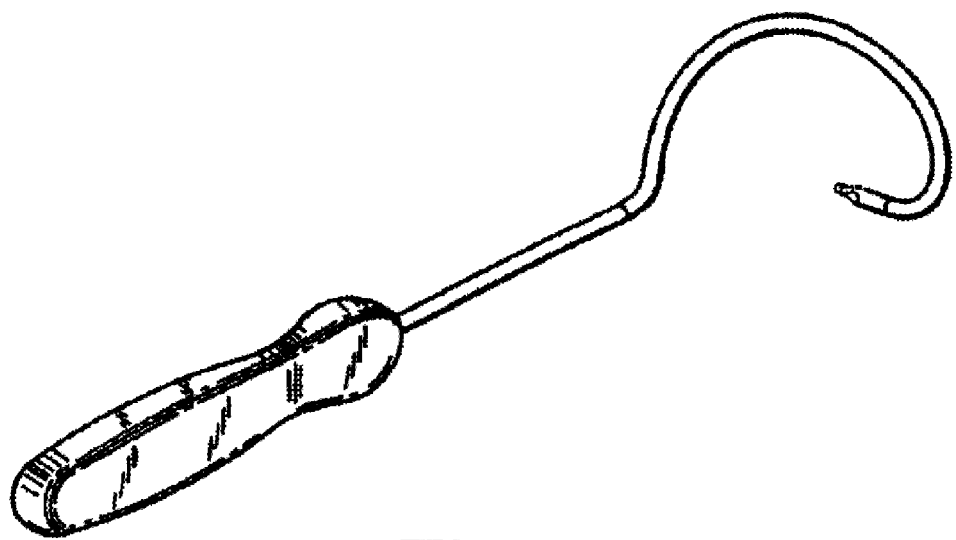
Figure 40:
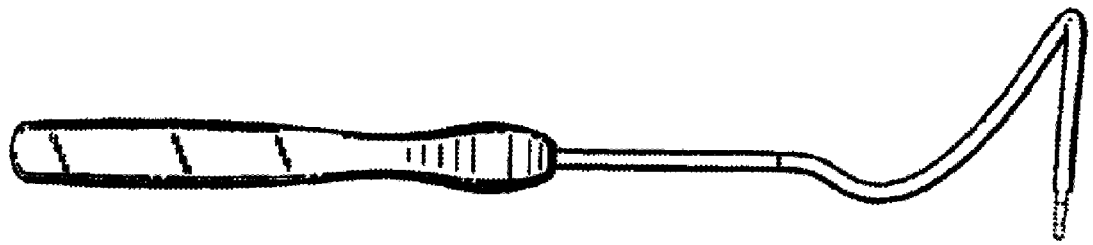
Figure 41:
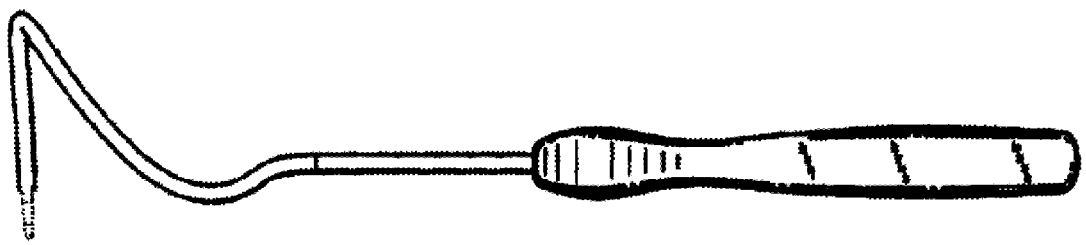
Figure 42:
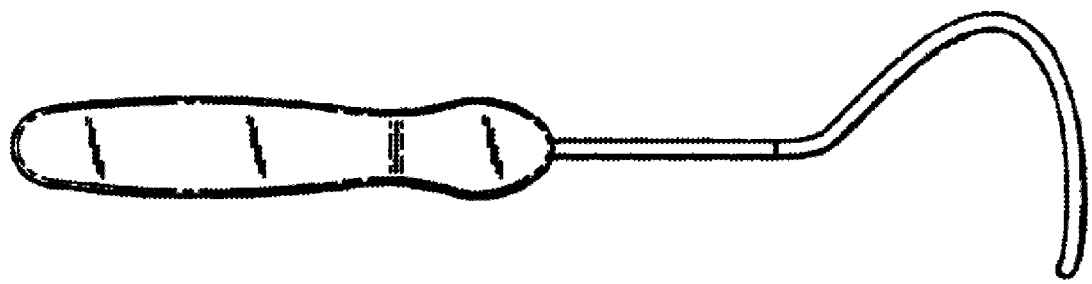
Figure 43:
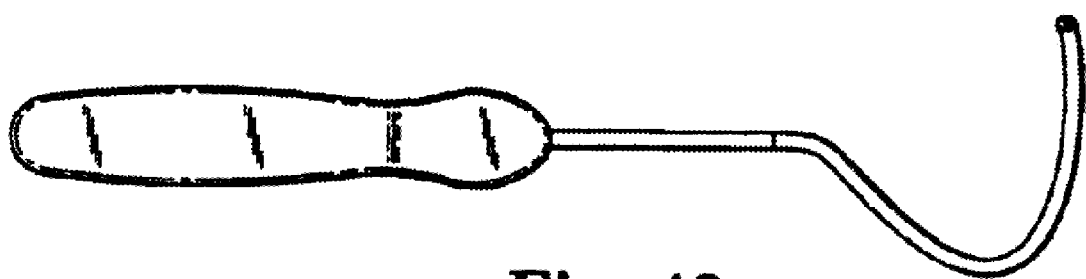
Figure 44:
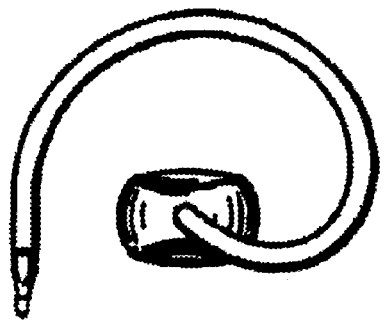
Figure 45:
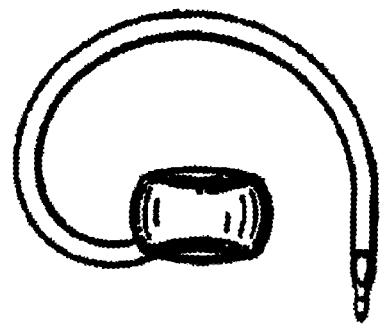
Figure 46:
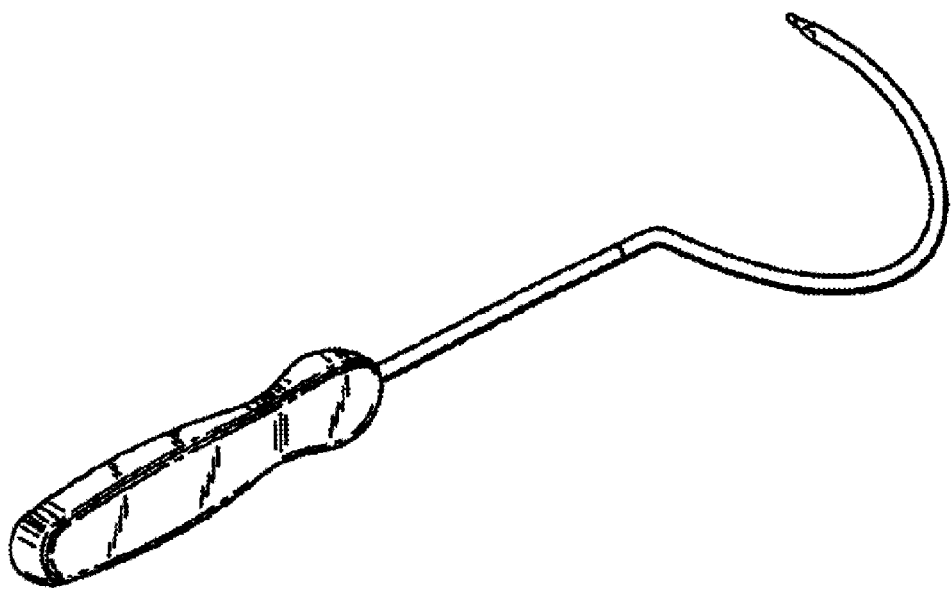
Figure 47:
Figure 48:
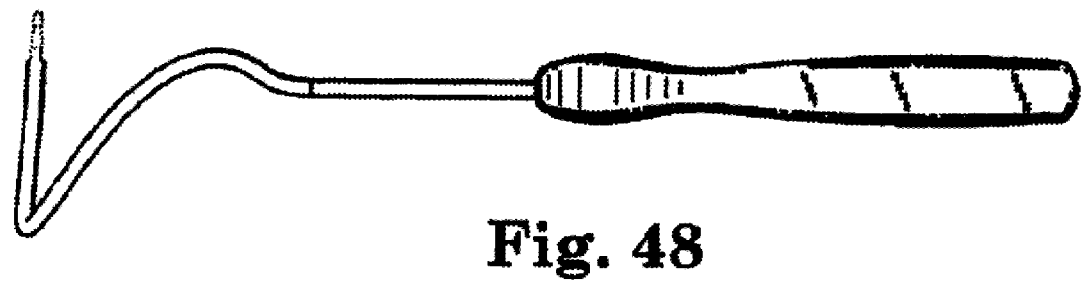
Figure 49:
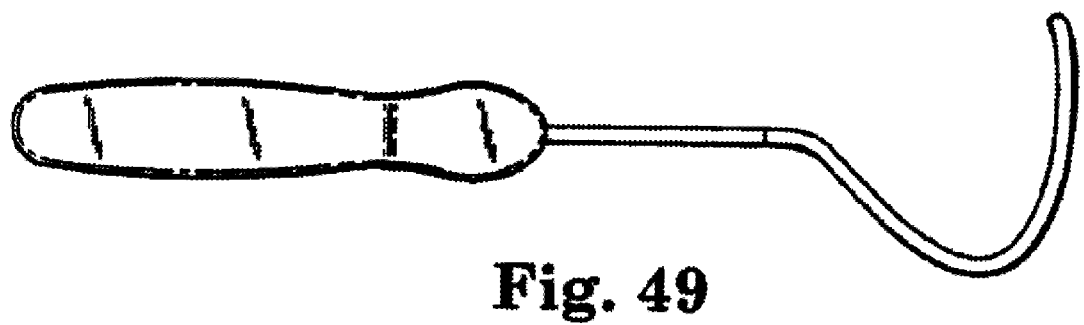
Figure 50:
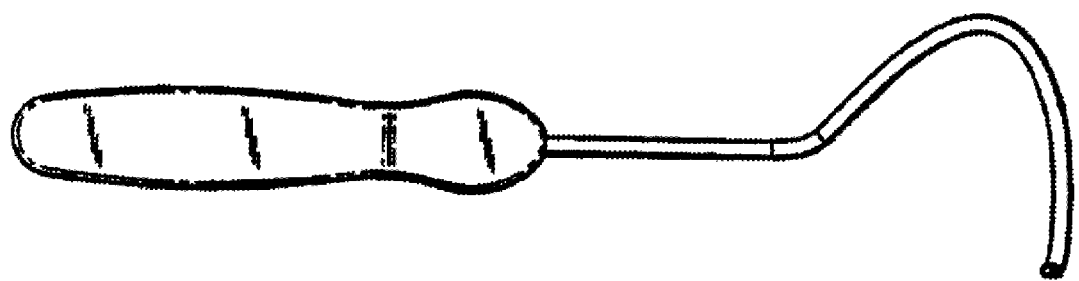
Figure 51:
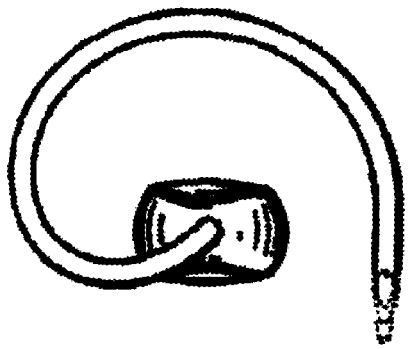
Figure 52:
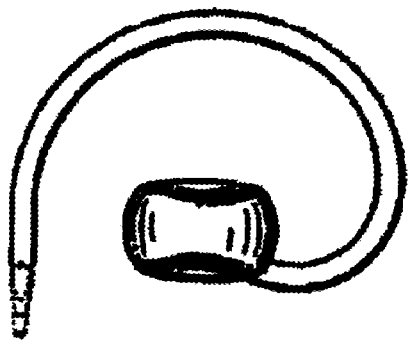
Figure 53:
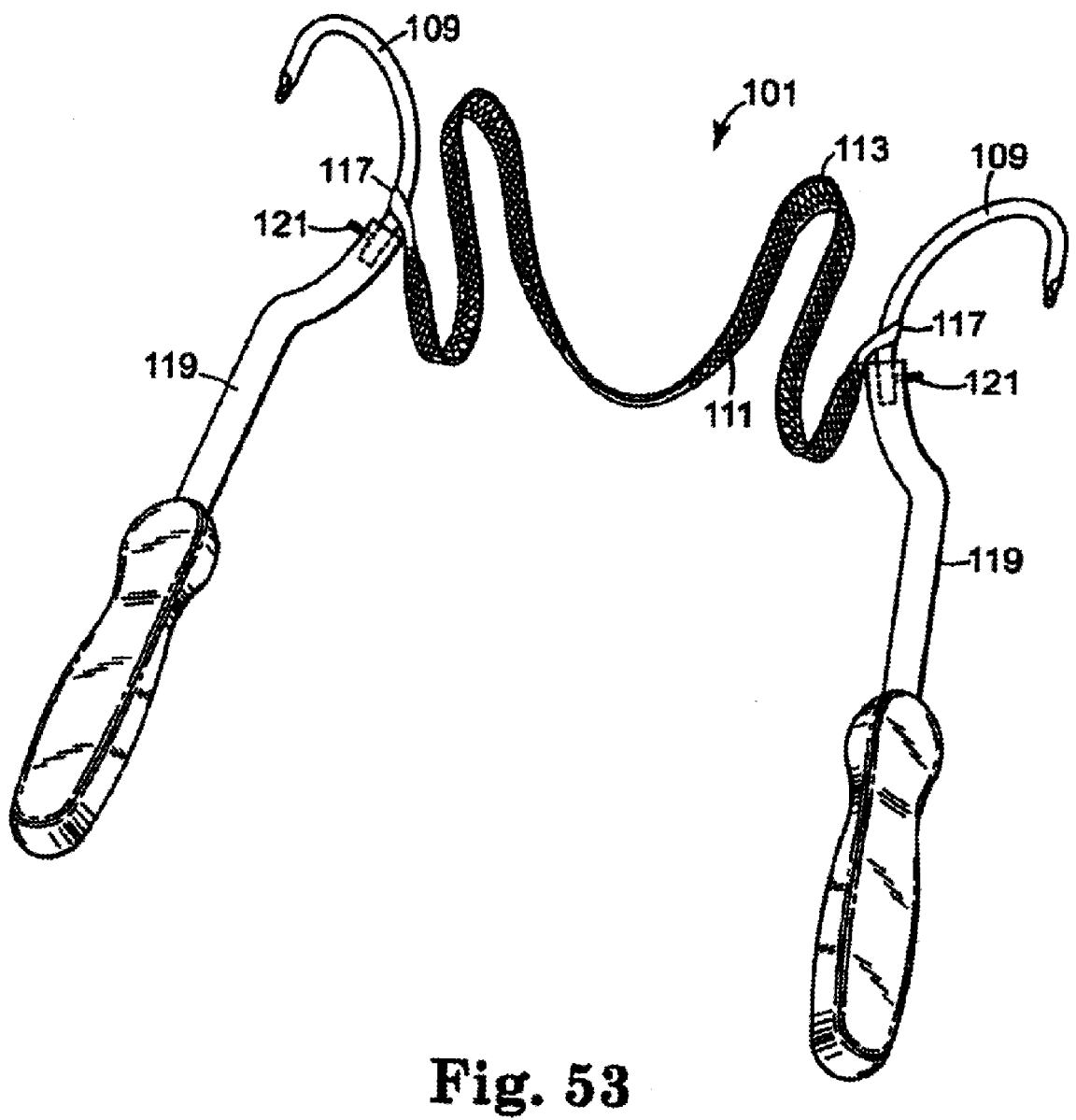
Figure 54:
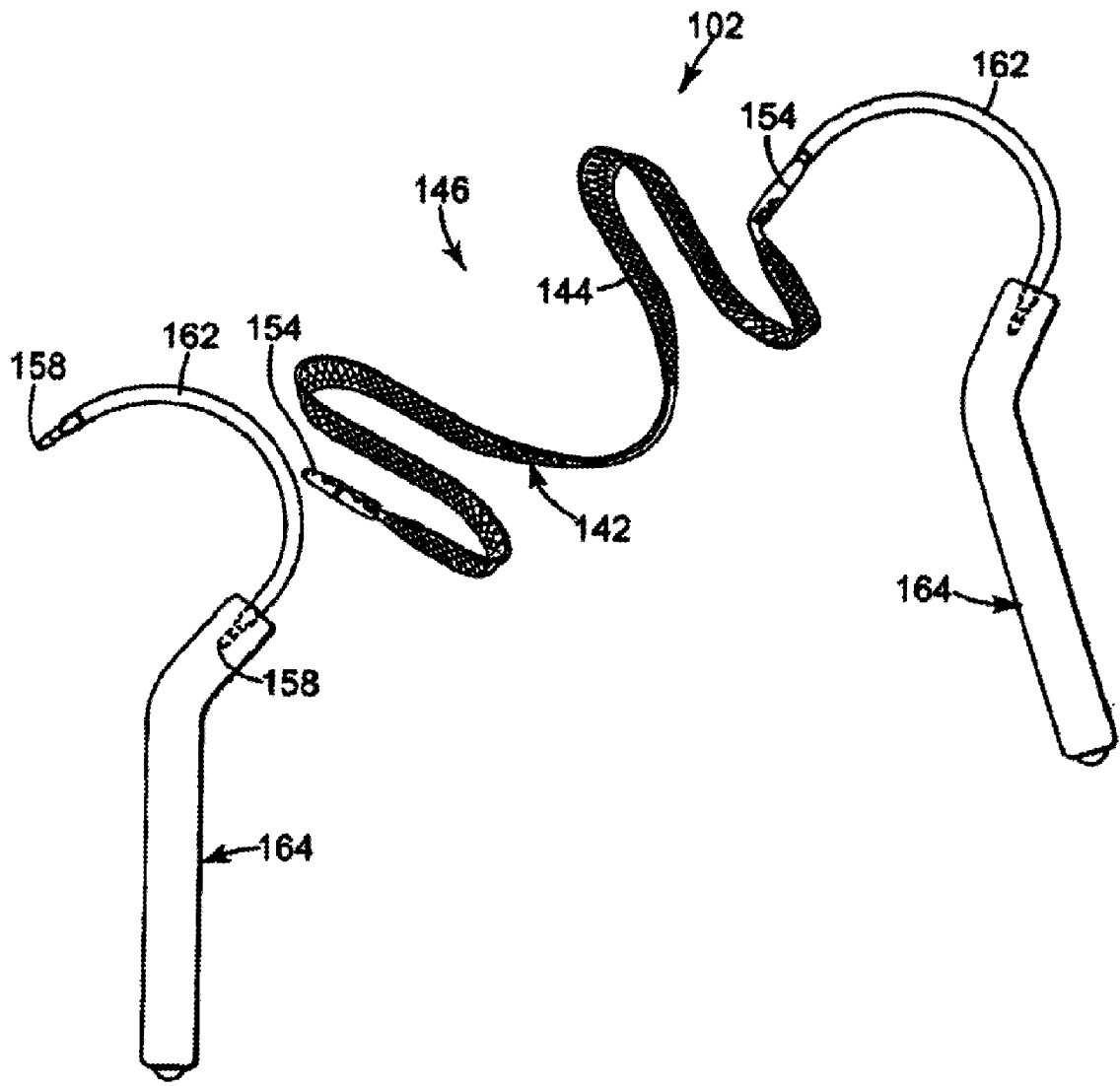
Figure 55:
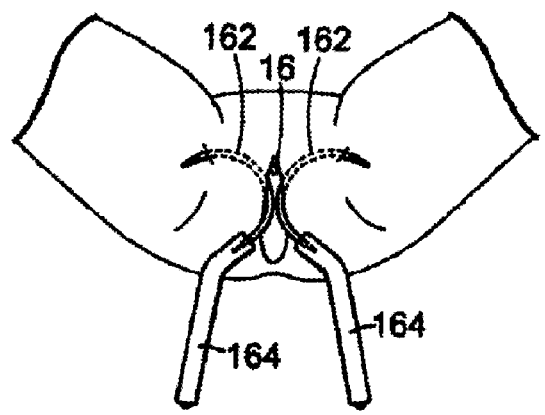
Figure 56:
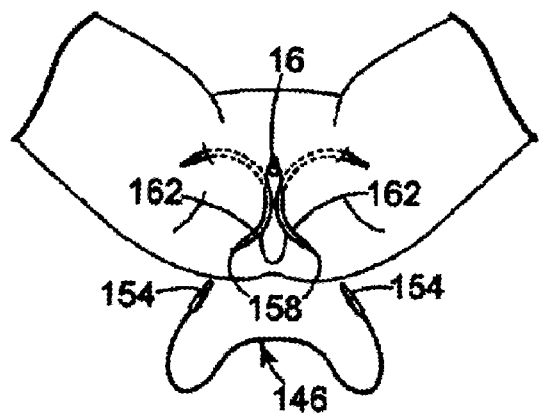
Figure 57:
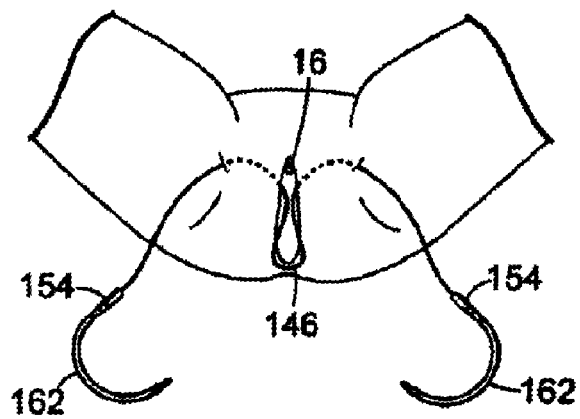
Figure 58:
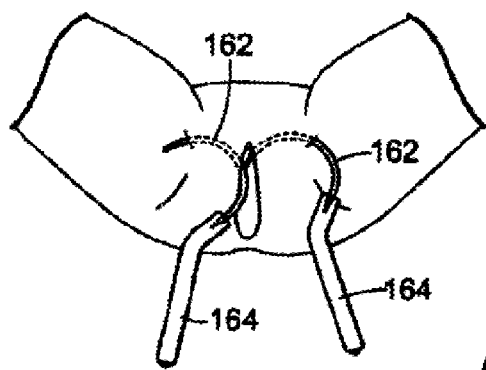
Figure 59:
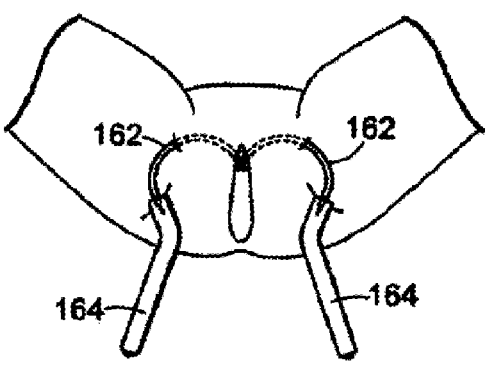
Figure 60:
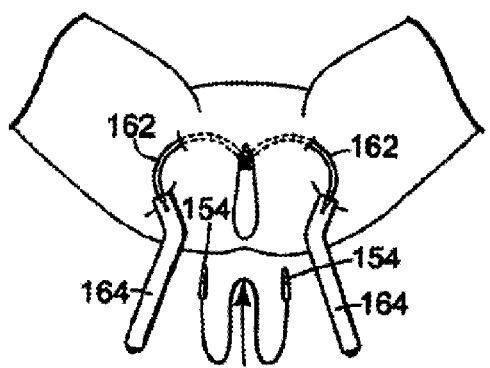
Figure 61:
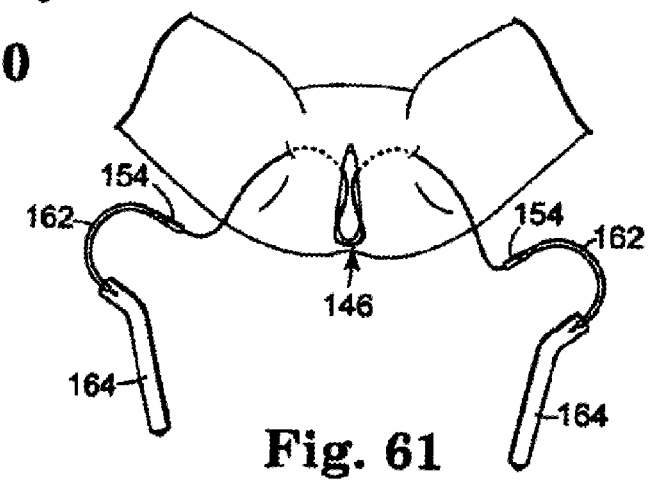
Figure 62:
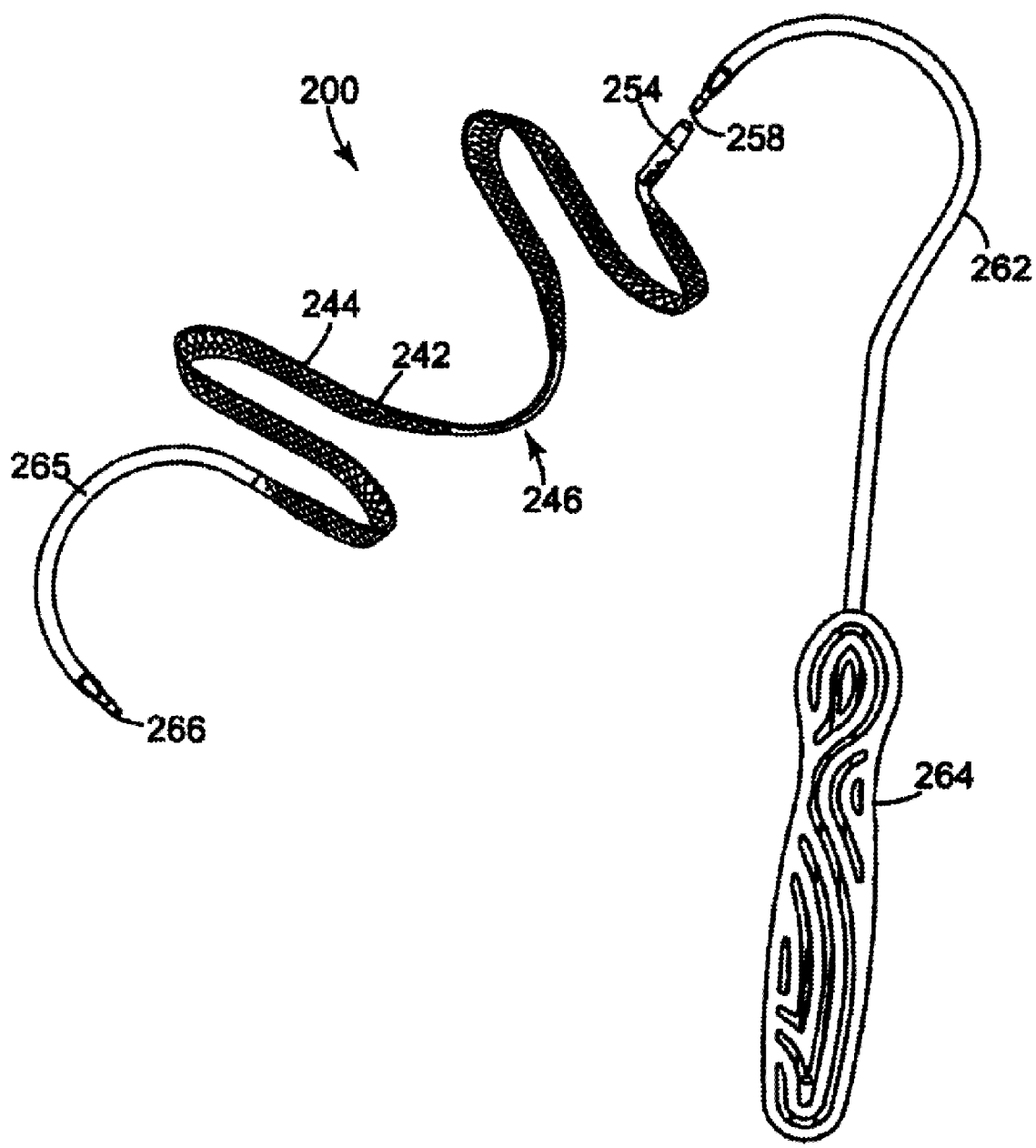
Figure 63:
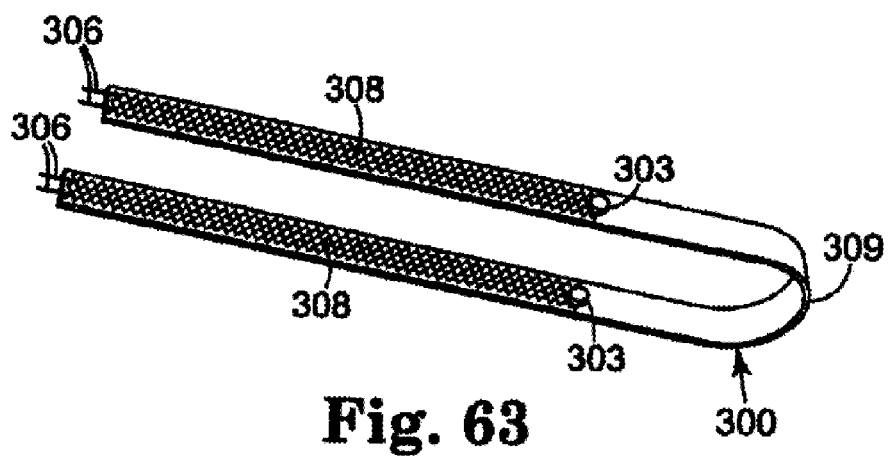
Figure 64:
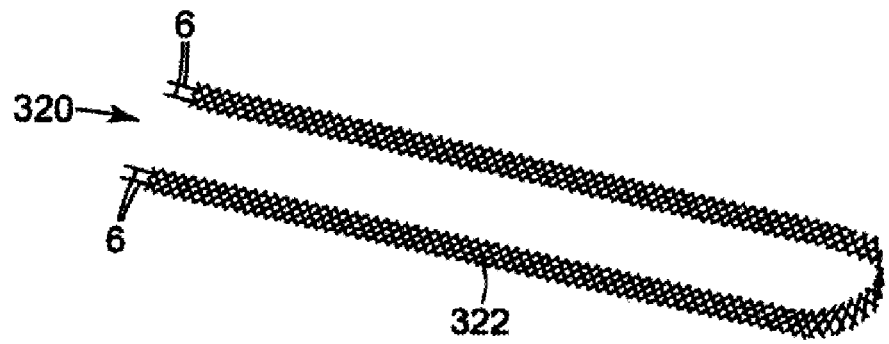
Figure 65:
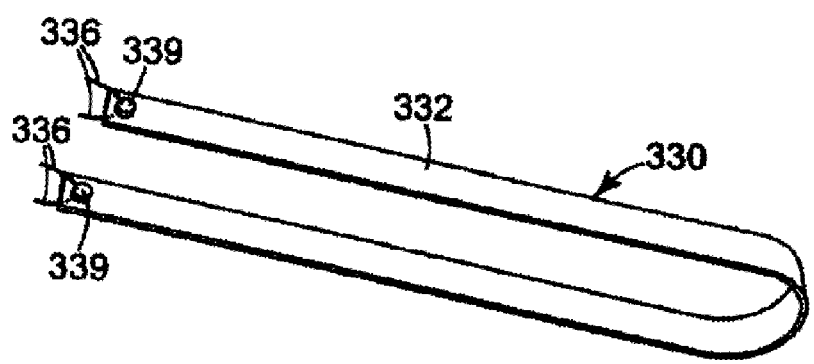
Figure 66:
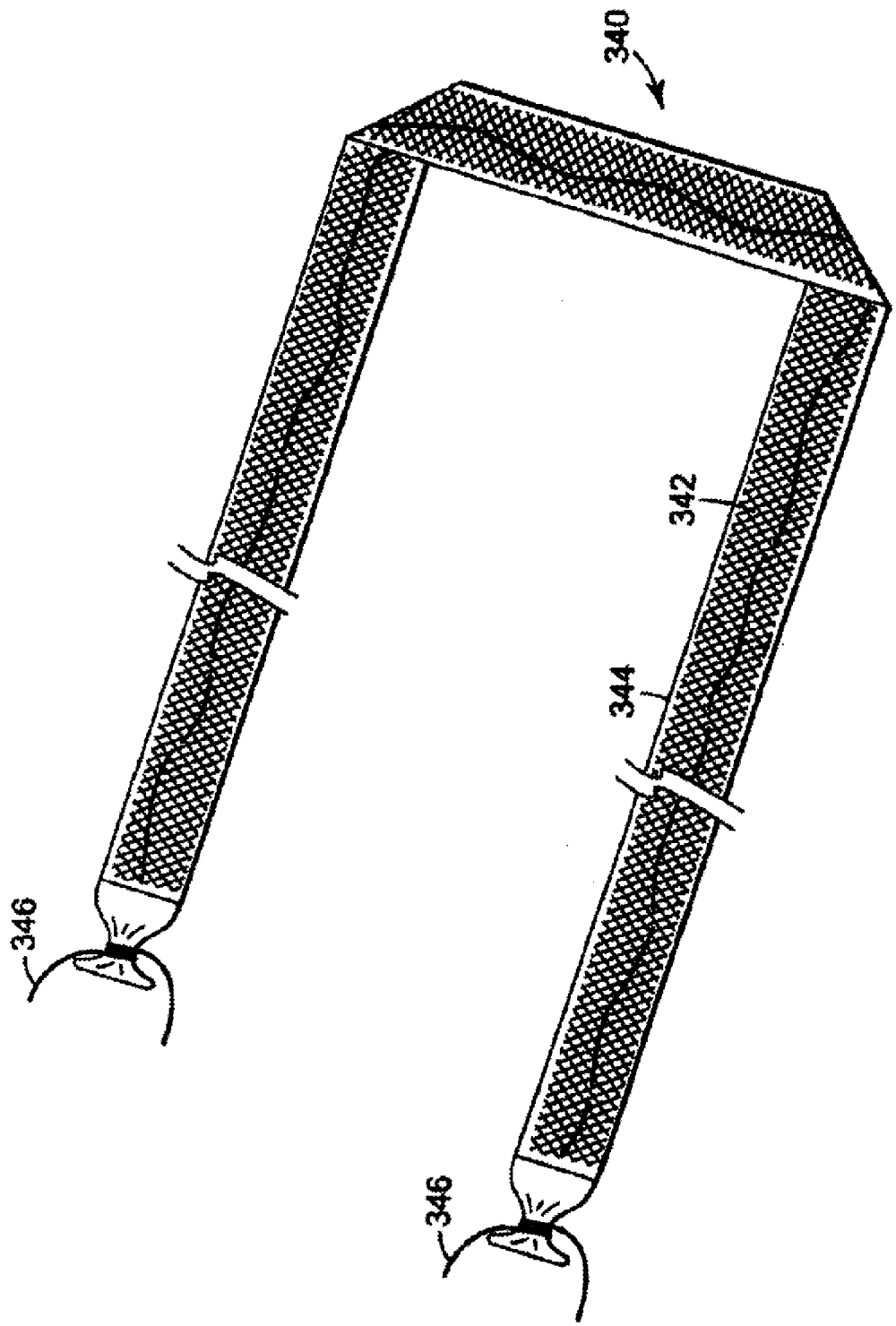
Figure 67:
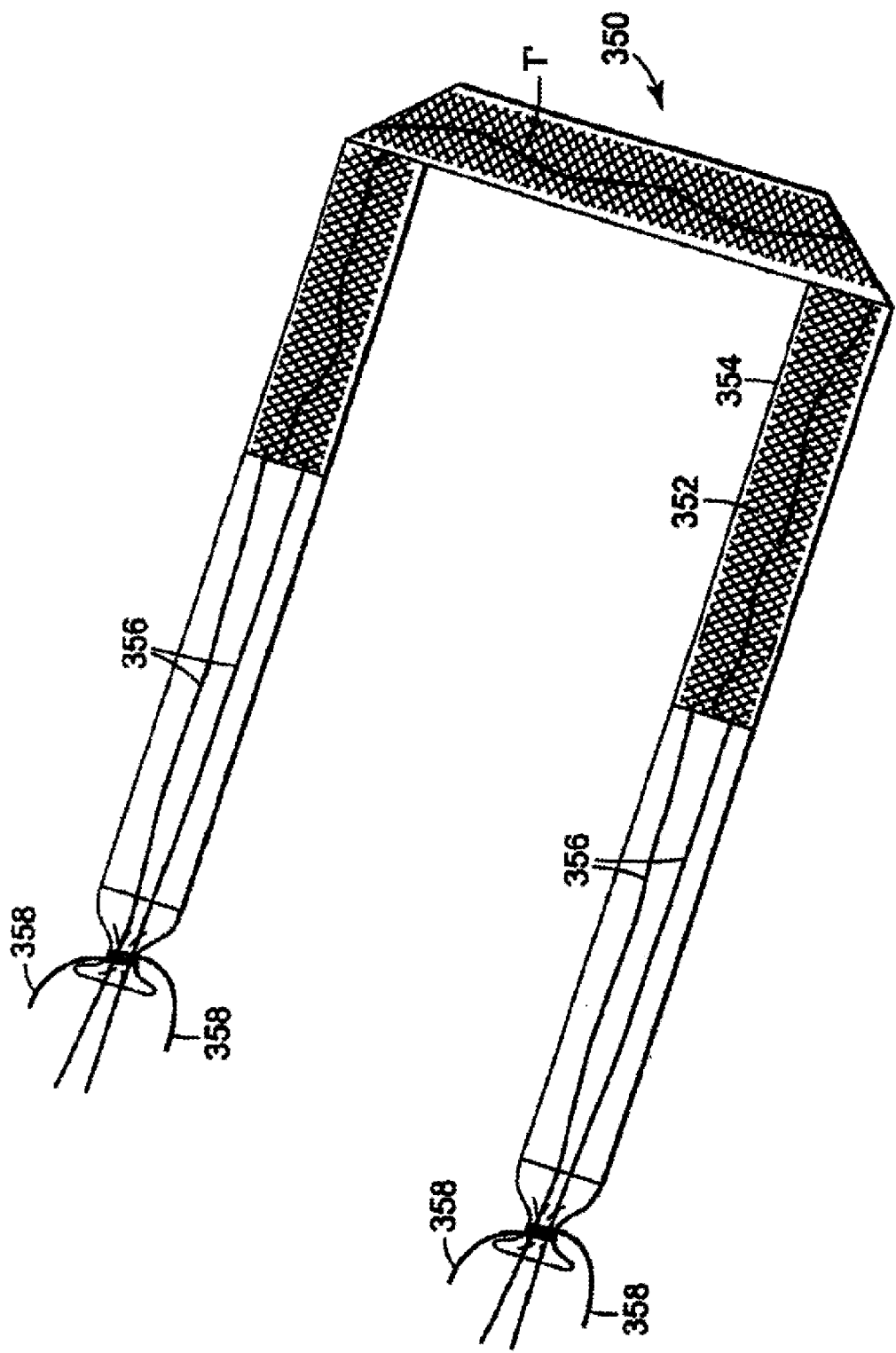

Other features and advantages of the present invention will be seen as the following description of particular embodiments progresses in conjunction with the drawings, in which:

FIG. 1 is a side view of a surgical needle according to one aspect of the present invention;

FIG. 2 is a perspective view of a needle, sling and additional optional elements for use in a kit according to an aspect of the present invention;

FIG. 3 is a top view of a kit according to one embodiment of the present invention;

FIGS. 4 through 10 are schematic views sequentially showing a surgical procedure in accordance with one aspect of the present invention, wherein:

FIG. 4 shows a needle just passing an incision on the right side of a patient's body with the tip of the needle shown in dotted lines;

FIG. 4A is a schematic view of an alternate approach, presented as an alternative to the step shown in FIG. 4, showing an inside-out approach using the needle of FIG. 1, which may be preferred by some surgeon's whose dominant hand is the right hand, the handle shown being a detachable handle that is movable from one end of the needle to the other, with solid lines being used to show the initial position of the handle and dashed lines and an arrow used to show a second position of the handle;

FIG. 5 illustrates a needle just passing an incision on the left side of a patient's body with the tip of the needle and part of the surgeon's finger shown in dotted lines;

FIG. 6 illustrates one side of a sling assembly and the needle of FIG. 5 as it emerges from the patient's vagina;

FIG. 7 shows the sling system of FIG. 6 after it is attached to the needle of FIG. 6;

FIG. 8 is a perspective view of a sling assembly being pulled through the body by a needle in accordance with the present invention;

FIG. 9 is a schematic view of the approximate relative positions of the pubic bone and the sling after the sling is inserted according to one aspect of the present invention;

FIG. 10 is an enlarged schematic view showing portions of FIG. 9;

FIG. 11 is a perspective view of another embodiment of the present invention;

FIG. 12 is a top view of another embodiment of sling for use in accordance with the present invention;

FIG. 13A is a front view of an optional handle suitable for use with the present invention;

FIG. 13B is a side view of the handle of FIG. 13A;

FIG. 14 is a perspective view of the handle of FIGS. 13A and 13B;

FIG. 15 is a perspective view of a surgical instrument particularly suitable for use on a right side of a patient's body, according to one aspect of the present invention;

FIG. 16 is an end view of the needle of FIG. 15;

FIG. 17 is a front view of the needle of FIG. 15;

FIG. 18 is a bottom view of the needle of FIG. 15;

FIG. 15A is a perspective view of a surgical instrument particularly suitable for use on a right side of a patient's body, which needle is similar, but not identical to the needle of FIG. 15;

FIG. 16A is an end view of the needle of FIG. 15A;

FIG. 17A is a front view of the needle of FIG. 15A;

FIG. 18A is a bottom view of the needle of FIG. 15A;

FIG. 19 is a perspective view of a surgical instrument particularly suitable for use on a left side of a patient's body, according to one aspect of the present invention;

FIG. 20 is an end view of the needle of FIG. 19;

FIG. 21 is a front view of the needle of FIG. 19;

FIG. 22 is a bottom view of the needle of FIG. 19;

FIG. 19A is a perspective view of a surgical instrument particularly suitable for use on a left side of a patient's body, which needle is similar, but not identical to the needle of FIG. 19;

FIG. 20A is an end view of the needle of FIG. 19A;

FIG. 20B is an end view of another embodiment of needle according to the present invention;

FIG. 21A is a front view of the needle of FIG. 19A;

FIG. 22A is a bottom view of the needle of FIG. 19A;

FIG. 23 is a perspective view of a short dilator for use in accordance with an aspect of the present invention;

FIG. 24 is an enlarged, sectional view of an internal portion of the dilator of FIG. 23 in accordance with an aspect of the present invention;

FIG. 25 is sectional view of the dilator of FIG. 23 in accordance with an aspect of the present invention;

FIGS. 25A and 26 are another sectional view of the dilator of FIG. 23 illustrating different features;

FIG. 26A is a sectional view illustrating a specially designed distal end portion of a needle inserted into the dilator of FIG. 25;

FIG. 27 is a side view of a distal end portion of a needle according to the present invention; showing a specially designed shape that is complementary to inner surfaces of the dilator of FIG. 23;

FIG. 28 is a perspective view of one embodiment of a sling assembly according to the present invention;

FIG. 29 is a side view of the sling assembly of FIG. 28;

FIG. 30 is a side view of a sling and tensioning suture according to an aspect of the present invention;

FIG. 31 is a schematic illustration of anatomical features, showing a pubic bone with dashed lines and incisions;

FIG. 32 is a schematic illustration of the relative positions of the patient's pubic bone and a novel needle according to the present invention, after at least partially inserting the needle;

FIG. 33 is a schematic illustration of the relative positions of the patient's pubic bone and a novel needle according to the present invention, after at least partially inserting the needle;

FIGS. 34 through 38 are perspective views sequentially showing a surgical procedure in accordance with another aspect of the present invention, wherein:

FIG. 34 shows a needle just passing an incision on the right side of a patient's body with the tip of the needle shown in dotted lines;

FIG. 35 illustrates a needle just passing an incision on the left side of a patient's body with the tip of the needle and part of the surgeon's finger shown in dotted lines;

FIG. 36 illustrates one side of a sling assembly and the needle of FIG. 35 as it emerges from the patient's vagina;

FIG. 37 shows the sling assembly of FIG. 36 after it is attached to the needle of FIG. 36;

FIG. 38 is a perspective view of a sling assembly being pulled through the body by a needle in accordance with the present invention;

FIG. 39 is a perspective view of a design of a surgical instrument according to another aspect of the present invention;

FIG. 40 is a top view of the instrument of FIG. 39;

FIG. 41 is a bottom view of the instrument of FIG. 39;

FIG. 42 is a front view of the instrument of FIG. 39;

FIG. 43 is a rear view of the instrument of FIG. 39;

FIG. 44 is a right end view of the instrument of FIG. 39;

FIG. 45 is a left end view of the instrument of FIG. 39;

FIG. 46 is a perspective view of a design of a instrument according to another aspect of the present invention;

FIG. 47 is a top view of the instrument of FIG. 46;

FIG. 48 is a bottom view of the instrument of FIG. 46;

FIG. 49 is a front view of the instrument of FIG. 46;

FIG. 50 is a rear view of the instrument of FIG. 46;

FIG. 51 is a right end view of the instrument of FIG. 46;

FIG. 52 is a left end view of the instrument of FIG. 46;

FIG. 53 is a perspective view of a system for use in an inside out procedure according to the present invention that includes a portion that is at least partially reusable;

FIG. 54 is a perspective view of a universal system capable of use in inside-out and outside in approaches according to the present invention, which system includes a needle having two ends capable of attachment to either a handle or a sling assembly;

FIGS. 55-57 sequentially illustrate use of the system of FIG. 54 wherein:

FIG. 55 illustrates passage of the needles using inside-out approaches,

FIG. 56 illustrates the needles after the handles have been removed, in preparation for attachment of a sling assembly on the ends of the needles previously occupied by the handles;

FIG. 57 illustrates the system during implantation of the sling;

FIG. 58 is a schematic illustration of the system of FIG. 54 used in an inside-out approach (the right side of the patient) and an outside-in (the left side of the patient) approach;

FIGS. 59-61 sequentially illustrate the system of FIG. 54 used in outside-in approaches wherein:

FIG. 59 illustrates the needles inserted initially through the patient's skin and thereafter emerging from a vaginal incision;

FIG. 60 illustrates the system just prior to attachment of a sling assembly;

FIG. 61 illustrates the system of FIG. 54 during implantation of the sling;

FIG. 62 is a perspective view of another embodiment of surgical assembly according to the present invention, with a needle suitable for an outside-in approach (e.g. on the left side of the patient's body) and a sling assembly with a needle attached thereto suitable for an inside-out approach (e.g. through the right side of the patient's body);

FIG. 63 is a perspective view of an alternative embodiment of sling assembly for use in accordance with the present invention;

FIG. 64 is a perspective view of an alternative embodiment of sling assembly for use in accordance with the present invention, which assembly does not include a sheath;

FIG. 65 is a perspective view of an alternative embodiment of sling assembly for use in accordance with the present invention;

FIG. 66 is a top plan view of an alternative embodiment of sling assembly for use in accordance with the present invention; and FIG. 67 is a top plan view of an alternative embodiment of sling assembly for use in accordance with the present invention.

The broken line showing of structures on the design of the surgical instruments in FIGS. 39 through 52 are for illustrative purposes only and form no part of the claimed design.

DETAILED DESCRIPTION

The following description is meant to be illustrative only and not limiting. Other embodiments of this invention will be apparent to those of ordinary skill in the art in view of this description.

The present invention is directed to surgical instruments, assemblies and implantable articles for treating pelvic floor disorders such as incontinence or stress urinary incontinence (SUI) in both men and women. The present invention is also directed to improved surgical procedures that utilize the surgical articles.

FIG. 1 is a side view of a sling assembly guide or needle 60 according to one aspect of the present invention. The needle 60 is preferably sized and shaped to be suitable for initial insertion through obturator fascia (see FIGS. 4 through 8). The needle 60 has a length sufficient to extend from the initial incision 400 adjacent the anterior side of the pubic bone, through the obturator foramen 3 (e.g. see FIG. 9) portion of the pubic bone to a position on the posterior side of the pubic bone, and to then emerge from a vaginal incision. While FIG. 1 is a side view or a species of the present invention, the present invention is not limited to the particular shape disclosed. It is expressly understood that a large number of different sizes, shapes and dimensions of needles are suitable for the present invention.

There are many vulnerable, sensitive pelvic anatomical structures and tissues in the region of the obturator foramen 3, including the pudendal artery (internal), the pudendal canal (Alcock), and nerves (e.g. the perineal and labial). The needle 60 is preferably sized and shaped to pass through the obturator foramen 3 along a path that is substantially free of vascular and nerve structures. The size and shape of the needle 60 help avoid the sensitive structures. For example, in one embodiment, the path may be in a region between the superior pubic ramus and the inferior pubic ramus (see e.g. FIGS. 4 through 10). The tip of the needle is preferably substantially blunt to help avoid damage to the sensitive structures. Alternatively, the tip may be slightly sharpened to assist in the initial passage of the needle.

Preferably, the needle 60 comprises three substantial linear portions 60A, 60B and 60C; each situated at an angle relative to the other linear portions. Preferably, the angles are different. The needle 60 preferably includes a leading portion 60A, an intermediate portion 60B and a trailing portion 60C.

The leading portion 60A of the needle 60 is sized to extend through the initial incision 400. The cross-sectional shape of the needle 60 is preferably substantially circular, but other cross sectional shapes such as, but not limited to, elliptical, polygonal, square and triangular are also contemplated herein. The diameter of the leading portion 60A is less than 5 mm, more preferably less than 4 mm, and even more preferably less than 3.5 mm to avoid damaging or displacing tissue. The sudden angle between the intermediate portion 60B of the needle and the leading portion 60A helps the surgeon avoid sudden lurches of the needle after the end 58 passes through the obturator fascia, as the intermediate 60B or trailing 60C portions of the needle can be grasped or abut external portions of the patient to stop an undesirable, sudden lurch through tissue. The angle also helps the surgeon steer the needle 60 along a desired or predetermined path.

The angle between the intermediate portion 60B and the trailing portion 60C is preferable greater than ninety degrees, more preferably, it is greater than one hundred and twenty degrees. The length of the trailing portion 60C should be sufficient to allow the surgeon to leverage the end 58 of the needle and drive it along its predetermined, desired path. This geometry helps direct the end of the needle 58 back toward the surgeon. This geometry also helps the surgeon pass the needle through this portion of the body and emerge from the vagina without undue tissue trauma.

FIG. 3 illustrates a kit 15 according to an aspect of the present invention. The kit 15 preferably comprises an implantable material (e.g. a sling mesh provided as part of a sling assembly 46), at least one (preferably two) optional handle 64, and at least one (preferably two) needle 60.

The handle 64 is entirely optional. The handle may be removably attached to the needle, or it may be repositionably attached to the needle. Alternatively, the handle may be permanently attached to the needle 60. FIGS. 13 and 14 illustrate an optional shape of handle 64A suitable for permanent attachment to the needle 60. Other suitable handles are disclosed, for example, in U.S. Provisional Patent Application Nos. 60/347,494; 60/336,884 and 60/343,658.

The needle 60 is preferably made of a durable, biocompatable surgical instrument material such as, but not limited to, stainless steel (e.g. 316 stainless steel or 17-4 stainless steel), titanium, Nitinol, polymers, plastics and other materials, including combinations of materials. The needle 60 should have sufficient structural integrity to withstand the various forces (e.g. forces caused by dilator attachment, and penetration/passage of the needle 60 through the various tissues) without undergoing any significant structural deformation. Optionally, the needles 60 could be sufficiently malleable to allow a practitioner or user of the device to modify the needle 60 to a desired shape and, thereby, optimize the procedural approach.

Needles 60 may be disposable or reusable (e.g. sterilizable by steam sterilization procedures). In another aspect of the present invention, the needles 60 may be provided in a kit, such as any of the kits described in any of published U.S. patent application Ser. Nos. 2002-0151762-A1; 2002-0147382-A1; 2002-0107430-A1, US-2002-0099258-A1 and US-2002-0099259-A1; and U.S. Provisional Application Ser. Nos. 60/263,472, filed Jan. 23, 2001; 60/269,829, filed Feb. 20, 2001; 60/281,350, filed Apr. 4, 2001; 60/295,068, filed Jun. 1, 2001; 60/306,915, filed Jul. 20, 2001, and U.S. Provisional Patent Application Ser. No. 60/332,330, filed Nov. 20, 2001.

One embodiment of kit includes the needle 60 and other needles (not shown, but for example including the needles shown in published U.S. patent application Ser. No. US-2002-0099258-A1) designed for placing a sling from the abdominal rectus fascia, under the urethra, and then back to the rectus fascia. If a traditional pubovaginal sling procedure seems to be an option for a patient but, during or prior to the surgical procedure, it becomes apparent that excessive scar tissue (e.g. due to a previous surgery) exists and would render the traditional procedure less desirable or impossible, then the needle 60 may be used in an alternative approach. Since the needles 60 are also provided in a kit, the surgeon has the option of conducting an alternative surgical procedure with the needles 60.

In another aspect of the present invention, a needle may optionally include the capacity to deliver a medicament (e.g. anesthesia) during the surgical procedure. For example, the needle 60 may be hollow with an open end. The needle may have a connector for associating with a medicament reservoir and delivery mechanism (e.g. a syringe).

The present invention may be utilized in conjunction with a wide variety of sling materials and sling assemblies. The sling may be integral, monolithic, or a composite of different components or segments of different components. Suitable non-synthetic materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium and fascia lata. Suitable synthetic materials for a sling include polymerics, metals and plastics and any combination of such materials.

Commercial examples of non-absorbable materials include Marlex™ (polypropylene) available from Bard of Covington, R.I., Prolene™ (polypropylene) and Mersilene (polyethylene terphthalate) Hernia Mesh available from Ethicon, of New Jersey, Gore-TeX™ (expanded polytetrafluoroethylene) available from W. L. Gore and associates, Phoenix, Ariz., and the polypropylene sling available in the SPARC™ sling system, available from American Medical Systems, Inc. of Minnetonka, Minn. Commercial examples of absorbable materials include Dexon™ (polyglycolic acid) available from Davis and Geck of Danbury, Conn., and Vicryl™ available from Ethicon. Other examples of suitable materials include those disclosed in U.S. patent application Ser. No. 09/939,098 filed Aug. 24, 2001 and published U.S. patent application Ser. No. 2002/0072694. More specific examples of synthetic sling materials include, but are not limited to polypropylene, cellulose, polyvinyl, silicone, polytetrafluoroethylene, polygalactin, Silastic, carbon-fiber, polyethylene, nylon, polyester (e.g. dacron) PLLA and PGA. The sling material may be resorbable, absorbable or non-absorbable. Optionally, some portions may be absorbable and other portions may be non-absorbable.

The synthetic slings may be knitted, woven, sprayed or punched from a blank. Some slings may be sufficiently robust to be inserted without a protective sleeve. In other embodiments, some synthetic slings may have an associated protective sleeve (described in greater detail below) to assist with the implantation.

In one aspect of the invention, the sling may comprise a mesh material. The mesh material comprises one or more woven, knitted or inter-linked filaments or fibers that form multiple fiber junctions throughout the mesh. The fiber junctions may be formed via weaving, knitting, braiding, bonding, ultrasonic welding or other junction forming techniques, including combinations thereof. In addition, the size of the resultant openings or pores of the mesh may be sufficient to allow tissue in-growth and fixation within surrounding tissue. As an example, not intended to be limiting, the holes may comprise polygonal shaped holes with diagonals of 0.132 inches and 0.076 inches.

The quantity and type of fiber junctions, fiber weave, pattern, and material type influence various sling properties or characteristics. As another example, not intended to be limiting, the mesh may be woven polypropylene monofilament, knitted with a warp tricot. The stitch count may be 27.5 courses/inch (+ or −2 courses) and 13 wales/inch (+ or −2 wales). The thickness of this example is 0.024 inches. This embodiment of sling is preferably associated with a protective sleeve (described in greater detail below). Non-mesh sling configurations are also included within the scope of the invention.

Referring to FIGS. 29 and 30, the sling mesh 42A is preferably elastic, as opposed to the substantially inelastic mesh available in Europe as Uratape® from Porges, and the tape described in Published U.S. patent application Ser. No. 2002/0099260. As an example, a mesh may be tested to determine whether it is elastic using a series IX Automated Materials Testing System (an Instron), available from Instron Corporation. A 1 cm wide sample of the mesh may be placed in the Instron with a crosshead speed set at 5 in/min and a gauge length of 1 inch. An elastic mesh exhibits at least a 7% elongation under a ½ pound load, more preferably about a 10% elongation under a ½ pound load, and more preferably about 14% under the ½ pound load. An inelastic mesh exhibits less than an 7% elongation under a ½ pound load.

The mid-portion of the sling mesh (the portion designed to reside underneath the midurethra) is preferably substantially free of any silicone coatings. In yet another embodiment (e.g. shown in FIG. 28), the mid-portion of the sling may comprise a non-synthetic material, constructed according to the teachings of U.S. Provisional Patent Appl. No. 60/405,139, filed Aug. 22, 2002. Other suitable synthetic slings are described in published U.S. Pat. No. 2002-0138025-A1, published Sep. 26, 2002.

In another embodiment the sling material may have one or more substances associated therewith through a process such as coating or they may be incorporated into the raw material of the sling. Examples of appropriate substances include, without limitation, drugs, hormones, antibiotics, antimicrobial substances, dyes, silicone elastomers, polyurethanes, radiopaque filaments or substances, anti-bacterial substances, chemicals or agents, including any combinations thereof. The substances may be used to enhance treatment effects, reduce potential sling rejection by the body, reduce the chances of tissue erosion, enhance visualization, indicate proper sling orientation, resist infection or other effects.

While the slings are preferably rectangular for treating SUI in females, other shapes are also contemplated. Depending on the treatment addressed (e.g. to provide hammock support for the bladder or bladder neck, or to address a rectocele, enterocele or prolapse) the slings may be any of a wide variety of shapes. As an example, the sling may be of the general shape of the slings described and shown in Moir et al., *The Gauze-Hammock Operation*, Journal of Obstetrics and Gynecology of the British Commonwealth, Volume 75, No. 1, Pps. 1-9 (1968).

FIG. 12 shows a sling 90 with a shape other than a purely rectangular shape. This embodiment of sling 90 includes a mid portion that is wider than the remaining portions of the sling 90. The mid portion is preferably placed under the urethra 16, along the mid portion of the urethra FIG. 2 illustrates a sling assembly 46 comprising sling 42 and sheath 44. Preferably, the overall dimensions of the sling assembly 46, including insertion sheath 44 and sling 42 are sufficient to extend from a superficial incision 400 near the obturator fascia (see FIGS. 4 through 8), to an undersurface of the urethra 16 and back to another incision 400 in obturator fascia that is opposite the first incision. The size of the sling can take into account the imprecision associated with the range of human anatomy sizes. In a preferred embodiment, the sheath length of the assembly of the present invention is approximately within the range of 10 cm to 50 cm, sheath width is approximately within the range of 1.0 cm to 2 cm, and sheath material thickness is approximately within the range of 0.127 mm to 0.203 mm, respectively. The associated sling 42 has a length, width and thickness approximately within the range of 7 cm to 50 cm; 1.0 cm to 2 cm; and 0.508 mm to 0.711 mm, respectively.

The sling 42 of the present invention can be implanted without the need for bone screws. The precise, final location of the sling 42 will depend on a variety of factors including the particular surgical procedure(s) performed, and any preconditions of the patient such as scar tissue or previous surgeries. For example, it may be preferred to place the sling 42 in close proximity to, but not in contact with, a mid portion of the urethra to treat incontinence. Alternatively, the sling may be placed near the bladder neck.

Preferably, the sling 42 has a tensioning filament or suture T as disclosed, for example, in U.S. Published patent application Ser. No. US-2002-0107430-A1. The tensioning suture T may be constructed from a permanent or absorbable material. Also preferably, the sling 42 comprises a substantially elastic, polypropylene sling such as a sling constructed from the polypropylene sling material available in the SPARC Sling System, available from American Medical Systems of Minnetonka, Minn.

FIG. 30 illustrates an embodiment with the tensioning filament T extending along end portions, but not extending along a mid-portion of the sling. The sling 42A comprises a polypropylene sling mesh 42A. It is constructed of polypropylene monofilament that is precut to about 1.1 cm width×35 cm length. The tensioning filaments T in this embodiment are fixed at each end to the sling material (e.g. a polypropylene mesh) by welding (e.g. ultrasonic), knotting, anchoring, adhering (e.g. with and adhesive) or the like. Absorbable tensioning sutures T are threaded into the length of the sling mesh 42A from each end to allow for tensioning adjustment of the sling mesh 42A after placement in the patient is achieved. The mid portion of the sling mesh 42A is preferably free of the tensioning sutures T. For example, approximately 5 mm may separate the ends of the two tensioning sutures T.

Two plastic sheaths 44A (see FIG. 29) that overlap in the center of the sling mesh cover the sling mesh and protect it during placement. The plastic covering over the mesh is designed to minimize the risk of contamination.

Referring to FIG. 2, a protective sheath 44 is preferred, especially when the sling 42 is elastic. A sheath is particularly desirable when the sling is elastic as the sheath 44 assists in introduction of the sling within tissue and avoids damage to the elastic sling material. The sheath 44 is used during insertion of a synthetic sling 42. After the sling 42 is implanted, the sheath 44 is removed and discarded. Preferably, the protective sheath 44 is constructed of a material that affords visual examination of the implantable sling material 42 and that affords convenient passage of the assembly 46 through tissue of the patient.

In a preferred embodiment, the sheath 44 is made of polyethylene. Other materials including, without limitation, polypropylene, nylon, polyester or Teflon may also be used to construct the sheath 44. The sheath 44 should also conveniently separate from the sling material 42 after the sling 42 is implanted without materially changing the position of the sling 42.

The sheath 44 may comprise two elongate, separable sections. Optionally, portions of the sheath 44 may detachably and telescopically overlap near the middle portion of the sling or it may be slit (e.g. longitudinally or perpendicular to the longitudinal axis) to afford convenient separation.

In another aspect, the present invention comprises a dilator 54 (FIG. 2) for use in a surgical sling procedure. Notably, the dilator is optional according to some aspects of the present invention as, for example, the sling and/or protective sheath may be directly connected to a novel needle of the present invention by virtue of an eyelet in the needle or other arrangements disclosed in greater detail below.

The dilator 54 comprises a body portion having first end portion 56 and second end portion 52 opposite the first end portion 56. The first end portion 56 has surfaces for associating the dilator with a needle (e.g. end 58 of needle 60). The second end portion 52 has sling association means for associating the article with a sling, sling assembly or component thereof. The sling association means may comprise a hole 90.

Preferably, the dilator 54 comprises a short article that dilates a needle track for ease of sling introduction and positioning within the patient. End 58 of the needle 60 is preferably keyed to allow for convenient, secure attachment of the needle 60 relative to the dilator 54. Preferably the attachment is permanent.

The kit shown in FIG. 3 includes two dilators 54. The dilators 54 atraumatically create and/or expand the passageway through the tissues for sling assembly delivery. The dilator 54 is preferably short relative to a needle 60 for ease of passage of the assembly and to reduce the overall amount of tissue that is deflected at one time. Preferably, the dilator is less than 2.5 inches in length, and more preferably, it is less than one inch in length, even more preferably, it is less than 0.7 inches in length. The maximum radius of a dilator 54 is preferably less than 10 mm, more preferably less than 7.5 mm, even more preferably less than about 5 mm. The tip or leading end of the dilator 54 is preferably blunt, as, in preferred embodiments, the leading tip of the dilator 54 will pass through tissue that has already been pierced by a needle 60. The dilator 54 may be made from a variety of biocompatible and sterilizable materials including, without limitation, acetal, polycarbonate, polypropylene, Delrin®, Acrylonitrile-Butadiene-Styrene (ABS), polyethylene, nylon and any combination of biocompatible materials.

The dilator 54 preferably includes means for associating with a surgical needle 60. In a preferred embodiment, the association means affords a permanent affixation between the dilator 54 and the needle 60. By "permanent affixation", it is meant that it would be very difficult to manually separate the dilator from the needle after they have become permanently affixed. After implantation of the sling 42, to separate the sling 42 from the dilator 54/needle 60, the surgeon cuts an end of the sling 42 as described more fully below. The association means preferably affords quick and convenient attachment of the dilator 54 to the needle 60 to avoid wasting time in the midst of a surgical procedure. The attachment should also be secure to avoid separation of the needle 60 and dilator 54 while the combination is passed through tissue.

In one embodiment, the means comprises a shoulder surface on the needle and complementary slot surfaces on the dilator 54. Referring to the embodiment of dilator shown in FIG. 2, the dilator 54 may be approximately 3.1 cm (1.2 inches) in length. The dilator 54 preferably includes a gentle taper near its first end 56. The dilator is sized and shaped to provide atraumatic passage through body tissue. The taper and relatively smooth outer surface of the dilator 54 facilitate atraumatic passage of the dilator 54 and attached sling assembly 46 through the various tissues of the patient. The presence of the dilator 54 allows a gentle transition between the diameter of the needle, to the shape of the dilator, and finally to the sling assembly 46.

Preferably, the attachment of the dilator 54 to the needle 60 is a substantially linear fashion, as opposed to a twisting or screw-like attachment. Preferably, the attachment is a snap-fit attachment to save time during the surgical procedure.

The second end 52 of the dilator 54 associates the dilator with one end of a sling 42, or sheath 44 or sling assembly 46. The sheath 44 or sling 42 is preferably attached to the dilator 54 via a first opening or through-hole located near the second end 52 of the dilator 54. In this embodiment, the opening operates as a universal sling material or assembly attachment point which can receive a variety of materials, such as fascia, autologous materials, synthetics, biologic tissues and any other similar tissues, including any combinations.

In the embodiment shown in FIG. 2, the end portion 48 or 50 of one end of the sheath 44 is threaded through the opening of the dilator 54 and secured to the sheath 44, thereby forming a loop. Alternatively, ends 48 or 50 may be fastened onto the sheath 44 via ultrasonic welding, bonding, melting, suturing, sealing or other attachment techniques. Further, the end 52 of the dilator 54 preferably includes a cut-away section to provide room to receive sling assembly material to reduce the overall profile of the sling assembly experienced by tissue during sling passage. Therefore, when the sheath is attached to the cut-away section, the additional sheath material is not apt to significantly increase the relative thickness, diameter or profile of the dilator 54. Unlike the showing in FIG. 3, the dilator 54 is preferably preattached to the sling assembly 46. In one embodiment, the sling 42 itself may be attached to the dilator, e.g. with a suture threaded through the opening of the dilator and tied to the sling.

One or more longitudinal slots located on the outer surface of the dilator 54 allow the wall of the dilator 54 to expand in a radially outward direction when the first end of the needle 60 is inserted into the opening of the dilator 54. When a shoulder of the dilator 54 passes the recess of the needle 60, the wall of the dilator 54 collapses around the needle 60 as the shoulder seats into the recess, thereby securing the dilator 54 on the needle 60 and blocking separation of the dilator 54 and needle 60.

A portion of the dilator 54 includes a taper having a decreasing profile toward the second end 56 of the dilator 54. The taper preferably gently cams tissue out of the path of the sling assembly 46 as the sling assembly is inserted in the body. The taper is also sized and shaped to reduce the amount of friction or resistance as the device is drawn through the tissues of the patient. The amount of force required to manipulate the device through the tissues is thereby reduced. This in turn provides the user of the assembly with additional control over device insertion and maneuverability through tissue and within the patient. In addition to tapered profiles, other dilator profiles such as conical, flared, frusto-conical, pyramid-shaped, elliptical or other applicable profiles may also be used.

A surgical kit according to the present invention may optionally include additional accessories. For example, a surgical drape specifically designed for urological procedures such as a sling procedure may be included in a kit of the present invention. Such a drape is disclosed in published U.S. patent application Ser. No. 2002-078964-A1. Alternatively, an article for objectively setting tension of the sling, such as one of the articles described in published U.S. patent application Ser. No. 09/968,239, filed Oct. 1, 2001 may be included in the kit.

The kits according to the present invention preferably include at least two needles. In some instances the needles may be substantially identical, in other instances, they may be different. Two or more needles reduce the need to reuse a non-sterile needle at a different location with a patient, thereby eliminating cross contamination issues. Additional needles, handles, dilators and other elements may also be included for surgical convenience, for avoidance of contamination from one portion of the body to another, for ease of manufacturing or sterilization or for surgical requirements. For example, two different types of needles may be included in a kit. One type of needle may be suitable for an outside-in (e.g. from the skin incision toward a vaginal incision) approach. Another type may be suitable for an inside-out (e.g. from the vaginal incision toward a skin incision) approach. Surgeons that prefer an approach dictated by the surgeon's dominant hand may prefer this embodiment. Alternatively, a universal needle (e.g one suitable for both an inside out and an outside in approach) may be utilized.

FIG. 53 illustrates a system 101 for use in an inside-out procedure. The system 101 comprises a pair of needles 109 that are sized and shaped for the inside-out approach. The system 101 also includes a sling assembly comprising a sling 111, and protective sheath 113. The sling assembly may be permanently attached to the needles 109 at ends 117. Alternatively, the needle 109 can include specially shaped structure (e.g. an eyelet) near end 117 that affords association between the needle 109 and sling or sling assembly after passage of the needle 109. The system 101 may optionally include releasable handle portions 119 that can be releasably attached to the needles 109 at ends 121.

FIG. 54 illustrates a system 102 for use in either an inside-out procedure or an outside-in procedure. The system 102 comprises a sling assembly 146 having a sling material 142, a sheath 144 and dilators 154. The system includes a handle portion 164 that is at least partially reusable. Needles 162 are suitable for either an inside-out or outside in procedure. The ends 158 of the needles 162 may be attachable to either a dilator 154 or the handle portion 164. Alternatively, the needles may be attachable to the implantable material itself or a sling and protective sleeve assembly without any dilator.

The system 102 allow the needles to be passed through tissue without requiring that they be attached to a sling or sling assembly. Thus, if the initial passage is not deemed to be optimum, the needles may be repassed without subjecting the sling or sling assembly to damage during the initial passage.

FIGS. 55-57 sequentially illustrate use of the system 102 using an inside-out approach. FIG. 55 illustrates passage of the needles 162 using inside-out approaches. The handles 164 are optional. If they are used, they are removed once the needles 162 have emerged from the skin incision. FIG. 56 illustrates the needles 162 after the handles 164 have been removed, in preparation for attachment of a sling assembly 146 on the ends 158 of the needles 162 previously occupied by the handles 164. FIG. 57 illustrates the system 102 during implantation of the sling.

FIG. 58 is a schematic illustration of the system 102 used in an inside-out approach (the right side of the patient) and an outside-in (the left side of the patient) approach. This combination may be utilized, by a right-handed surgeon who prefers to pass the leading edge of the needle with his or her dominant hand. Alternatively, the combination may be reversed for a left handed surgeon. The remainder of the surgical procedure may be substantially identical to that depicted in FIGS. 56 and 57. Notably, the handle 164 utilized on the right side of the patient's body may optionally be placed on the other side of the needle after it emerges from the patient's body to conveniently assist the surgeon in moving the needle 162 and sling assembly 146 through the tissue.

FIGS. 59-61 sequentially illustrate the system 102 used in outside-in approaches. FIG. 59 illustrates the needles 162 inserted initially through the patient's skin and thereafter emerging from a vaginal incision. FIG. 60 illustrates the system 102 just prior to attachment of a sling assembly 146. FIG. 61 illustrates the system 102 during implantation of the sling.

Referring to FIG. 62, there is shown another system 200 according to the present invention. The system 200 comprises a needle 262 suitable for an outside-in approach on the left side of the patient's body and associated handle 264. The system 200 also includes a sling assembly 246 comprising a sling 242, protective sheath 244 and dilator 254 at one end. The dilator 254 is designed to mate with the end 258 of the needle 262. At the other end of the sling assembly 246, a needle 265 may be permanently attached to the sling assembly 246. The needle 265 is sized and shaped to be suitable for an inside-out approach on the right side of a patient's body. The needle 265 includes a leading end 266 suitable for that purpose. The leading end 206 may be substantially blunt or, alternatively somewhat sharpened. The system 200 is particularly suitable for a surgeon that desires to initially pass needles with his or her dominant hand. The depicted system 200 is suitable for a right handed surgeon. A mirror image or reverse system is particularly suitable for a left handed surgeon that desires to initially pass a needle with his or her left hand.

Optionally, the system 200 could include a detachable handle for the needle 265 to assist in passage of the needle 265. Also optionally, the needle 264 may be omitted from the system. Instead, the needle 265 may be used to pass the sling initially using an outside-in approach on one side of the body and then continuing to insert the sling using an inside out approach on the other side of the body.

In a preferred embodiment a kit comprises two surgical instruments such as those shown in FIGS. 15-22, and a polypropylene sling mesh assembly with attached dilators as shown in FIG. 28. Such a kit may be provided for the placement of a pubourethral sling for the treatment of female stress urinary incontinence (SUI) resulting from urethral hypermobility and/or intrinsic sphincter deficiency.

The individual elements of the kits of the present invention may be packaged together, separately or in subassemblies depending on a variety of factors such as shelf life and sterilization requirements. They may be assembled at the manufacturing location or at the healthcare location. Any suitable sterilization procedure may be utilized to sterilize the contents of a kit. Suitable sterilization techniques include, but are not limited to steam, ethylene oxide, electron beam, vapor (e.g. hydrogen peroxide or peracetic acid), gamma or plasma procedures. For example, the surgical instrument may be reusable or single use devices.

FIG. 11 shows another embodiment of the present invention. In this embodiment, the needle 60 acts as a surgical guide needle (e.g. with a diameter of about 4 mm, or less, preferably about 3 mm) for a relatively larger sling transport needle 604 (e.g. with a diameter of about 5 mm or less). Preferably, the sling transport member has a sling assembly 610 (e.g. a sling mesh and insertion sheath) attached thereto. Alternatively, the sling transport needle 604 may have a more exaggerated hook shape, similar to the shape shown in PCT WO 02/39890.

The guide needle 60 serves a different purpose than the surgical transport needle 604. The surgical guide needle 60 is preferably small and has a blunt tip. The blunt tip is initially inserted through incision 400 adjacent obturator fascia and then through a vaginal incision. Inserting a small, blunt needle in this fashion provides the surgeon with addition control in maneuvering through the anatomy of a patent and in avoiding sensitive tissue.

A surgical kit according to an aspect of the present invention may include a dilator 54 for placement on the end of needle 60. The sling transport needle 604 may optionally include a sharp tip. The dilator 54 receives the tip of the needle 604. Pushing sideways on the sling transport needle 604 with one hand while steering the tip of the needle 604 by holding guide needle 60 with the other hand may be used to implant the sling.

Alternatively, the dilator 54 can include surfaces for firmly engaging and attaching to needle 604. Those surfaces can include mechanical interlocking structures, grasping structures or interlocking structures. As a result, the needle 60 need not have specially shaped surfaces 58 for engaging the dilator and can instead have cylindrical surfaces adapted to be received within the dilator.

Referring to FIGS. 15, 16, 17 and 18, there is shown a novel needle 60R according to the present invention. The needle 60R is particularly suitable for passage on the right side of a patient's body, initially from an incision in the region of the patient's obturator foramen and subsequently emerging through a vaginal incision. The needle 60R includes a handle 64R and a leading end portion 62R. Referring to FIG. 27, the leading end portion 62R includes a substantially blunt distal tip 63R and specially designed surfaces 67R and 65R suitable for mating with complementary surfaces on a dilator or connector (described in more detail below). Notably, in one aspect of the present invention, a novel needle of the present invention may utilize an eyelet near its distal tip to afford a suture attachment to a sling or sling assembly without the use of a dilator.

As shown in FIGS. 15-18, the needle 60R has substantial structure in three dimensions, as opposed to, for example, the substantially flat needle shown in FIG. 1 (or an Emmet needle) that only includes substantial structure in two dimensions. Having substantial structure in three dimensions helps the surgeon pass the needle through the obturator foramen and subsequently through a vaginal incision by affording greater surgeon control. The handle of the needle allows the surgeon to move the distal end of the needle with an ergonomic wrist roll action FIGS. 15A, 16A, 17A and 18A show another embodiment of novel needle 60R' that is similar, but not identical to the needle 60R. The needle 60R' is also particularly suitable for passage on the right side of a patient's body, initially from an incision in the region of the patient's obturator foramen and subsequently emerging through a vaginal incision.

FIGS. 19, 20, 21 and 22 show another novel needle 60L according to the present invention. The needle 60L is particularly suitable for passage on the left side of a patient's body, initially from an incision in the region of the patient's obturator foramen and subsequently emerging through a vaginal incision. The needle 60L includes a handle portion 64L and a leading end portion 62L. Like the needle 60R, the needle 60R includes substantial structure in three dimensions.

FIGS. 19A, 20A, 21A and 22A show another embodiment of novel needle 60L' that is similar, but not identical to the needle 60L. The needle 60L' is also particularly suitable for passage on the left side of a patient's body, initially from an incision in the region of the patient's obturator foramen and subsequently emerging through a vaginal incision.

Yet another embodiment of novel needle is shown in FIG. 20B. The novel needle 64L" is substantially similar to the needle 64L', except that the tip T of the needle lies substantially in the plane P of the handle H of the needle 64L". It is believed that such an arrangement of the elements may assist some surgeons in conjuring a mental image of the location of the tip T of the needle 64L" relative to the body while the needle is being passed through a patient outside the surgeon's direct vision. The arrangement of the tip and the handle affords visual feedback concerning the approximate location of the tip of the needle when the tip is not under direct vision. Instead of a snap-in feature for connection to a dilator, this needle 64L" includes an eyelet E for threading a suture so that the needle 64L" can be tied to an implantable material or assembly such as a knitted polypropylene sling with an associated sheath.

FIGS. 63 through 67 show various embodiments of sling assemblies suitable for use in the present invention. These assemblies may be used in systems that do not include a dilator. FIG. 63 illustrates a sling assembly 300 having sutures 306 for threading through an eyelet of a needle to associate the assembly 300 with a needle. The assembly 300 may comprise a composite assembly with synthetic portions 308 and a non-synthetic mid portion 309 connected with fasteners 303.

FIG. 64 shows a sling assembly 320 comprising only a synthetic mesh material 322. Sutures 6 may be threaded through an eyelet of a needle to associate the assembly 320 with a needle. Optionally, a sheath may be added to the assembly 320, especially when the mesh 322 is elastic.

FIG. 65 illustrates a sling assembly 330 comprising a non-synthetic sling 332. Sutures 336 may be threaded through an eyelet of a needle to associate the assembly 330 with a needle. Optionally, suture anchors or pledgets may be utilized to avoid suture pull through.

FIG. 66 illustrates a sling assembly 340 comprising a sling mesh 342 and a sheath 344. In this embodiment, the ends of the sling mesh 342 may be attached to the ends of the sheath 340 by welding, suturing, or other suitable means. Sutures 346 may be tied about the ends of the sheath 344 to form a dilator-like structure for pushing tissue out of the way of the assembly 340 during implantation. The sutures 346 may be threaded through an eyelet of a needle to associate the assembly 340 with a needle. FIG. 66 also shows a tensioning suture, but this is optional and can be omitted.

FIG. 67 illustrates another sling assembly 350 comprising a synthetic mesh 352 and a sheath 354. Sutures 356 may be threaded through an eyelet of a needle to associate the sling 352 with a needle. Sutures 358 may be tied about the ends of the sheath 354 to form a dilator-like structure for pushing tissue out of the way of the assembly 350 during implantation. FIG. 67 also shows a tensioning suture T', but this is optional and can be omitted.

Preferably, the handles of the surgical instruments shown in FIGS. 15-20B includes indicia indicating the proper side of the patient. For example, the indicia may be any suitable information conveying word, symbol or depiction. The indicia may simply be "right" or "left." For those instruments designed for use on the right side of the patient, the indicia may include a drawing similar to FIG. 32. For the instruments designed for use on the left side of the patient, the indicia may include a drawing similar to FIG. 33.

The various embodiment of three dimensional needles described above preferably include a substantially straight spacer portion emerging from an end of the handle portion preferably along the handle axis. This helps afford convenient passage of the needle using an ergonomic wrist roll adopted by some surgeons. The three dimensional needles also include a structure that can be described as a variable spiral portion extending from the distal end of the straight spacer portion. As shown, the spiral portion is preferably variable as the angle of the spiral portion changes between the end of the straight portion and the distal end of the needle. The shape of the spiral portions help avoid over insertion of the needle into the body which helps avoid damage to the sensitive structures in this region of the body.

The variable spiral portions of the three dimensional needles have tissue clearance depth TCD of greater than about 1.5 inches and less than about 2.5 inches, more preferably the tissue clearance depth is between 1.75 inches and about 2.25 inches, even more preferably it is about 2 inches. The tissue clearance depth TCD is the distance between the end of the straight spacer portion and a point along an extension of the axis of the straight spacer portion which is defined by a line that is normal to the axis and that intersects the distal tip of the needle. The tissue clearance depth TCD helps space the distal end of the needle from the distal end of the straight portion to reduce interference in needle passage by the distal end of the straight portion.

The variable spiral portions of the three dimensional needles have a maximum width MW that is preferably great enough to afford passage around the inferior pubic ramus and through the natural opening of the pubic bone, but small enough to avoid sensitive structure in this region of the body. Preferably, the maximum width MW is greater than about 1.25 inches and less than about 3 inches, more preferably, it is between about 2 and about 2.225 inches and more preferably, it is about 2.15 inches.

Referring to FIGS. 23, 24, 25, 25A and 26, there is shown a novel dilator 54S according to another aspect of the present invention. The dilator 54S includes a hole 90S for receiving a sling or a sheath or both in order to associate the dilator with a sheath.

Due to the more tortuous path associated with a transobturator route and the tighter radial passage, a shorter dilator is preferred to reduce tissue trauma and afford convenient, easy passage. Rotation of a helical needle can cause a substantially straight dilator to skid or plow through tissue instead of moving in a direction parrallel to the longitudinal axis of the dilator. A shorter dilator will reduce tissue trauma associated with such plowing or skidding. Alternatively, a slightly curved or arcuate dilator may be used to reduce plowing or skidding.

The length L of a substantially straight dilator 54S is substantially short, preferably less than about 30 mm (1.2 inches) more preferably less than about 18 mm, 0.7 inches. The outermost diameter D of the dilator 54S is preferably less than about 6 mm 0.24 inches, more preferably less than about 5 mm, even more preferably, less than about 4 mm. The dilator 54S preferably has surfaces 51S that provide a smooth transition between the needle (e.g. 60L) and the sling assembly. The angle theta is preferably less than about 15 degrees and more preferably less than about 12 degrees.

In one embodiment of the present invention, one substantially straight dilator 54S may be used with either a left or a right side needle. Preferably, such a combination includes a distal end of the needle that is substantially straight. This length (e.g. L" in FIG. 26A) is preferably short, preferably less than 0.9 inches, more preferably less than 0.8 inches, more preferably about 0.42 inches. In one embodiment, the length L' in FIG. 25 may be 0.3 inches.

It is noted that the dilator is preferably capable of being "permanently affixed" to the needle. Preferably, the needle is attached to the dilator without a suture. FIG. 26A illustrates one example of a permanently affixed needle and sling assembly. By "permanent affixation", it is meant that it would be very difficult to manually separate the dilator from the needle after they have become permanently affixed. After implantation of the sling, to separate the sling from the dilator/needle subassembly, the surgeon cuts an end of the sling assembly (e.g. a cut is made through the mesh and protective sleeve) to separate the mesh from the needle/ dilator subassembly. The connection between the needle and dilator preferably affords quick and convenient attachment of the dilator to the needle to avoid wasting time in the midst of a surgical procedure. The attachment should also be secure to avoid separation of the needle and dilator while the combination is passed through tissue.

To accomplish the preferred attachment, the dilator 54S includes an internal stop surface 57S that is complementary with specially shaped surfaces on a needle (e.g. 62R, FIG. 27). As best seen in FIG. 26A, the stop surface 57S is designed to engage complementary shoulder surface (e.g. 65R, FIG. 27) to achieved the desired convenient, but permanent affixation.

Also preferably, the needle is attached to the dilator without any screw-type connector. Preferably, the connection is a snap-fit, quick connection for secure, convenient use by the surgeon. Also preferably, the connection is a press on connection that does not require substantial rotation of elements (especially elements that are within the body) as such a connection is less likely to displace a needle or otherwise injure the patient.

Referring to FIG. 28, the dilators 54S may form a portion of a sling assembly that includes synthetic sling end portions 42A', sheaths 44A' covering at least some of the sling end portions 42A' and a non-synthetic mid-portion 45'. A composite sling assembly may be assembled by the surgeon or provided preassembled using the teachings or components of published U.S. patent application Ser. Nos. 2002-0147382-A1 or 2002-0082619-A1.

In another aspect, the present invention comprises the ornamental design for a surgical instrument, as shown in FIGS. 39 through 45 and described in the Brief Description of the Drawings.

In another aspect, the present invention comprises the ornamental design for a surgical instrument, as shown in FIGS. 46 through 52 and described in the Brief Description of the Drawings.

The broken line showing in FIGS. 39-52 are for illustrative purposes only and form no part of the claimed design.

The above-described surgical instruments may be disposable or reusable. Optionally, portions of the surgical instrument may be reusable (sterilizable) and other components may be disposable.

EXAMPLES OF SURGICAL PROCEDURES

Several methods are contemplated herein. Although the methods of use as disclosed herein generally relate to female incontinence conditions and treatments/procedures, male incontinence conditions and treatments/procedures are also included within the scope of the present invention. Further, the term "urethra," with respect to sling positioning, is used for brevity and reader convenience. It should be noted that the present invention is particularly suitable for placing a sling in a therapeutically effective position. The method may be utilized to support a variety of structures at different anatomical locations. Variations of these methods may occur due to individual surgeon's techniques or a patient's particular anatomy.

Referring to FIGS. 4 through 10, a preferred embodiment of surgical procedure is disclosed. The present invention utilizes an obturator passage of the needle, preferably in a direction from the anterior to the posterior side of the pubic bone. An obturator approach affords a sling procedure where previous scarring in the region of the retropubic space or other anatomical features would prevent or restrict a traditional pubovaginal sling procedure. An obturator approach is also likely to avoid bladder perforations, a possible but rare complication with some prior art pubovaginal procedures. It may also be more convenient to conduct a concomitant repair (e.g. cystocele repair) with a sling inserted with a side approach as the sling is placed in a more horizontal position (e.g. see FIGS. 9 and 10) than the U-shaped sling procedures of the prior art.

Initially, the patient is placed under local, spinal or general anesthesia. A catheter 2 (e.g. Foley) may be inserted through the urethra 16. A small incision (e.g. a transverse incision) is made in the anterior vaginal wall 20 of a patient followed by a transurethral dissection. The amount of dissection may vary according to surgeon preference. Preferably, dissection is sufficient to allow the surgeon's finger to meet the end 58 of the needle 60 just after it passes through the obturator fascia.

Two small stab incisions 400 are also made near the obturator fascia to afford needle entry. Notably, the precise location of the stab incisions 400 may vary according to surgeon preference. For example, some surgeons may place the incision adjacent the obturator opening of the pubic bone. Other surgeons may slightly offset the incision in order to use the bias provided by the patient's tissue to urge the tip of the needle in a direction toward the posterior surface of the pubic bone.

Referring to FIG. 4, the end 58 of needle 60 is shown just passing an incision 400 on the patient's right side. The surgeon's finger is initially placed in the vaginal incision sufficient to meet the end 58 of the needle 60 after it passes through the obturator fascia and the obturator foramen 3 (see FIG. 9). A path for the needle 60 through the obturator foramen 3 that is substantially free of vascular and nerve passages is selected. To select the path, the surgeon preferably initially identifies the anatomical structures of the pelvis such as the ischial tuberosity and obturator foramen 3 by palpation of the tissue.

If optional handle 64 is used, it may be adjusted relative to needle 60 according to surgeon preference and securely associated with the end 62 of the needle 60. FIG. 5 shows the end 58 of needle 60 just passing an incision 400 on the patient's left side.

Preferably, after the end 58 of the needle 60 meets the surgeon's finger, the surgeon seeks to use the posterior portion of the patient's pubic bone as an anatomical guide to controllably move the end 58 of the needle toward the vaginal incision and to help avoid damaging structures. The surgeon exploits the tactile feel provided by the posterior portion of the pubic bone to controllably pass the end of the needle 58. This approach is preferred as it helps keep the needle 60 away from the bladder and other vulnerable tissues.

FIG. 6 illustrates the needle of FIG. 5 as it emerges from a vaginal incision. The shape and size of needles 60 help provide precise passage of the needles 60 to the vaginal incision. The steps described above are repeated as needed for both sides of the urethra 16. FIG. 6 also illustrates one side of a sling assembly 46 prior to association with the needle 60.

FIG. 7 is a perspective view of one side of a sling system after it is associated with needle 60. The dilators 54 of the sling assembly 46 are preferably snapped irreversibly into place on the needles 60 for a secure connection. Next, if a synthetic sling assembly is used, the plastic sheath 44 is oriented so that an optional center orientation indicia (e.g. a blue mark) is facing away from the surgical field, toward the surgeon.

After the dilators 54 are attached to the needles 60, the sling assembly 46 is properly oriented so that the sling assembly 46 is not twisted when attached to the dilators 54. After the dilators 54 and sling assembly 46 are properly positioned, dilators 54 and sling assembly 46 are pulled through the tissues of the patient.

Referring to FIG. 8, once the dilators 54 are securely attached, the needles are pulled through the incisions 400, taking care to avoid contact with sensitive tissue. The sling is then clamped with surgical clamps (not shown). During this portion of the process, the attached dilators 54 and sling assembly 46 are atraumatically pulled through the needle paths, advancing the sling assembly 46 adjacent to and beneath the urethra 16 or target site. A portion of each end of the sling assembly 46 extending beyond the incisions 400 is clamped and then cut to release the needles 60 and attached dilators 54.

The sling is placed in a therapeutically effective position. FIGS. 9 and 10 show one example of a therapeutically effective position. Other positions are contemplated herein. The precise anatomical position will depend upon a variety of factors including the type and degree of anatomical damage or insufficiency, location of significant scar tissue, whether the sling procedure is combined with other procedures and other surgeon decisions. Typically, the sling is placed midurethra, without tension, but in position to support the midurethra. Alternatively, the sling could be placed to support the bladder neck and/or UV junction.

Once the sling assembly 46 is carefully positioned under the midurethra or target site to provide sufficient support to the target site, the overlapping portion of the sheath 44 located near the center of the sling assembly 46 and an optional tensioning member (i.e. tensioning filament) may then be used to center and properly position the sling assembly 46 under the midurethra. The sheath 44 is then removed.

Sling tension may be tightened by placing a device, such as a clamp, across one or both ends of the sling 42. Generally, the surgeon grasps the mesh and tensioning filament together adjacent the incision 400 and pulls to increase the degree of tightness of the mesh.

After the dilators 54 are trimmed off, the plastic sheath 44 is removed from the sling mesh 42 by pulling on both sides of the sheath 44, preferably one at a time. Optionally, to avoid overtightening the sling mesh 42 while removing the sheath 44, a forceps or other blunt instrument may be placed between the sling and the urethra.

FIGS. 9 and 10 illustrate one embodiment of the final placement of the sling 42 relative to anatomical structures such as the pubic bone, urethra and vagina. The sling is flatter than the U-shaped slings of the prior art which extend to the rectus fascia of the patient's abdomen.

In another embodiment of the invention, shown with reference to FIG. 11, a method includes the steps of providing a surgical kit comprising at least one guide needle 60 constructed for an obturator approach, and at least one sling transport needle 604 with a sharp tip, a sling 610 attached to the sling transport needle 604, and a dilator 54 having tip receiving surfaces for receiving the sharp tip of the sling transport needle 604. The needle 60 has a relatively small diameter (e.g. less than 4 mm). The method includes the steps of creating at least one vaginal incision, creating two obturator stab incisions, and initially passing a guide needle 60 through the obturator incision and then through the vaginal incision. The dilator 54 is then attached or associated with the needle 60.

Needles 604 are initially guided through a vaginal incision and toward one of the obturator incisions 400. Guiding the sharp tip of the large sling transport needle 604 in this fashion is believed to help avoid contact between the sharp tip of needle 604 and sensitive structures. Optionally the adapter with receiving surfaces may be integrally formed in the needle 604 to avoid the need to separately attach the adapter to the needle 604.

FIG. 4A shows an alternative step according to an aspect of a method according to the present invention. This illustrates a method wherein the needle 60 of FIG. 1 is initially inserted through a vaginal incision and then emerges from a skin incision. In this embodiment, the sling assembly may then be attached to the end of the needle previously occupied by a removable and repositionable handle 64. The handle 64 may then optionally be placed on the other end of the needle 60 to assist the surgeon in passing the sling assembly and needle through the body. This is shown by the arrow in FIG. 4A adjacent the dotted line showing of the handle 64.

The method preferably includes the step of removing the handle 64 and attaching an end of the sling assembly to the end of the needle previously occupied by the handle 64. The needle and attached sling assembly is then passed completely through the body, in substantially the same direction as the initial insertion, to place one side of the sling assembly. As a result, it can be seen that the needle 60 is a universal needle (i.e. one that can be utilized for either an "outside-in" surgical approach or an "inside-out" approach).

Referring now to FIGS. 31-38, there is shown another embodiment of method according to the present invention. This embodiment is believed to be suitable for patients under local, regional or general anesthesia. This embodiments utilizes needles specially shaped for use on a predetermined side (e.g. right or left) of the patient.

A small incision may be made in the anterior vaginal wall followed by pariurethral dissection. Two small stab incisions are also made above the obturator foramen for instrument passage.

The patient is preferably placed in a modified lithotomy position with hips flexed, legs elevated. The bladder is emptied and a weighted vaginal retractor may be used.

The surgeon palpates the inferior portion of the ischiopubic ramus, palpates the edge of the bone and notes where the ischiopubic branch gets wider and the obturator membrane is tactily sensed. Just below this location and lateral to the bone is a preferred mark for the skin incisions. The surgeon preferably confirms that both marks lie in a straight line approximately at the level of the clitoris.

In the anterior wall of the vagina, the surgeon may draw a vertical mark approximately 0.5 cm below the meatus. The incision may be approximately 2 cm in length. An Allis forceps may be placed on the incision margin to expose the incision.

The surgeon incises the vaginal wall and extend the dissection laterally (parurethral) with, for example, a Metzenbaum scissors. The surgeon then may dissect the pariurethral attachment to the vagina. The surgeon may then insert the tip of a blunt instrument (e.g. the Metzenbaum scissors laterally), spread and advance the scissors until the tip of the scissors touches the inferior portion of the bone (about 1-1.5 cm). This may be accomplished bilaterally. The vaginal dissection is preferably large enough for a finger tip to enter in both directions.

The instrument is then passed through the obturator foramen. The surgeon preferably palpates the interior portion of the ischiopubic ramus, palpates the edge of the bone and preferably moves his or her finger cephalad until muscle firmness is felt. Just below this location and lateral to the bone may be the mark for the skin incisions. The surgeon may confirm that both marks lie approximately in a straight line at the level of the clitoris.

The surgeon may then insert the index finger into the vaginal dissection and probe to the ipsilateral outer obturator foramen mark to confirm needle path. The surgeon makes a small vertical skin incision on the same side over the skin mark denoting the foramen. If patient side specific instruments are used (e.g. those shown in FIGS. 15-22), the instrument designated for the patients left side 60L may be removed from the package. The surgeon points the instrument tip perpendicular to the skin and proceeds to the level of the obturator fascia.

With a finger in vaginal incision, the surgeon moves the finger laterally to meet the needle tip (see FIG. 35). When passing the needle 60L on the patient's left side, the surgeon preferably keeps his or her right hand on the needle handle and left index finger in the vaginal incision. The surgeon's left thumb may optionally be on the outside curve of the needle 60L to control the needle movement. The surgeon's left thumb preferably pushes the needle through the muscles and obturator fascia. The needle tip preferably penetrates until resistance of the tissue stops—about 0.5 cm.

The surgeon then preferably immediately locates the ischial pubic ramus with the needle tip 62L and rotates the needle handle 64L (see FIG. 33) to allow the needle to follow the posterior ischial pubic ramus surface. The index finger tip should palpate the needle tip. If not, the surgeon should move the needle to meet the finger tip. If the needle tip cannot be located, then the needle should be withdrawn just behind the ischial pubic ramus and advanced again.

Using the index finger, the surgeon preferably guides the instrument tip medially towards the vaginal incision until the instrument tip extends through the incision (see FIG. 36).

The above steps are repeated on the patient's right side. See FIGS. 32 and 34. Cystoscopy may not be required but can be done at the surgeon's discretion.

The surgeon then attaches the dilating connectors (that are pre-attached to the sling mesh) to the ends of the instruments 60L and 60R that emerge from the vaginal incision. One dilating connector 54S should be attached to each of the instruments 60L and 60R on the ends protruding from the vagina. If optional blue markings are used on the sling assembly, the surgeon orients the blue markings on the sheath facing outward, away from the urethra 16. The surgeon may use the blue markings to help ensure that the sling mesh lies flat and that the mesh is not twisted prior to attaching the second dilator 54S as the dilators cannot be removed once they are snapped into place.

The surgeon then pulls the assembly through the lateral incision. This is shown for the left side of the patient's body in FIG. 37. Next the surgeon cuts the sling mesh just below the level of the connector and discards the needle and dilator. In FIG. 38, this has been accomplished for the portion of the system on the right side of the patient's body.

The surgeon preferably keeps the blue centering marks on the plastic sheath in the midline. This is repeated on the contralateral side.

If vaginal retraction has been used, it should be removed to adjust the tension of the sling. The sling may be finely tensioned by placing a blunt instrument (e.g. a Metzenbaum scissors or small instrument) between the sling and urethra.

The surgeon removes the plastic protective sheaths 44A and discards them.

Under spinal or regional anesthesia, the position of the sling can be improved by the cough test after filling up the bladder, at the discretion of the surgeon.

To loosen the mesh, the surgeon place an instrument (e.g. Metzenbaum clamp) between the sling mesh and the urethra. The surgeon ensures that both the mesh and the tensioning suture are located beneath the clamp. The clamp may be used to pull down and loosen the sling mesh as desired.

To tighten the sling mesh, the surgeon places a clamp (e.g. hemostat) across the sling mesh at the lateral incisions 400. The surgeon ensures that both the tensioning suture and the complete width of the sling are captured within the clamp. The sling mesh may be rolled around the clamp to improve the grip. The surgeon pulls up to tighten the sling mesh as desired. If needed, this can be repeated on the contralateral side.

To complete the procedure, the surgeon trims the sling mesh at the level of the subcutaneous tissue. A multi-layer closure of the vaginal incision and the skin incisions may then be completed.

All patents, patent applications, and publications cited herein are hereby incorporated by reference in their entirety as if individually incorporated.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

Passage of the guides and mesh are not limited to, through the vagina. The guides can also be inserted through the anus and penetrate the rectum to exit the ischial fossa or obturator fossa to suspend mesh through those portals. Additional combinations of passage routes include; from the iliac crest to the pubis; from the Ischial spine to the pubis; from right Ischial spine to left Ischial spine and others.

Additional configurations of the mesh include:

FIG. #21 a ladder shape with multiple strands connecting the strips.

FIG. #22 an "X" connecting the strips.

FIG. #23 perpendicular and diagonal strands connecting the strips.

FIG. #25 diagonal strands connecting the strips. In order to enhance the passage of the guide through the abdominal cavity it will be necessary for some procedures to have guides, which have different shapes and lengths. The basic guide has a single curve in the shaft, FIG. #26. Other configurations can have "S" curves, FIG. #27. Further shapes can be curves in multiple planes. The shaft can also contain a hinged section which is rotateable and lockable. The direction of the guide can be accomplished with a simple hinge or complex hinges along the shaft. Additional designs can include flexible shafts, directable shafts, and stearable shafts. Other designs can incorporate sections, which are rigid and sections, which are flexible or stearable. The use of certain materials can also enhance the passage of the guides through the body. Materials, which can be used, are shape memory alloys and plastics, which deploy to specific shapes under changes in temperature. These materials can also include a super elastic property, which allows significant bending with low force applied and without permanent deformation. The superelastic material can be combined with a cannula so that the cannula makes the initial passage and the memory material is extended beyond the cannula to finish the curved track. Additionally, the superelastic material can be passed through a curved cannula and as it exits continues on a straight path. In this instance the shaft can be constructed from a single or double central core wire which is wrapped with a tight coil of wire producing a configuration which has the flexibility of a spring without the elongation.

The invention claimed is:

1. A surgical assembly for treating incontinence comprising: a first surgical instrument for use on a right side of a patient, the first surgical instrument comprising a handle portion and a substantially helical needle portion having substantial structure in three dimensions and a distal end, the needle portion having a portion that is sized and shaped to extend between an incision substantially adjacent the obturator foramen on the patient's right side and a vaginal incision;
a second surgical instrument for use on a left side of a patient, the second surgical instrument comprising a handle portion and a substantially helical needle portion having substantial structure in three dimensions and a distal end, the needle portion having a portion that is sized and shaped to extend between an incision substantially adjacent the obturator foramen on the patient's left side and a vaginal incision; and
a sling assembly including a mesh material.

2. The assembly of claim 1 wherein the sling assembly comprises a synthetic material.

3. The assembly of claim 1 wherein the sling assembly comprises a knitted polypropylene material.

4. The assembly of claim 1 wherein the sling assembly comprises a sheath.

5. The assembly of claim 1 wherein at least a portion of the sling assembly comprises a non-synthetic material.

6. The assembly of claim 1 wherein the mesh material comprises a woven or knitted material.

7. The assembly of claim 1 wherein the mesh material comprises interlinked fibers that form multiple junctions.

8. The assembly of claim 1 wherein the needle portions of the first and second surgical instruments have structure near the distal ends for associating the first and second surgical instruments with the sling assembly.

9. The assembly of claim 1 wherein the needle portions of the first and second surgical instruments further comprise substantially straight spacer portions along an elongate axis of the handles.

10. The assembly of claim 1 wherein the substantially helical needle portions of the first and second surgical instruments are variable spiral portions.

11. The assembly of claim 1 wherein the needle portions of the first and second surgical instruments include a substantially circular cross sectional shape with a diameter of less than about 4 mm.

12. The surgical assembly of claim 1 wherein the handle portion of the first surgical instrument includes indicia indicating the first surgical instrument is for use on the right side of the patient, and
the handle portion of the second surgical instrument includes indicia indicating the second surgical instrument is for use on the left side of the patient.

13. The assembly of claim 1 wherein the handle portions of the first and second surgical instruments are detachable from the substantially helical needle portions.

14. The assembly of claim 1 wherein the handle portions of the first and second surgical instruments consist of a single handed adapted to removably attach to the substantially helical needle portions of the first and second surgical instruments.

15. A surgical assembly for treating incontinence comprising: a first surgical instrument for use on a right side of a patient, the first surgical instrument comprising a handle portion, and a needle portion having a substantially straight portion projecting from the handle and a variable spiral portion with a distal end, the variable spiral portion being sized and shaped to extend between an incision substantially adjacent the obturator foramen on the patient's right side and a vaginal incision;
a second surgical instrument for use on a left side of a patient, the second surgical instrument comprising a handle portion, and a needle portion having a substantially straight portion projecting from the handle and a variable spiral portion with a distal end, the variable spiral portion being sized and shaped to extend between an incision substantially adjacent the obturator foramen on the patient's left side and a vaginal incision; and
a sling assembly including a mesh material.

16. The assembly of claim 15 wherein the variable spiral portions of the first and second surgical instruments have a tissue clearance depth of greater than about 1.5 inches and less than about 2.5 inches.

17. The assembly of claim 15 wherein the variable spiral portions of the first and second surgical instruments have a maximum width of greater than about 1.25 inches and less than about 3 inches.

18. A surgical assembly for treating incontinence comprising: a first substantially helical needle having a leading end, a trailing end and substantial structure in three dimensions, the needle having a portion that is sized and shaped to extend between an incision substantially adjacent the obturator foramen on a patient's right side and a vaginal incision;
a second substantially helical needle having a leading end, a trailing end and a substantial structure in three dimensions, the needle portion having a portion that is sized and shaped to extend between an incision substantially adjacent the obturator foramen on the patient's left side and a vaginal incision;
a handle removably attachable to the trailing ends of the first and second substantially helical needles; and
a sling assembly including a mesh material.

19. The surgical assembly of claim 18 wherein the handle is removably attachable to the leading ends of the first and second substantially helical needles.

20. A method of treating incontinence in a patient comprising the steps of:
creating a vaginal incision;
creating an incision substantially adjacent the patient's obturator foramen,
providing an elongate, substantially helical surgical instrument comprising first and second ends, with at least one of the ends having a securement surfaces;
providing a sling assembly having an implantable sling for treating the incontinence, the sling assembly having surfaces complementary to the securement surfaces,
passing the instrument between the incisions,
then snap fitting the instrument to the sling assembly to provide a substantially permanent attachment between the instrument and the assembly,
then passing the implantable material through tissue from the vaginal incision toward the incision substantially adjacent the patient's obturator foramen.

21. A method of treating incontinence in a patient comprising the steps of:
creating a vaginal incision,
creating an incision substantially adjacent the patient's obturator foramen,
providing a substantially helical, elongate surgical instrument comprising first and second ends, the instrument having substantial structure in three dimensions,
providing an implant for treating the incontinence,
passing the instrument between the incisions,
then associating the implant with the instrument, and
passing the implant through tissue and through the patient's obturator foramen with the instrument.

22. A method according to claim 21 wherein the step of passing the implant through tissue includes the step of passing the implant along a substantially three dimensional path.

23. A method according to claim 21 wherein the step of providing an elongate surgical instrument includes the step of providing an instrument with an elongate handle portion having an axis, and
the step of passing the instrument between the incisions includes the step of rotating the instrument about the axis of the handle portion.

24. A method of treating incontinence in a patient comprising the steps of:
creating a vaginal incision,
creating an incision substantially adjacent the patient's obturator foramen,
providing an elongate surgical instrument comprising a handle portion, a needle portion having a substantially straight portion projecting from the handle portion and a variable spiral portion with a distal end,
providing an implant for treating the incontinence,
passing at least a portion of the variable spiral portion between the incisions by initially passing the distal end through the incision substantially adjacent the patient's obturator foramen and then through the vaginal incision,
then associating the implant with a portion of the instrument that has emerged from the vaginal incision, and
then moving the distal end of the instrument with the implant associated therewith from the vaginal incision toward the patient's obturator foramen to pass the implant through tissue.

25. A method according to claim 24 wherein the step of associating the implant with a portion of the instrument that has emerged from the vaginal incision includes the step of using a suture to tie the implant to an eyelet in the distal end of the needle.

26. A method of treating incontinence in a patient comprising the steps of:
creating a vaginal incision,
creating an incision substantially adjacent the patient's obturator foramen,
providing a substantially helical, elongate surgical instrument comprising a pair of ends,
providing an assembly having an implant for treating incontinence,
initially passing one end of the instrument initially through the vaginal incision toward the incision substantially adjacent the patient's obturator foramen in a path through the patient's obturator foramen until one end of the instrument emerges from the incision substantially adjacent the patient's obturator foramen, leaving the other end of the needle projecting from the vaginal incision,
then associating the end of the instrument that projects from the vaginal incision with the assembly, and
then moving the instrument out of the patient's body to pass the implant through tissue from the vaginal incision toward the incision substantially adjacent the patient's obturator foramen to place the implant in a therapeutically effective position.

\* \* \* \* \*

UNITED STATES PATENT AND TRADEMARK OFFICE
CERTIFICATE OF CORRECTION

PATENT NO. : 7,070,556 B2  Page 1 of 1
APPLICATION NO. : 10/306179
DATED : July 4, 2006
INVENTOR(S) : Kimberly A. Anderson et al.

It is certified that error appears in the above-identified patent and that said Letters Patent is hereby corrected as shown below:

Amend the claims as follows:

Column 11, Line 49, in Claim 1, insert --right helical-- following "having a";
Column 11, Line 57, in Claim 1, insert --left helical-- following "having a";
Column 12, Line 41, in Claim 15, insert --right-- following "handle and a";
Column 12, Line 42, in Claim 15, insert --right-- following "distal end, the";
Column 12, Line 49, in Claim 15, insert --left-- following "handle and a";
Column 12, Line 50, in Claim 15, insert --left-- following "distal end, the";
Column 12, Line 66, in Claim 18, insert --right helical-- following "the needle having a";
Column 13, Line 5, in Claim 18, delete "portion having a" and insert --having a left helical--;
Column 13, Line 7, in Claim 18, change "foraxnen" to --foramen--;
Column 13, Line 22, in Claim 20, delete "a" before securemen;
Column 14, Line 10, in Claim 24, delete the first "," after portion;
Column 14, Line 50, in Claim 26, uncapitalize the "o" in "out"

Signed and Sealed this

Eleventh Day of November, 2008

JON W. DUDAS
*Director of the United States Patent and Trademark Office*